United States Patent [19]

Narula et al.

[11] Patent Number: 5,100,872
[45] Date of Patent: Mar. 31, 1992

[54] SUBSTITUTED AND UNSUBSTITUTED ALKYL CYCLOHEXYLMETHYL AND CYCLOHEXENYLMETHYL CARBONATES AND PERFUMERY USES THEREOF

[75] Inventors: Anubhav P. S. Narula, Hazlet; Leroy John, Hillsborough; Anton V. Ouwerkerk, Livingston, all of N.J.; Vincent F. Kuczinski, Staten Island; Sophia Grojsman, Brooklyn, both of N.Y.

[73] Assignee: International Flavors & Fragrances Inc., New York, N.Y.

[21] Appl. No.: 729,381

[22] Filed: Jul. 12, 1991

Related U.S. Application Data

[63] Continuation-in-part of Ser. No. 666,031, Mar. 7, 1991.

[51] Int. Cl.$^5$ .................................................. A61K 7/46
[52] U.S. Cl. ........................................... 512/22; 558/60
[58] Field of Search ............................. 512/22; 558/60

[56] References Cited

U.S. PATENT DOCUMENTS

| | | | |
|---|---|---|---|
| 4,033,993 | 7/1977 | Bruns et al. | 260/463 |
| 4,080,309 | 3/1978 | Bruns et al. | 252/522 |
| 4,301,022 | 11/1981 | Sprecker et al. | 252/174.11 |
| 4,397,789 | 8/1983 | Boden et al. | 260/463 |
| 4,436,331 | 3/1984 | Licciardello et al. | 260/463 |

*Primary Examiner*—James H. Reamer
*Attorney, Agent, or Firm*—Arthur L. Liberman

[57] ABSTRACT

Described are alkyl cyclohexylmethyl and cyclohexenylmethyl carbonates defined according to the generic structure:

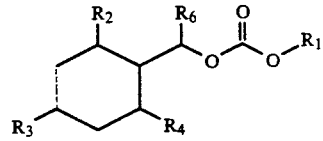

wherein $R_1$ is methyl or ethyl; $R_2$, $R_3$, $R_4$ and $R_6$ represents hydrogen or methyl; $R_5$ represents hydrogen, methyl or methylene; and $R_7$ represents hydrogen or $C_1$–$C_4$ straight chain lower alkyl or isopropyl or $R_7$ is no moiety; each of the dashed lines represents a carbon-carbon single bond or a carbon-carbon double bond; the wavy line represents a carbon-carbon single bond or no bond; with the provisos that:

(a) at least three of the dashed lines each represents a carbon-carbon single bond;
(b) when $R_7$ is no moiety, the dashed line at the "1-6" position is a carbon-carbon double bond;
(c) when the wavy line is a carbon-carbon single bond then $R_5$ is methylene and the carbon-carbon bond at the "4–5" position and at the "5–6" position is a carbon-carbon single bond;

and uses thereof in augmenting or enhancing the aroma of perfume compositions, colognes and perfumed articles, such as solid or liquid anionic, cationic, nonionic or zwitterionic detergents, fabric softeners, fabric softener articles, hair sprays, shampoos, bath oils and perfumed polymers.

22 Claims, 105 Drawing Sheets

GLC PROFILE FOR EXAMPLE I.
CRUDE

GLC PROFILE FOR EXAMPLE I, BULKED DISTILLATION FRACTIONS 7-12.

FIG.3 EXAMPLE I,
NMR SPECTRUM FOR/GLC PEAK 22 OF FIG.2.

IR SPECTRUM FOR EXAMPLE I, GLC PEAK 22 OF FIG. 2.

GLC PROFILE FOR EXAMPLE II.
CRUDE

IR SPECTRUM FOR GLC PEAKS 71 & 72 OF FIG. 7.

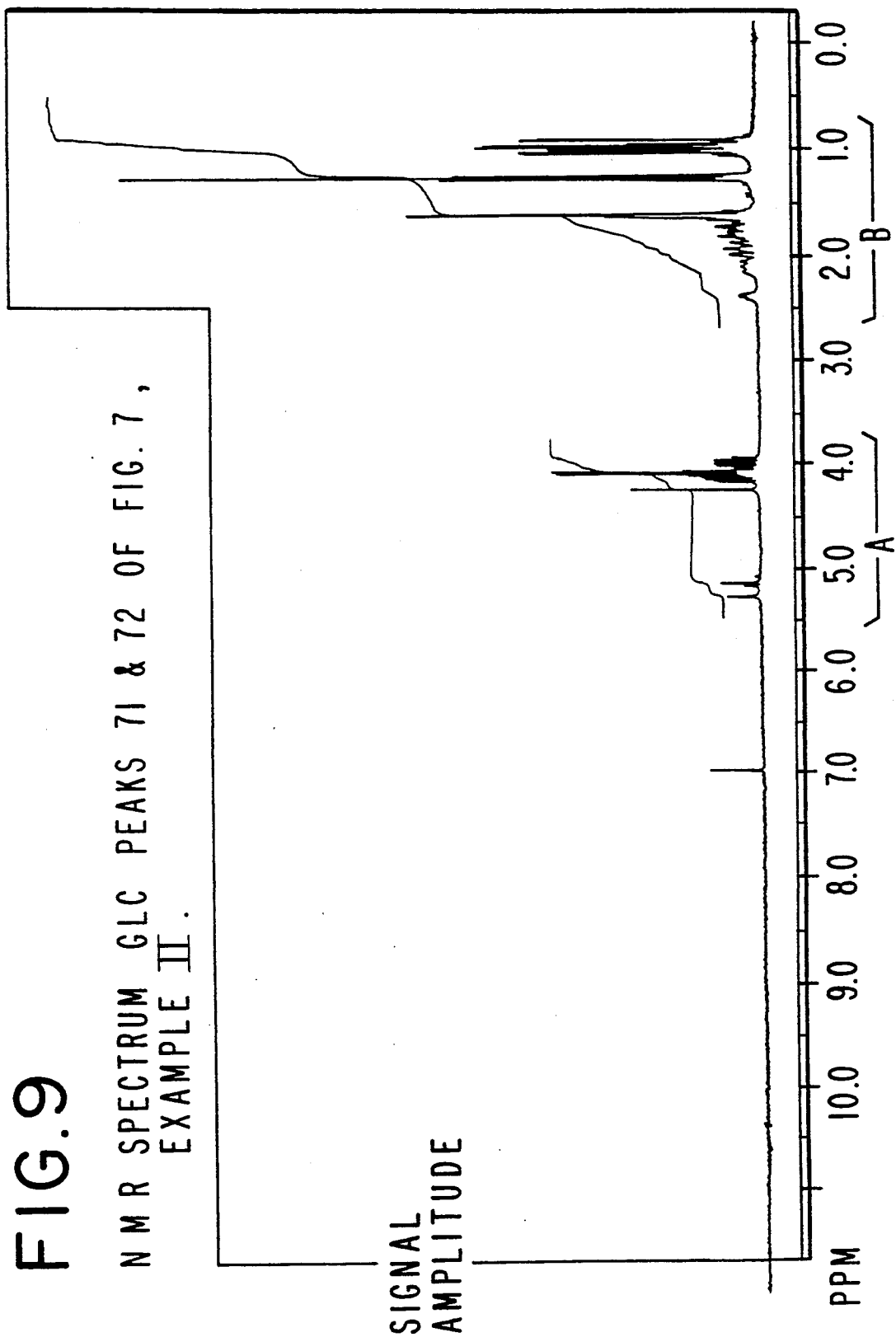
FIG. 9 NMR SPECTRUM GLC PEAKS 71 & 72 OF FIG. 7, EXAMPLE II.

FIG.9-A
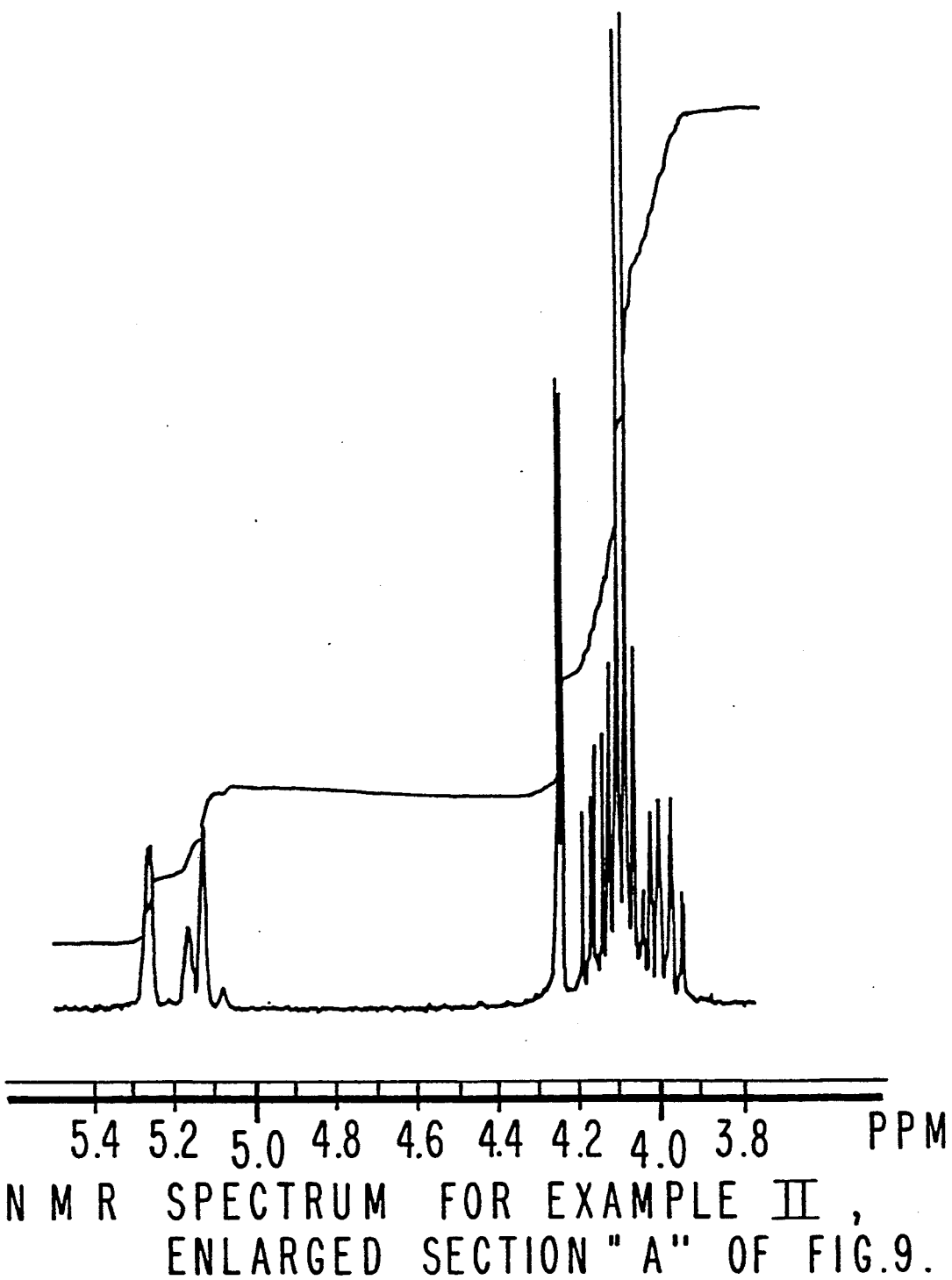
NMR SPECTRUM FOR EXAMPLE II, ENLARGED SECTION "A" OF FIG.9.

FIG.9-B
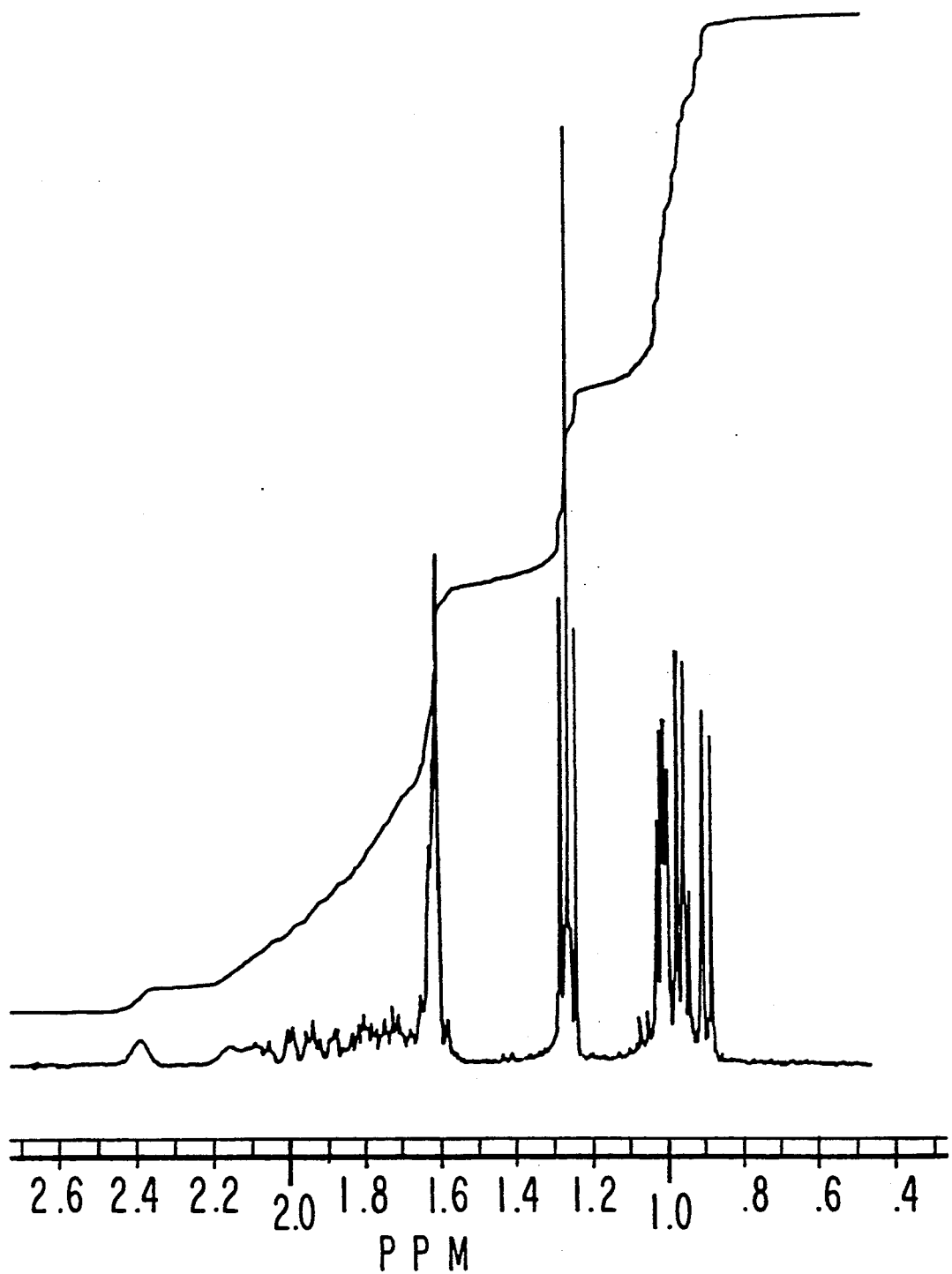
NMR SPECTRUM FOR EXAMPLE II,
ENLARGED SECTION "B" OF FIG.9.

GLC PROFILE FOR EXAMPLE III.

FIG. 11 NMR SPECTRUM FOR EXAMPLE III, PEAKS 103 AND 104 OF FIG. 10.

GLC PROFILE FOR EXAMPLE IV.

FIG. 14 NMR SPECTRUM FOR EXAMPLE IV, PEAK 132 OF FIG. 13.

IR SPECTRUM FOR EXAMPLE IV, PEAK 132 OF FIG.13.

GLC PROFILE FOR EXAMPLE V.

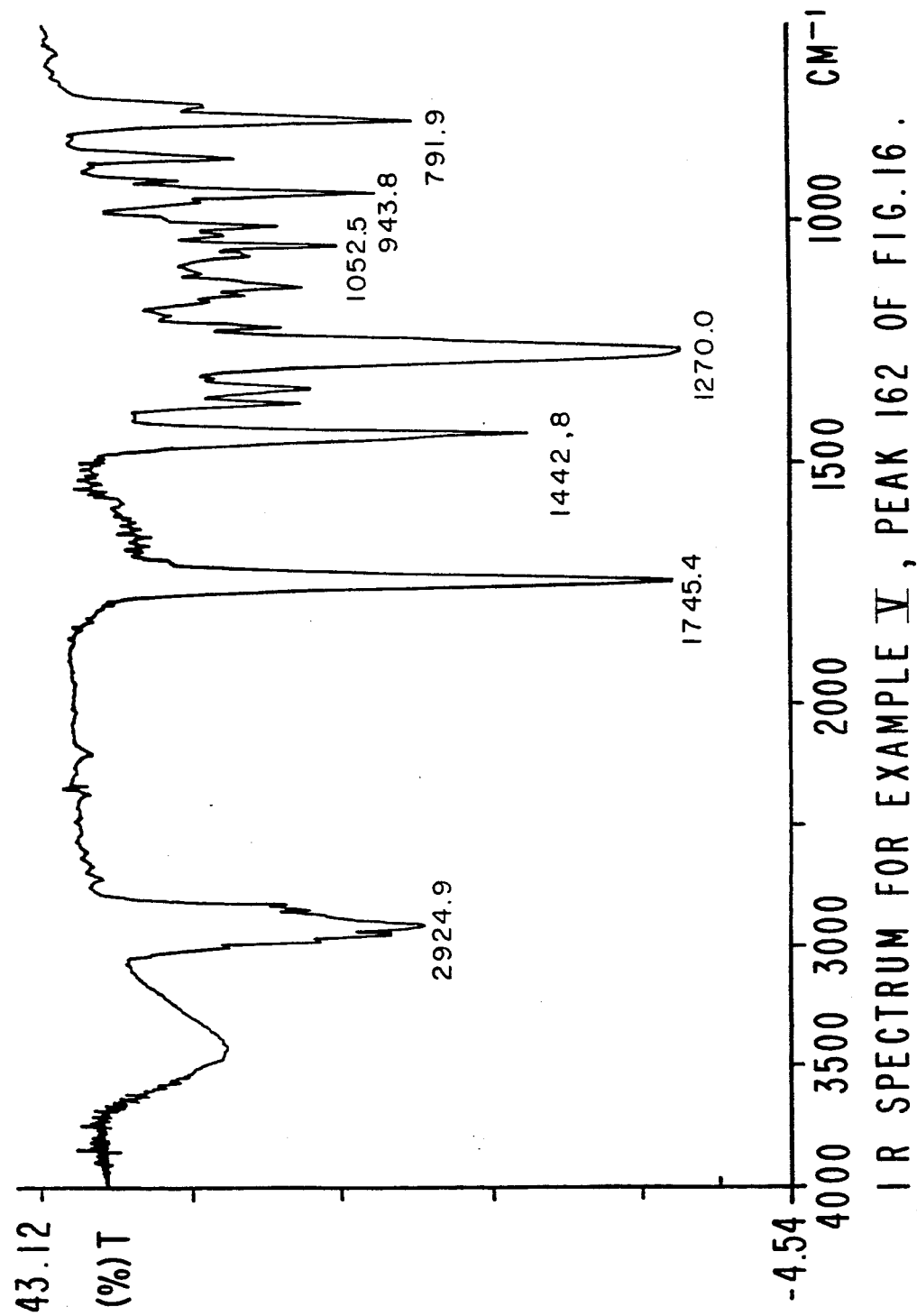

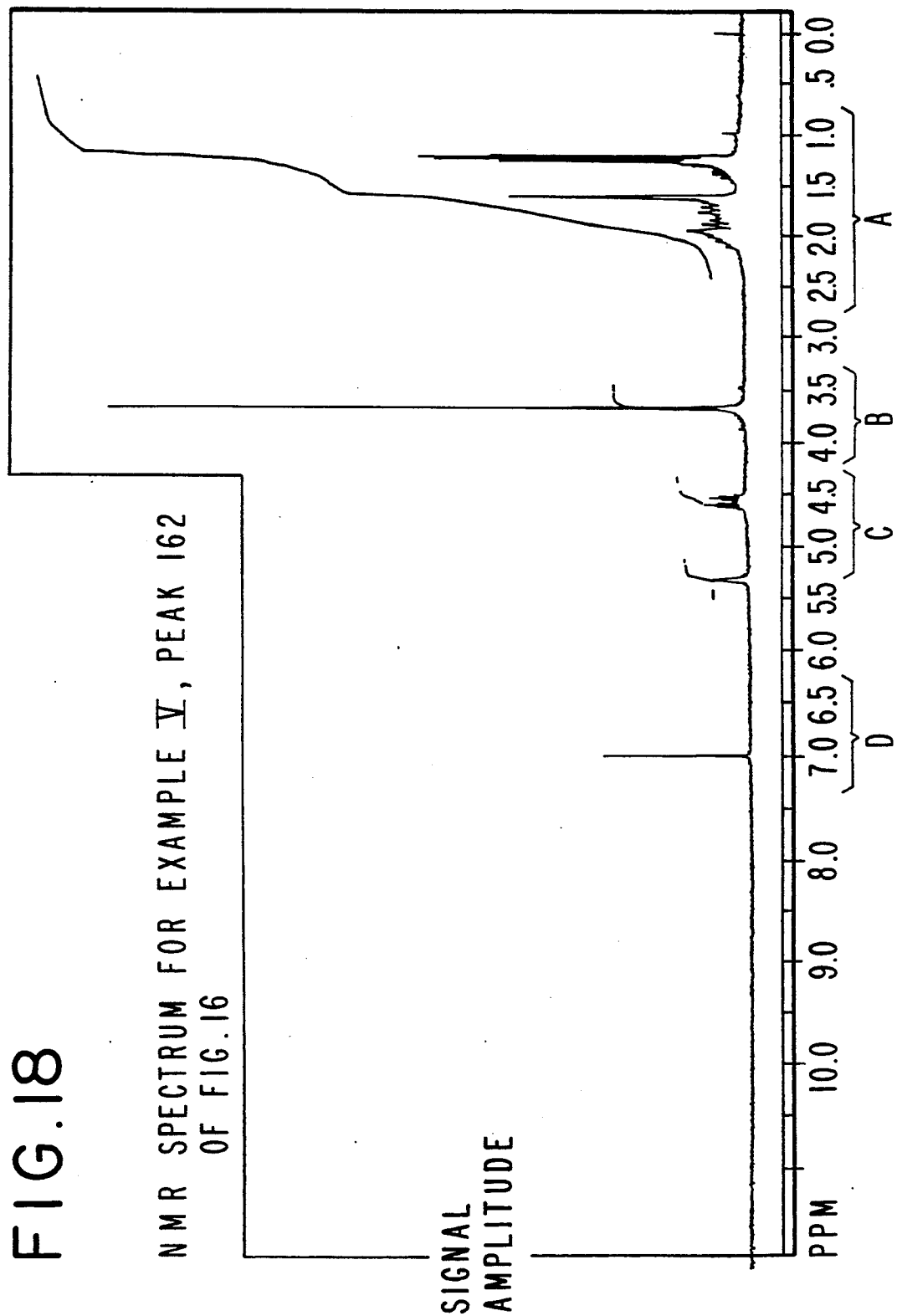
FIG. 18 NMR SPECTRUM FOR EXAMPLE V, PEAK 162 OF FIG. 16

FIG. 18-A
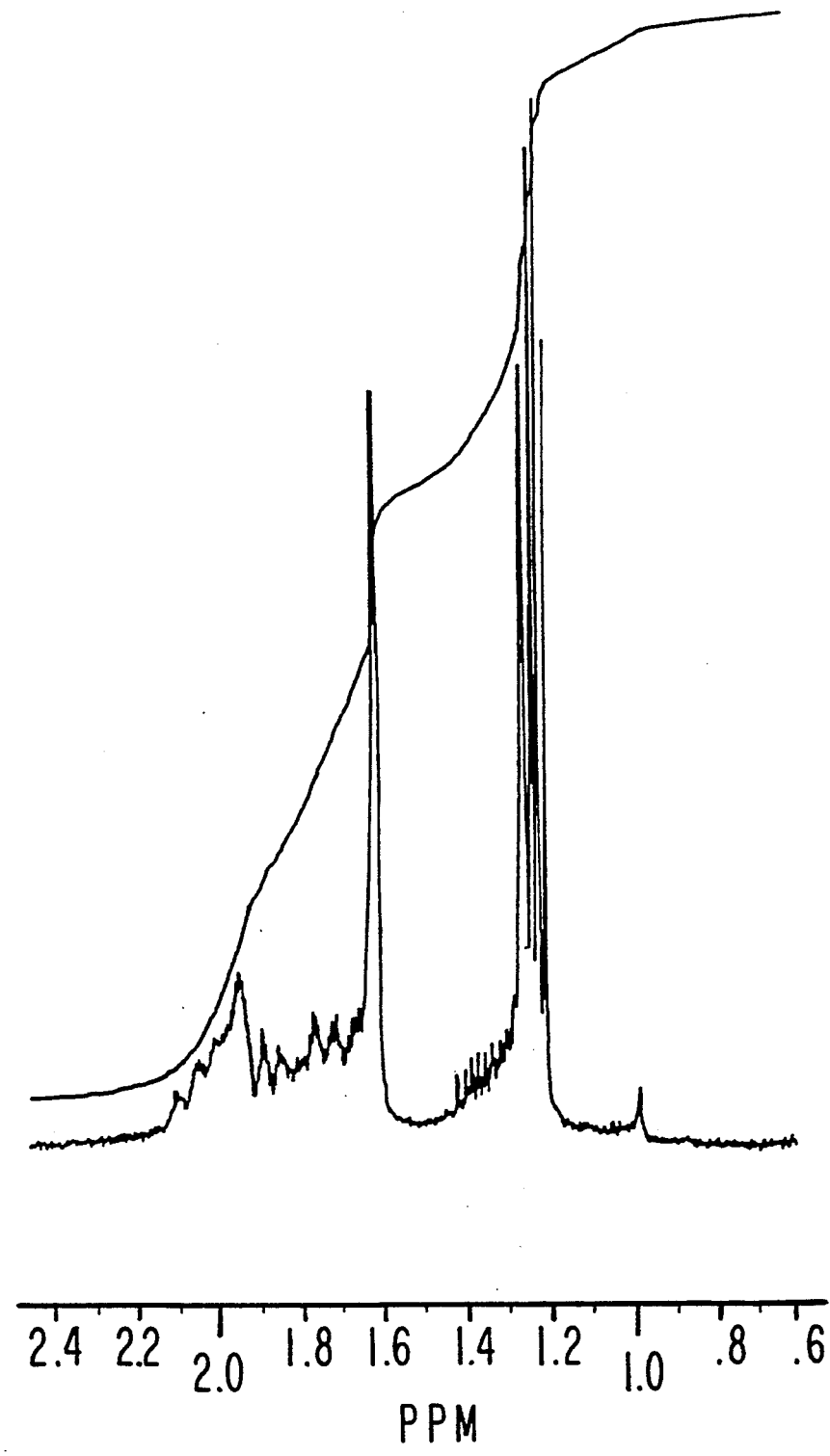

FIG. 18-B
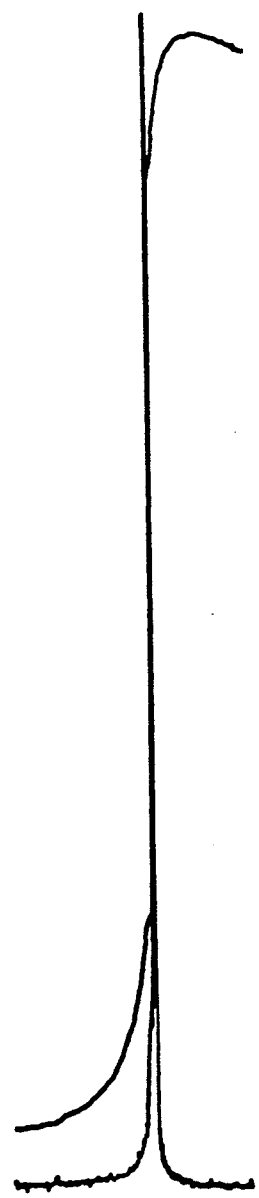
3.8 3.6
PPM

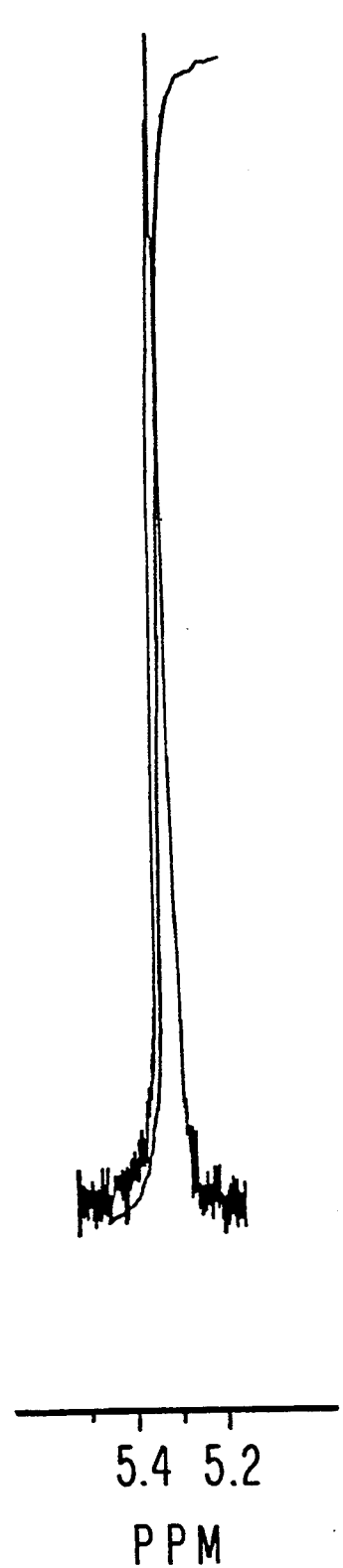
FIG.18-D
5.4 5.2
PPM
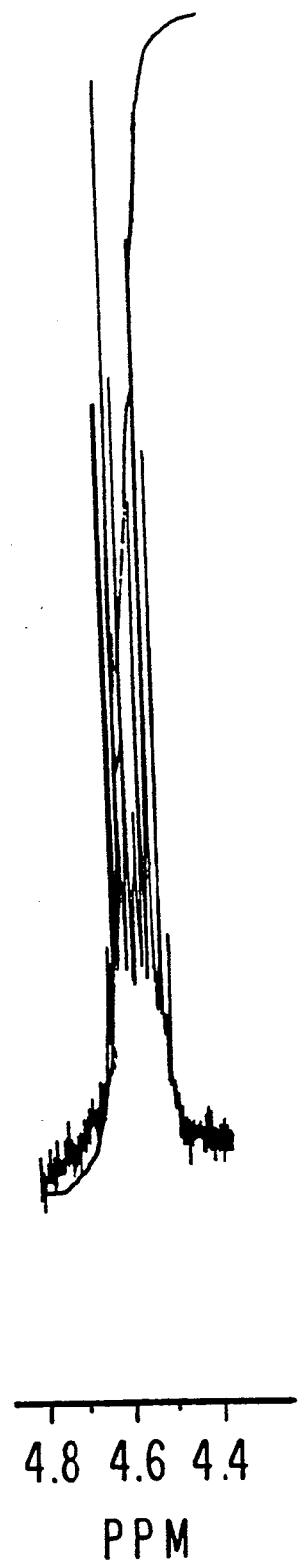
FIG.18-C
4.8 4.6 4.4
PPM

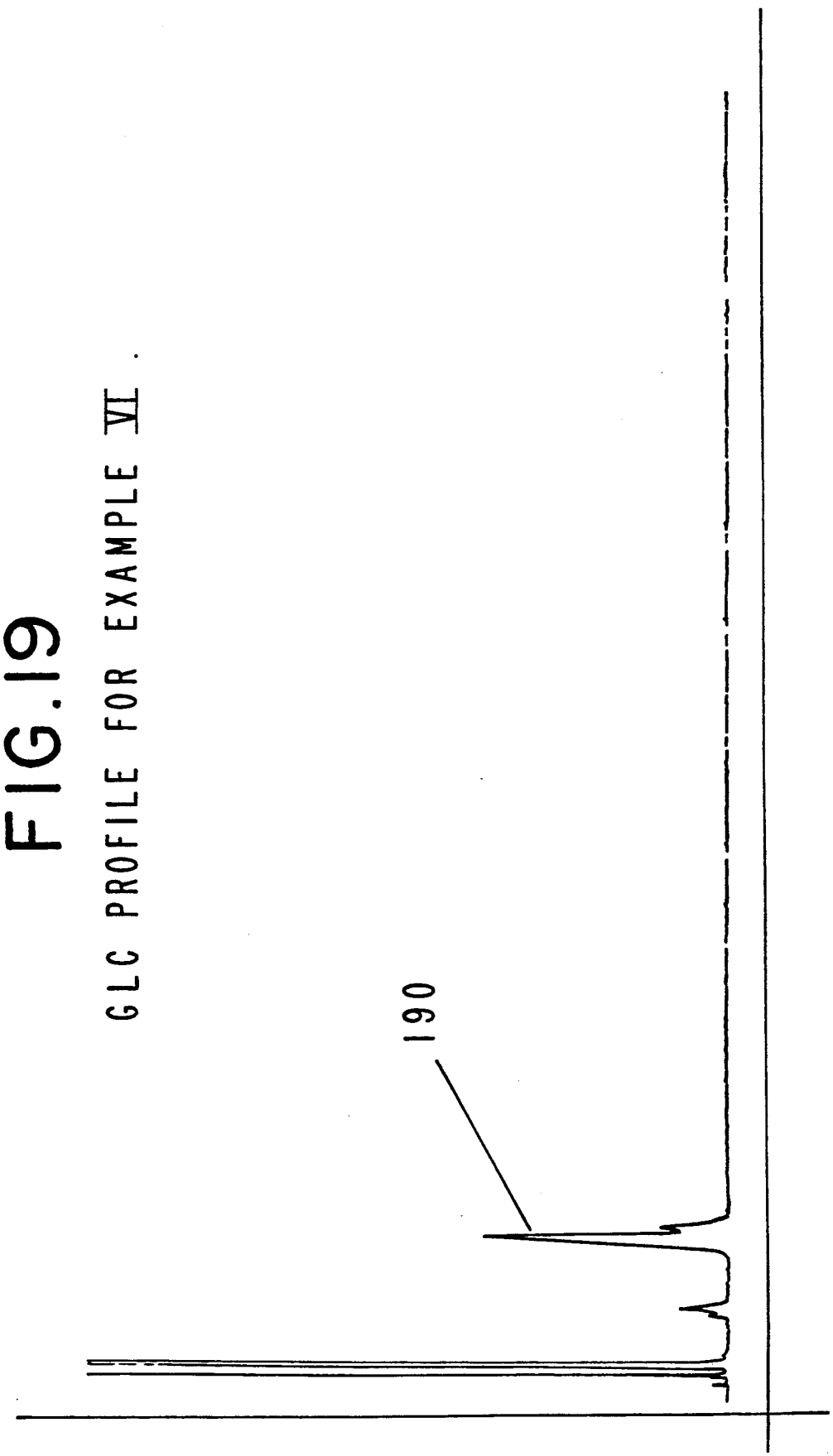
FIG.19 GLC PROFILE FOR EXAMPLE VI

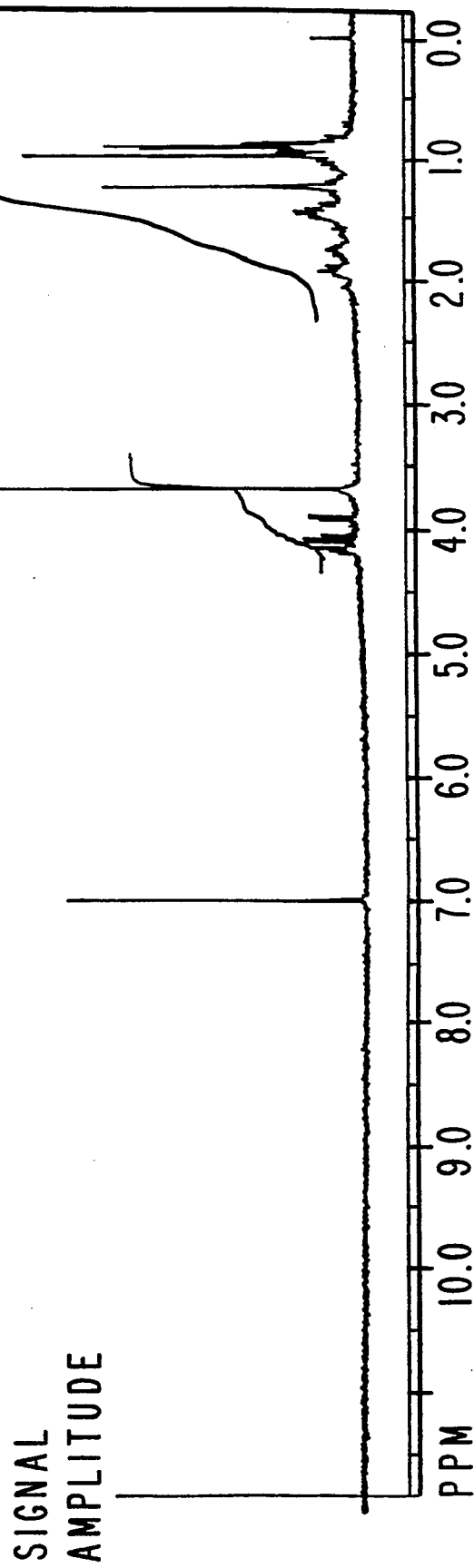
FIG. 20 NMR SPECTRUM FOR EXAMPLE VI, PEAK 190 OF FIG. 19.

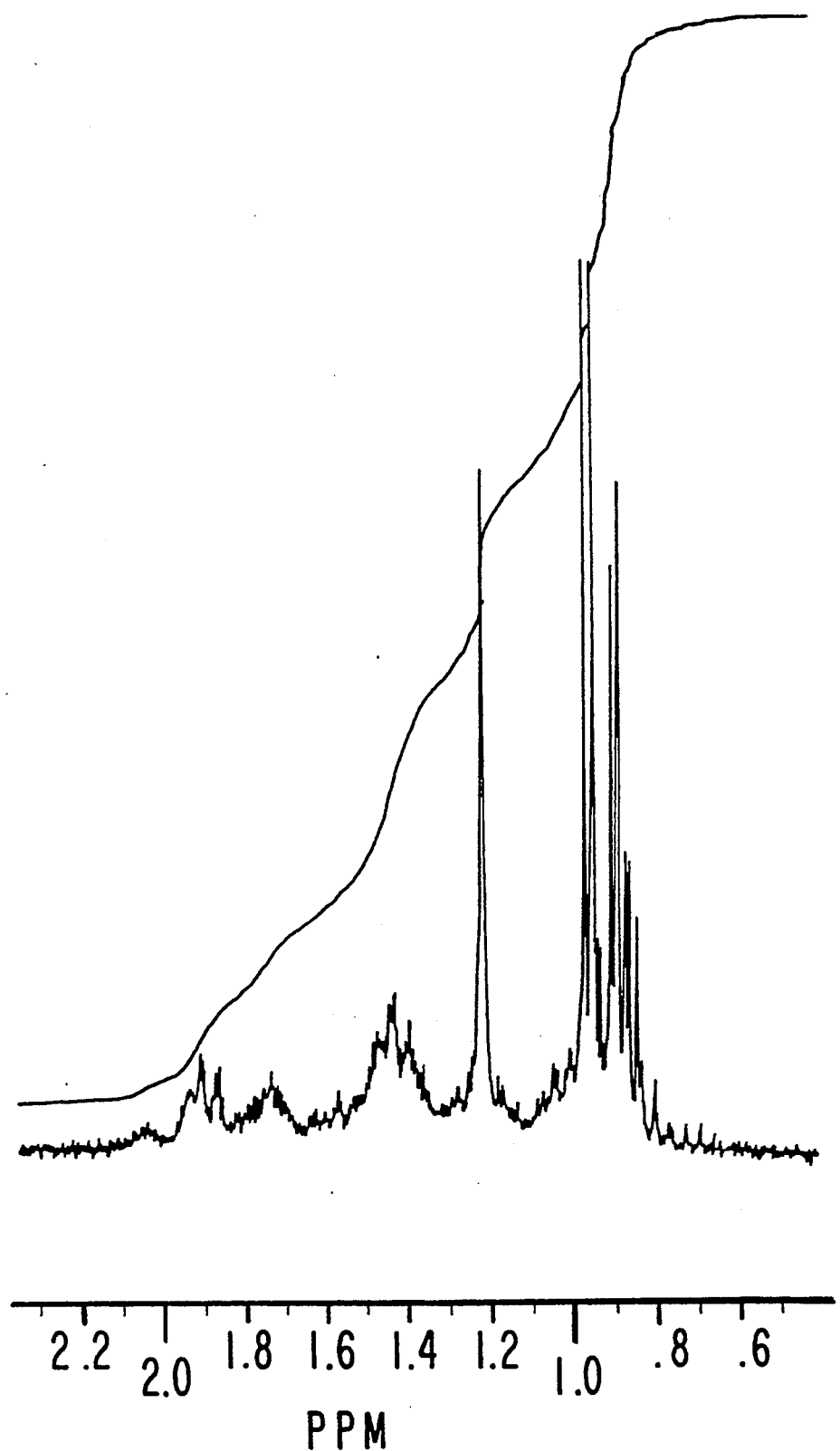
FIG.20-A

FIG. 20-B
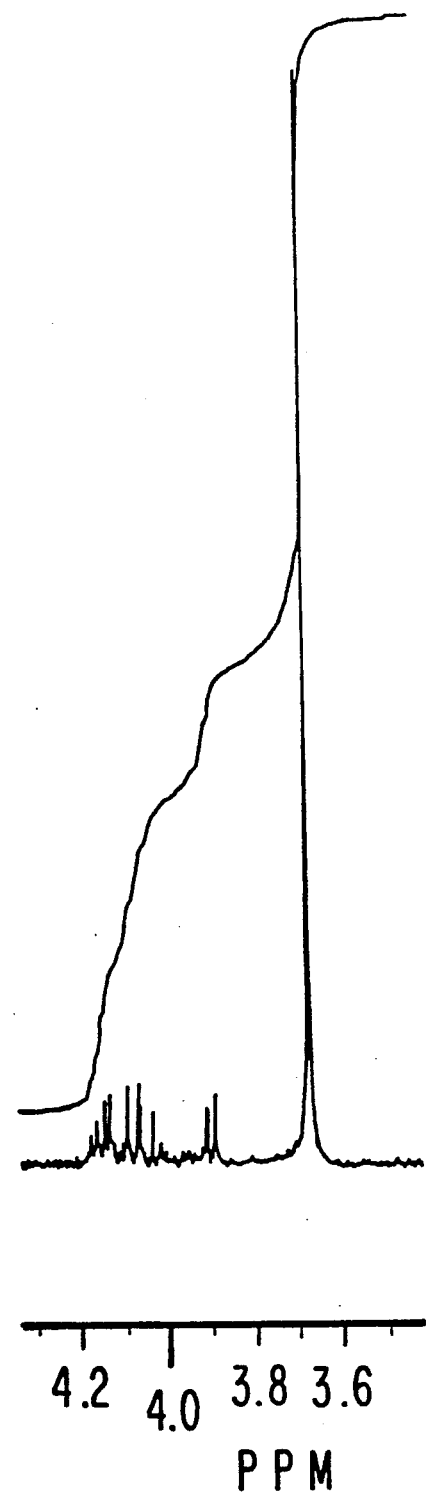

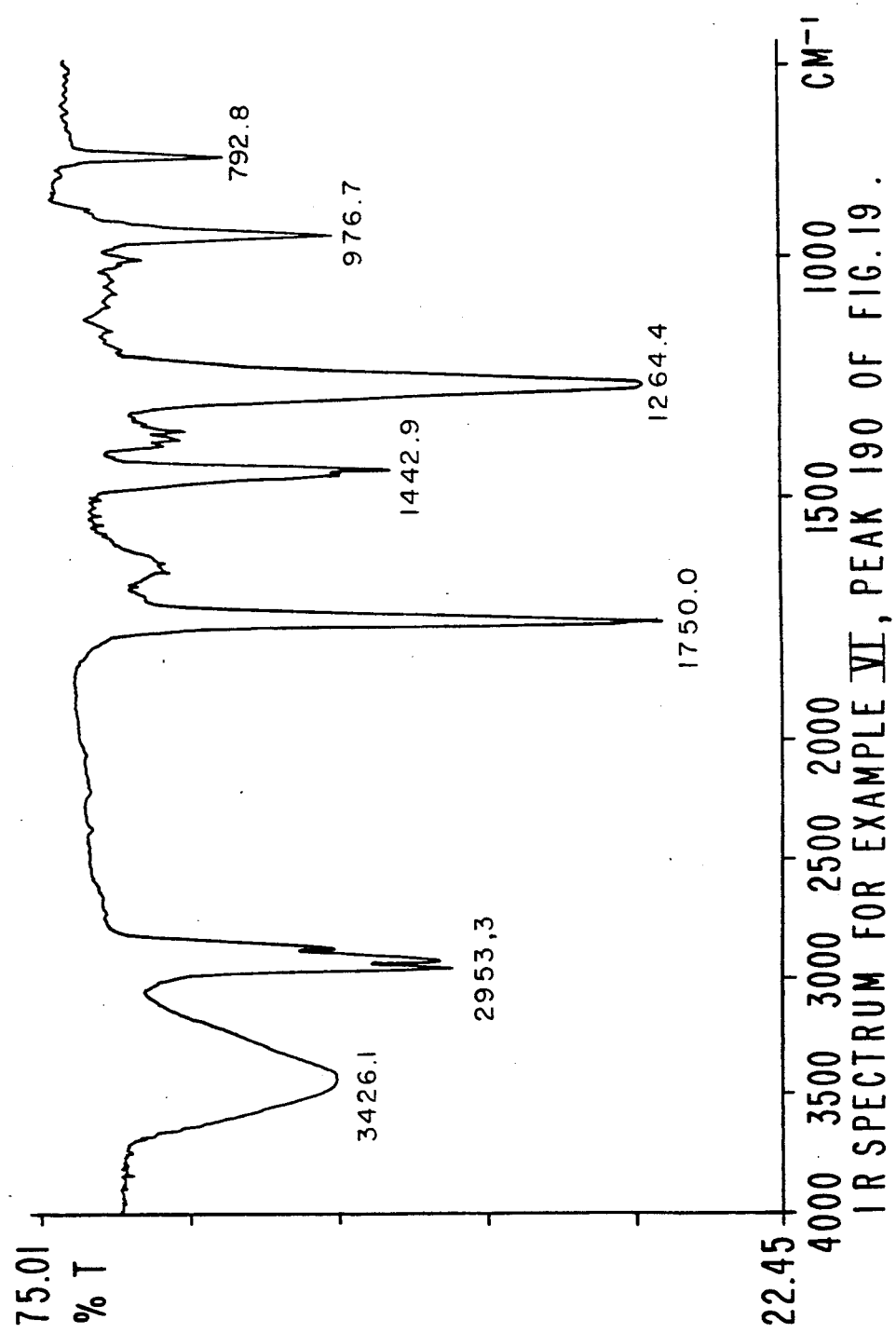

GLC PROFILE FOR EXAMPLE VII.

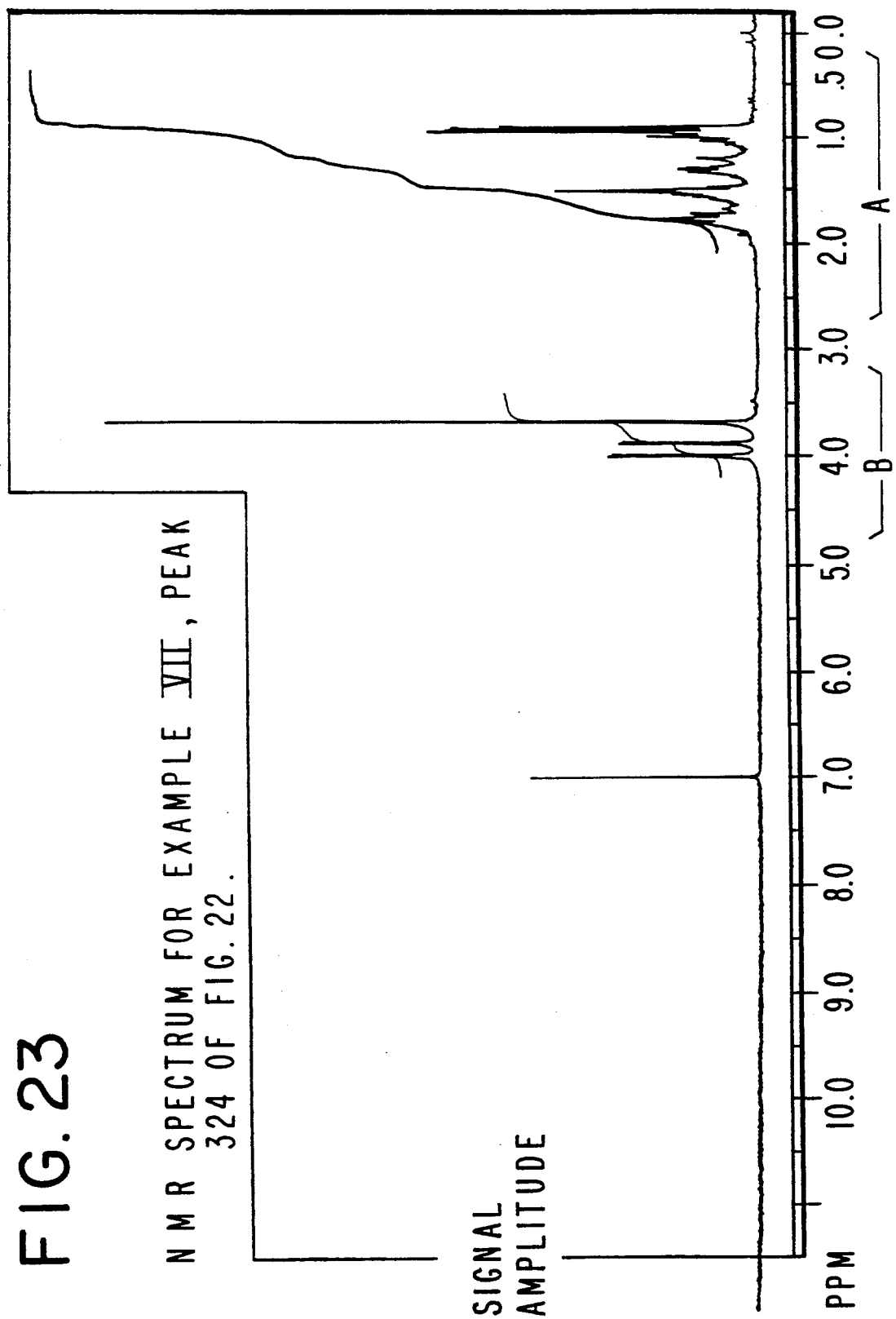
FIG. 23 NMR SPECTRUM FOR EXAMPLE VII, PEAK 324 OF FIG. 22.

FIG. 23-A
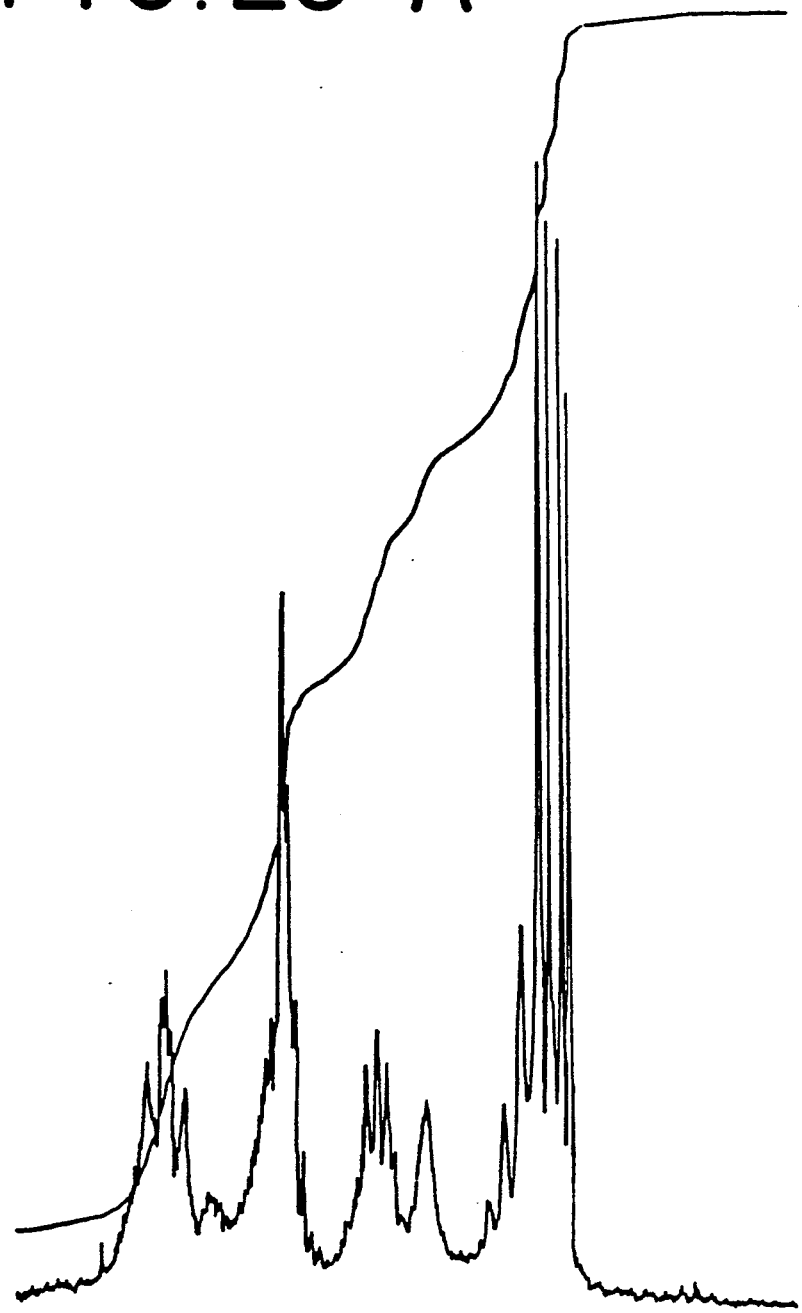

FIG.23-B
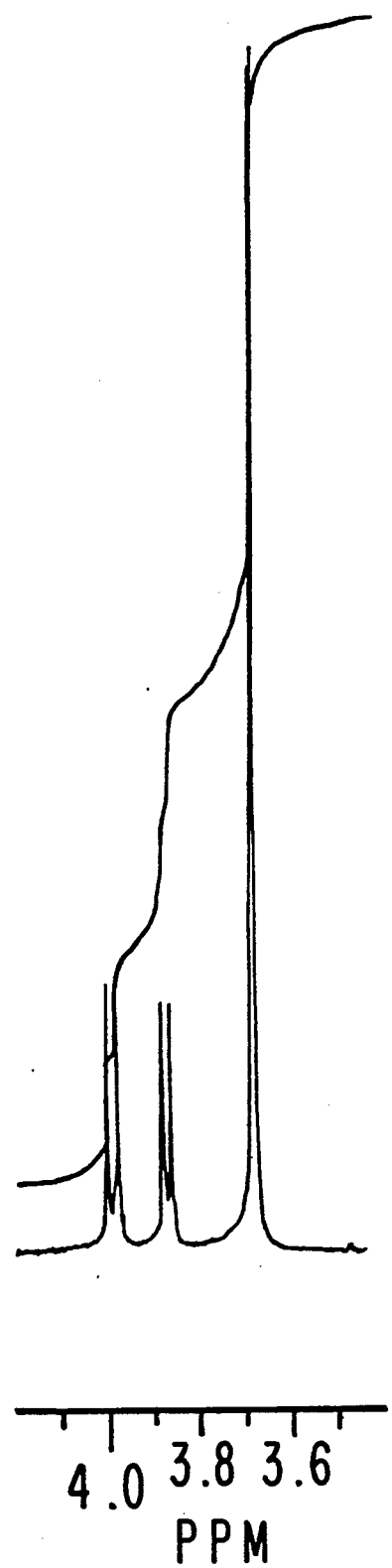

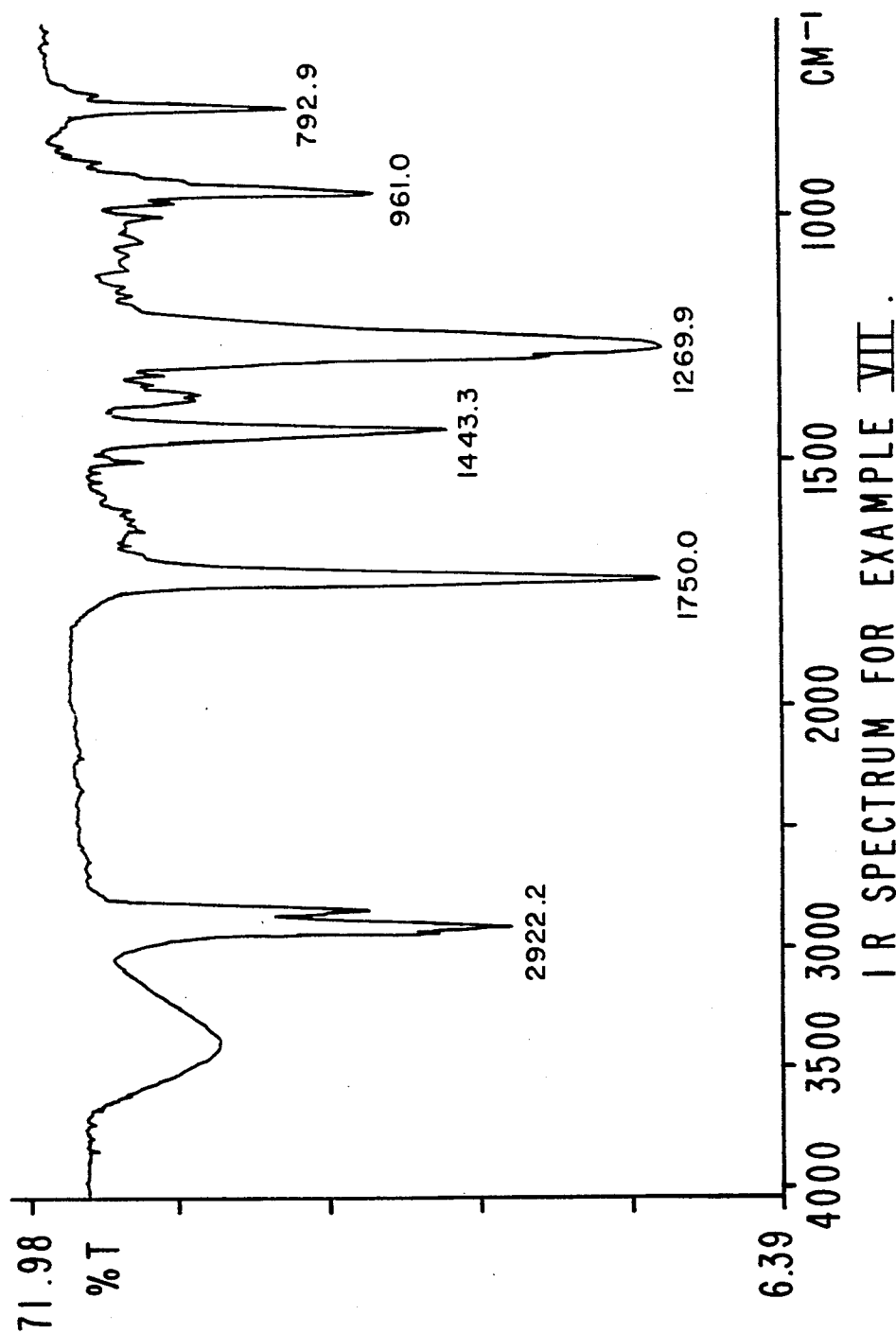
FIG. 24 IR SPECTRUM FOR EXAMPLE VII.

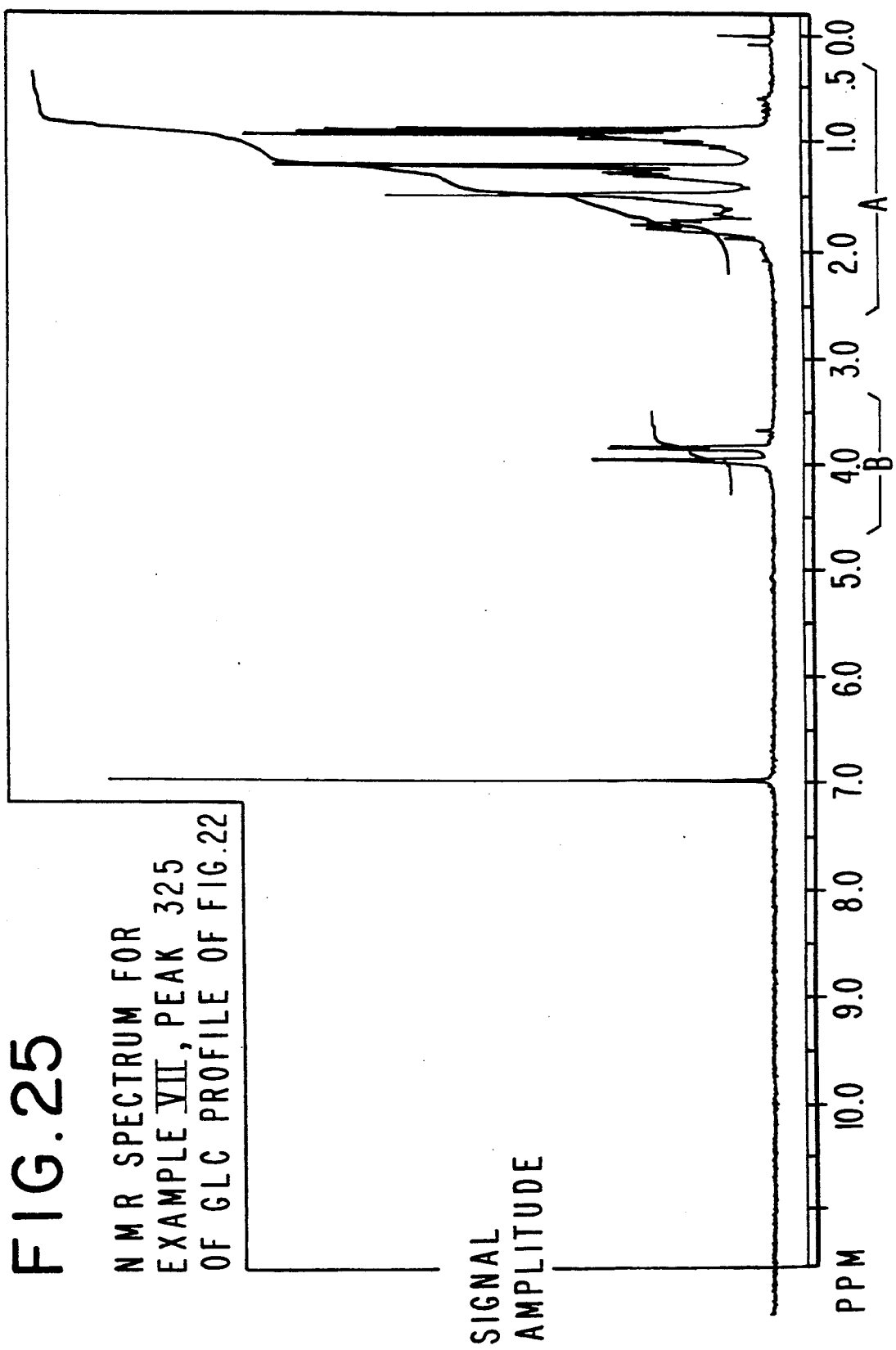
FIG. 25 NMR SPECTRUM FOR EXAMPLE VII, PEAK 325 OF GLC PROFILE OF FIG. 22

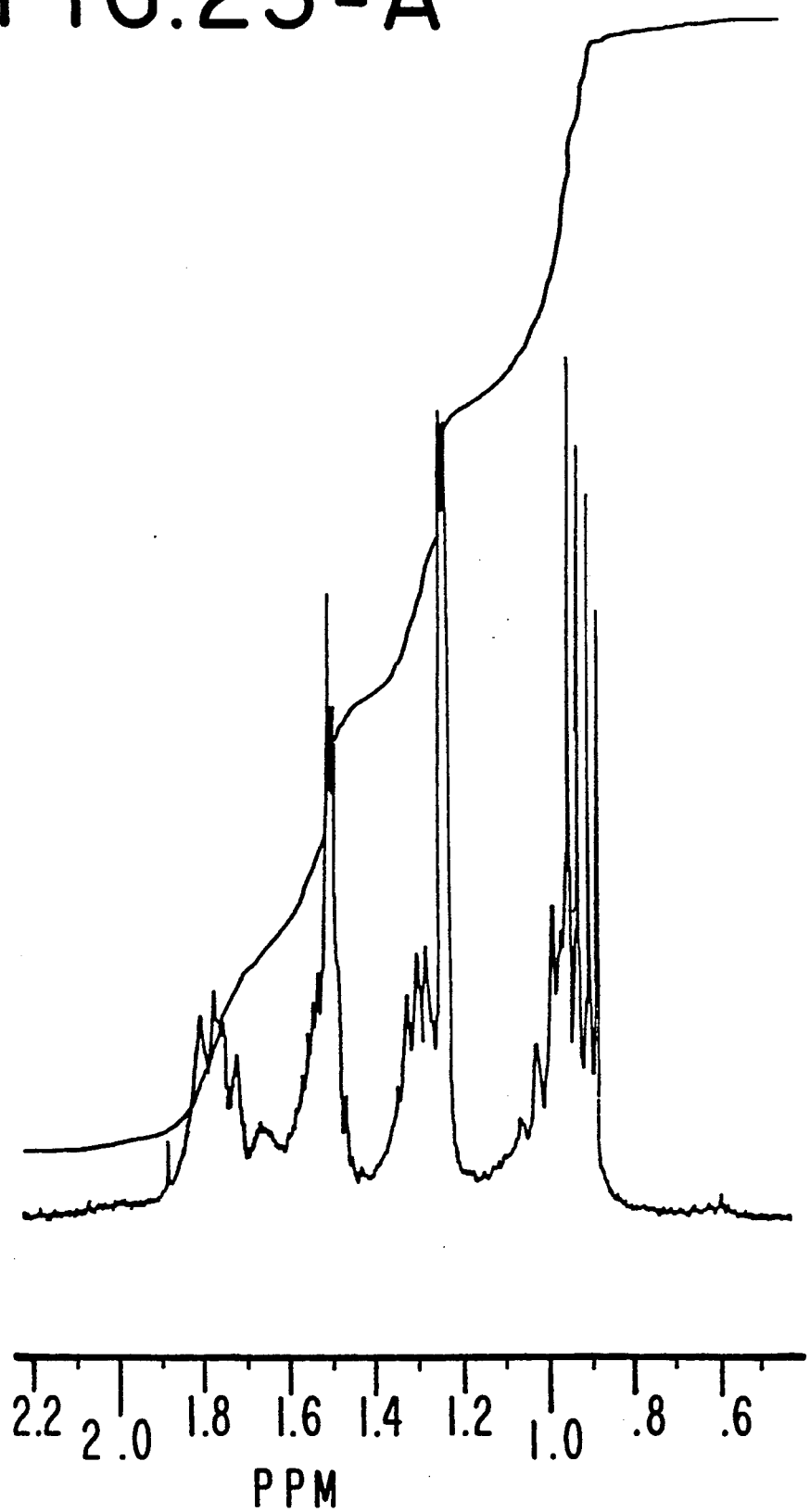
FIG.25-A

FIG. 25-B
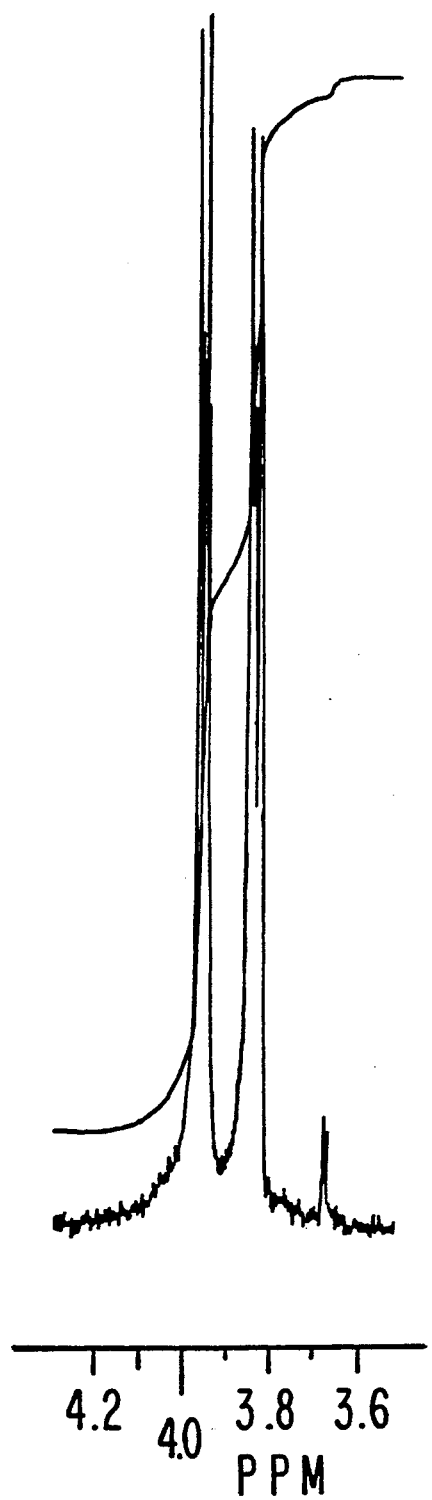

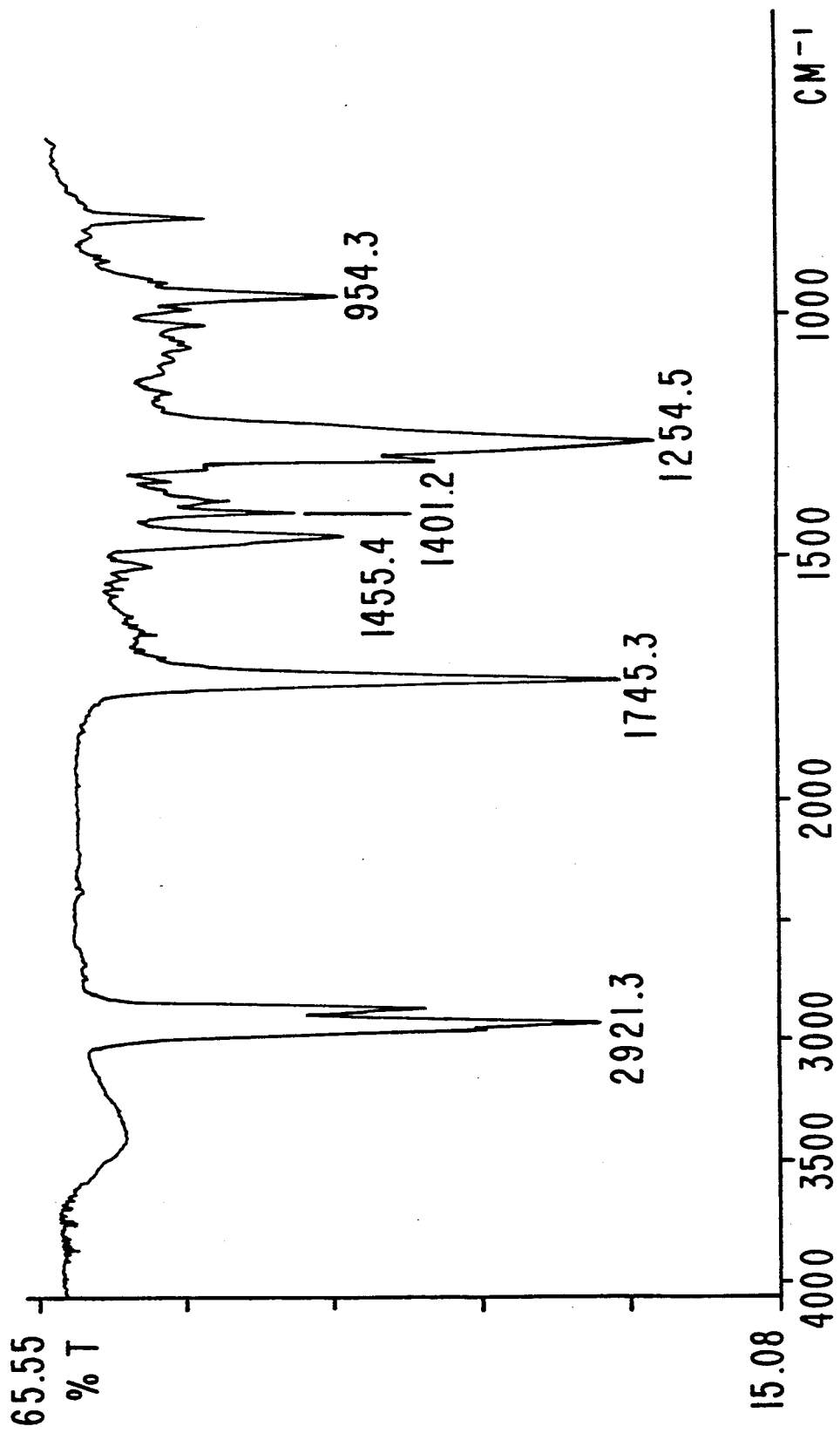

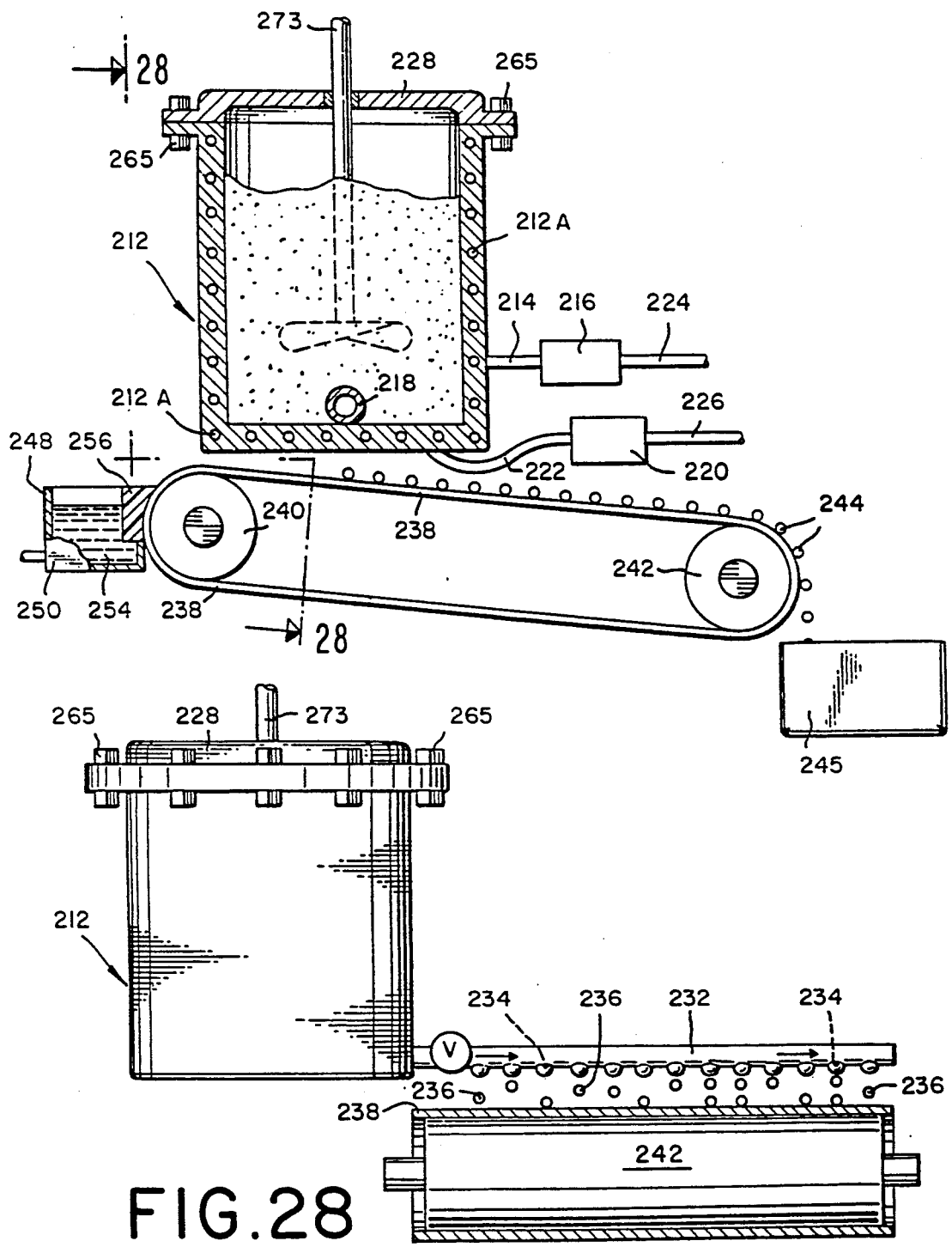

GLC PROFILE FOR EXAMPLE VIII.

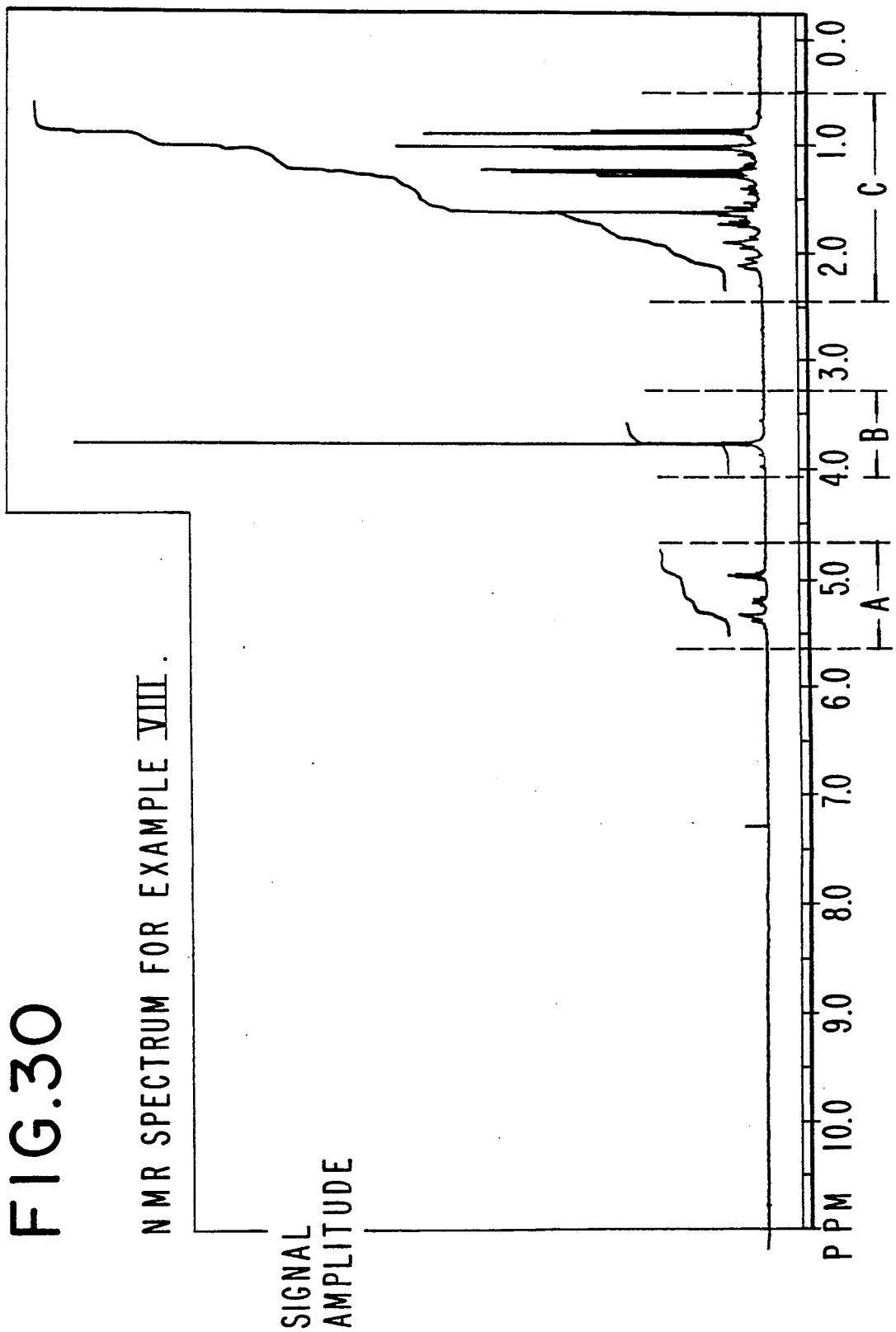
FIG. 30 NMR SPECTRUM FOR EXAMPLE VIII.

FIG. 30-A
FIG. 30-B
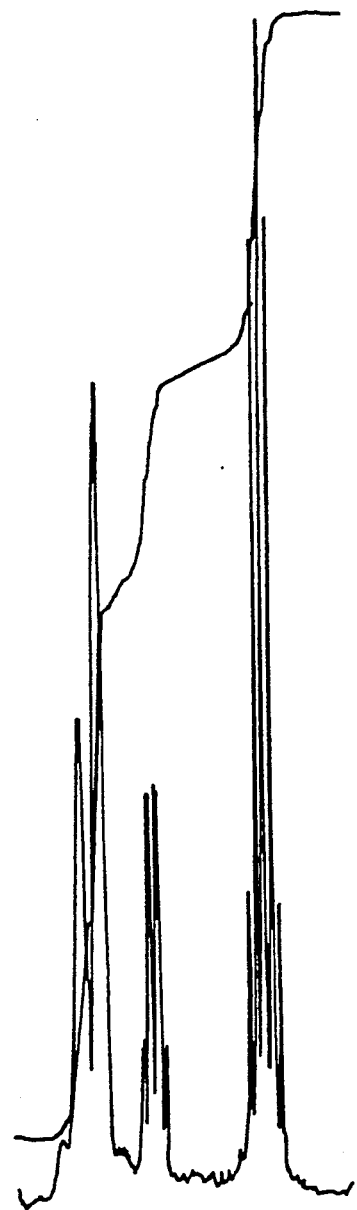
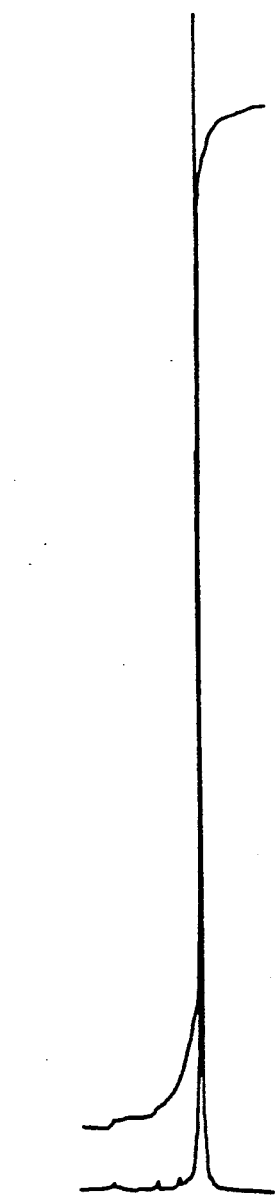

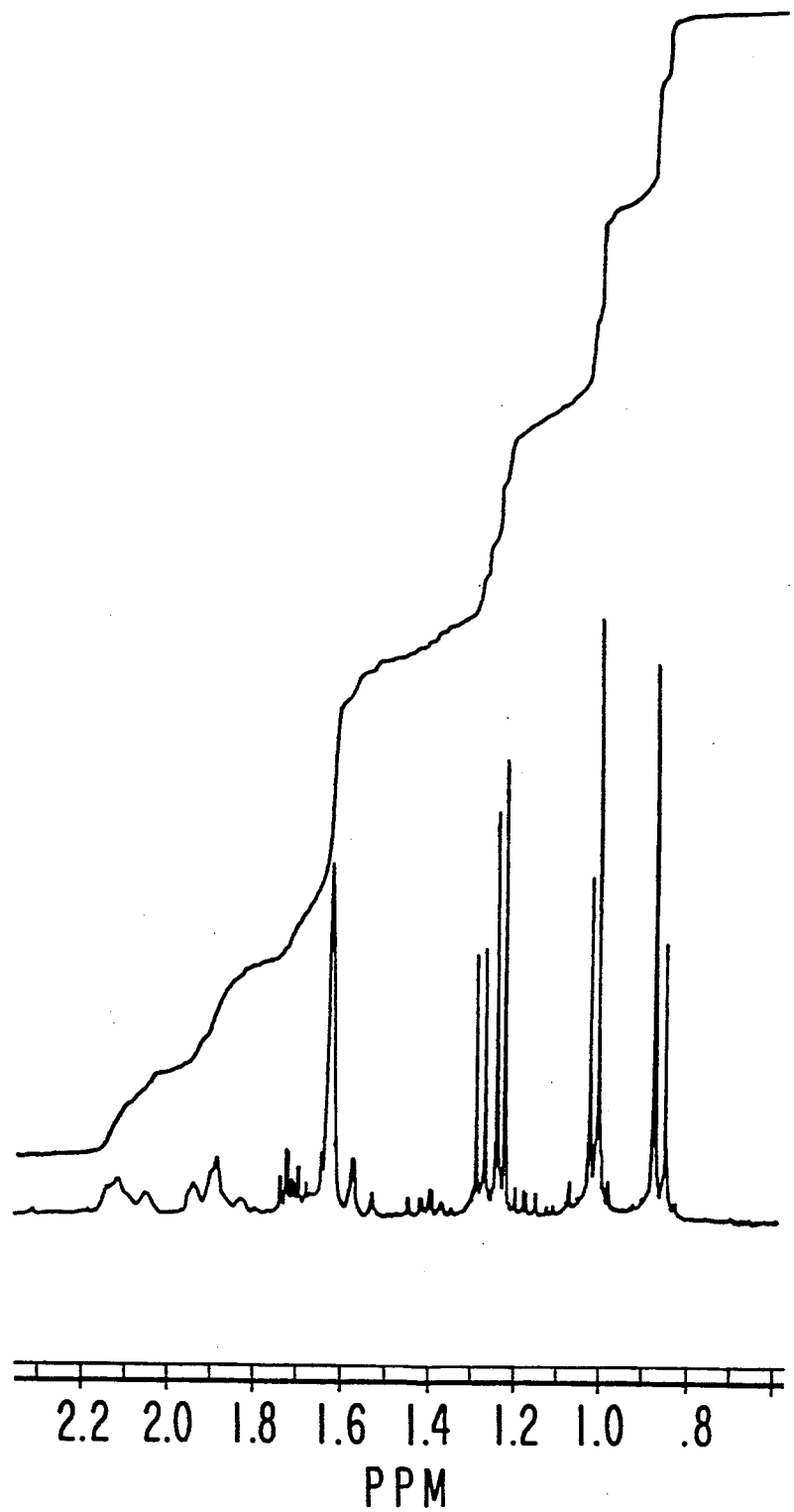
FIG.30-C

GLC PROFILE FOR EXAMPLE IX.

GLC PROFILE FOR EXAMPLE IX.

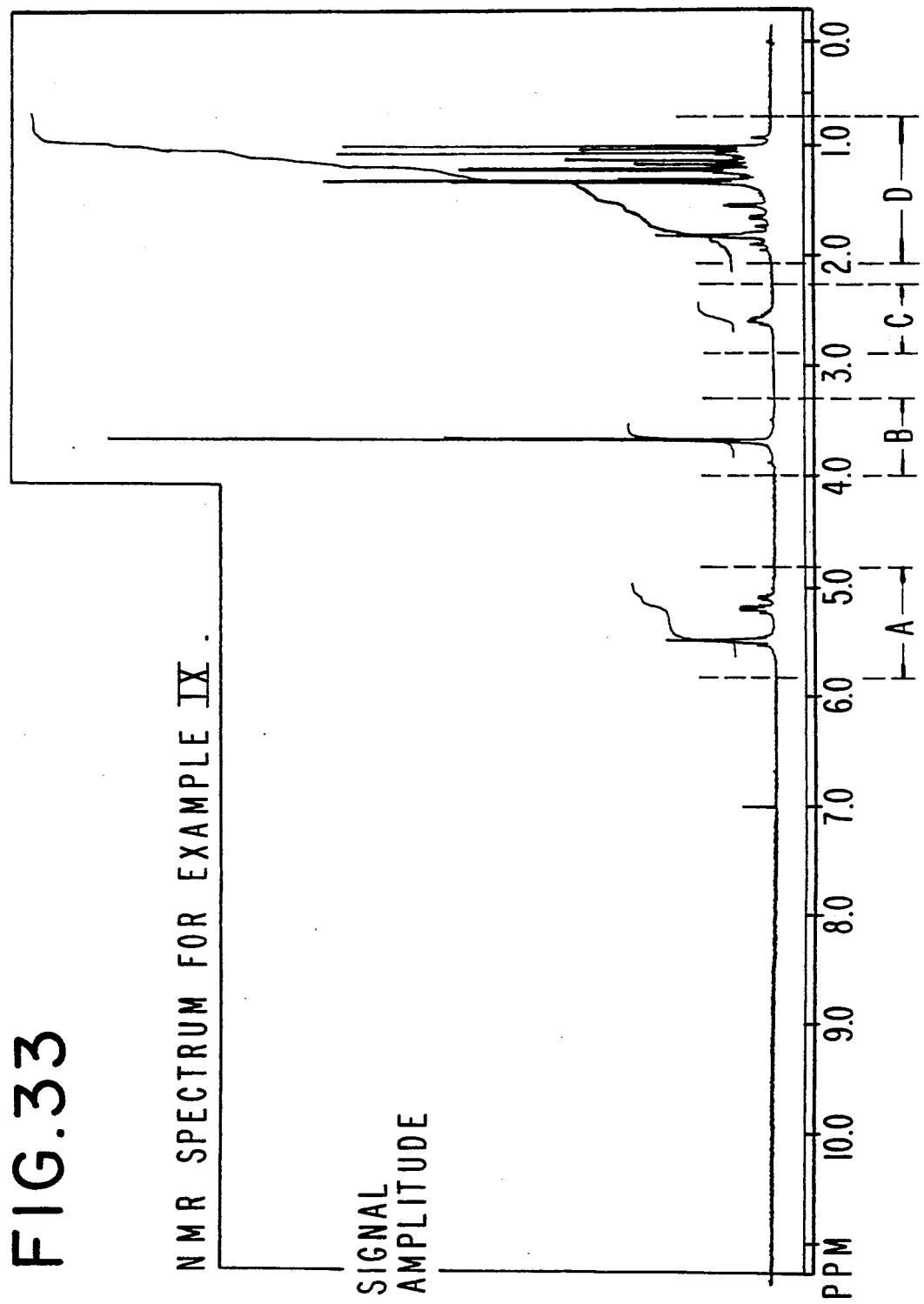

FIG.33A
FIG.33B
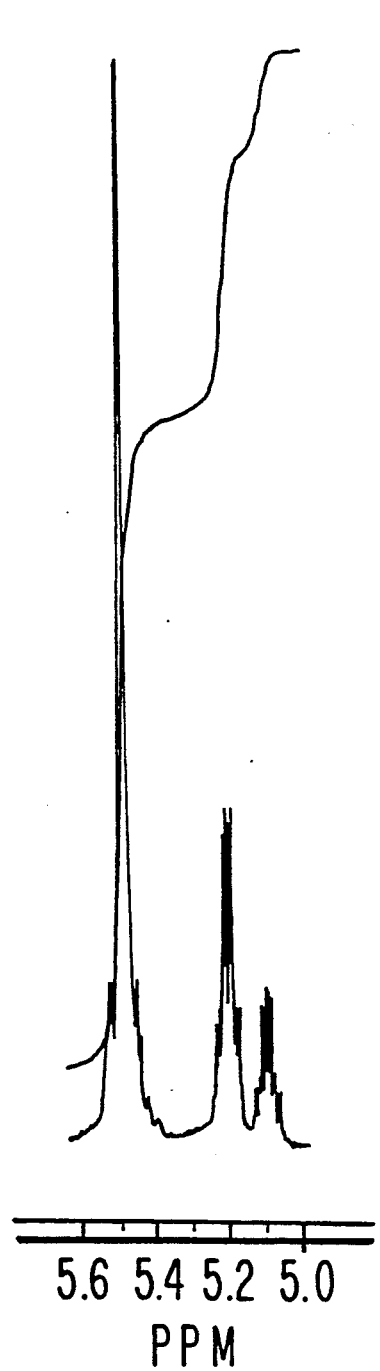
5.6 5.4 5.2 5.0
PPM
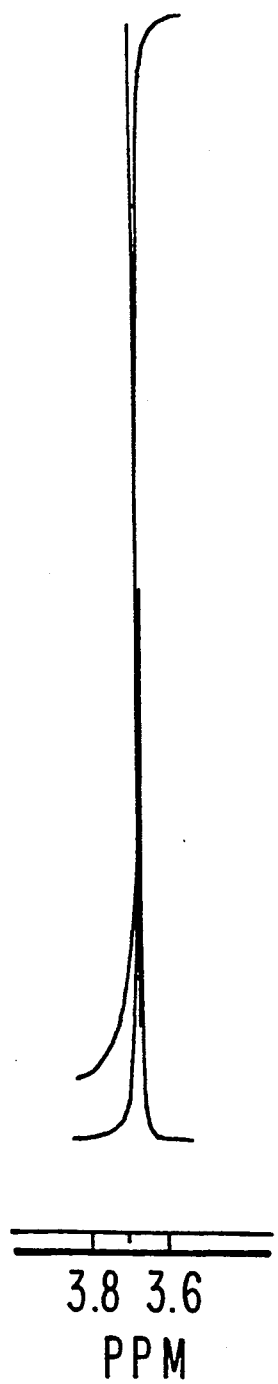
3.8 3.6
PPM

FIG.33C
FIG.33D
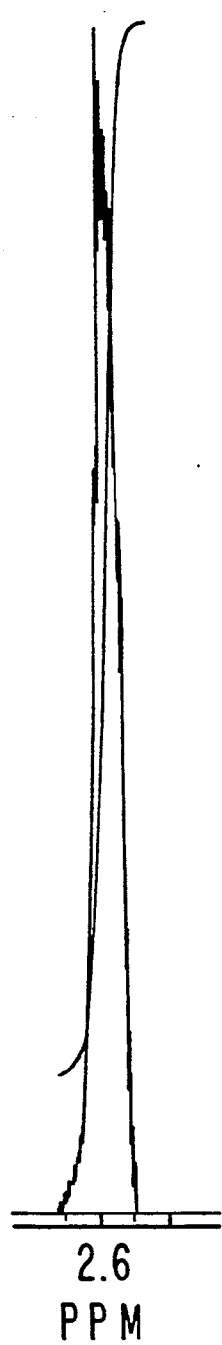
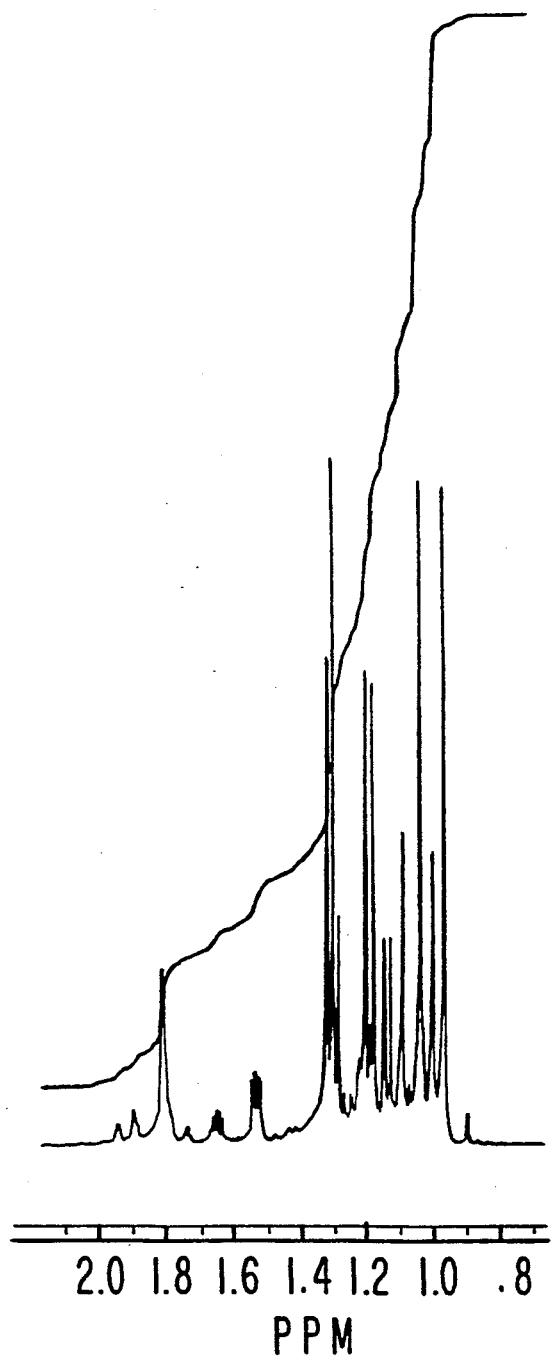

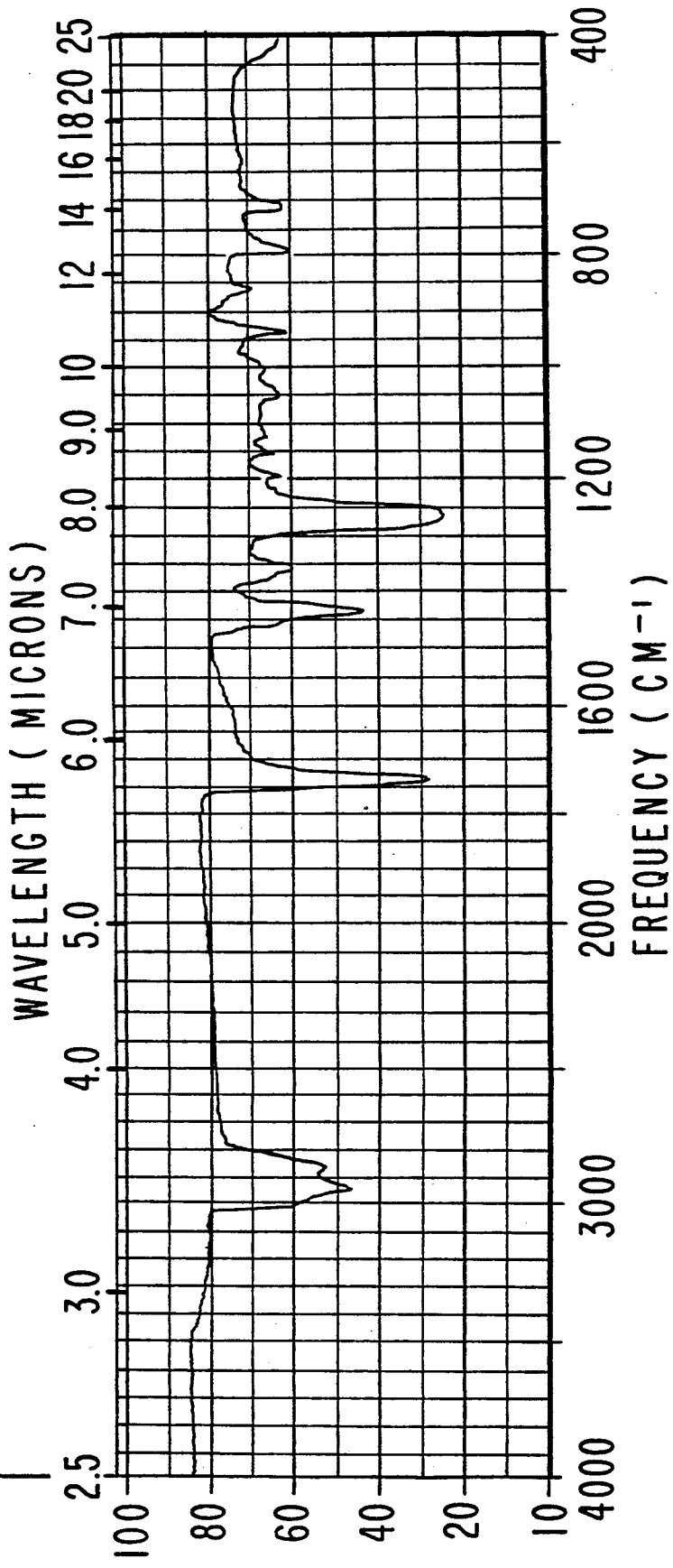

GLC PROFILE FOR EXAMPLE X.

IR SPECTRUM FOR EXAMPLE X.

NMR SPECTRUM FOR EXAMPLE X.

FIG.37A
FIG.37B
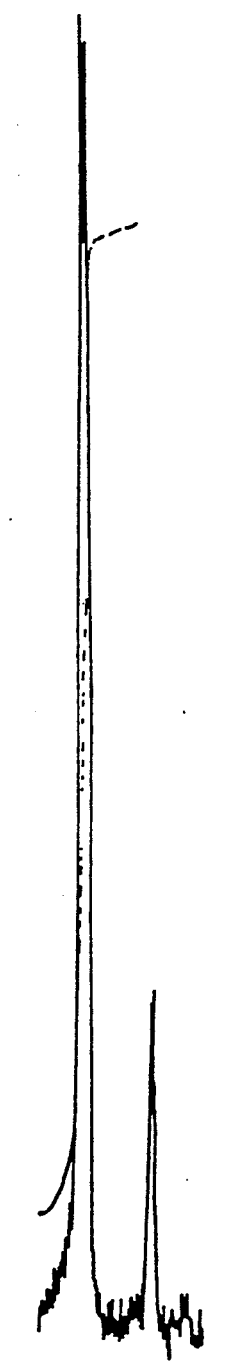
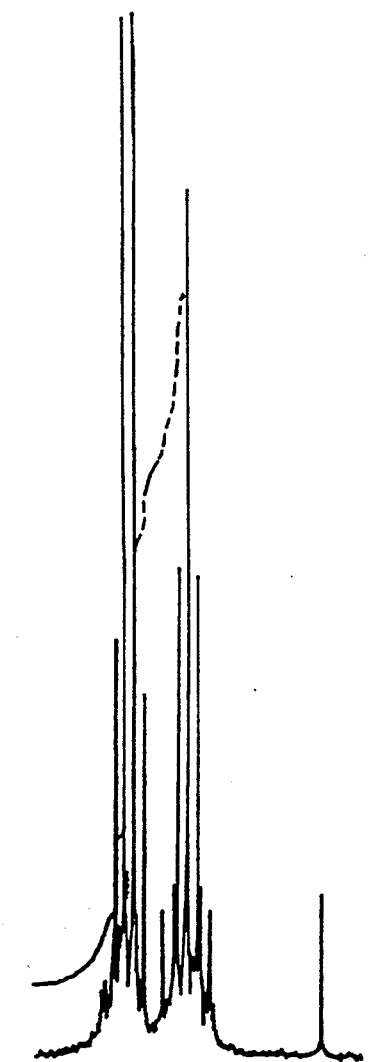

GLC PROFILE FOR EXAMPLE XI.

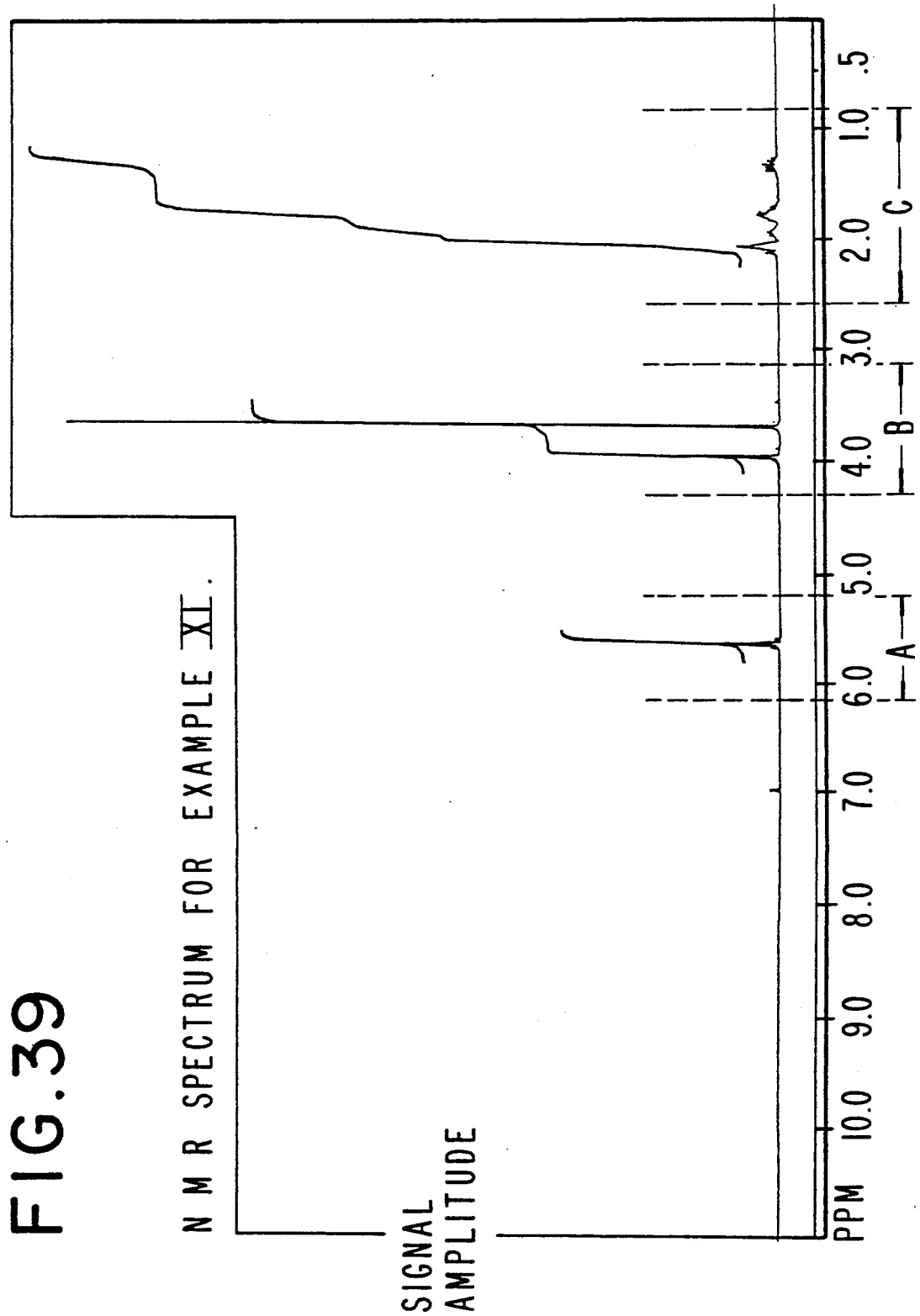
FIG. 39 NMR SPECTRUM FOR EXAMPLE XI.

IR SPECTRUM FOR EXAMPLE XI.

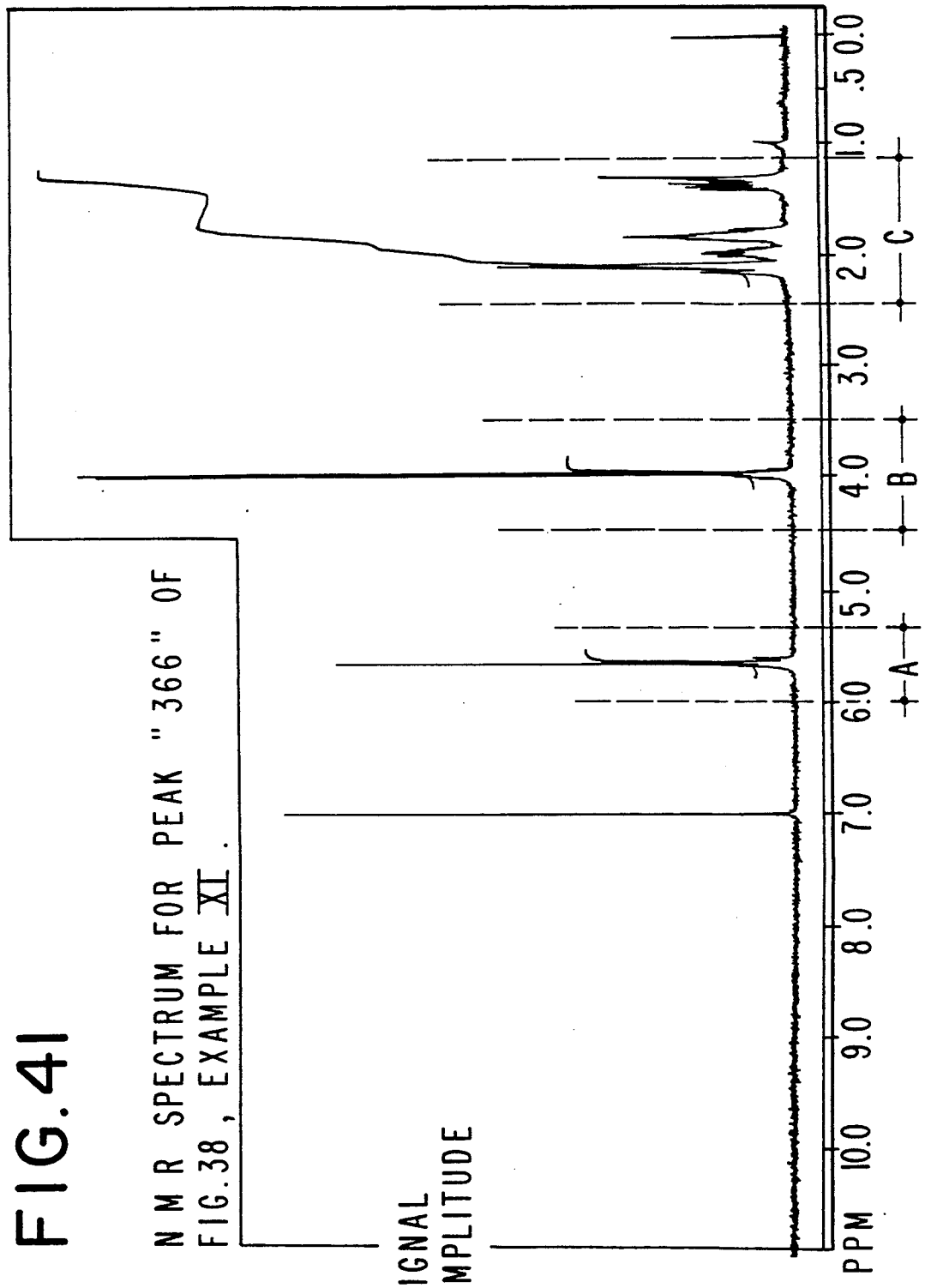
FIG. 41 NMR SPECTRUM FOR PEAK "366" OF FIG. 38, EXAMPLE XI.

PPM 5.6

4.0 PPM

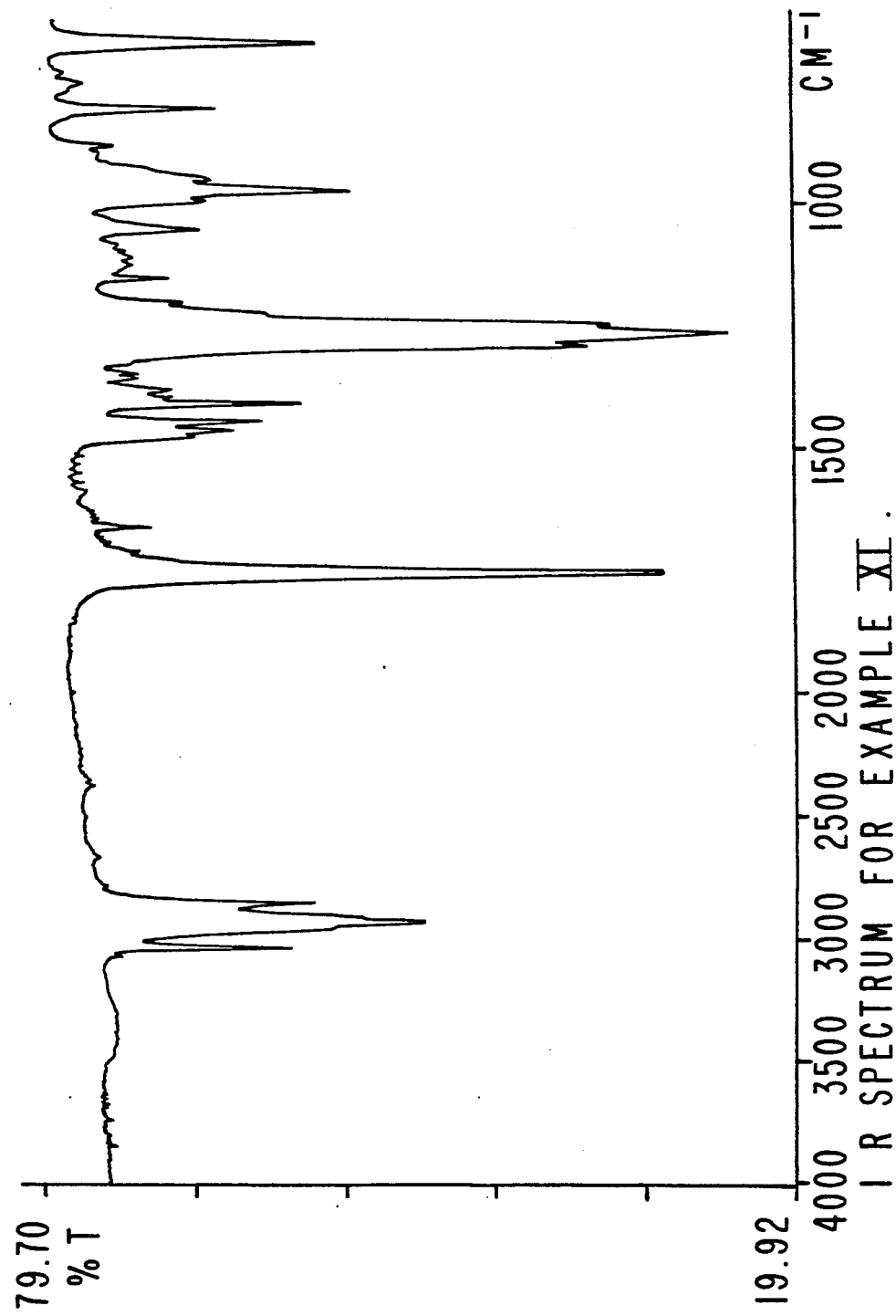

GLC PROFILE FOR EXAMPLE XII.

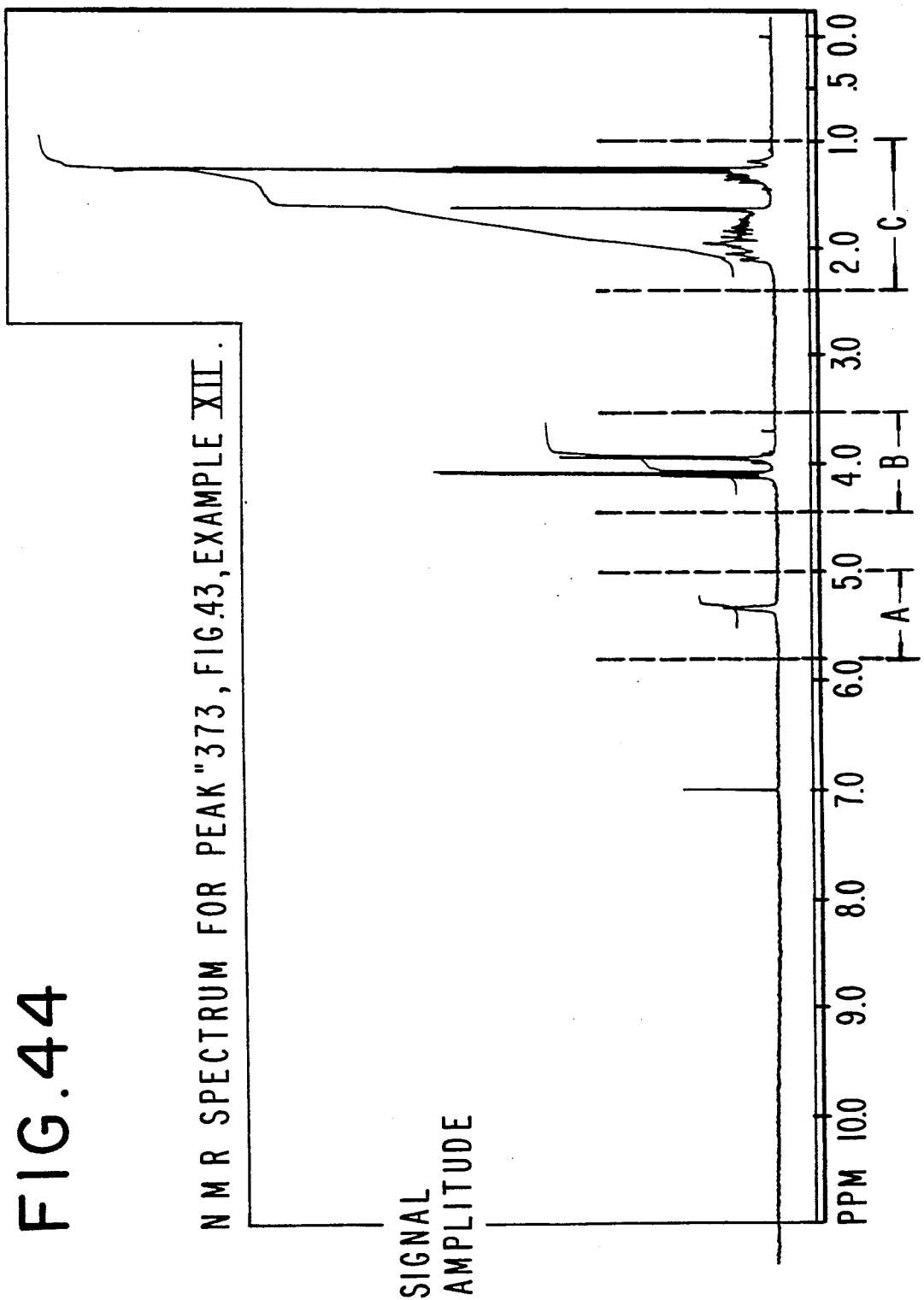
FIG.44 NMR SPECTRUM FOR PEAK "373", FIG.43, EXAMPLE XII.

5.4
PPM 4.2  4.0  3.8
PPM

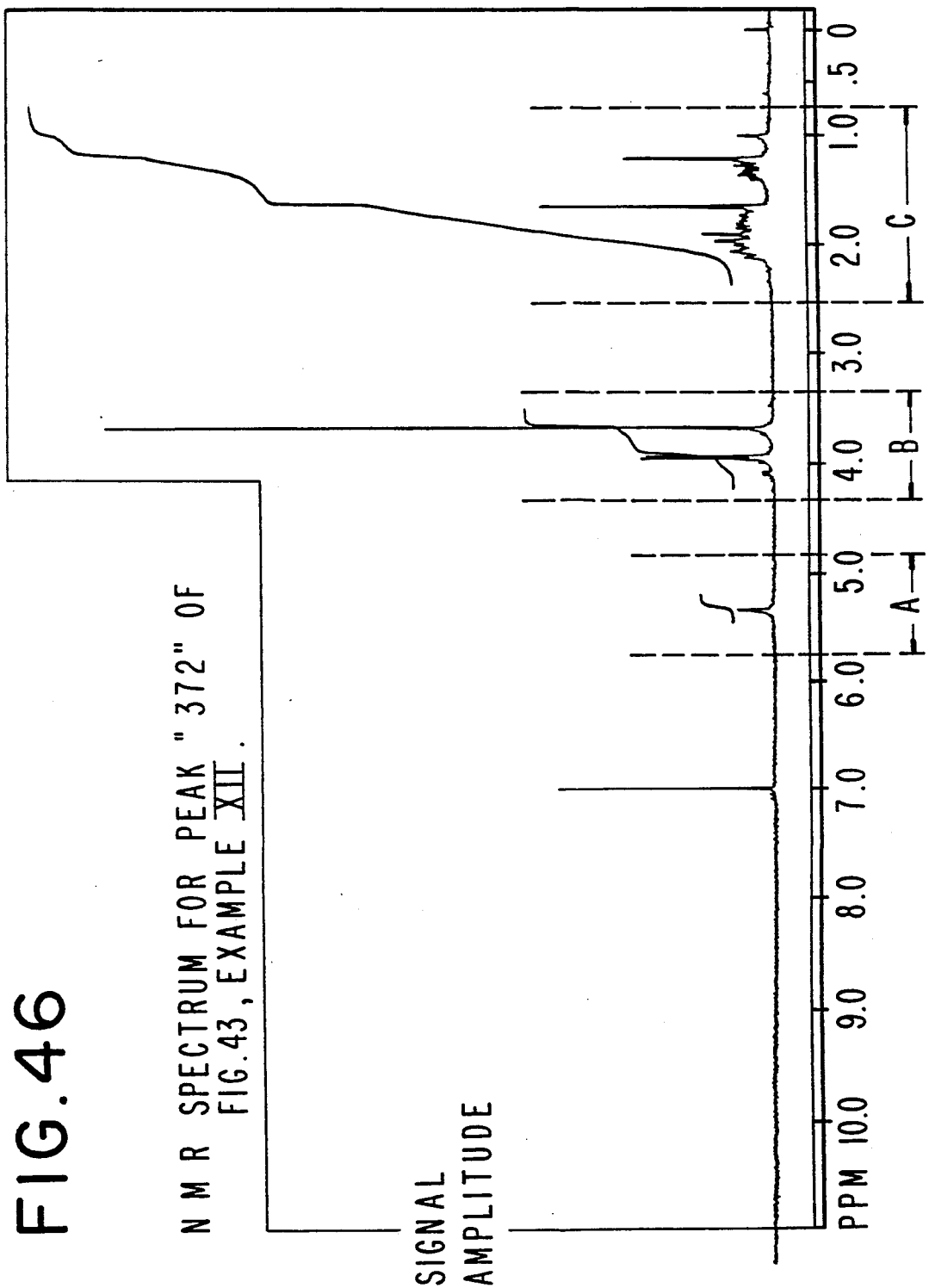
FIG. 46 NMR SPECTRUM FOR PEAK "372" OF FIG. 43, EXAMPLE XII.

5.4
PPM 4.2  4.0  3.8  3.6
PPM

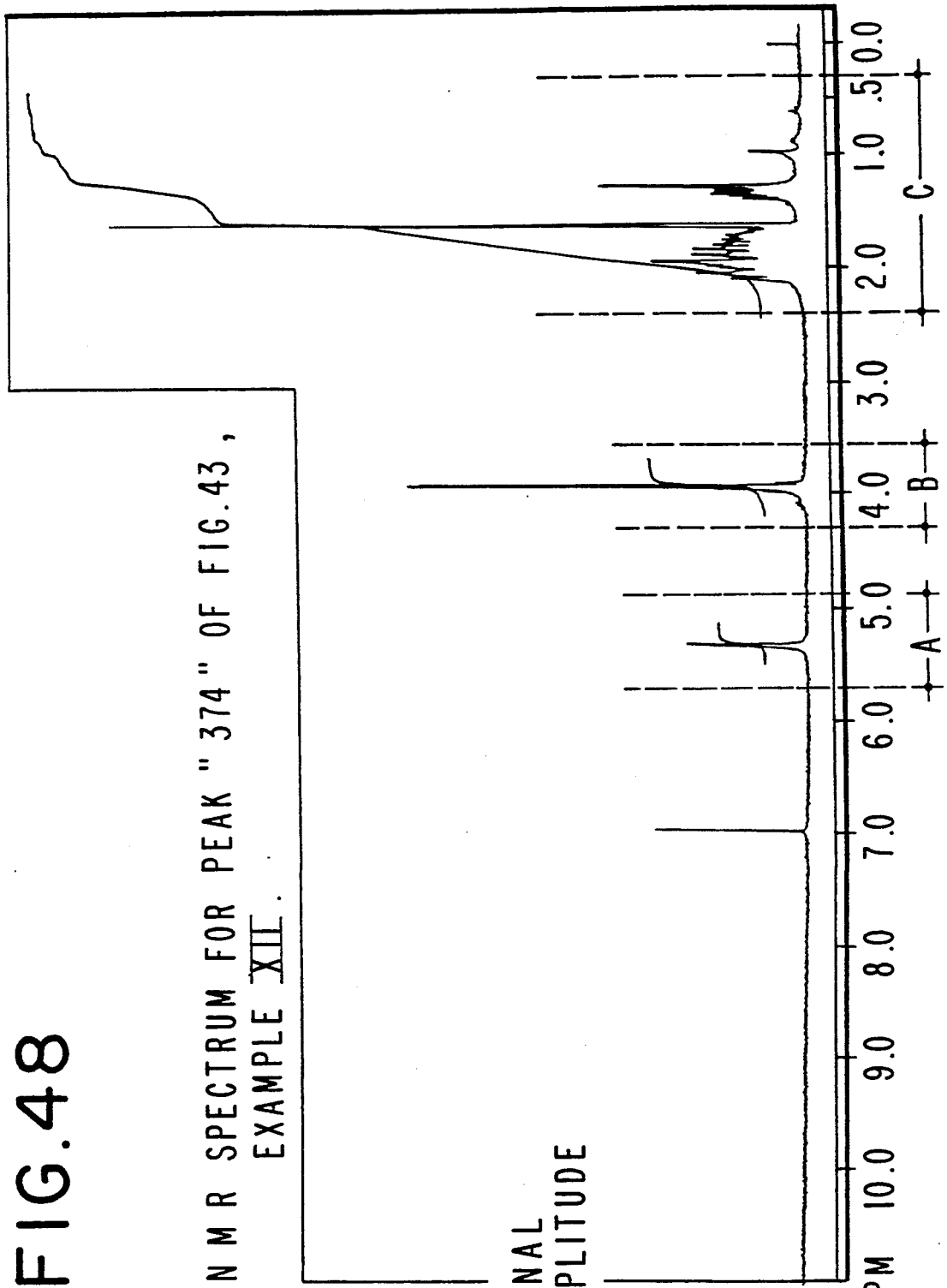
FIG. 48 NMR SPECTRUM FOR PEAK "374" OF FIG. 43, EXAMPLE XII.

FIG. 48 A
FIG. 48 B
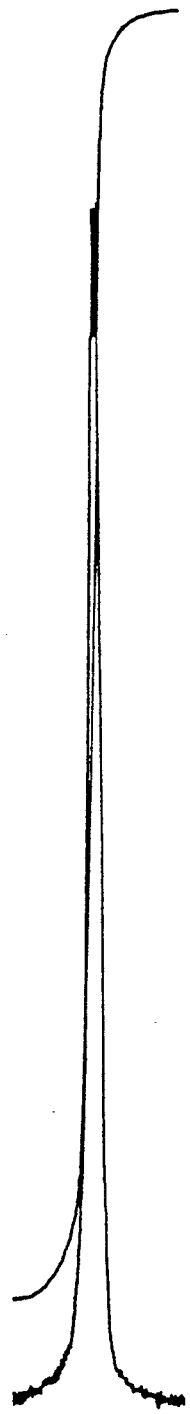
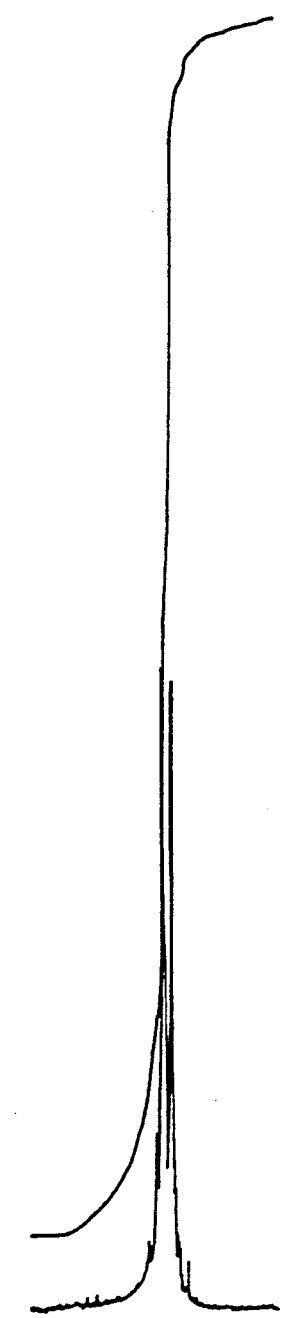
5.4  5.2 PPM              4.0  3.8 PPM

GLC PROFILE FOR EXAMPLE XIII.

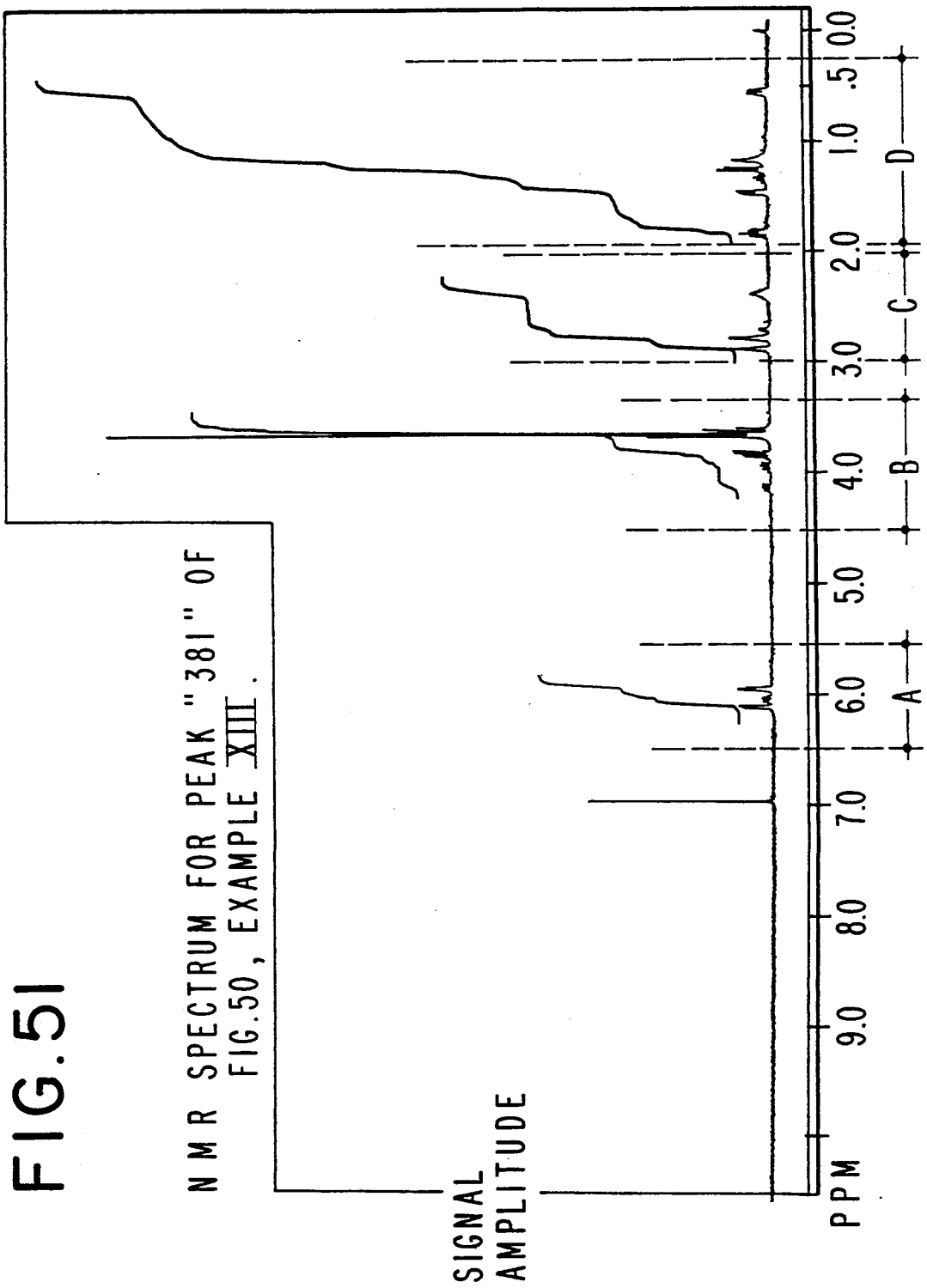
FIG. 51 NMR SPECTRUM FOR PEAK "381" OF FIG. 50, EXAMPLE XIII.

FIG.51C
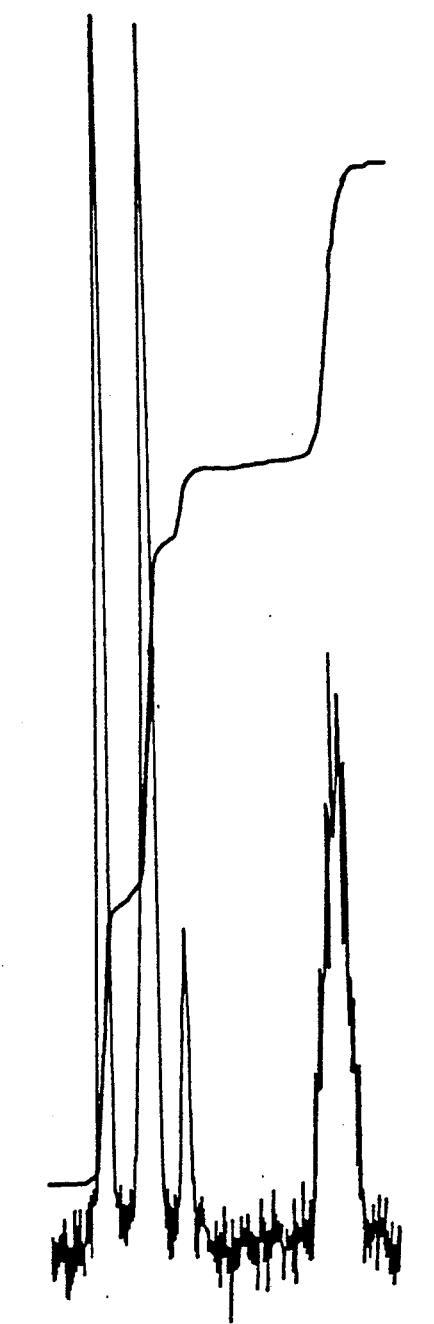
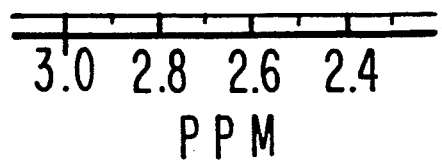

GLC PROFILE FOR EXAMPLE XIV.

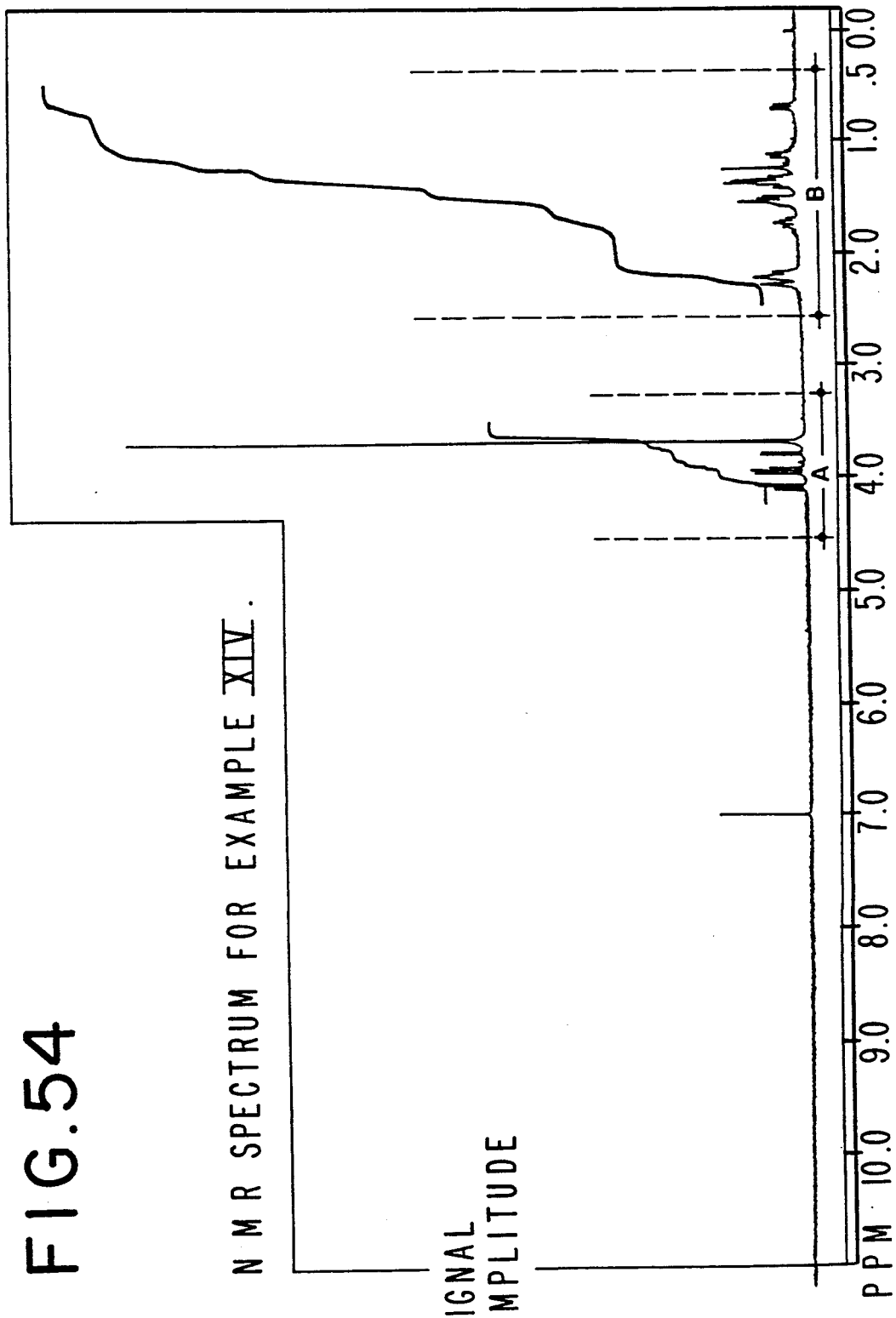
FIG. 54 NMR SPECTRUM FOR EXAMPLE XIV.

GLC PROFILE FOR EXAMPLE XV.

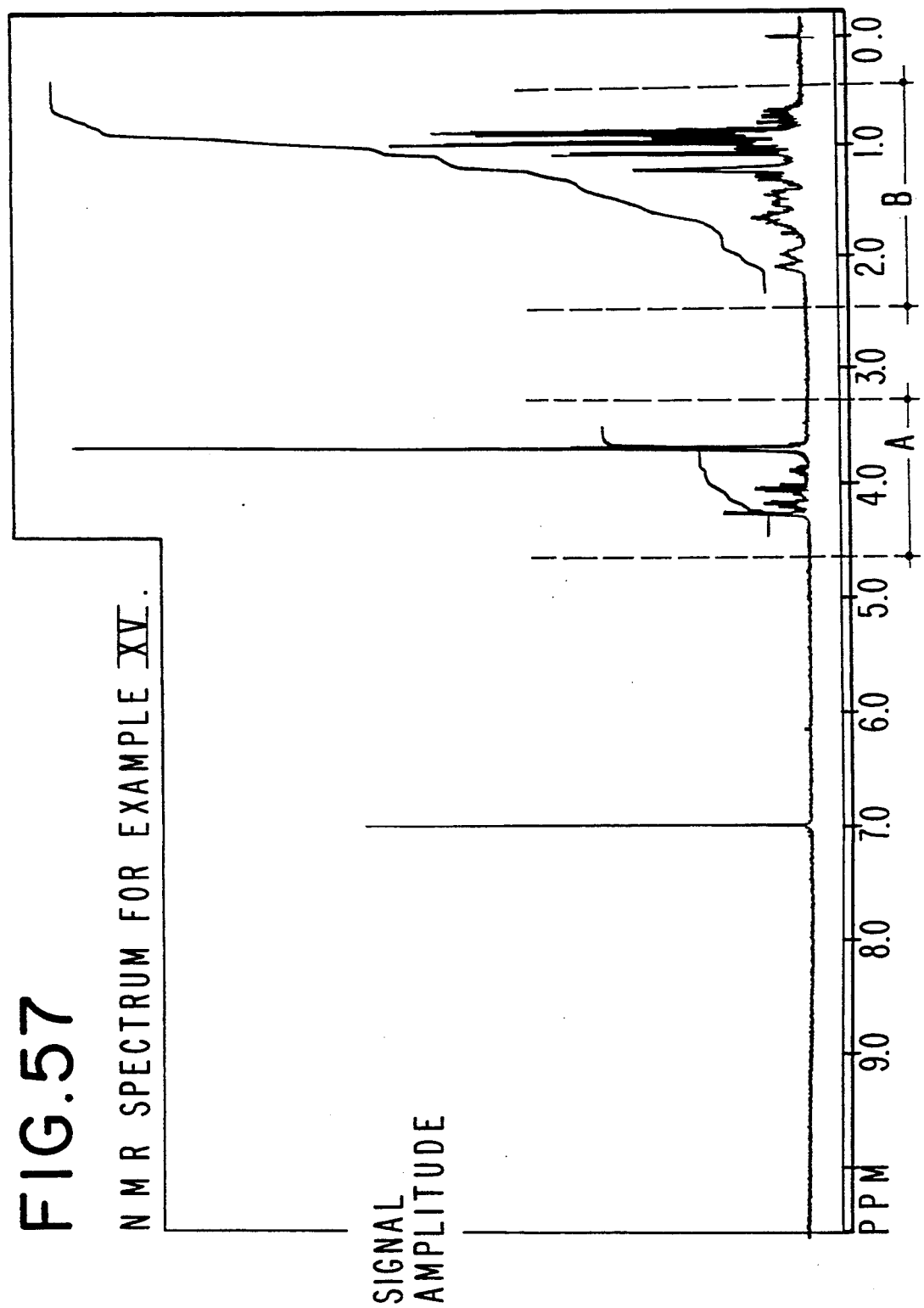

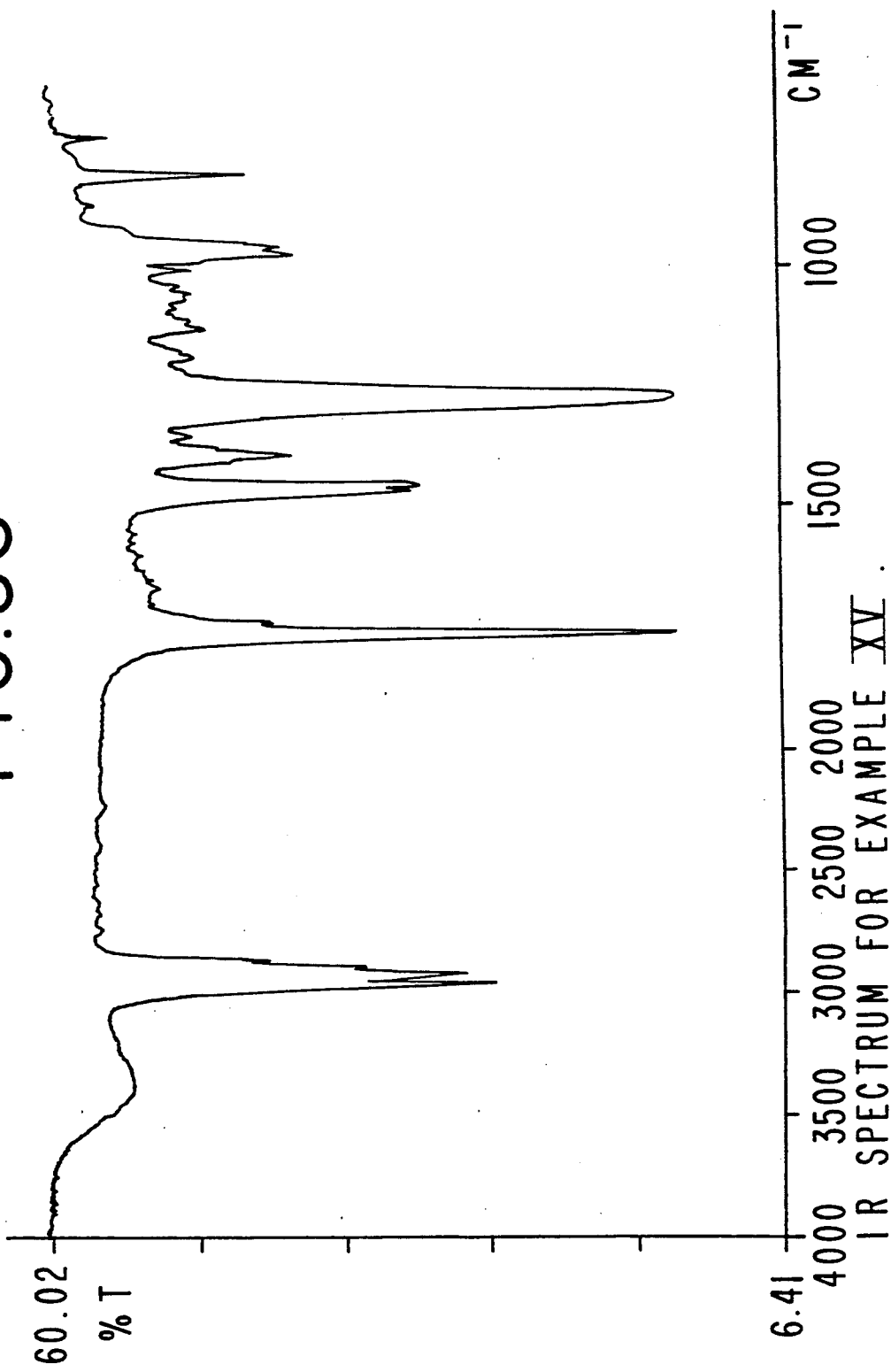

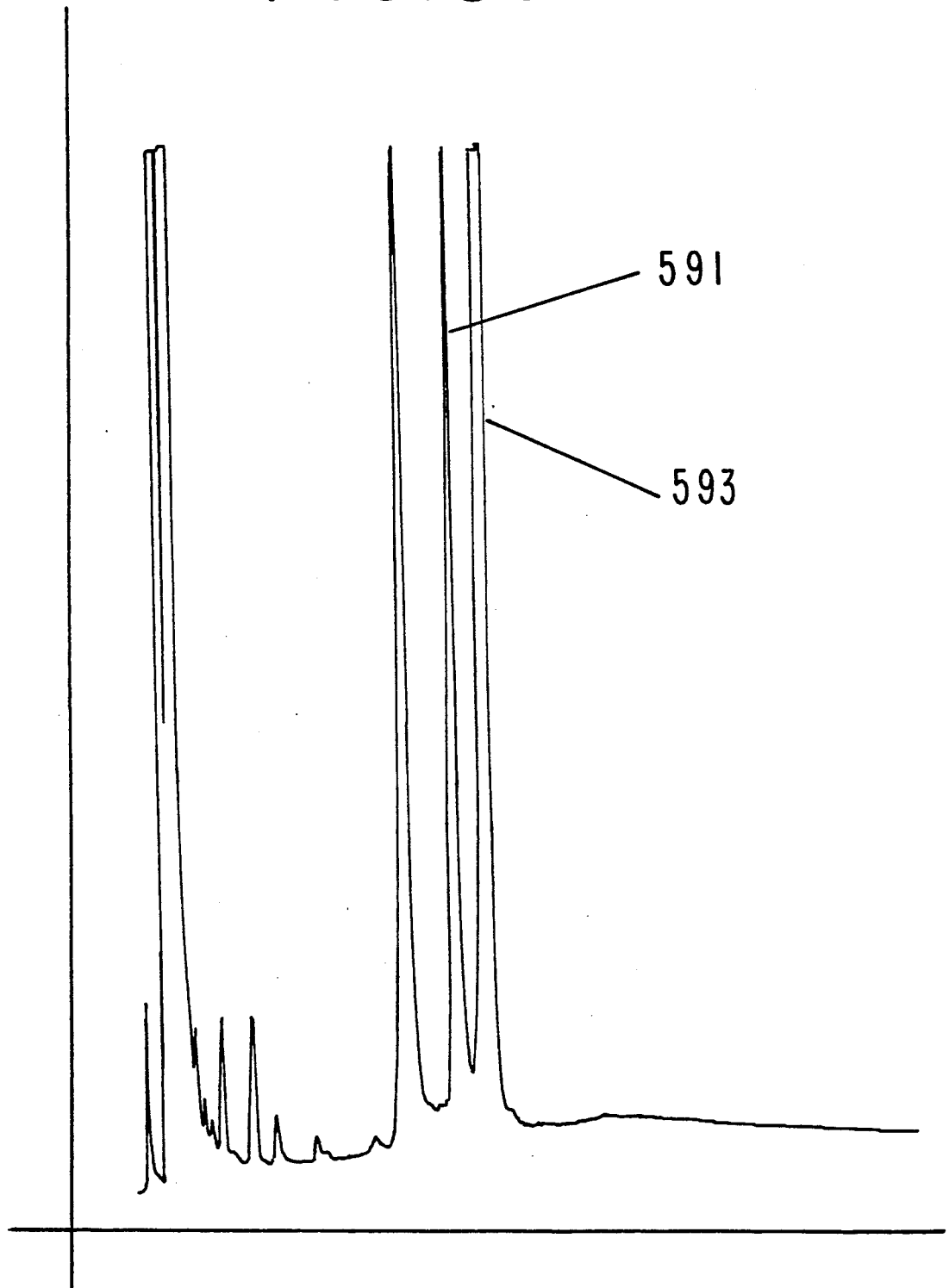

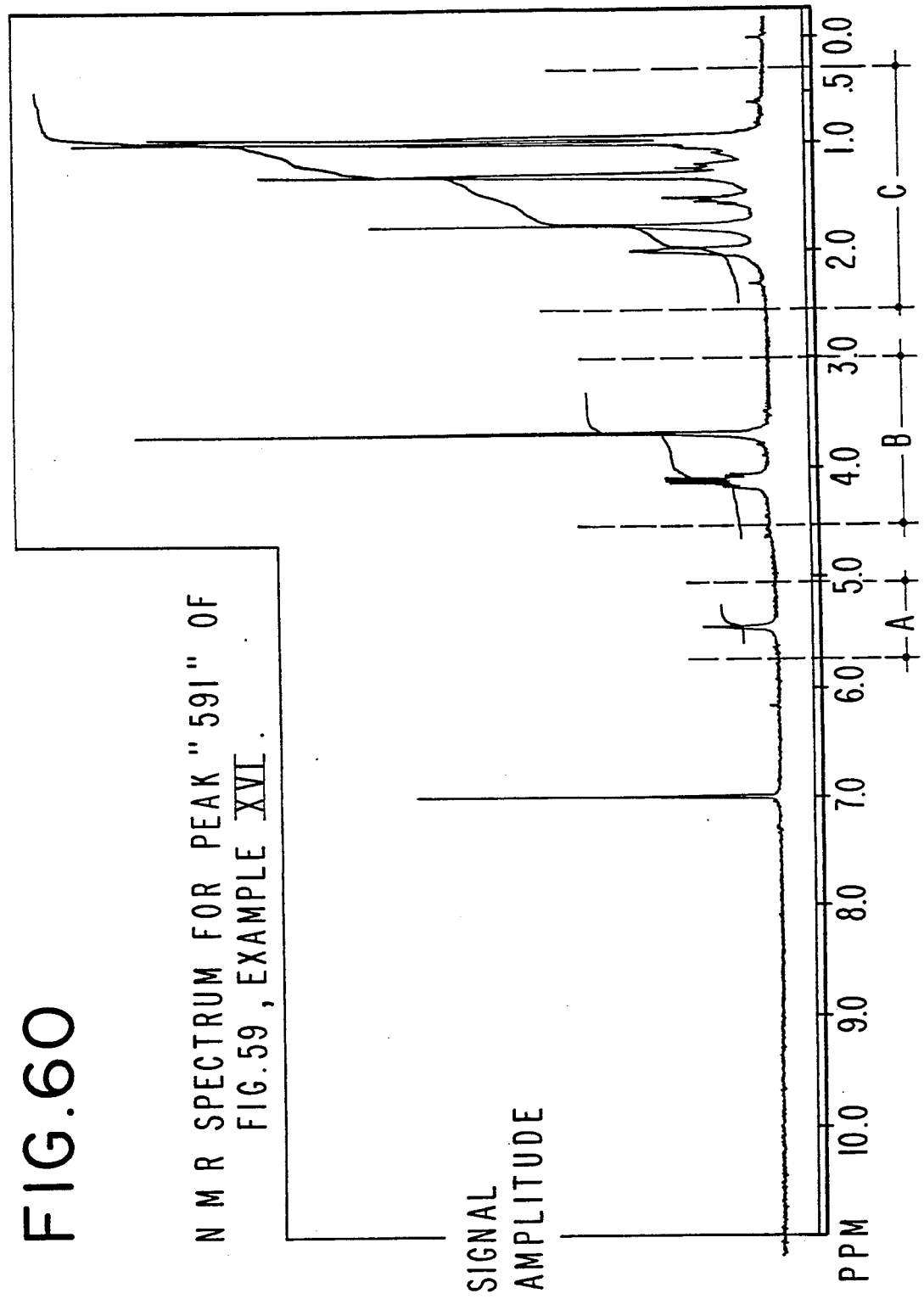
FIG. 60 NMR SPECTRUM FOR PEAK "591" OF FIG. 59, EXAMPLE XVI.

FIG. 60A
FIG. 60B
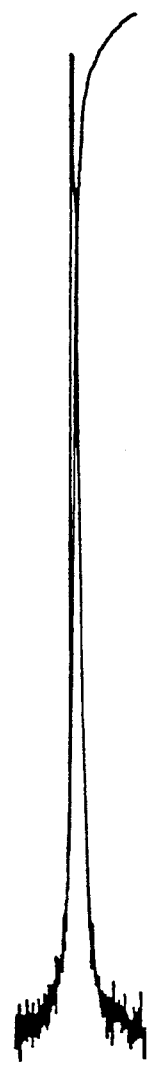
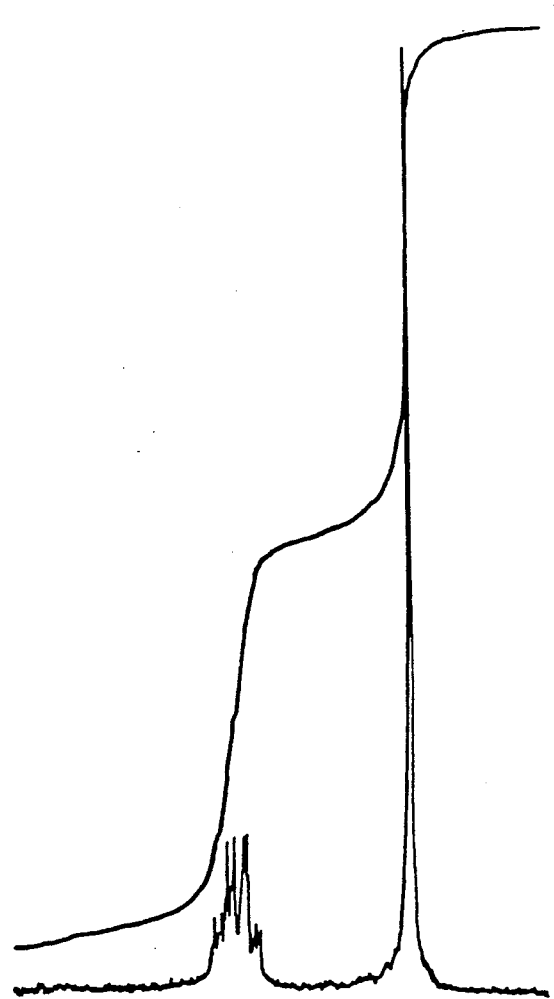

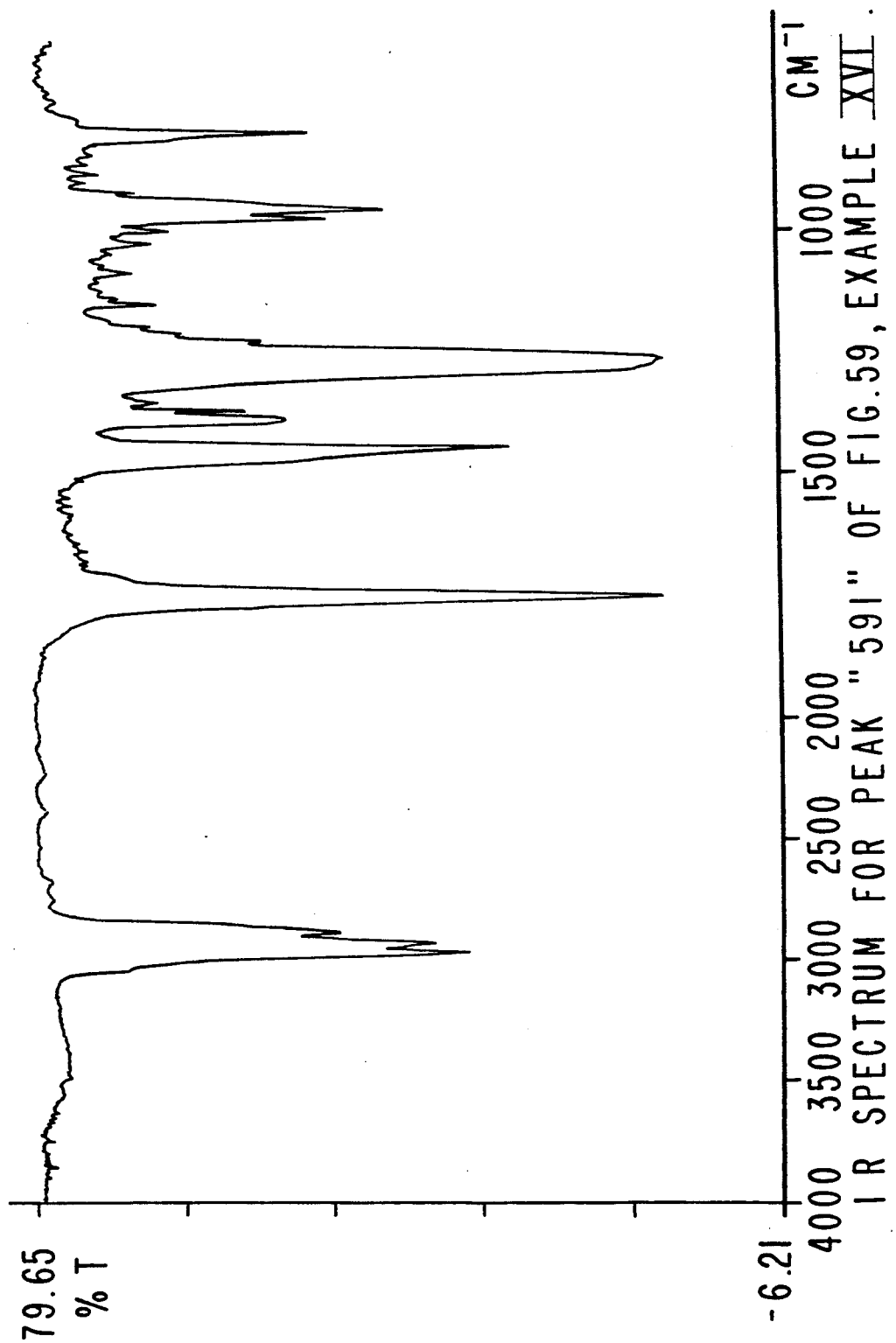

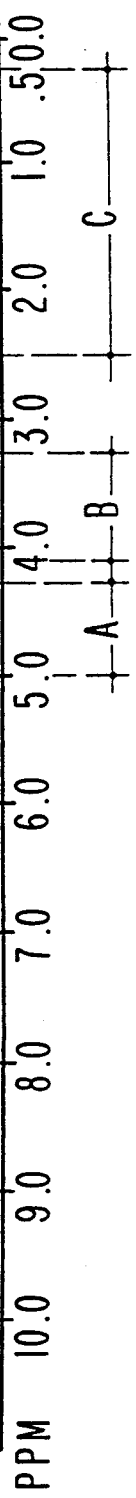
FIG. 62 NMR SPECTRUM FOR PEAK "593" OF FIG. 59, EXAMPLE XVI 4.6
PPM 3.8  3.6
PPM

GLC PROFILE FOR EXAMPLE XVII.

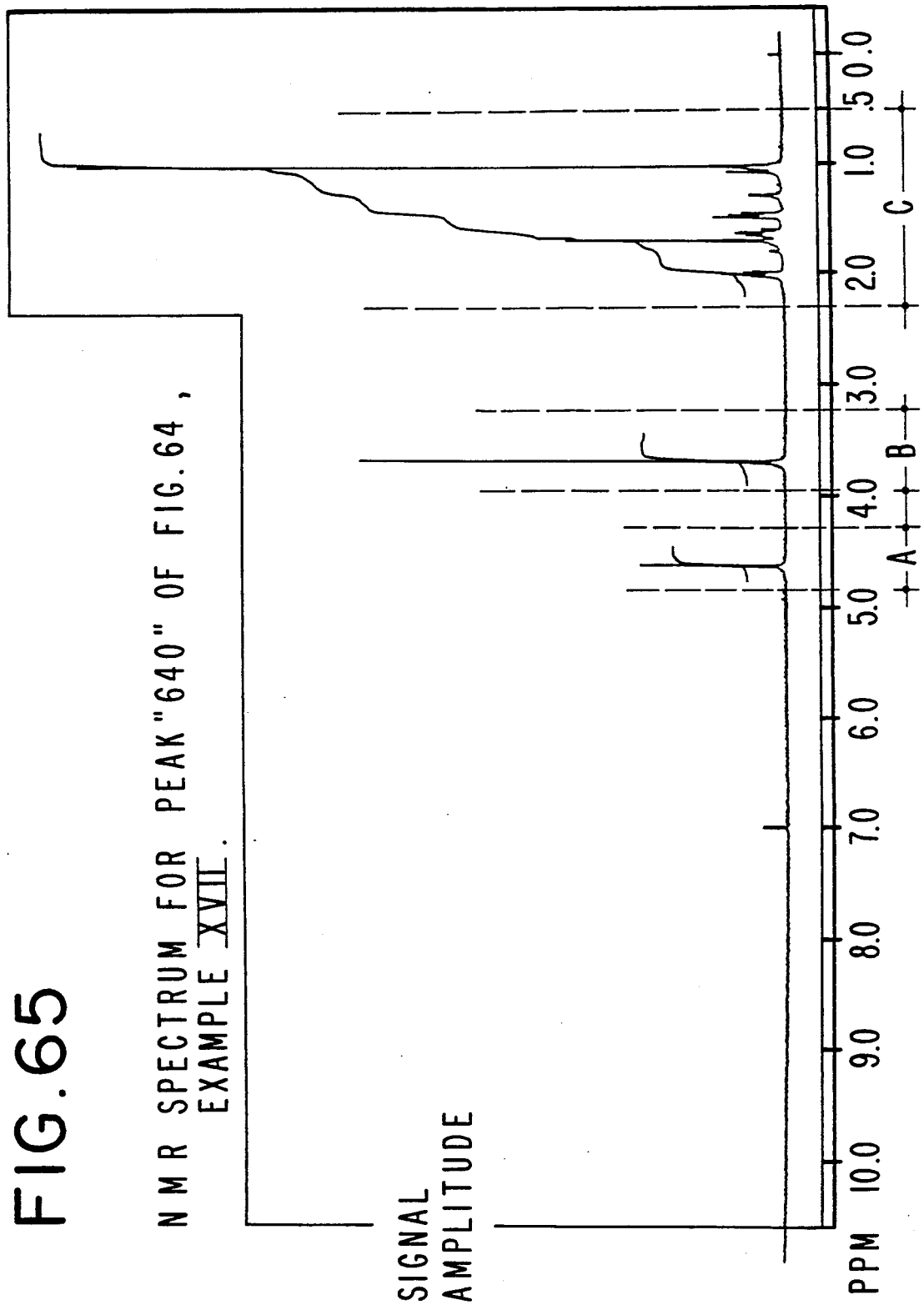

4.6
PPM 3.8 3.6
PPM

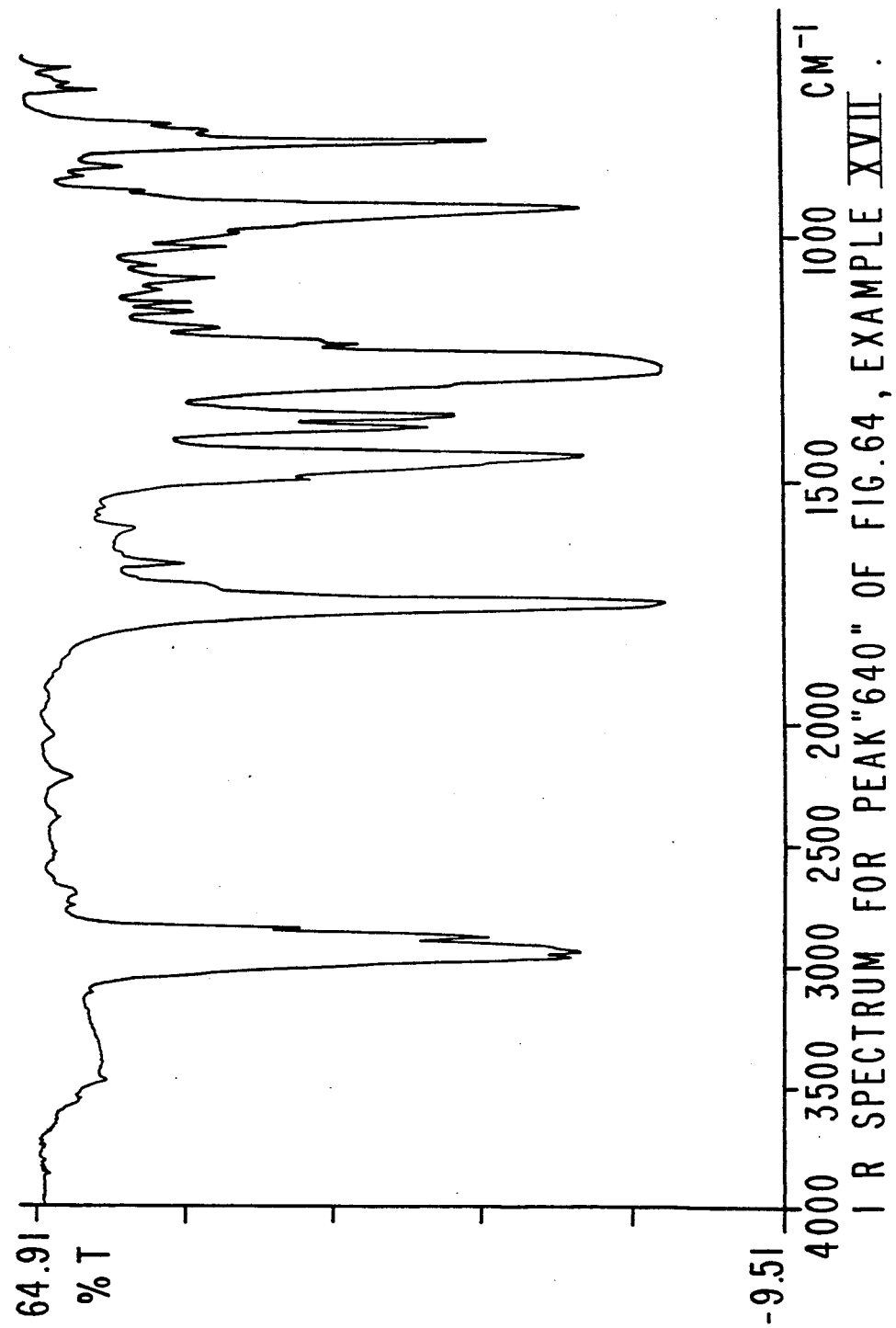

SUBSTITUTED AND UNSUBSTITUTED ALKYL CYCLOHEXYLMETHYL AND CYCLOHEXENYLMETHYL CARBONATES AND PERFUMERY USES THEREOF

This application is a continuation-in-part of application for United States Letters Patent, Ser. No. 666,031 filed on Mar. 7, 1991.

BACKGROUND OF THE INVENTION

Our invention relates to and provides novel alkyl cyclohexylmethyl and cyclohexenylmethyl carbonates having the generic structure:

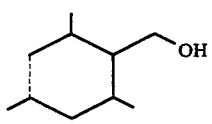

wherein $R_1$ is ethyl or methyl; $R_2$, $R_3$, and $R_4$ and $R_6$ each represents hydrogen or methyl; $R_5$ represents hydrogen, methyl or methylene; $R_7$ represents hydrogen or $C_1$-$C_4$ straight chain lower alkyl or isopropyl or $R_7$ is no moiety; each of the dashed lines is a carbon-carbon single bond or a carbon-carbon double bond; and the wavy line represents a carbon-carbon single bond or no bond; with the provisos that:

(a) at least three of the dashed lines is a carbon-carbon single bond;
(b) when $R_7$ is no moiety, the dashed line at the "1–6" position is a carbon-carbon double bond; and
(c) when the wavy line is a carbon-carbon single bond then $R_5$ is methylene and the carbon-carbon bonds at the "4–5" position and at the "5–6" position represent carbon-carbon single bonds; and uses thereof for their organoleptic properties in consumable materials.

Chemical compounds which can provide earthy, minty, eucalyptus, leathery, myrrh-like, sweet, green, herbal, fruity, banana, blueberry, ozoney, fresh air-dried clothing, floral, rose, violet, tulip, spicy, anisic, lavender, sweet, basic, woody, camphoraceous, winey and cognac aromas, with floral, rose, green, cognac-like, balsamic, rum-like, sweet, air-dried clothing, ozoney and anisic topnotes and early morning forest path, earthy, rooty, eucalyptus, camphoraceous, minty, floral, rose, violet, tulip, green, sweet, aubepine, anisic, stemmy, fruity, pear-like, figgy, woody, spicy and clove-like undertones are highly desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

There is, accordingly, a continuing effort to find synthetic materials which will replace, enhance or augment the essential fragrance notes provided by natural essential oils or compositions thereof having the above properties. Unfortunately, many of these synthetic materials either have the desired nuances only to a relatively small degree or else contribute undersirable or unwanted odor to the compositions.

Esters defined according to the generic structure:

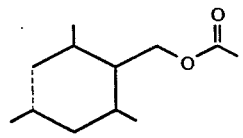

wherein the dashed line represents a carbon-carbon single bond or a carbon-carbon double bond as well as their corresponding alcohols defined according to the generic structure:

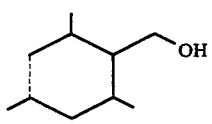

and defined according to the structures:

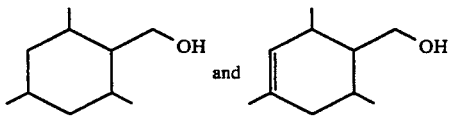

are known to be useful in augmenting or enhancing the aroma of perfume compositions and perfumed articles as disclosed in U.S. Pat. No. 4,301,022 issued on Nov. 17, 1981, the specification for which is incorporated by reference herein. The carbon esters of our invention however, have structures and perfumery properties which are different in kind from the structures and perfumery properties of the esters and alcohols of U.S. Pat. No. 4,301,022 issued on Nov. 17, 1981. The perfumery properties of the carbonates of our invention have unexpected, unobvious and advantageous perfumery properties when compared with the esters of U.S. Pat. No. 4,301,022 as well as the alcohols thereof.

U.S. Pat. No. 4,397,789 issued on Aug. 9, 1983 discloses carbonate esters useful in augmenting or enhancing the aroma of perfume compositions, colognes or perfumed articles and these carbonate esters are defined according to the structures:

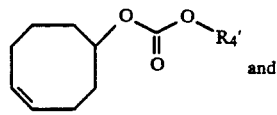
and
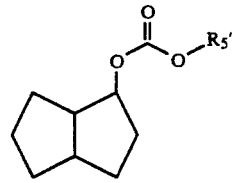

wherein $R_4'$ and $R_5'$ are methyl or ethyl.

Reference to U.S. Pat. Nos. 4,080,309 and 4,033,993 issued on July 5, 1977 is made in said U.S. Pat. No. 4,397,789.

U.S. Pat. No. 4,033,993 issued on July 5, 1977 as well as U.S. Pat. No. 4,080,309 issued on Mar. 21, 1978 disclose compounds defined according to the generic structure:

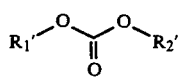

for use in augmenting or enhancing perfume compositions. Thus, such compounds as described in said U.S. Pat. Nos. 4,033,993 and 4,080,309 having the generic structure:

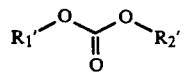

wherein $R_1'$ is a member having from 8 to 12 carbon atoms selected from the group consisting of alkylcyclohexyl, alkenylcyclohexyl, alkynylcyclohexyl and cycloalkyl, and $R_2'$ is a member selected form the group consisting of alkyl having from 1 to 5 carbon atoms, alkenyl having from 2 to 5 carbon atoms and alkynyl having from 2 to 5 carbon atoms indicated to have pleasing and persistent scents. Specifically, said U.S. Pat. Nos. 4,033,993 and 4,080,309 describe interalia compounds having the structures:

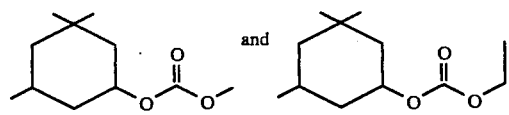

but do not describe unsaturated cyclohexylmethyl carbonates and do not describe any cyclohexylmethyl carbonates. The alkyl cyclohexylmethyl and cyclohexenylmethyl carbonates of our invention have structures and organoleptic properties which are different in kind from the carbonate derivatives of said U.S. Pat. Nos. 4,033,993 and 4,080,309. The alkyl cyclohexylmethyl and cyclohexenylmethyl carbonates of our invention have organoleptic properties which are unobvious, unexpected and advantageous over the carbonates described in U.S. Pat. Nos. 4,033,993 and 4,080,309.

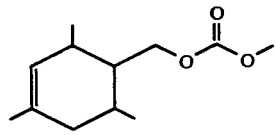

Figure 2:
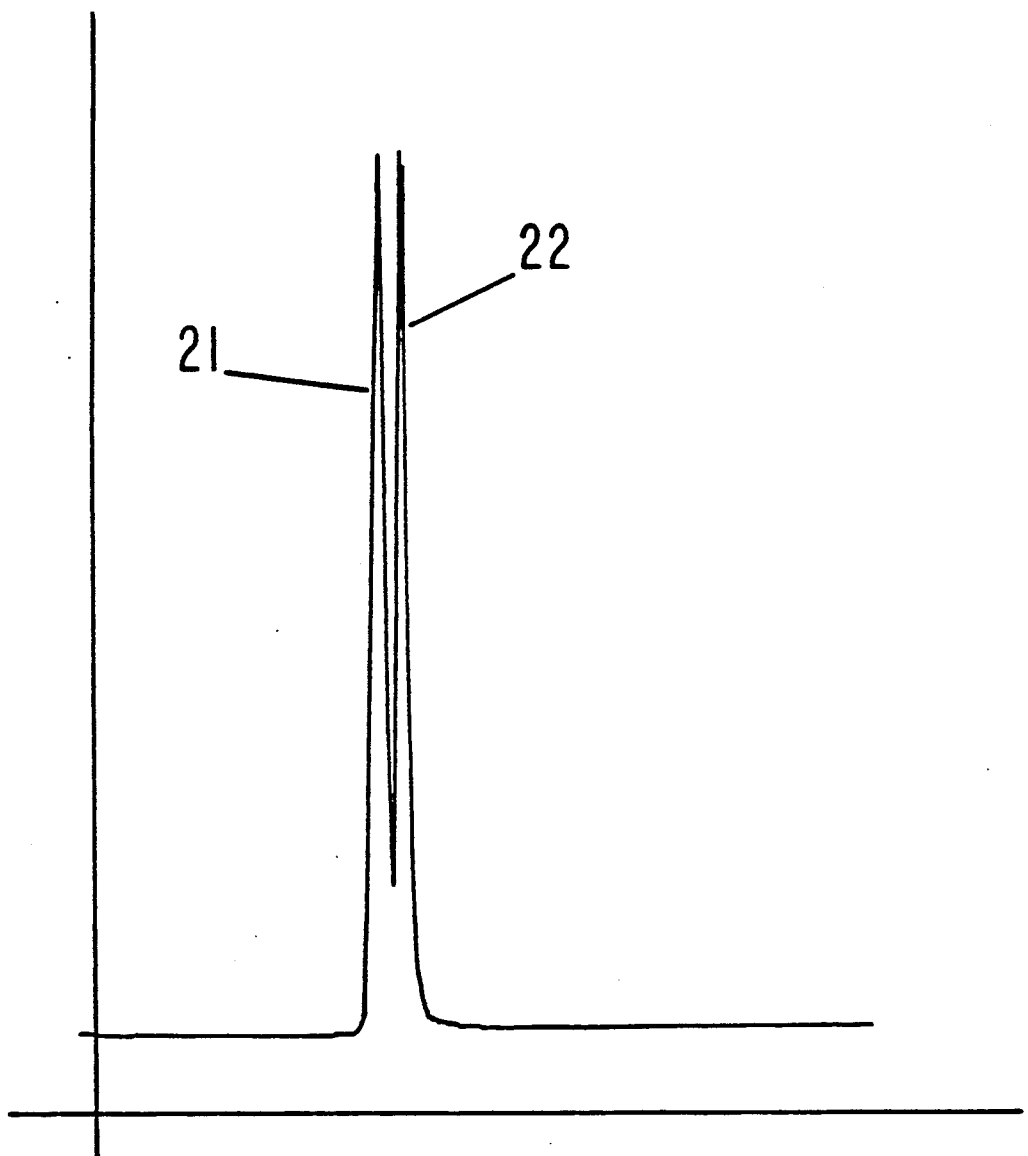

FIG. 2 is the GLC profile for bulked distillation fractions 7–10 of the distillation of the reaction product of Example I containing the compound having the structure:

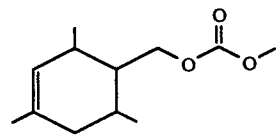

Figure 3:
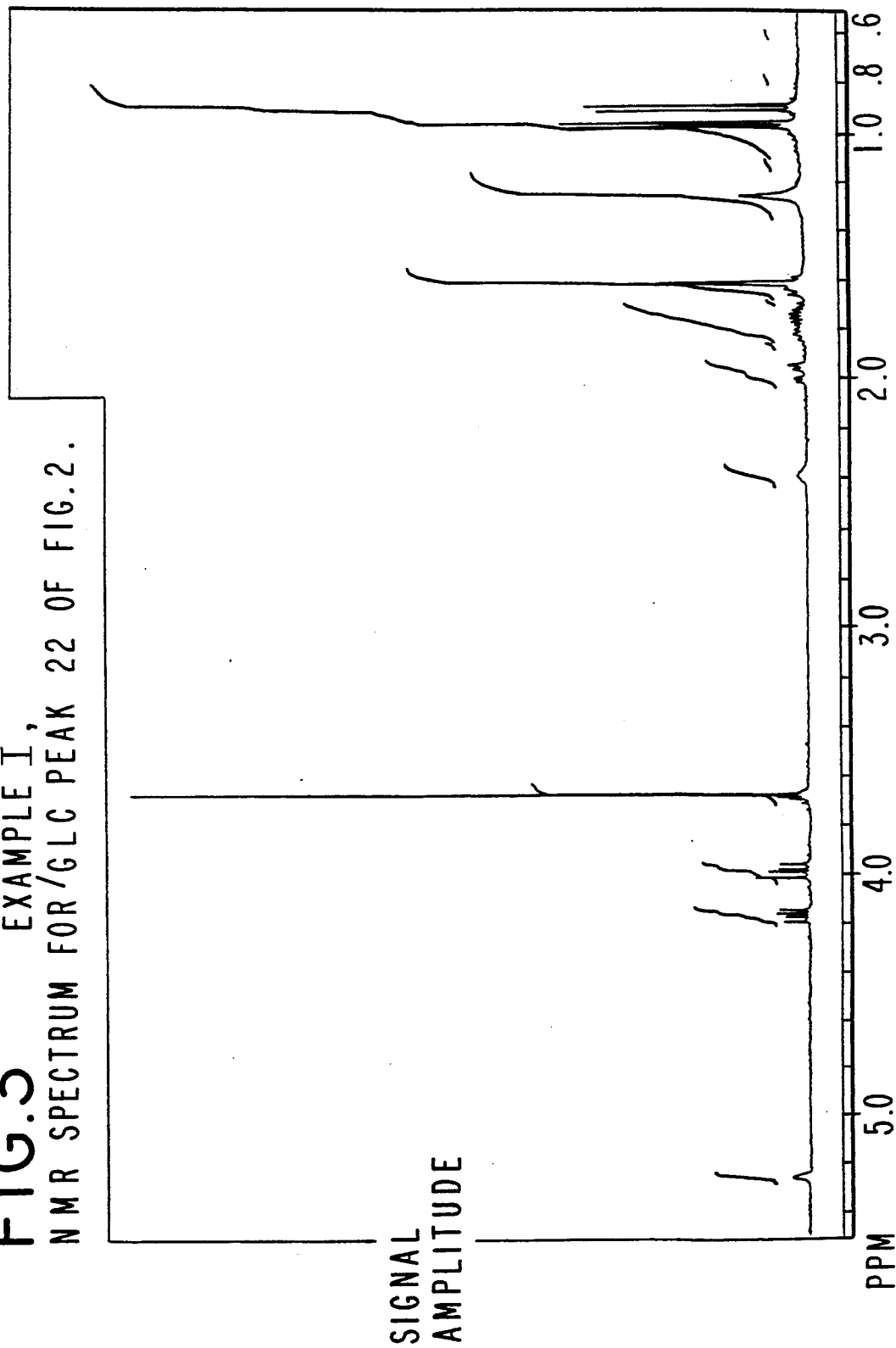

FIG. 3 is the NMR spectrum for peak 22 of the GLC profile of FIG. 2; for an isomer of the compound having the structure:

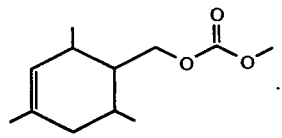

Figure 4:
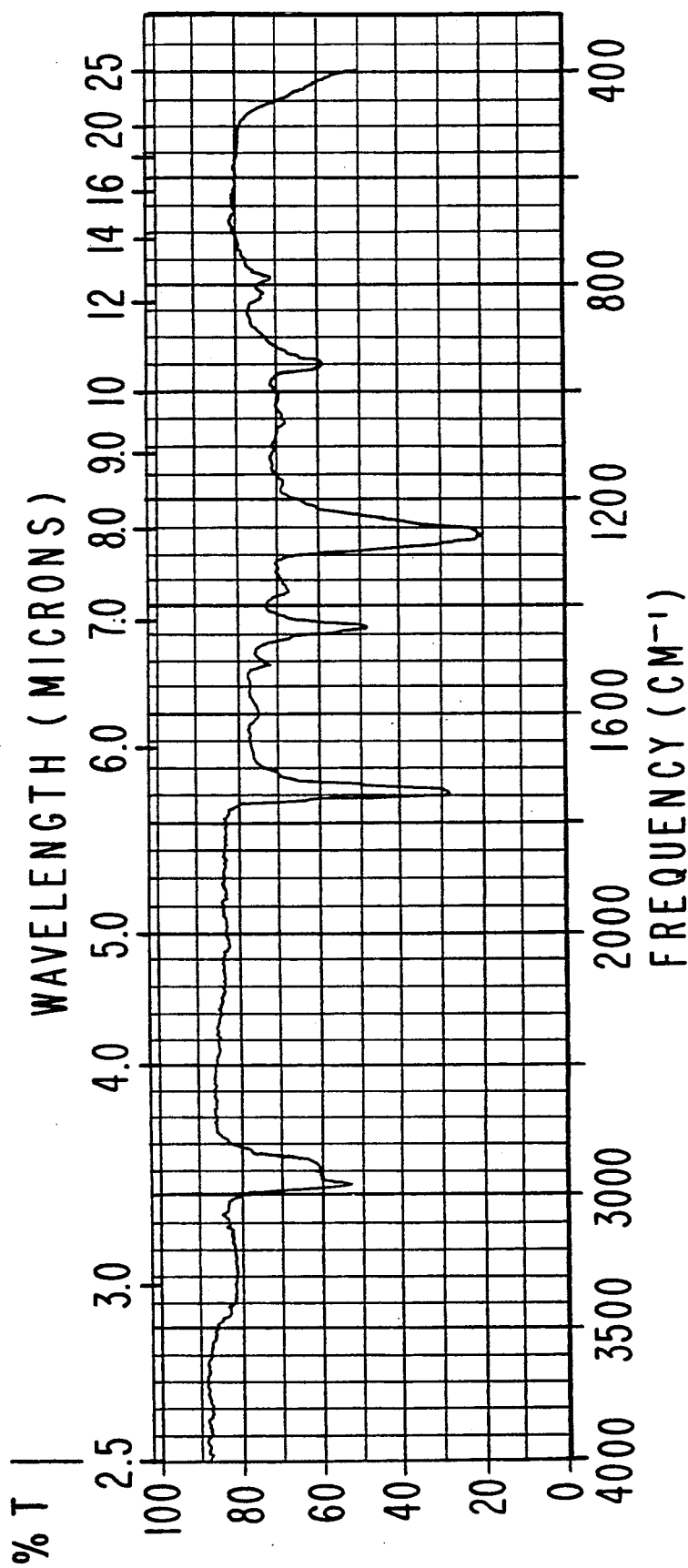

FIG. 4 is the infra-red spectrum for peak 22 of the GLC profile of FIG. 2; for an isomer of the compound having the structure:

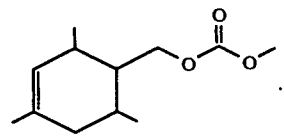

Figure 5:
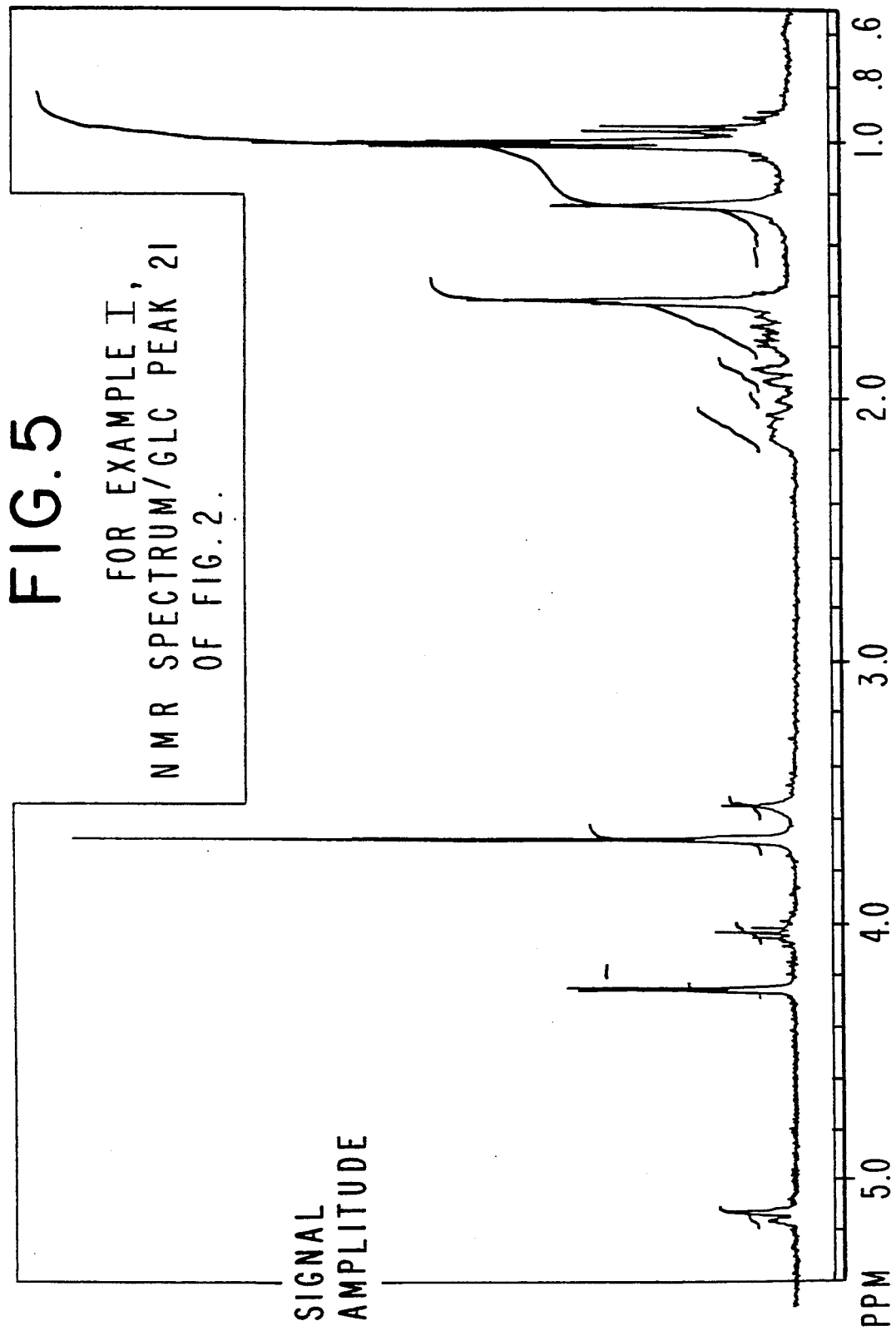

FIG. 5 is the NMR spectrum for peak 21 of the GLC profile of FIG. 2; for an isomer of the compound having the structure:

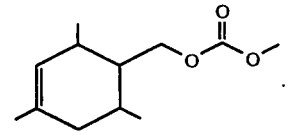

Figure 6:
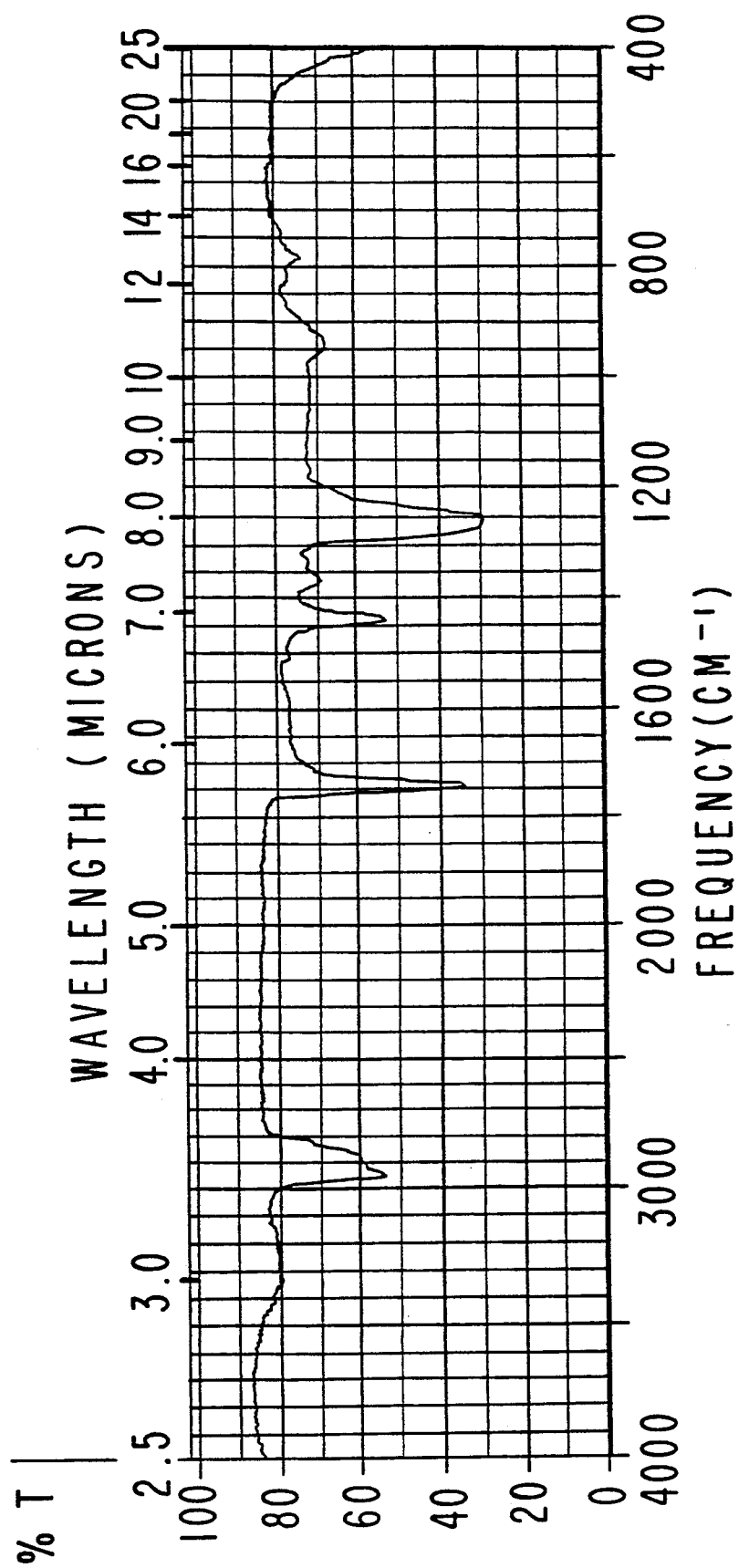

FIG. 6 is the infra-red spectrum for peak 21 of the GLC profile of FIG. 2; for an isomer of the compound having the structure:

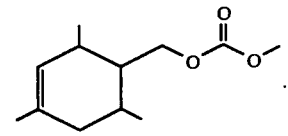

Figure 7:
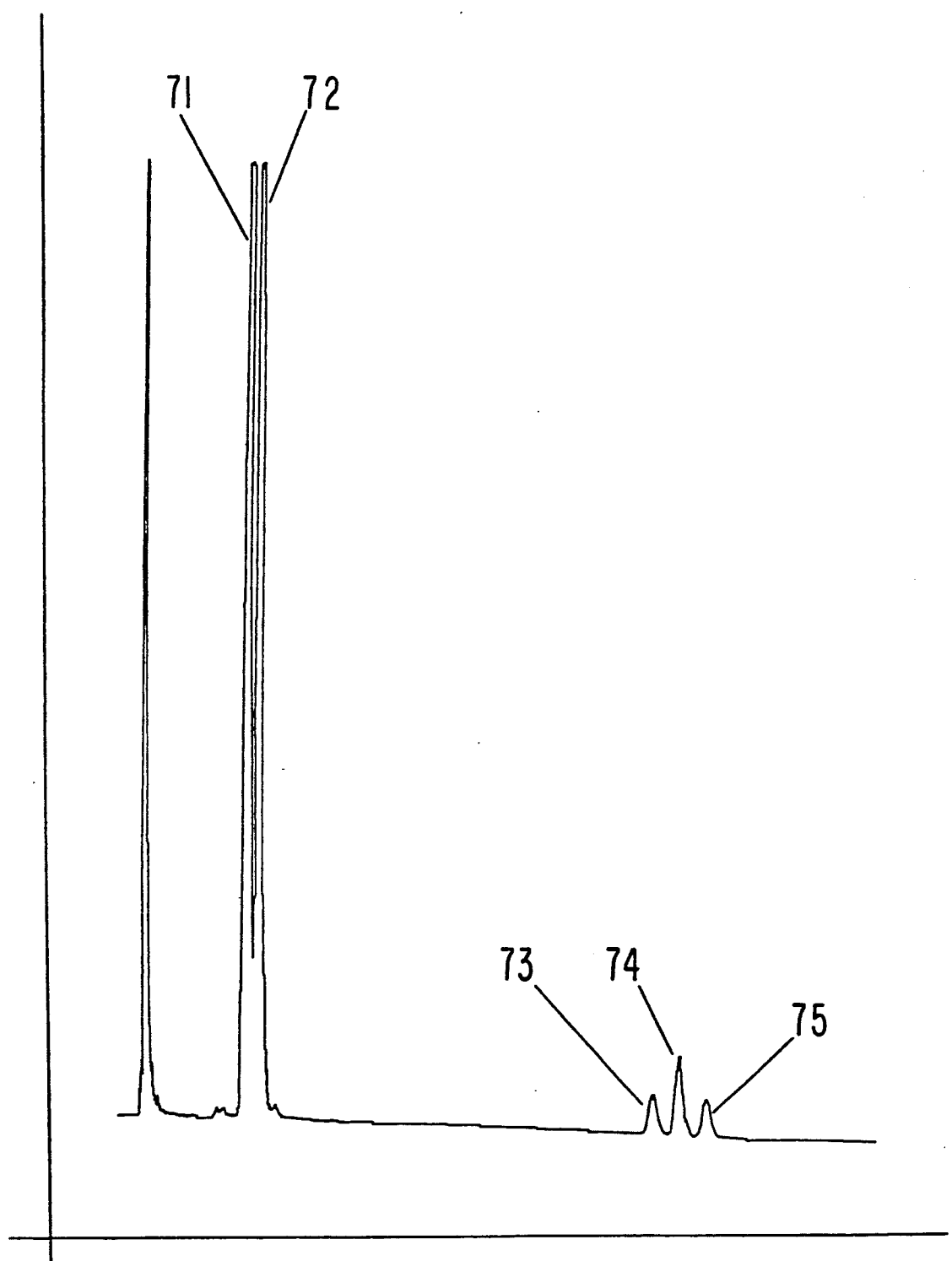

FIG. 7 is the GLC profile for the crude reaction product of Example II containing the compound having the structure:

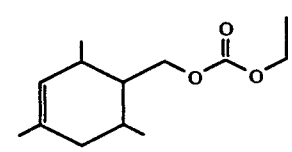

as well as the compound having the structure:

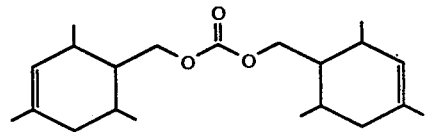

Figure 8:
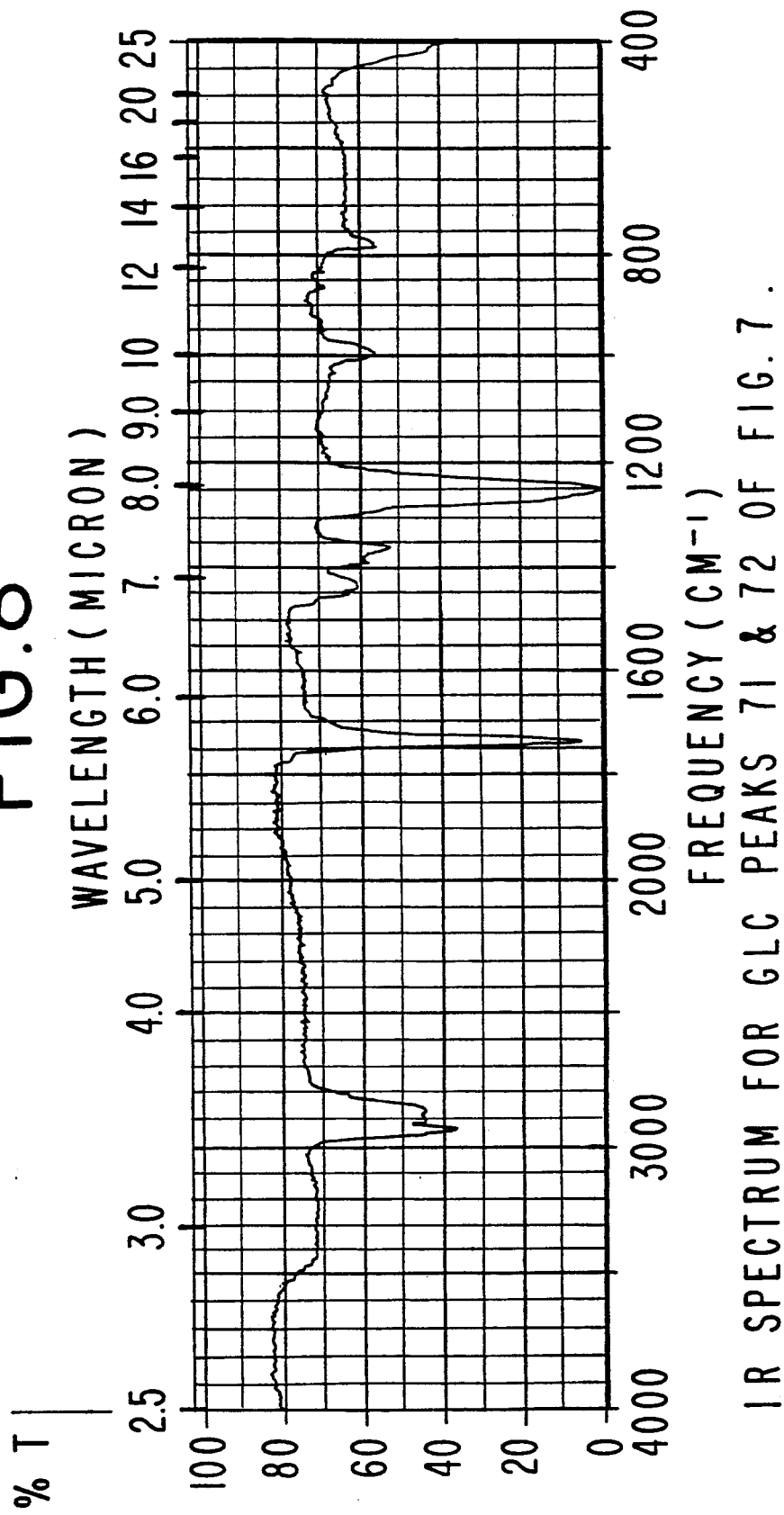

FIG. 8 is the infra-red spectrum for peaks 71 and 72 of the GLC profile of FIG. 7; for the compound having the structure:

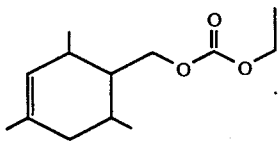

FIG. 9 is the NMR spectrum for peaks 71 and 72 of the GLC profile of FIG. 7; for the compound having the structure:

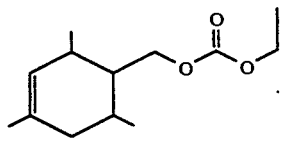

FIG. 9A is a detailed section "A" of the NMR spectrum of FIG. 9.

FIG. 9B is a detailed section "B" of the NMR spectrum of FIG. 9.

Figure 10:
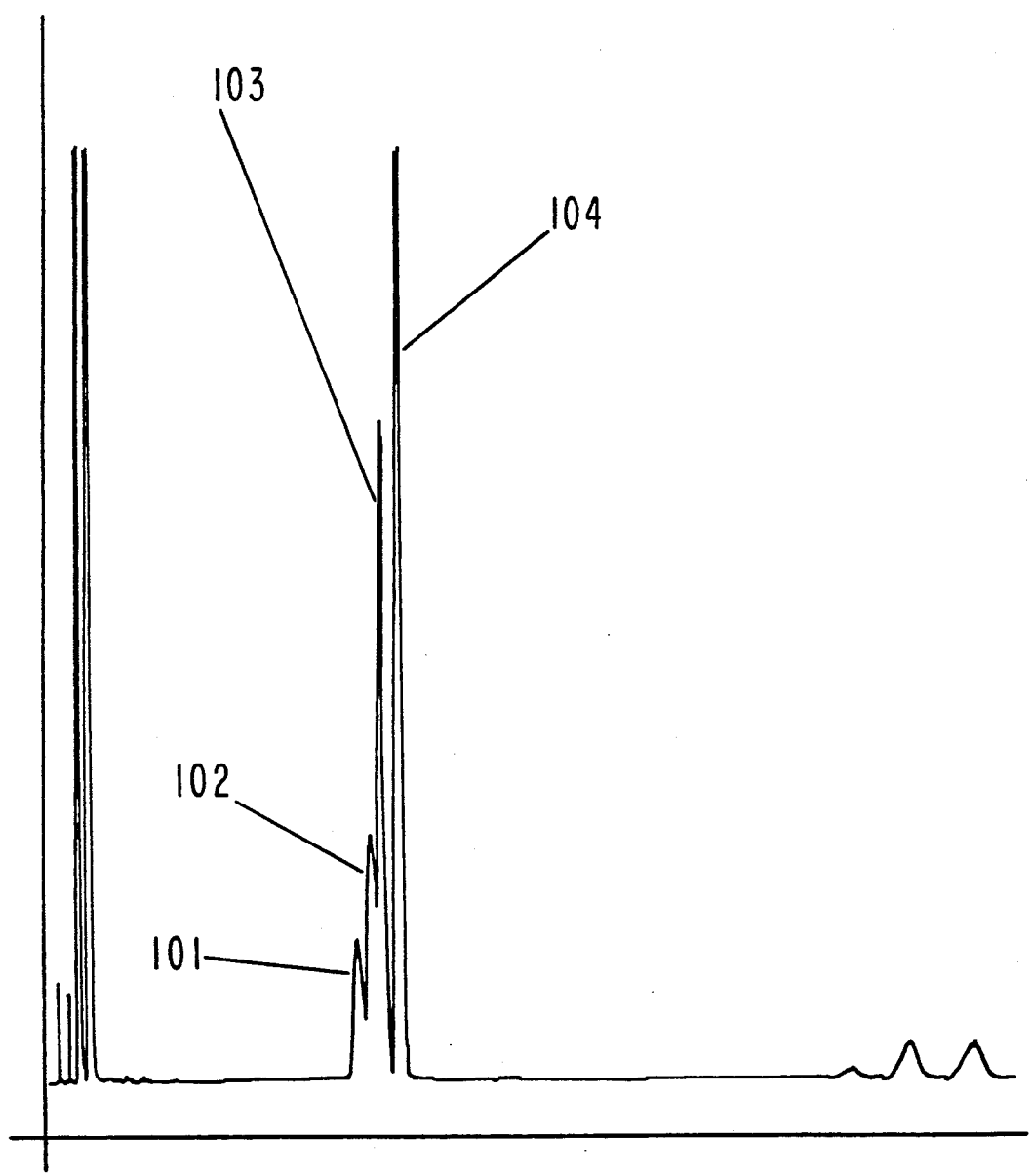

FIG. 10 is the GLC profile of the crude reaction product of Example III containing the compound having the structure:

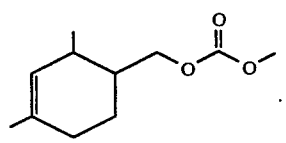

Figure 11:
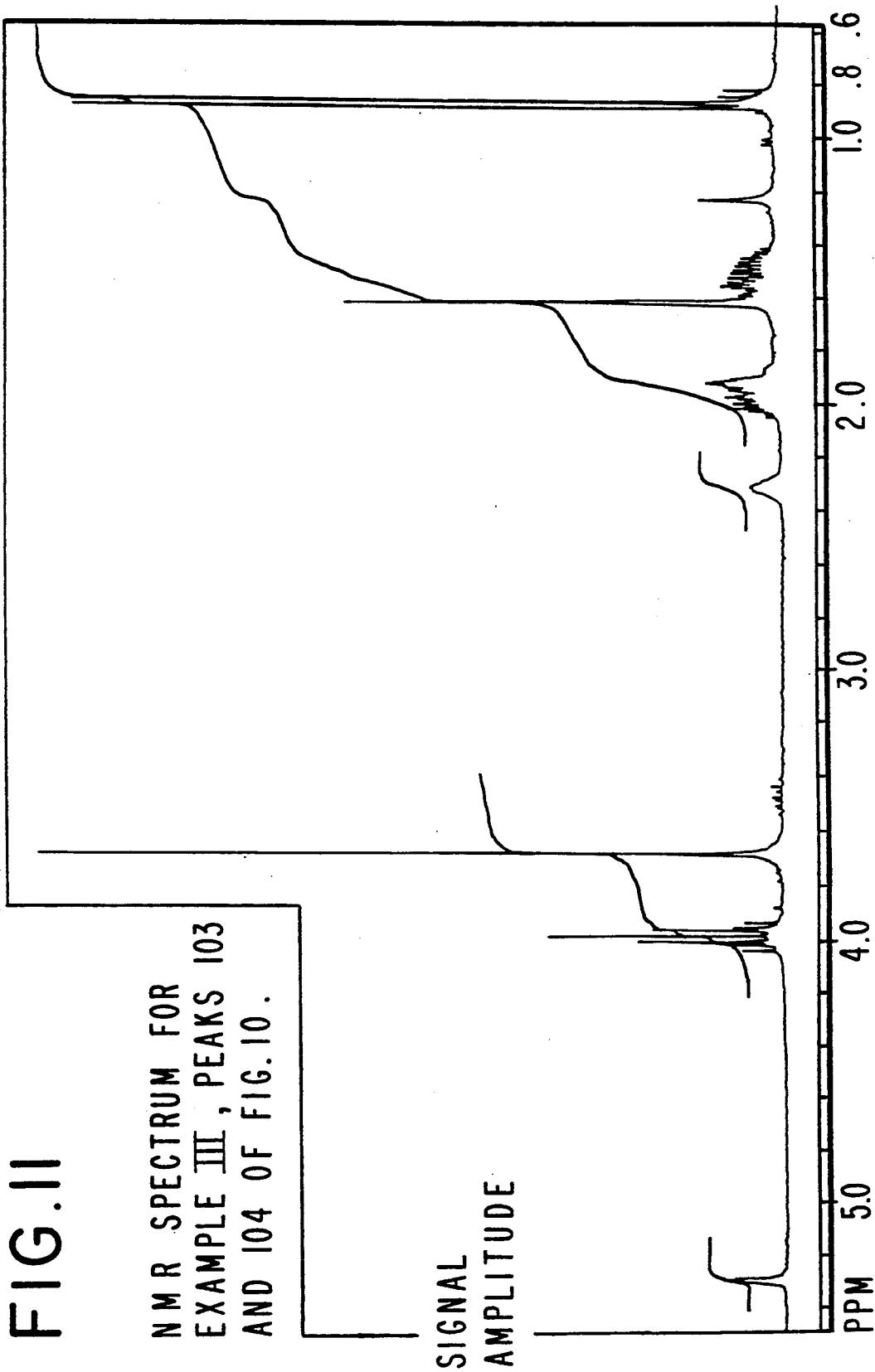

FIG. 11 is the NMR spectrum for peaks 103 and 104 of the GLC profile of FIG. 10; for the compound having the structure:

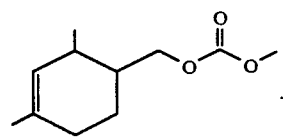

Figure 12:
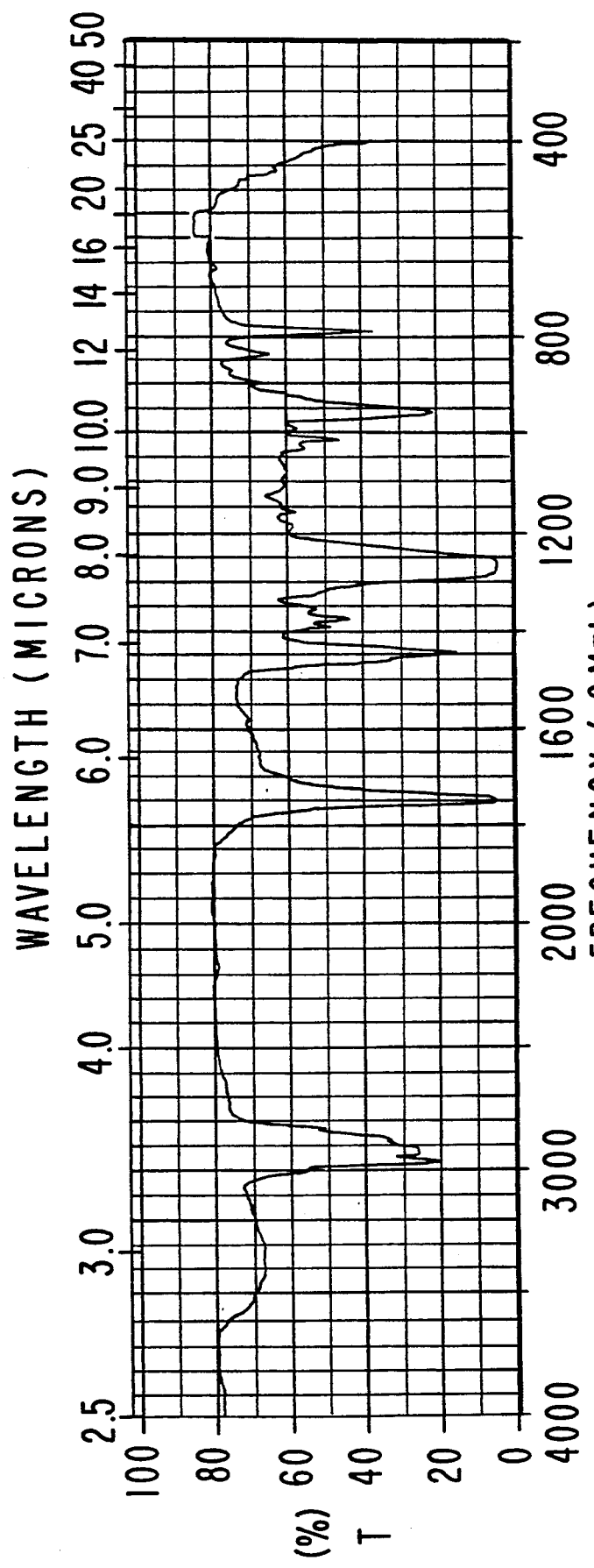

FIG. 12 is the infra-red spectrum for peaks 103 and 104 of the GLC profile of FIG. 10; for the compound having the structure:

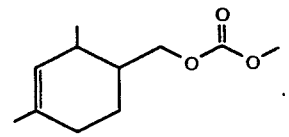

Figure 13:
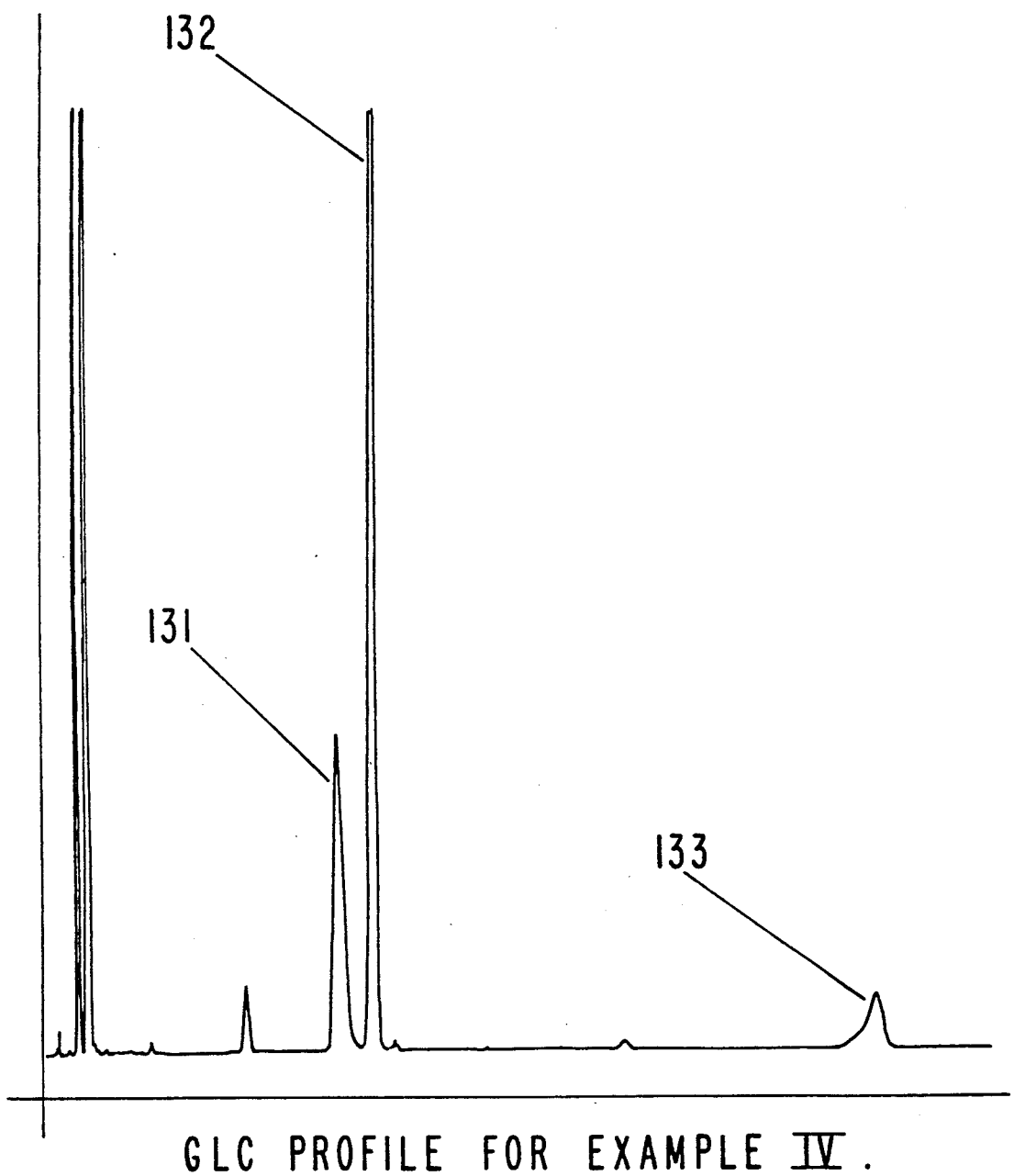

FIG. 13 is the GLC profile for the crude reaction product of Example IV containing the compound having the structure:

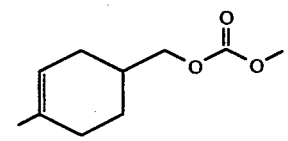

as well as the compound having the structure:

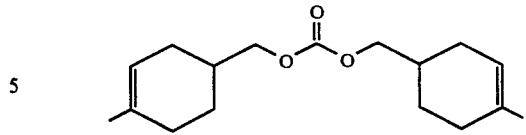

Figure 14:
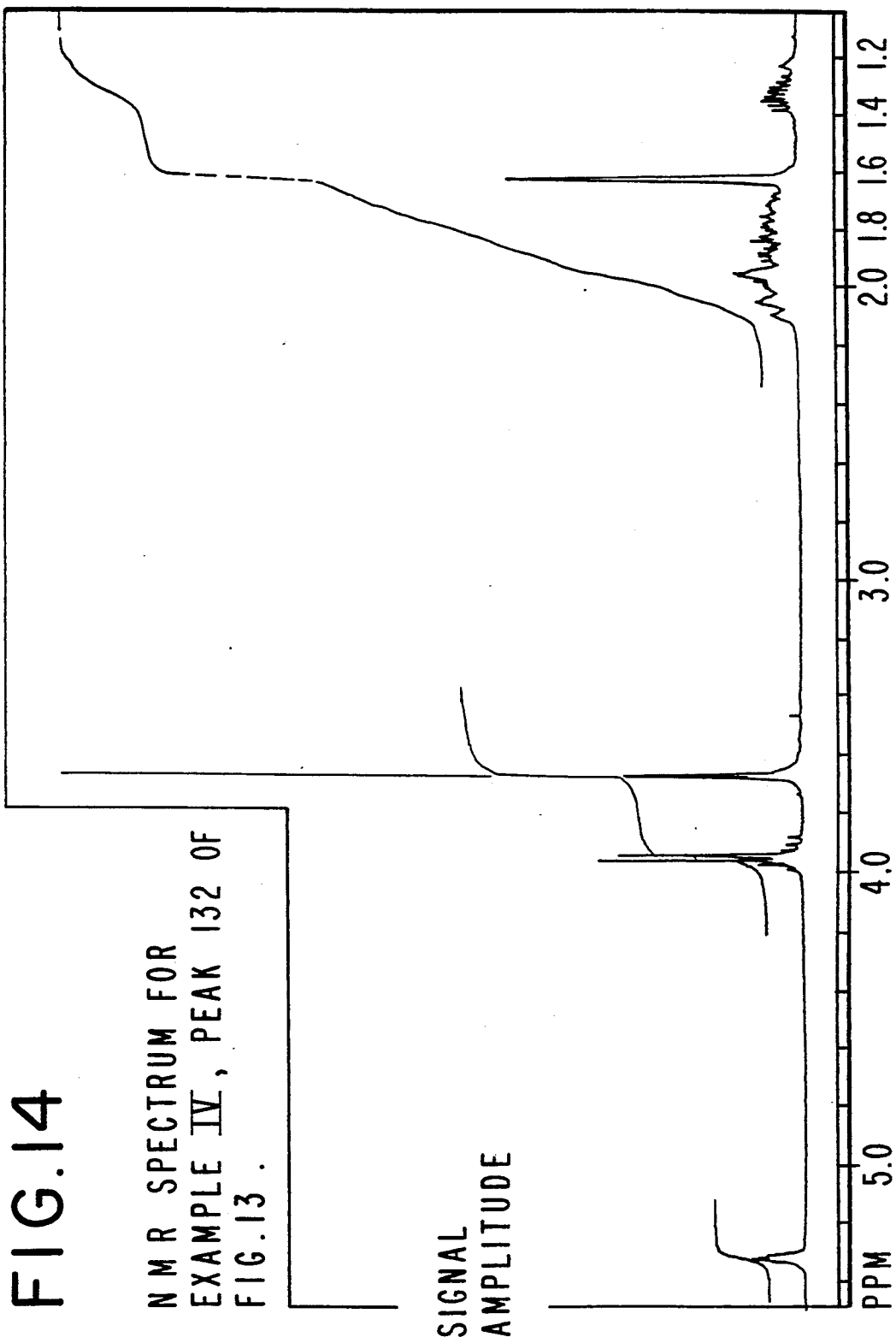

FIG. 14 is the NMR spectrum for the peak indicated by reference numeral 132 of the GLC profile of FIG. 13 for the compound having the structure:

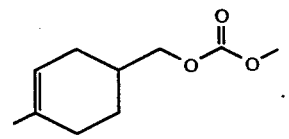

Figure 15:
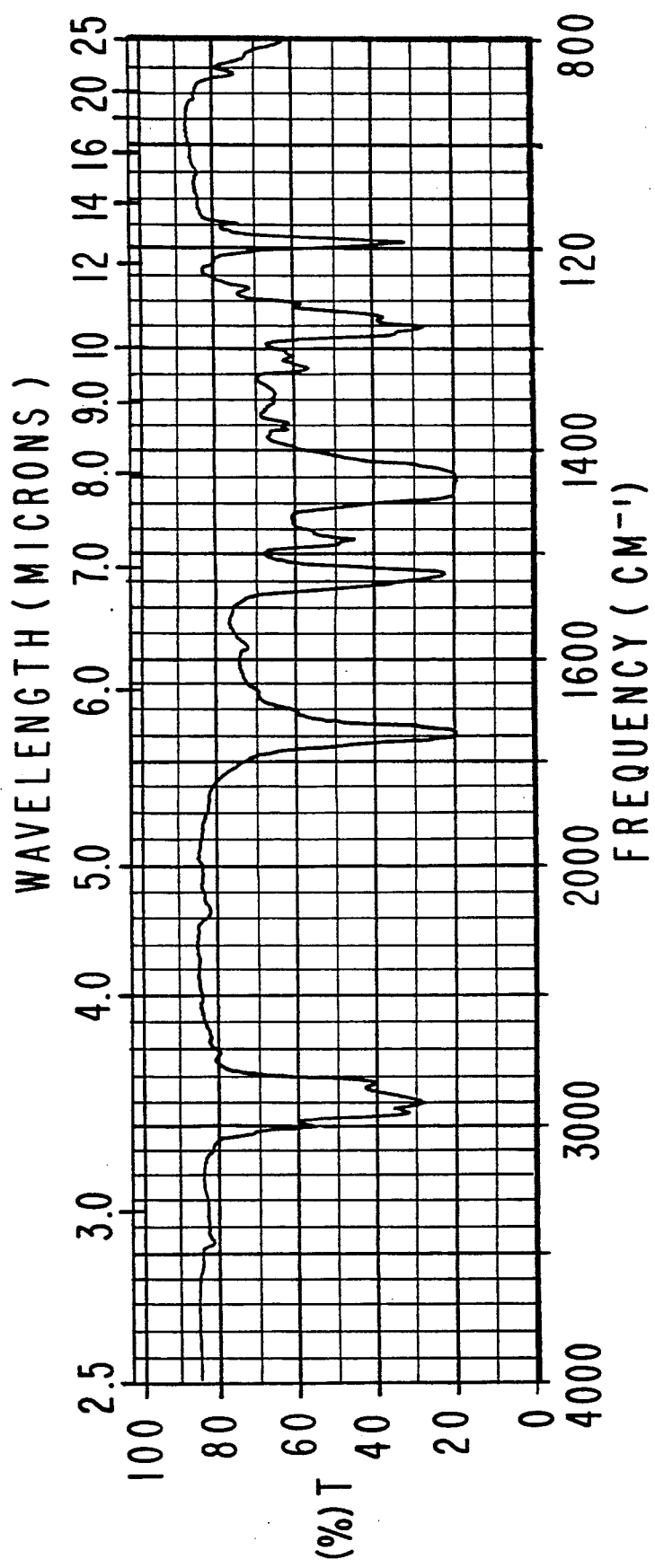

FIG. 15 is the NMR spectrum for the peak indicated by reference numeral 132 of the GLC profile of FIG. 13 for the compound having the structure:

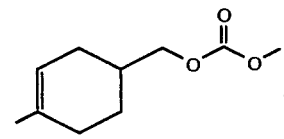

Figure 16:
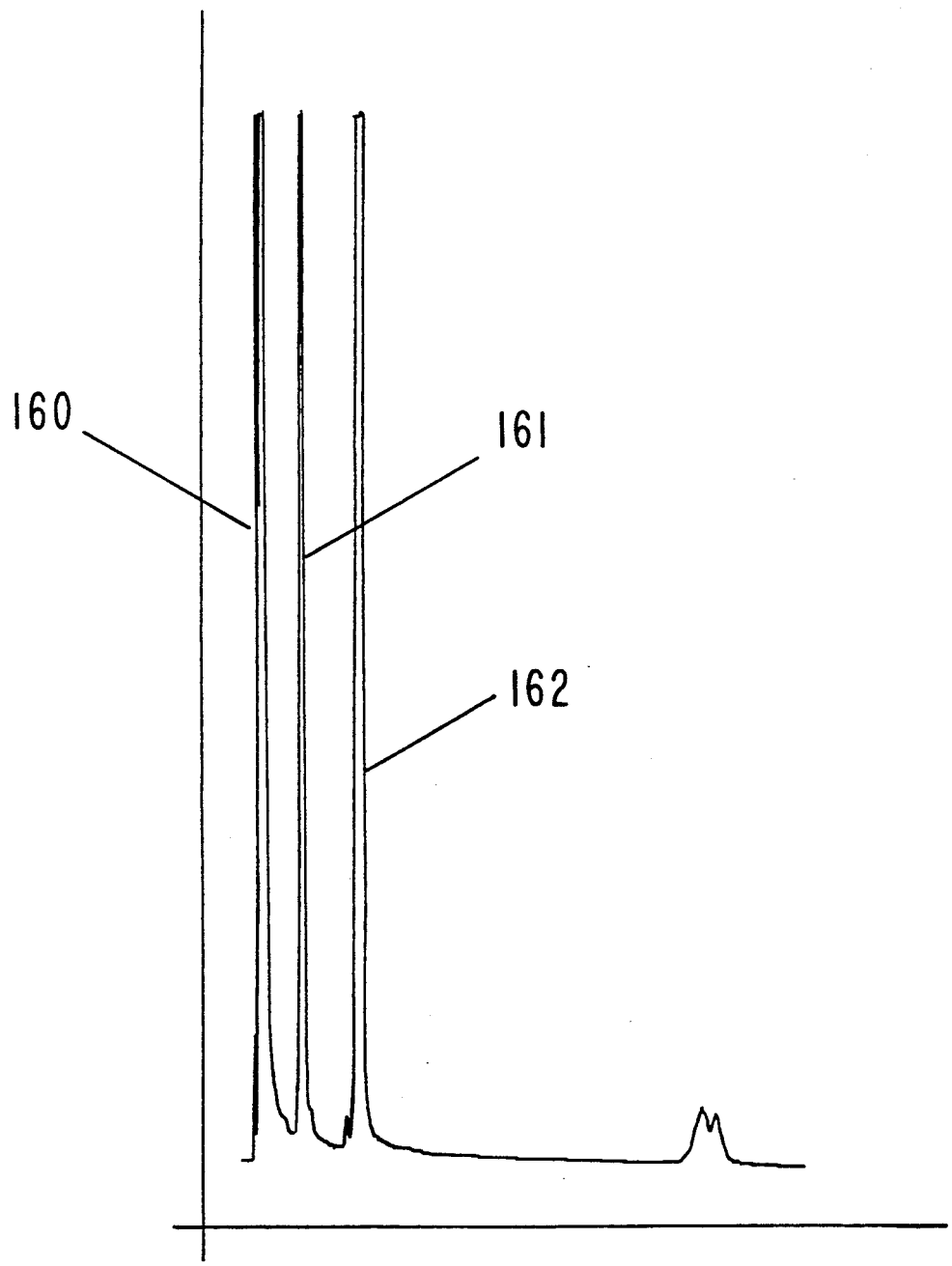

FIG. 16 is the GLC profile for the reaction product of Example V containing the compound having the structure:

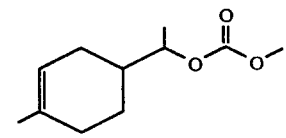

FIG. 17 is the infra-red spectrum for the peak indicated by reference numeral 162 of the GLC profile of FIG. 16 for the compound having the structure:

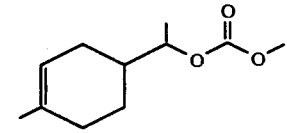

FIG. 18 is the NMR spectrum for the peak indicated by reference numeral 162 of the GLC profile of FIG. 16 for the compound having the structure:

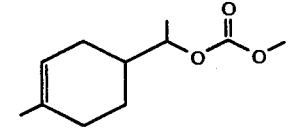

FIG. 18A is the detailed portion "A" of the NMR spectrum of FIG. 18.

FIG. 18B is the detailed portion "B" of the NMR spectrum of FIG. 18.

FIG. 18C is the detailed portion "C" of the NMR spectrum of FIG. 18.

FIG. 18D is the detailed portion "D" of the NMR spectrum of FIG. 18.

FIG. 19 is the GLC profile for the crude reaction product of Example VI containing the compound having the structure:

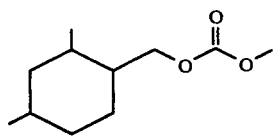

(Conditions: SE-30 column programmed at 150°-220° C. at 8° C. per minute).

FIG. 20 is the NMR spectrum for the peak indicated by reference numeral 190 of the GLC profile of FIG. 19 for the compound having the structure:

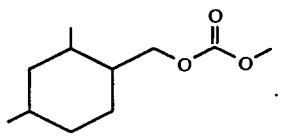

FIG. 20A is the detailed section "A" of the NMR spectrum of FIG. 20.

FIG. 20B is the detailed section "B" of the NMR spectrum of FIG. 20.

FIG. 21 is the infra-red spectrum for the peak indicated by reference numeral 190 of the GLC profile of FIG. 19 for the compound having the structure:

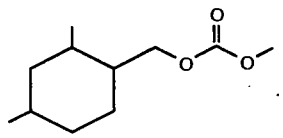

Figure 22:
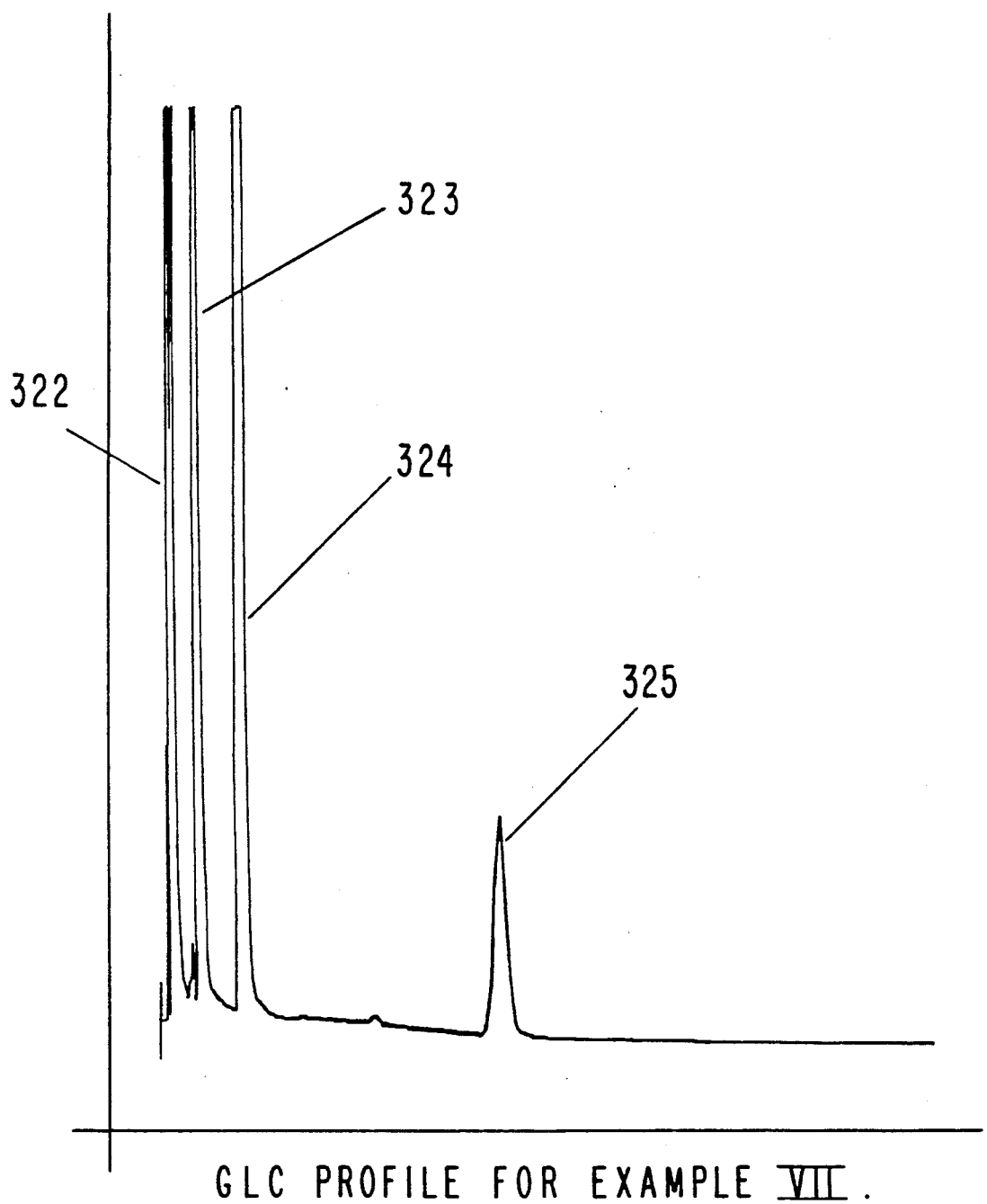

FIG. 22 is the GLC profile for the crude reaction product of Example VII containing the compound having the structure:

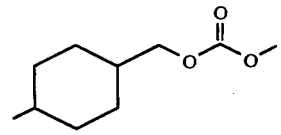

as well as the compound having the structure:

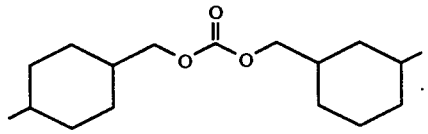

FIG. 23 is the NMR spectrum for the peak indicated by reference numeral 324 of the GLC profile of FIG. 22 containing the compound having the structure:

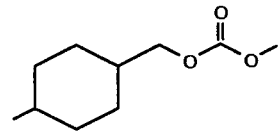

FIG. 23A is the detailed section "A" of the NMR spectrum of FIG. 23.

FIG. 23B is the detailed section "B" of the NMR spectrum of FIG. 23.

FIG. 24 is the infra-red spectrum for the peak indicated by reference numeral 324 of the GLC profile of FIG. 22 for the compound having the structure:

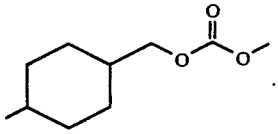

FIG. 25 is the NMR spectrum for the peak indicated by reference numeral 325 of the GLC profile of FIG. 22 for the compound having the structure:

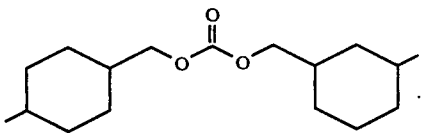

FIG. 25A is the detailed section "A" of the NMR spectrum of FIG. 25.

FIG. 25B is the detailed section "B" of the NMR spectrum of FIG. 25.

FIG. 26 is the infra-red spectrum for peak 325 of the GLC profile of FIG. 22 for the compound having the structure:

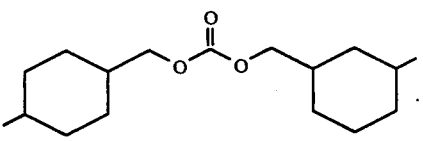

FIG. 27 is a cut-away side elevation view of apparatus used in producing polymeric fragrances containing at least one of the alkyl cyclohexylmethyl and cyclohexenylmethyl carbonates of our invention.

FIG. 28 is the front elevation view of the apparatus of FIG. 27 looking in the direction of the arrows along lines 28—28 of FIG. 27.

Figure 29:
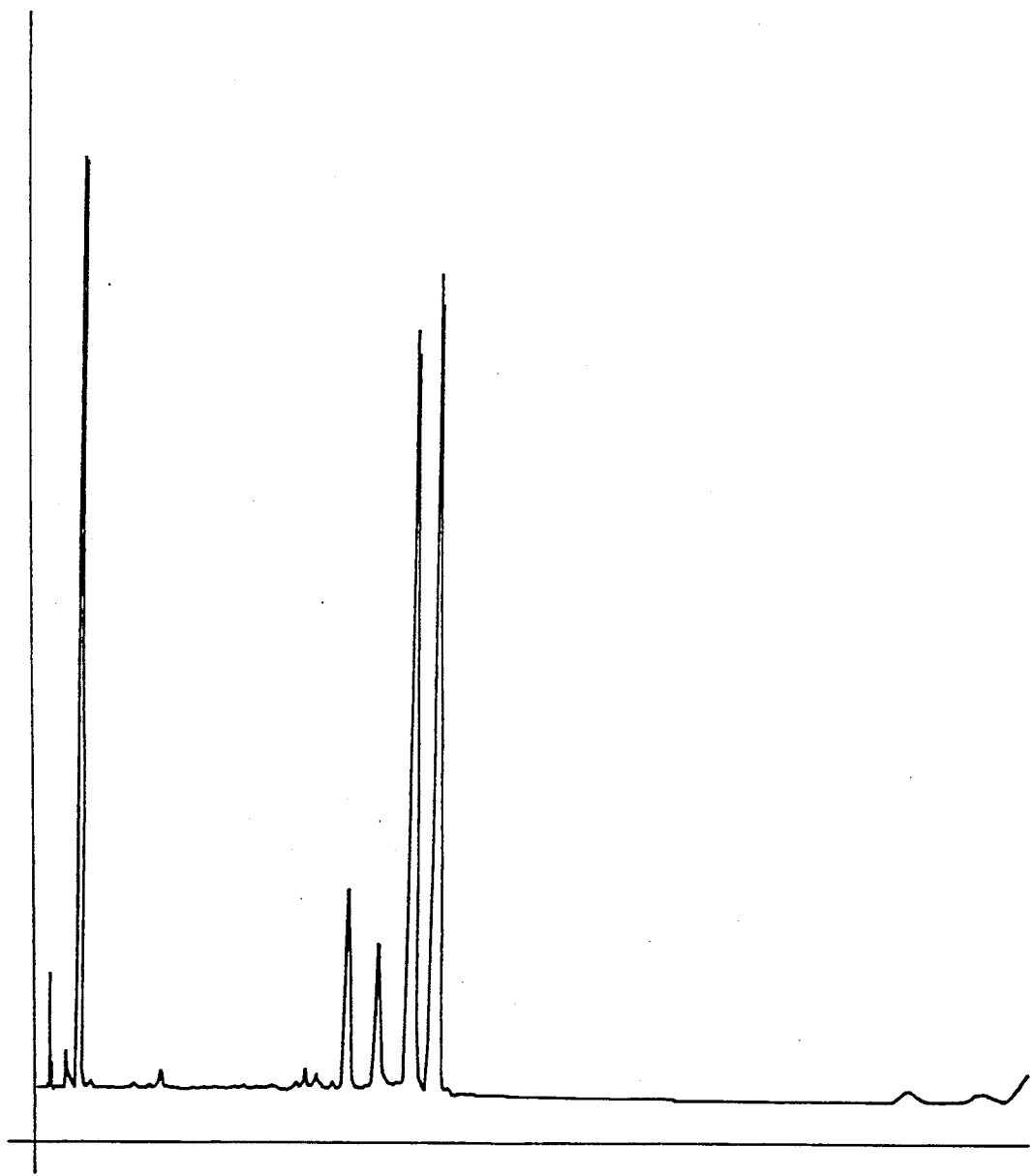

FIG. 29 is the GLC profile for the reaction product of Example VIII containing the compound having the structure:

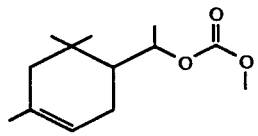

(Conditions: Carbowax 100 column programmed at 220° C. isothermal).

FIG. 30 is the NMR spectrum for the compound having the structure:

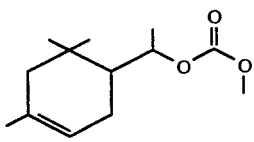

prepared according to Example VIII.

FIG. 30A is the detailed portion "A" of the NMR spectrum of FIG. 30.

FIG. 30B is the detailed portion "B" of the NMR spectrum of FIG. 30.

FIG. 30C is the detailed portion "C" of the NMR spectrum of FIG. 30.

Figure 31:
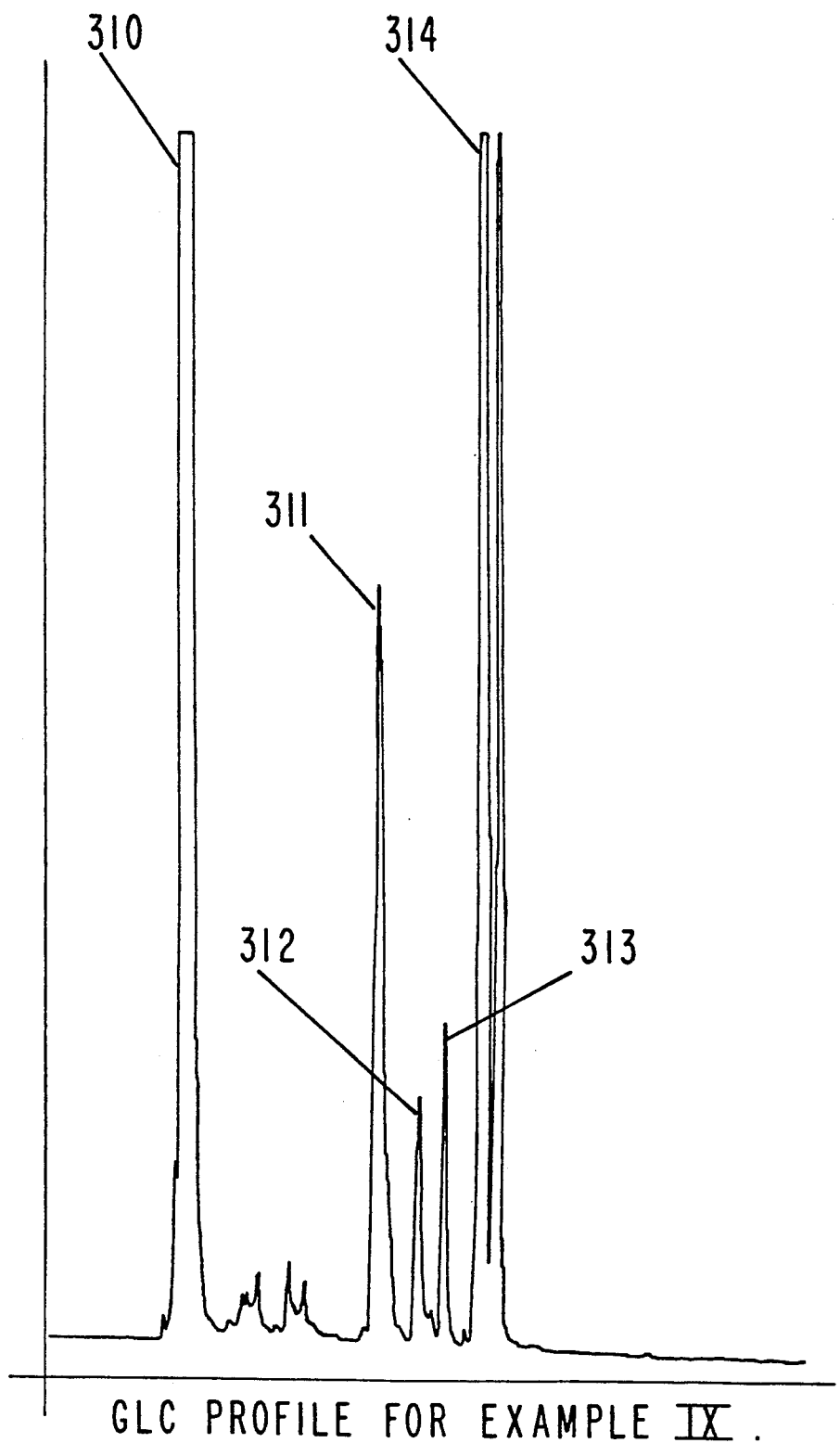

FIG. 31 is the GLC profile for the reaction product of Example IX containing the compound having the structure:

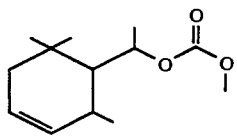

(Conditions: Carbowax column programmed at 150°-220° C. at 8° C. per minute) (capillary GLC).

Figure 32:
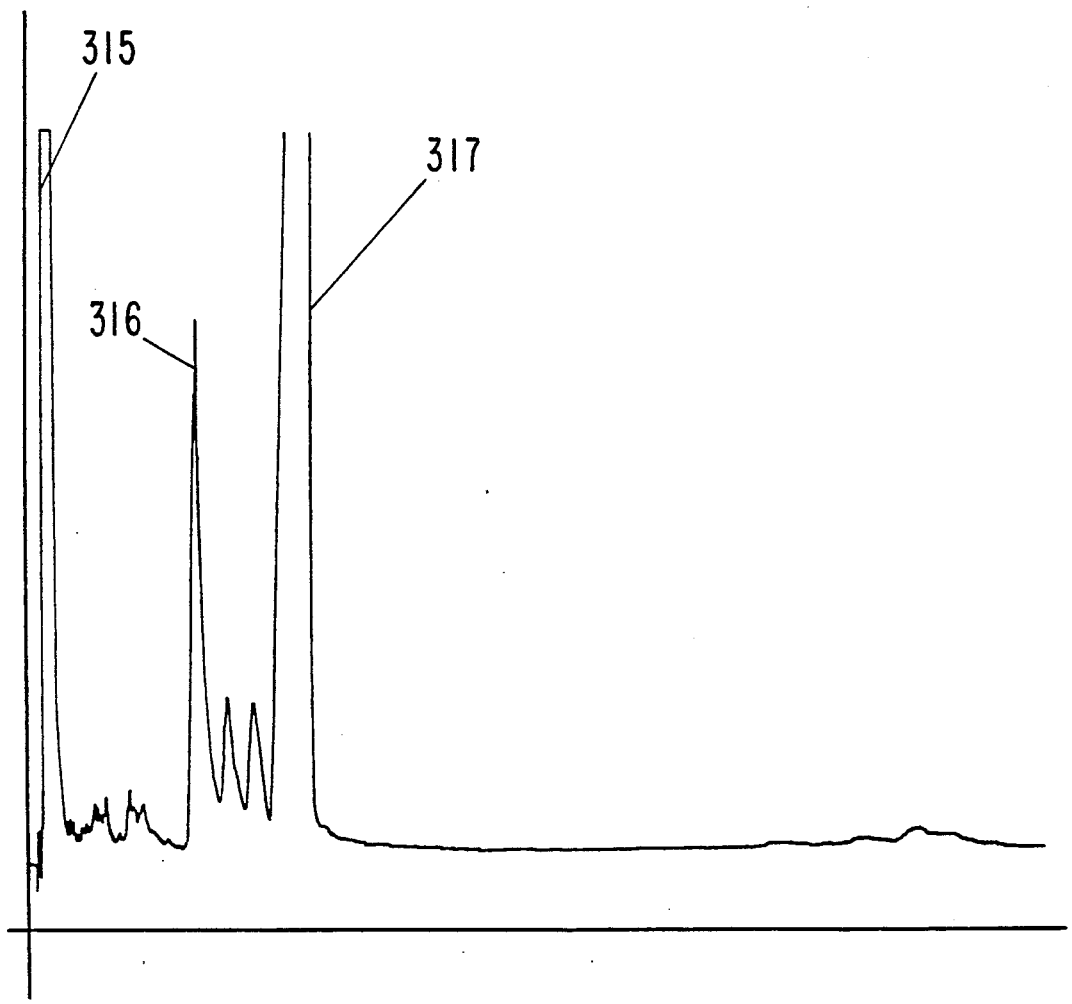

FIG. 32 is the GLC profile for the reaction product of Example IX containing the compound having the structure:

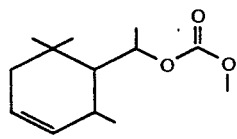

(10 foot column used for trapping) (Conditions: Carbowax column programmed at 150°-220° C. at 8° C. per minute).

FIG. 33 is the NMR spectrum for the compound having the structure:

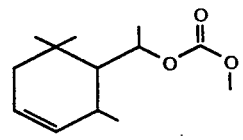

prepared according to Example IX.

FIG. 33A is the detailed portion "A" of the NMR spectrum of FIG. 33.

FIG. 33B is the detailed portion "B" of the NMR spectrum of FIG. 33.

FIG. 33C is the detailed portion "C" of the NMR spectrum of FIG. 33.

FIG. 33D is the detailed portion "D" of the NMR spectrum of FIG. 33.

FIG. 34 is the infra-red spectrum for the compound having the structure:

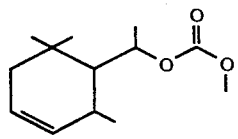

prepared according to Example IX.

Figure 35:
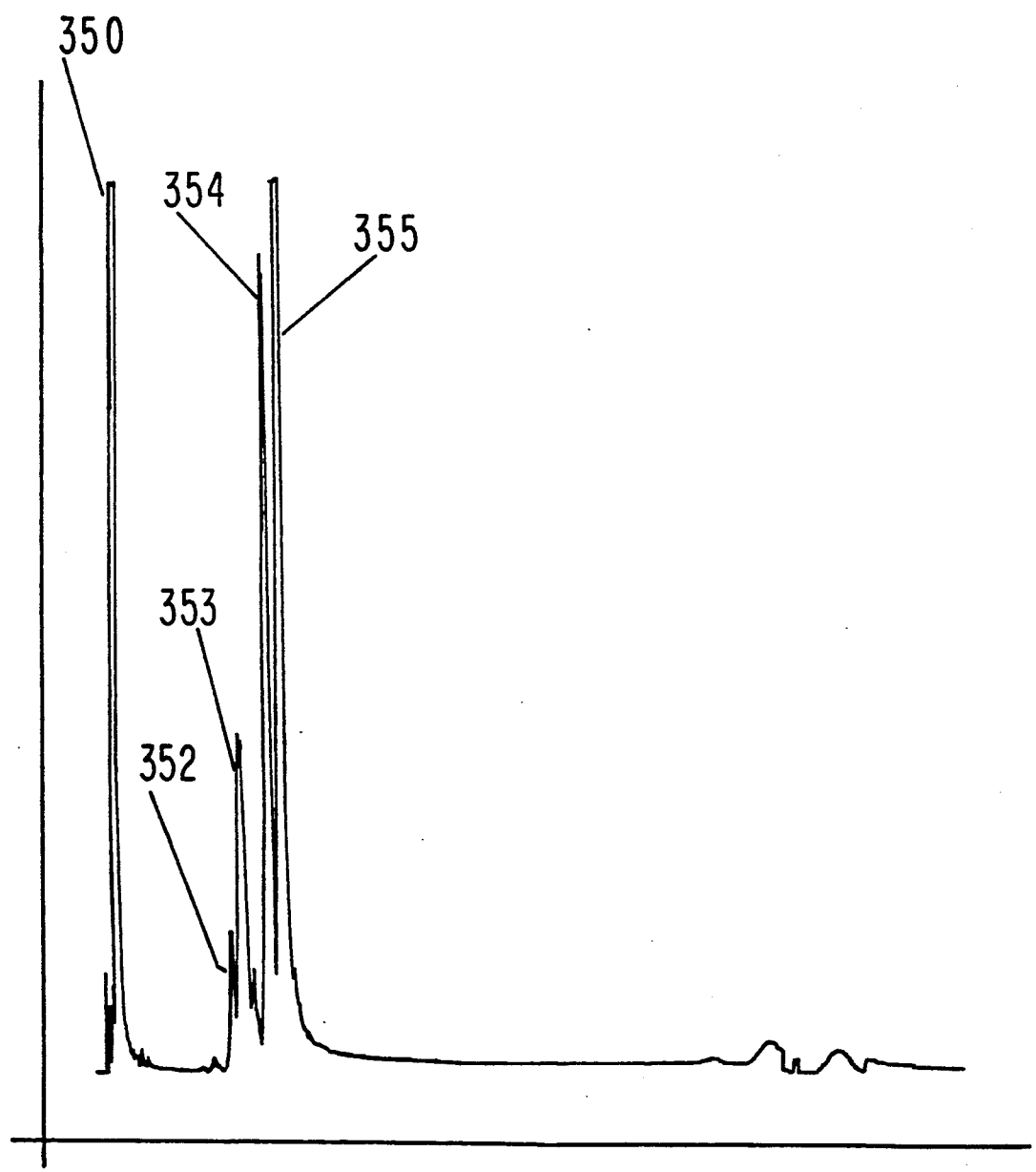

FIG. 35 is the GLC profile for the reaction product of Example X containing the compound having the structure:

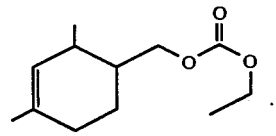

Figure 36:
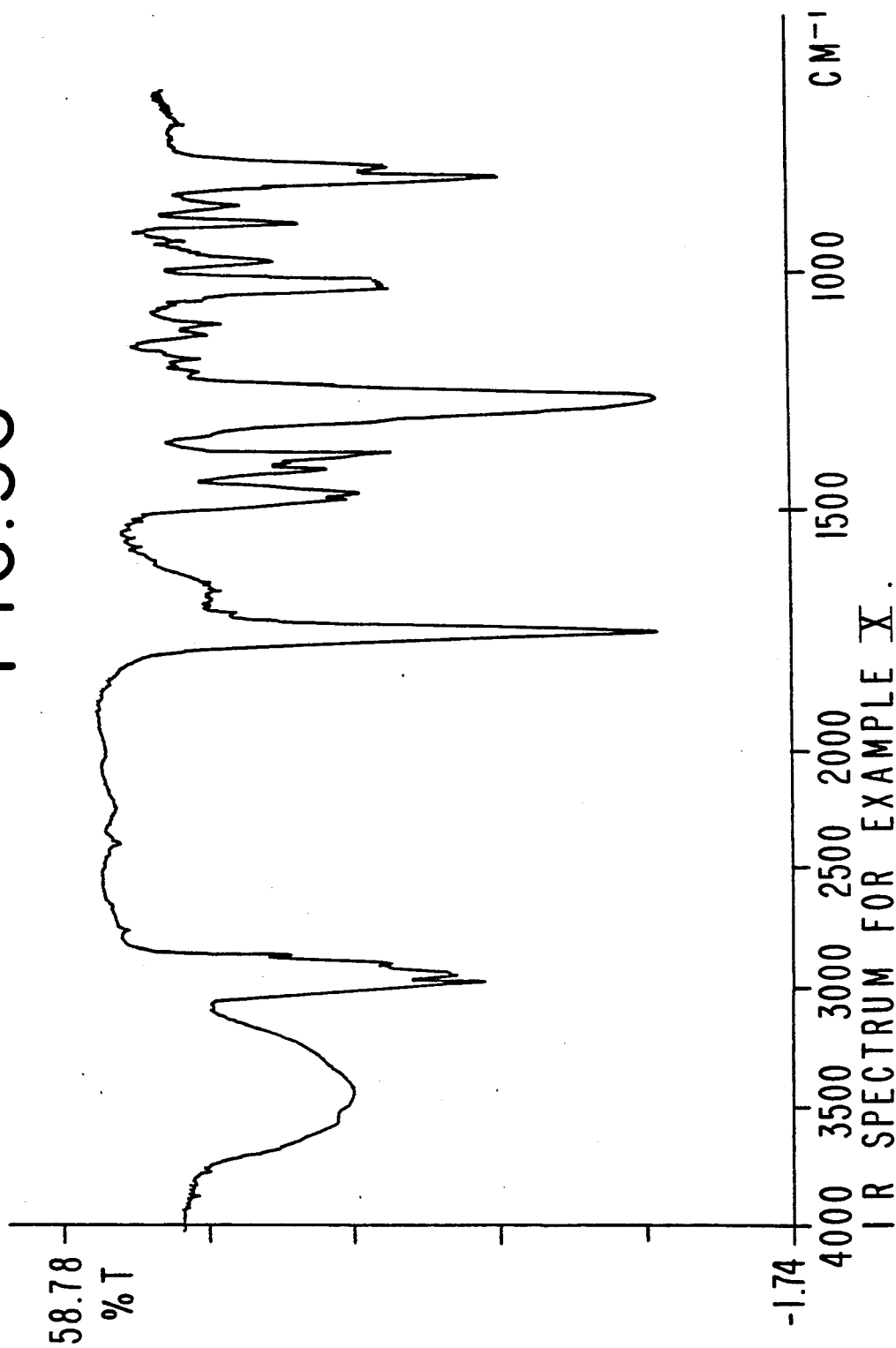

FIG. 36 is the infra-red spectrum for the compound having the structure:

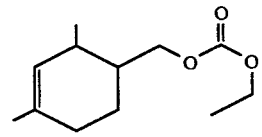

prepared according to Example X.

Figure 37:
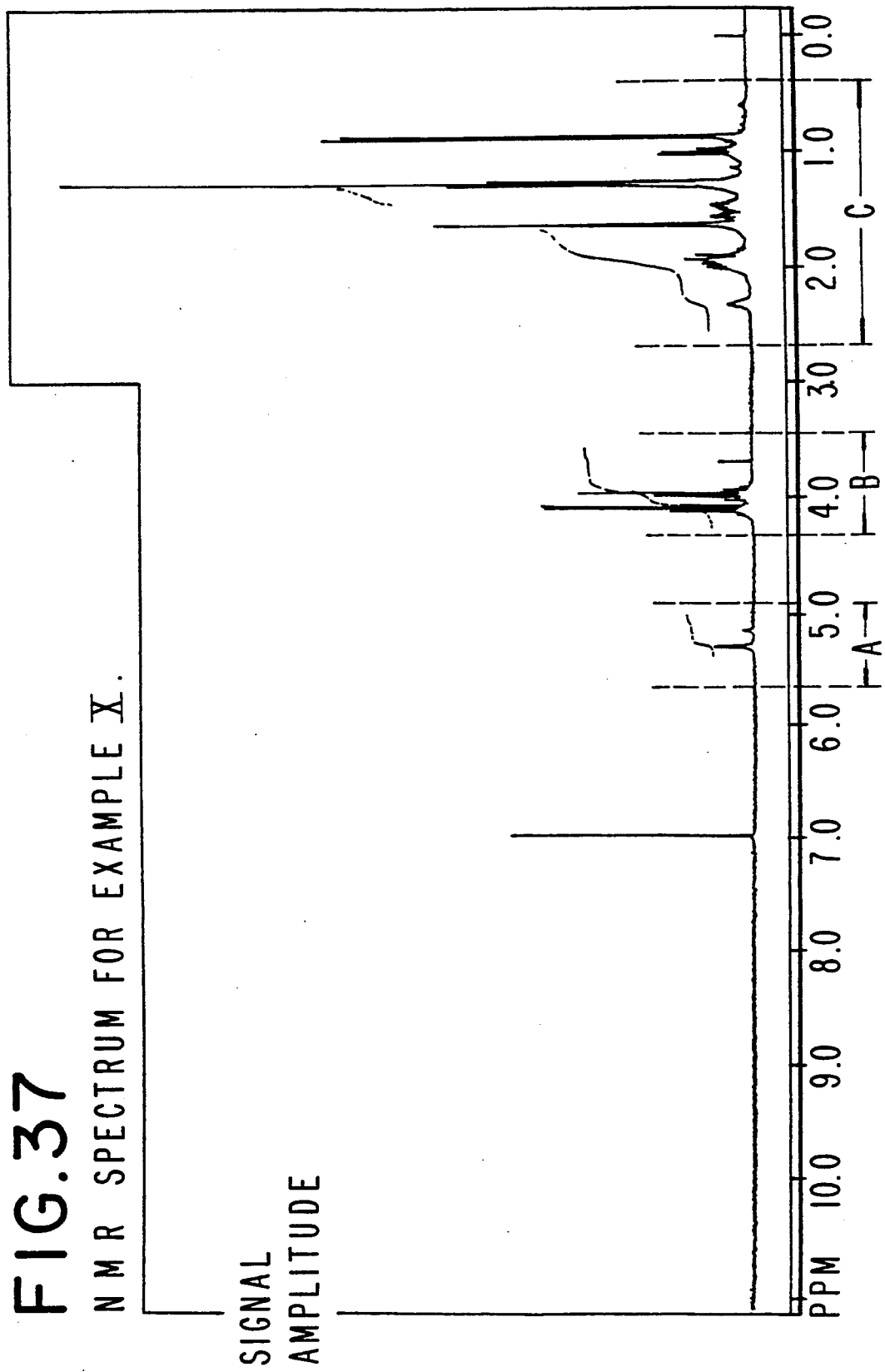

FIG. 37 is the NMR spectrum for the compound having the structure:

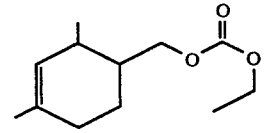

prepared according to Example X.

FIG. 37A is the detailed portion "A" of the NMR spectrum of FIG. 37.

FIG. 37B is the detailed portion "B" of the NMR spectrum of FIG. 37.

Figure 37C:
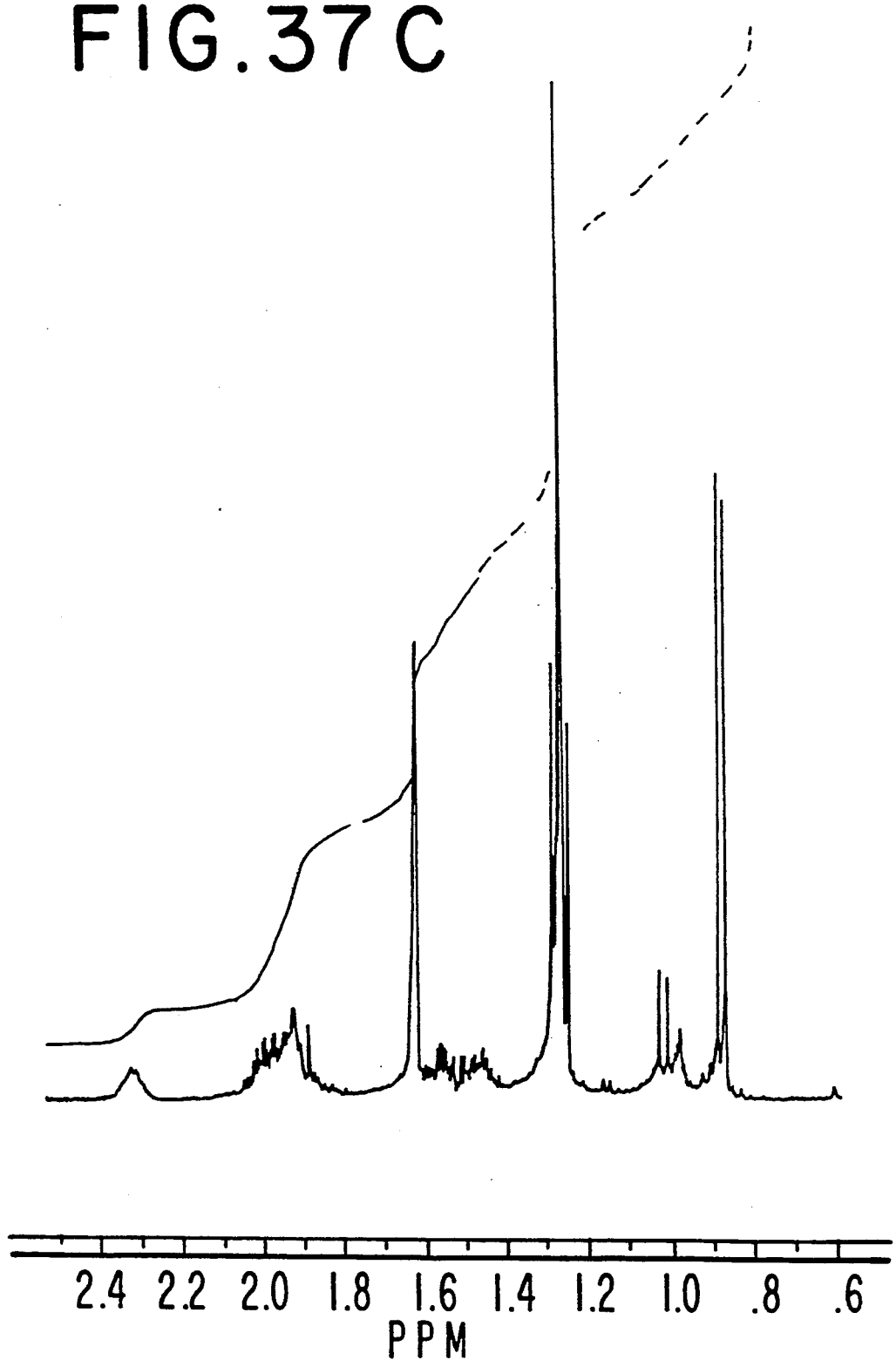

FIG. 37C is the detailed portion "C" of the NMR spectrum of FIG. 37.

Figure 38:
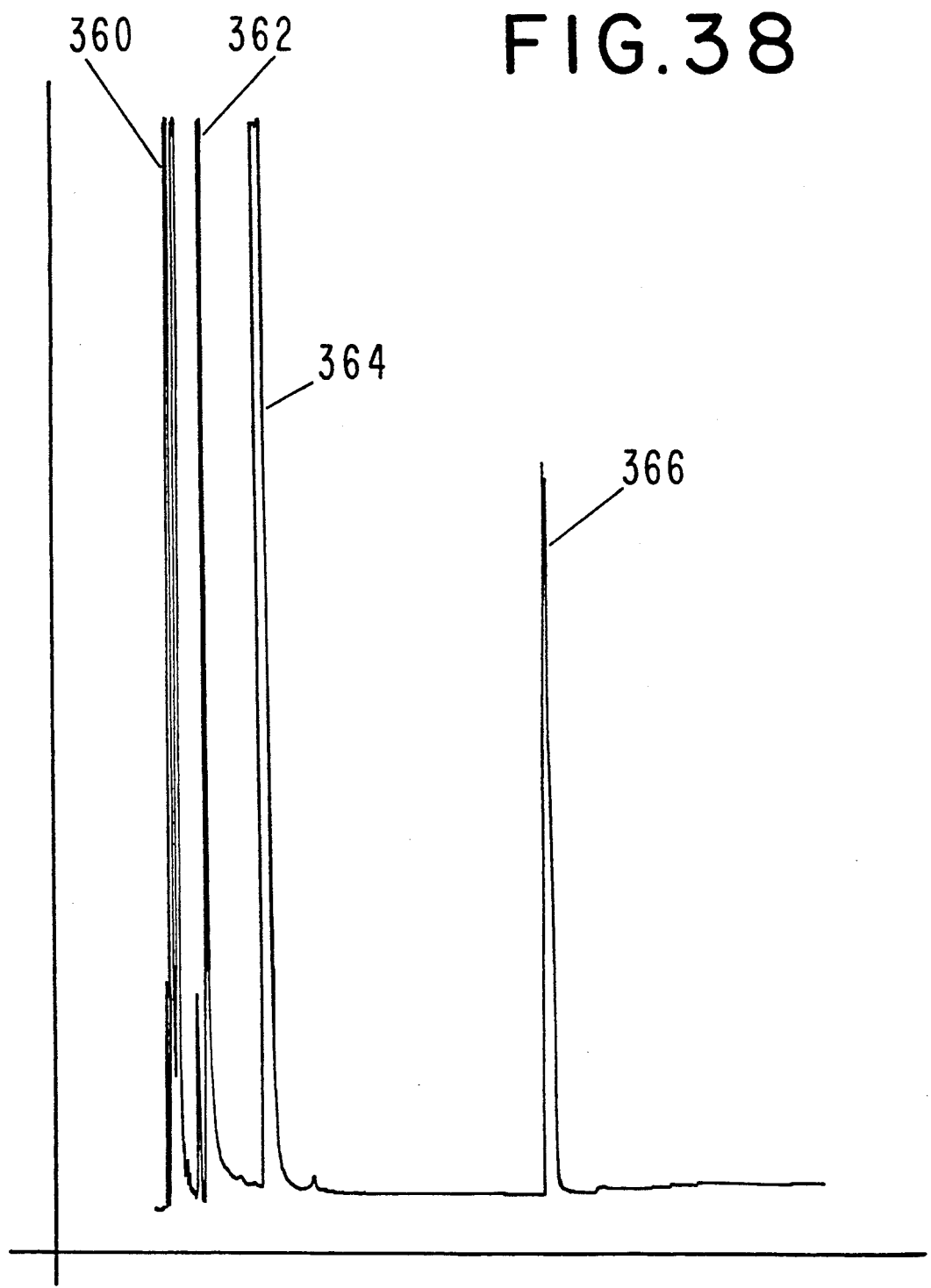

FIG. 38 is the GLC profile for the reaction product of Example XI containing the compound having the structure:

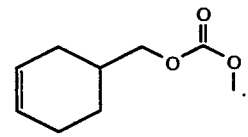

FIG. 39 is the NMR spectrum for the compound having the structure:

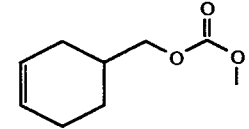

prepared according to Example XI.

Figure 39A:

FIG. 39A is the detailed portion "A" of the NMR spectrum of FIG. 39.

Figure 39B:
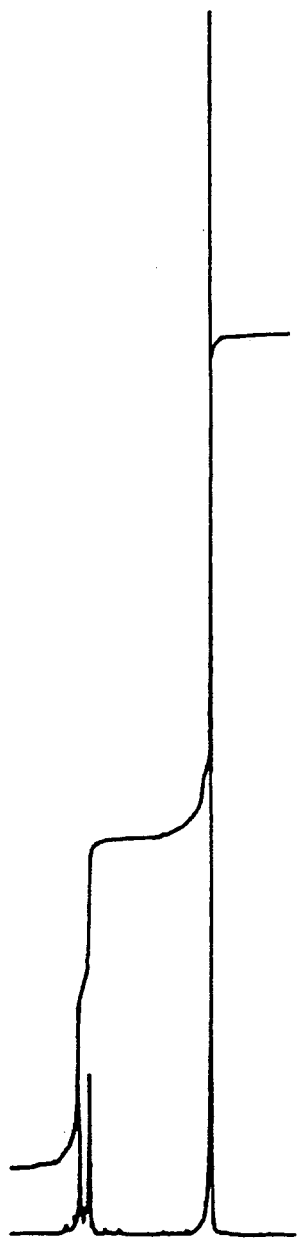

FIG. 39B is the detailed portion "B" of the NMR spectrum of FIG. 39.

Figure 39C:

FIG. 39C is the detailed portion "C" of the NMR spectrum of FIG. 39.

Figure 40:
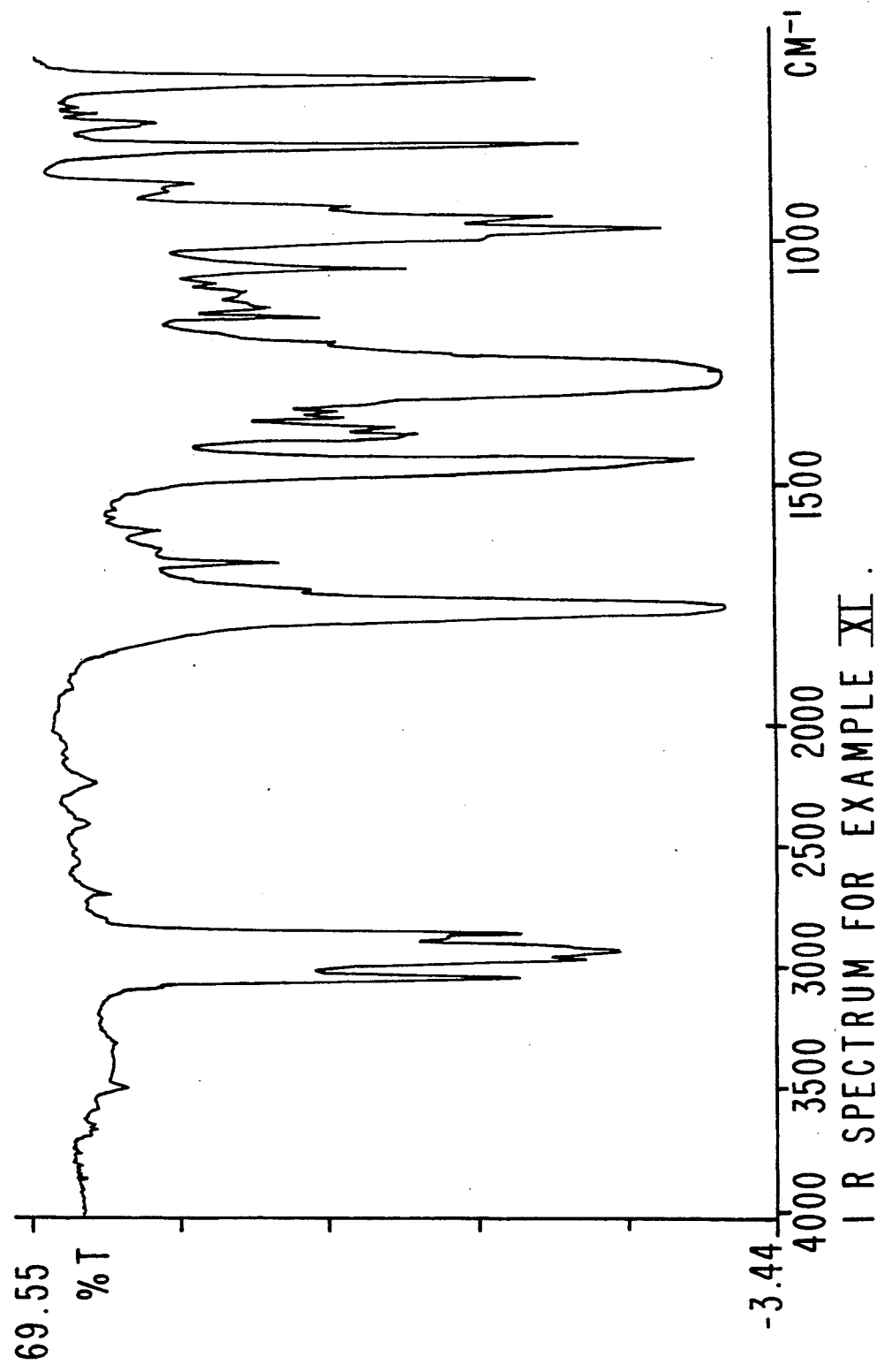

FIG. 40 is the infra-red spectrum for the compound having the structure:

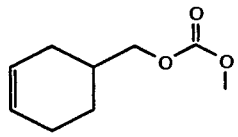

prepared according to Example XI.

FIG. 41 is the NMR spectrum for the compound having the structure:

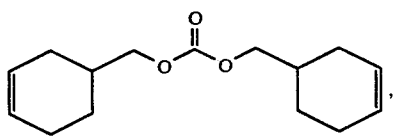

peak "366" of FIG. 38 prepared according to Example XI.

Figure 41A:

FIG. 41A is the detailed portion "A" of the NMR spectrum of FIG. 41.

Figure 41B:
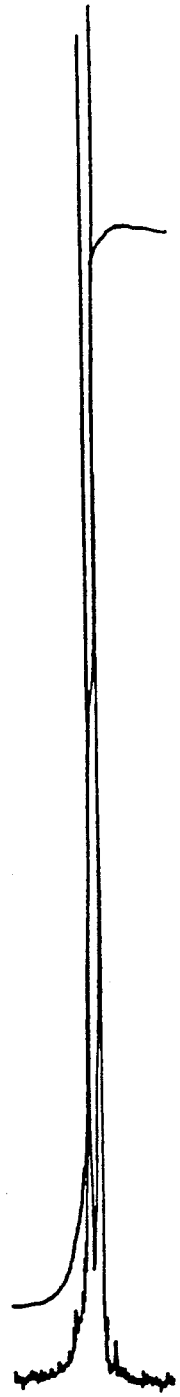

FIG. 41B is the detailed portion "B" of the NMR spectrum of FIG. 41.

Figure 41C:
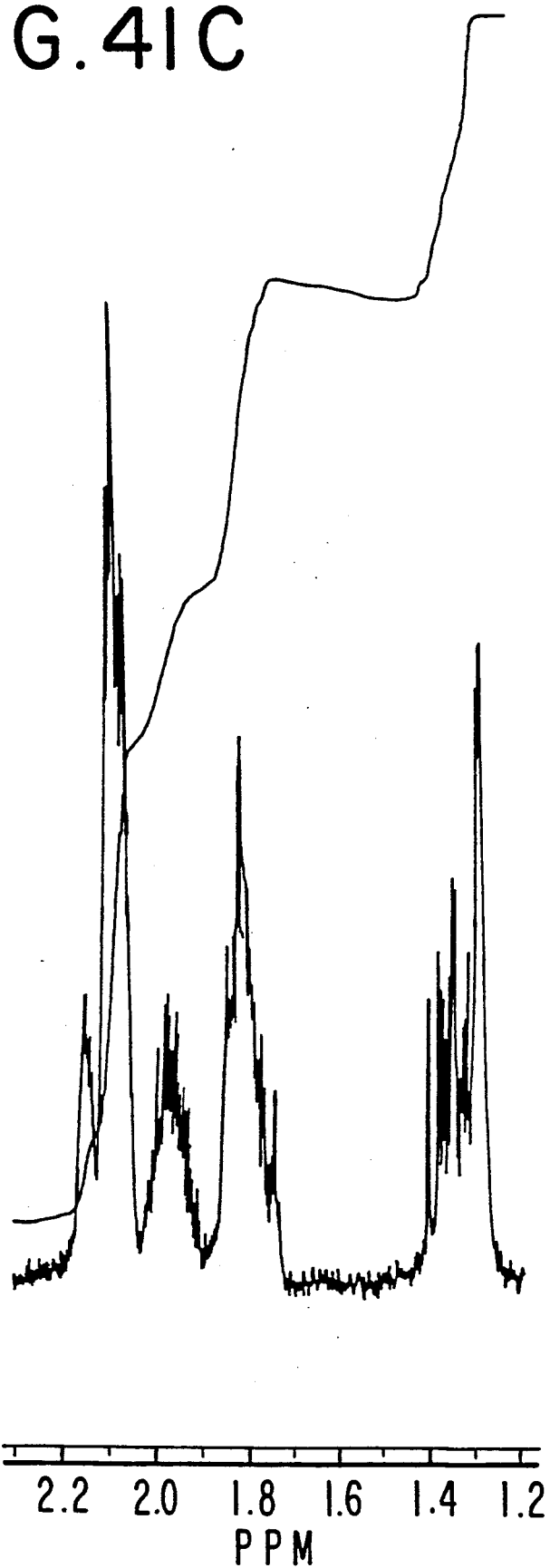

FIG. 41C is the detailed portion "C" of the NMR spectrum of FIG. 41.

FIG. 42 is the infra-red spectrum for the compound having the structure:

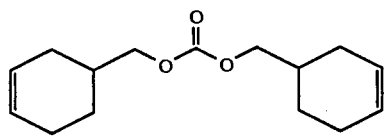

prepared according to Example XI.

Figure 43:
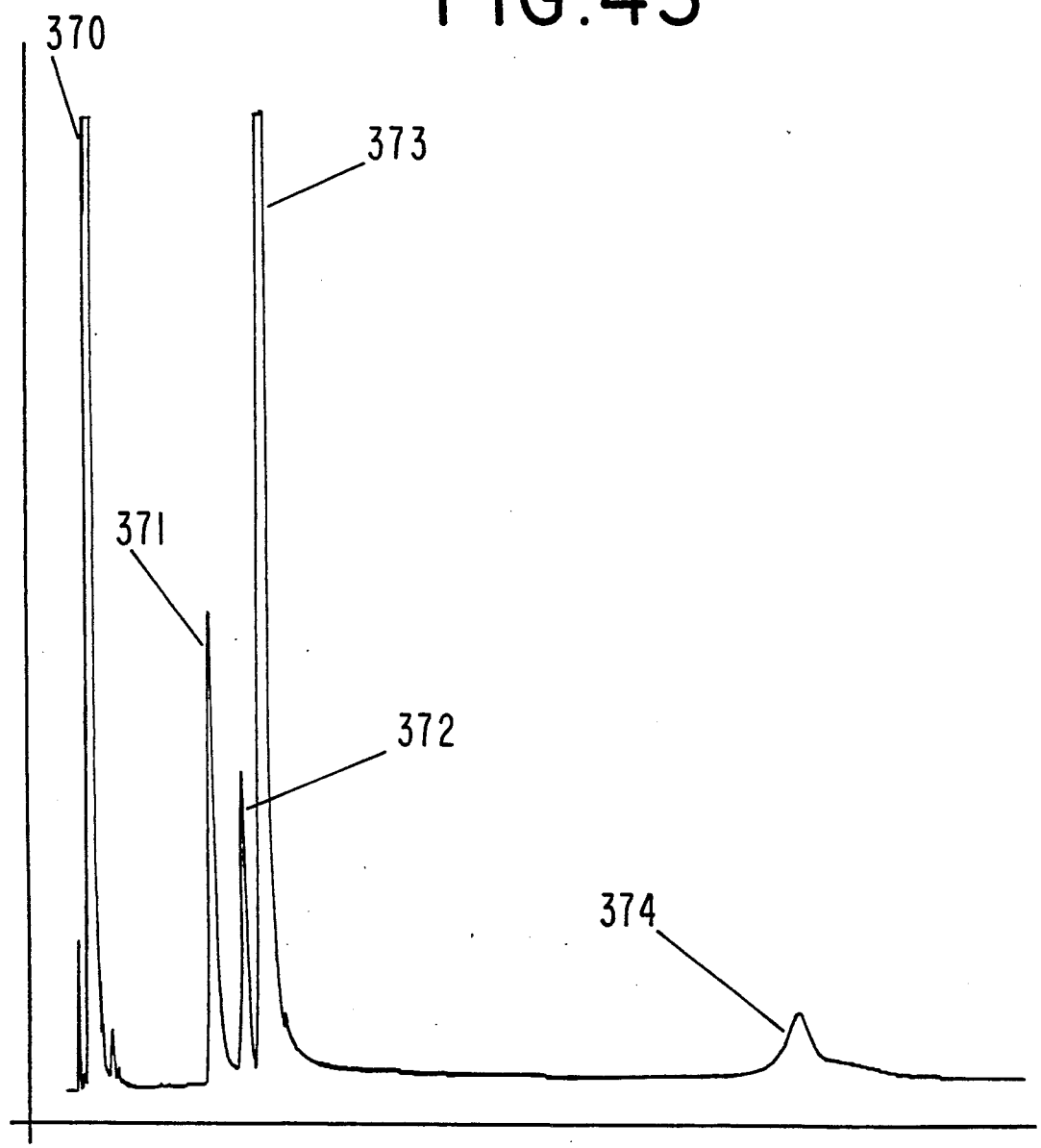

FIG. 43 is the GLC profile for the reaction product of Example XII containing the compounds having the structures:

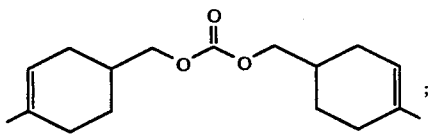

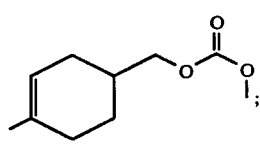

and

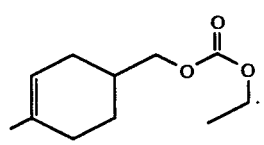

Figure 44:
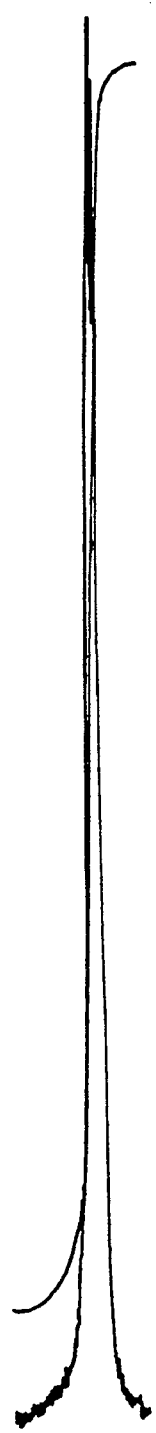
Figure 44:
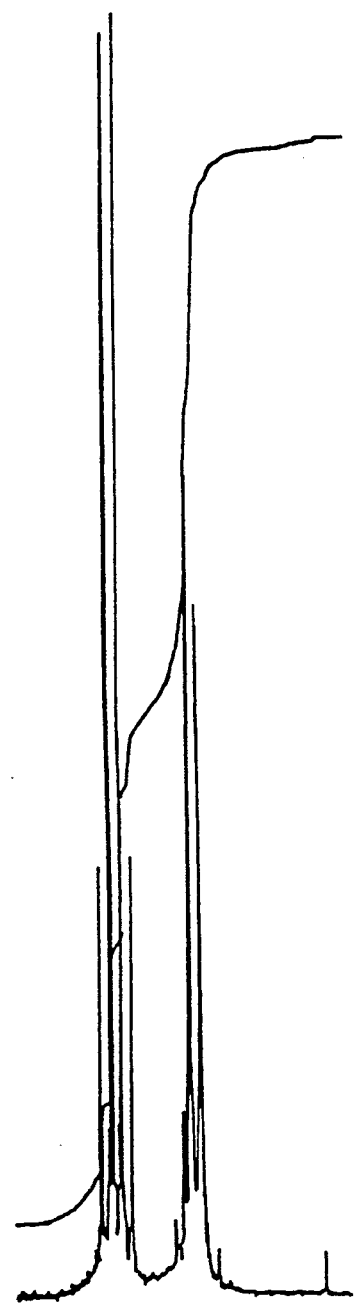

FIG. 44 is the NMR spectrum for the peak indicated by reference numeral 373 of FIG. 43 for the compound having the structure:

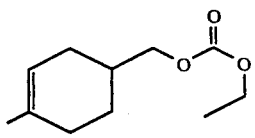

prepared according to Example XII.

FIG. 44A is the detailed portion "A" of the NMR spectrum of FIG. 44.

FIG. 44B is the detailed portion "B" of the NMR spectrum of FIG. 44.

Figure 44C:
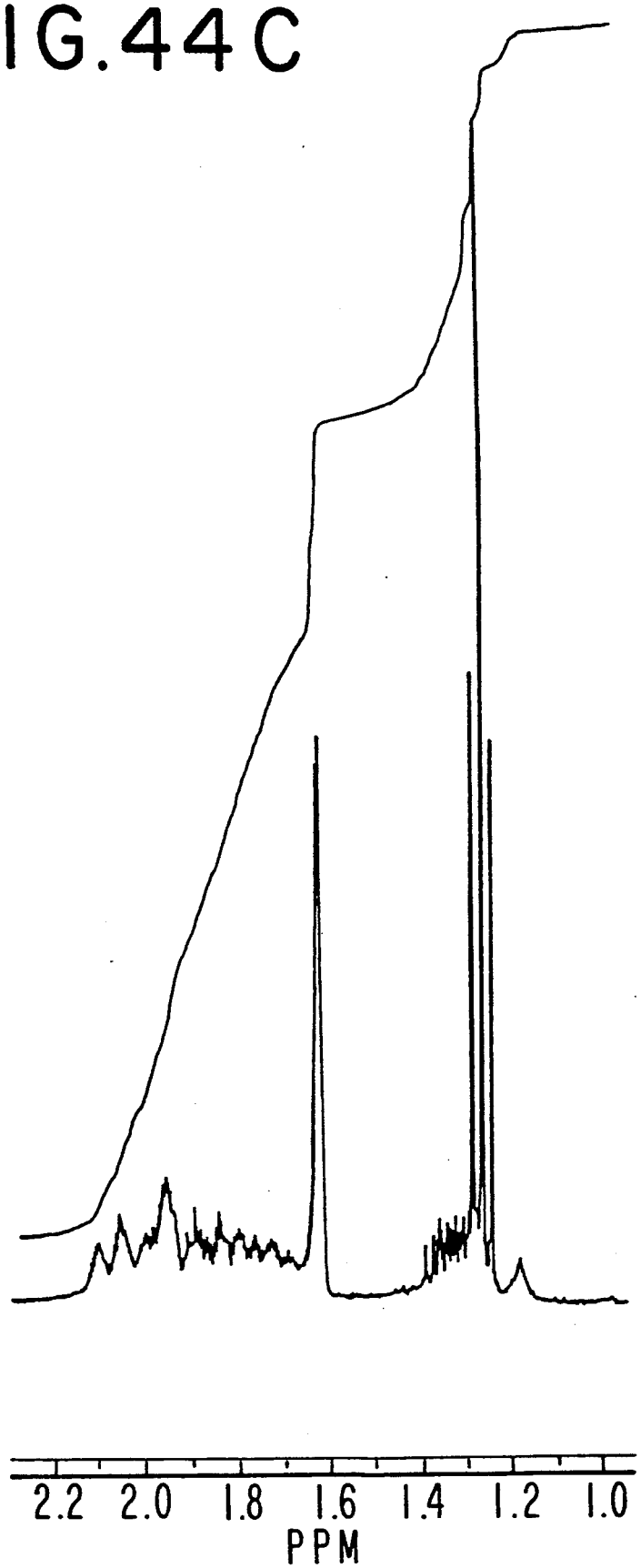

FIG. 44C is the detailed portion "C" of the NMR spectrum of FIG. 44.

Figure 45:
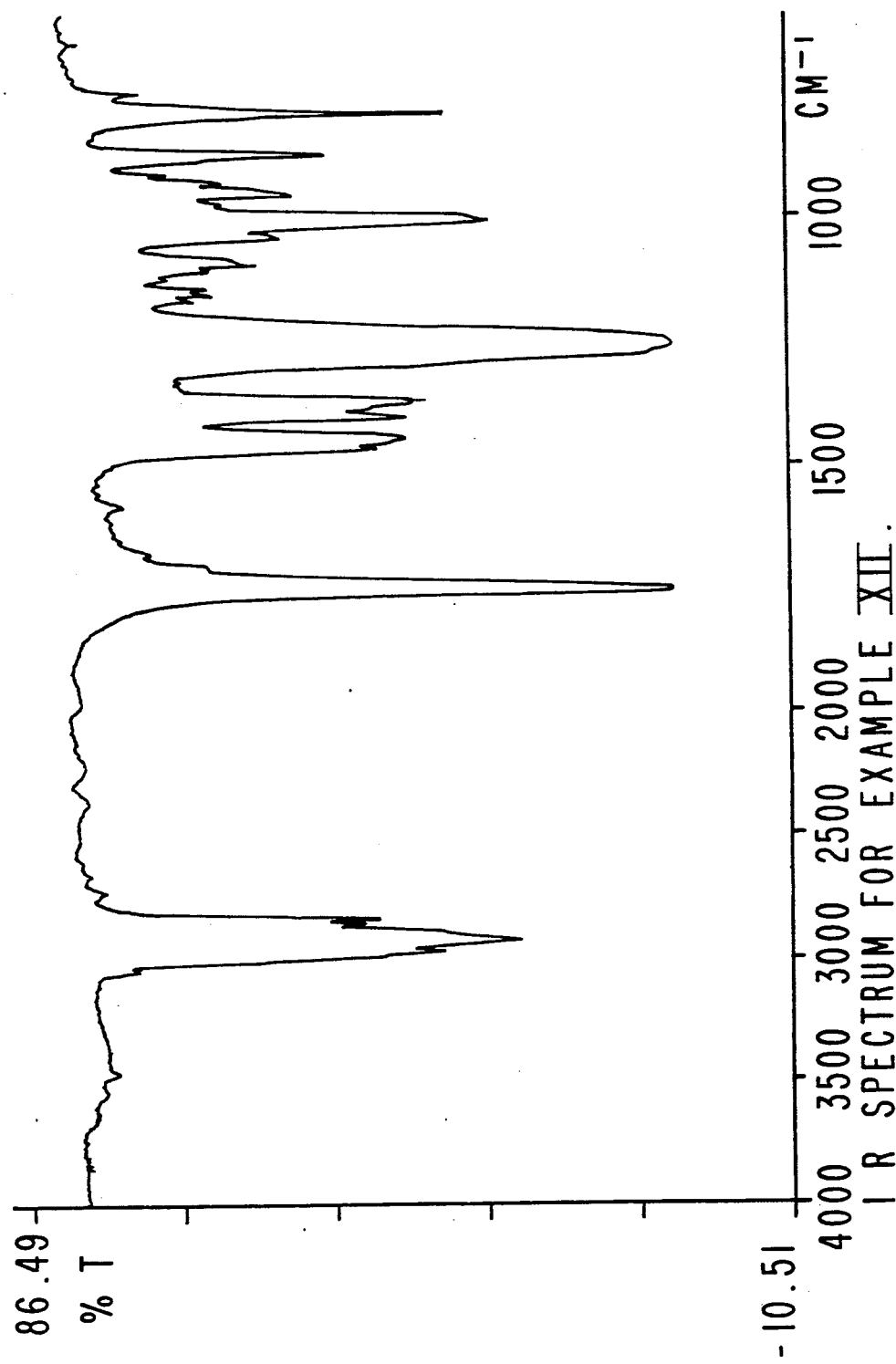

FIG. 45 is the infra-red spectrum for the compound having the structure:

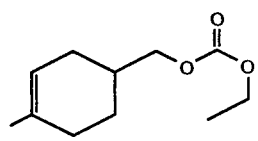

prepared according to Example XII.

FIG. 46 is the NMR spectrum for the compound having the structure:

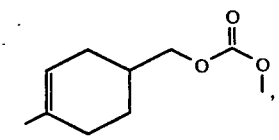

indicated by peak 372 of FIG. 43.

Figure 46A:
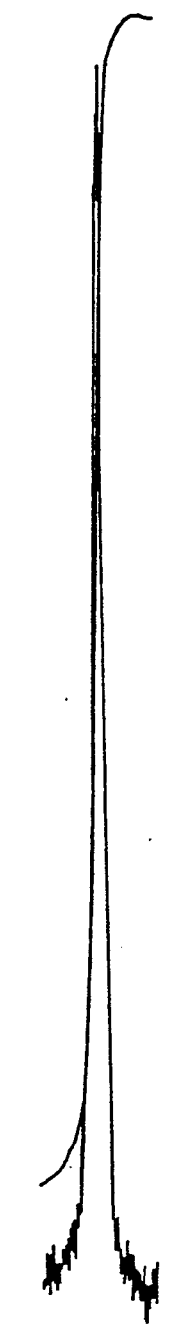

FIG. 46A is the detailed portion "A" of the NMR spectrum of FIG. 46.

Figure 46B:
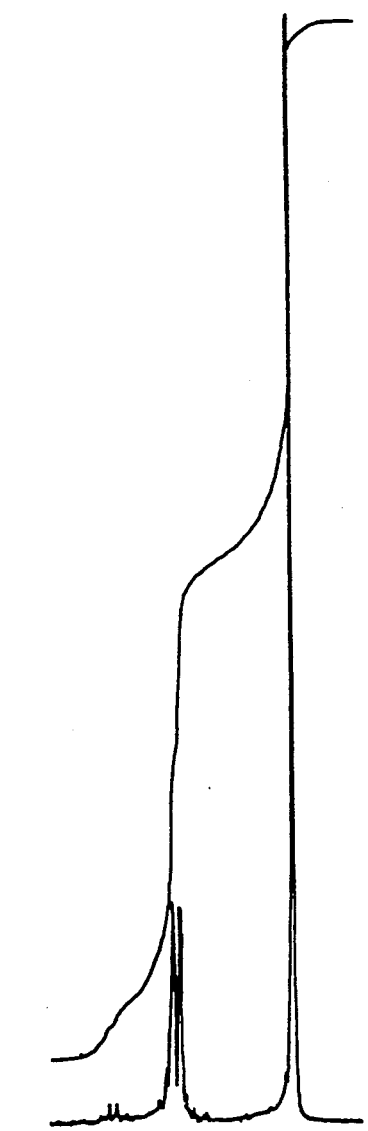

FIG. 46B is the detailed portion "B" of the NMR spectrum of FIG. 46.

Figure 46C:
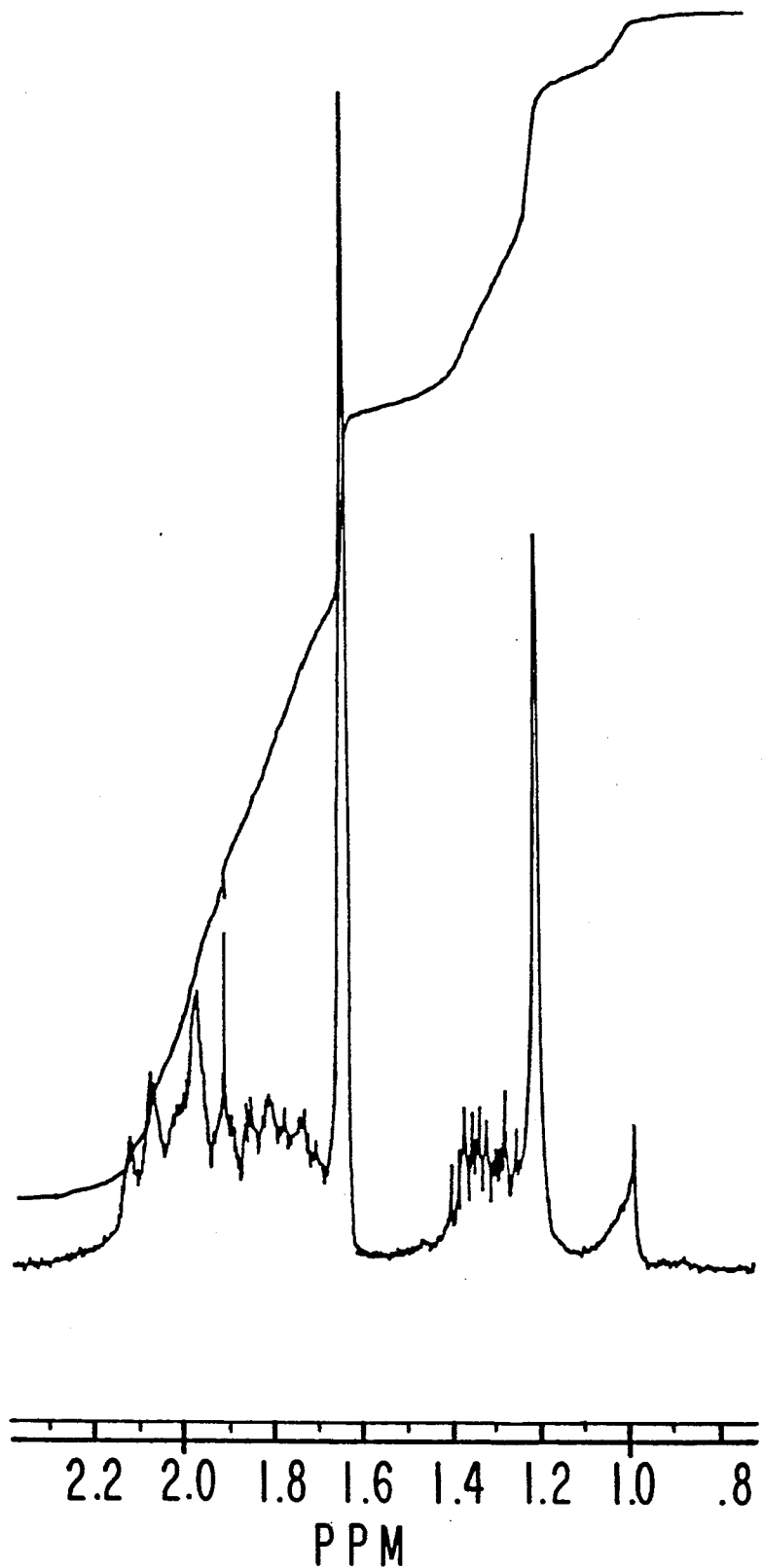

FIG. 46C is the detailed portion "C" of the NMR spectrum of FIG. 46.

Figure 47:
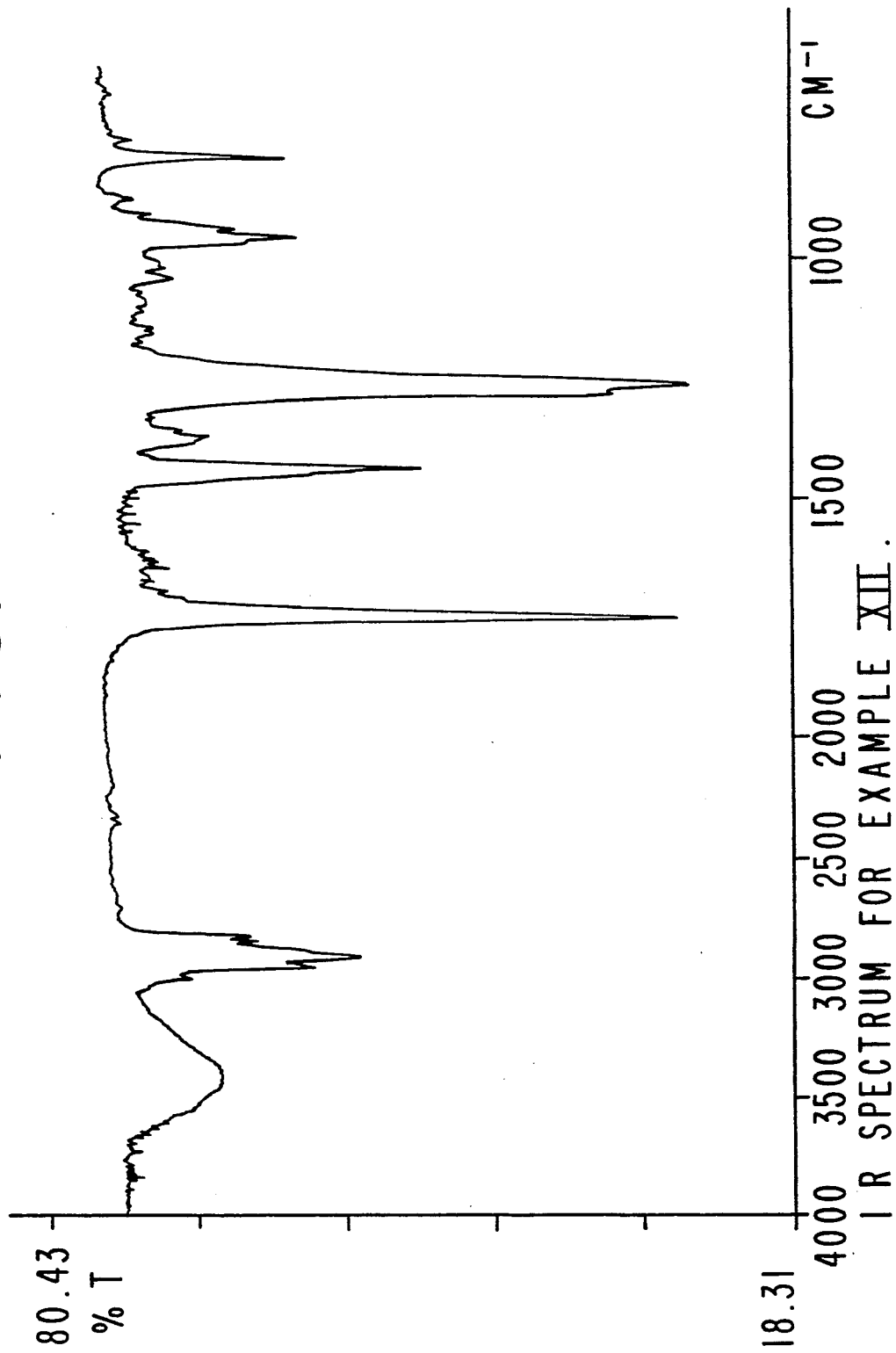

FIG. 47 is the infra-red spectrum for the compound having the structure:

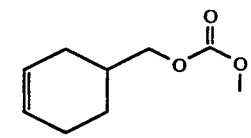

prepared according to Example XII.

Figure 48:
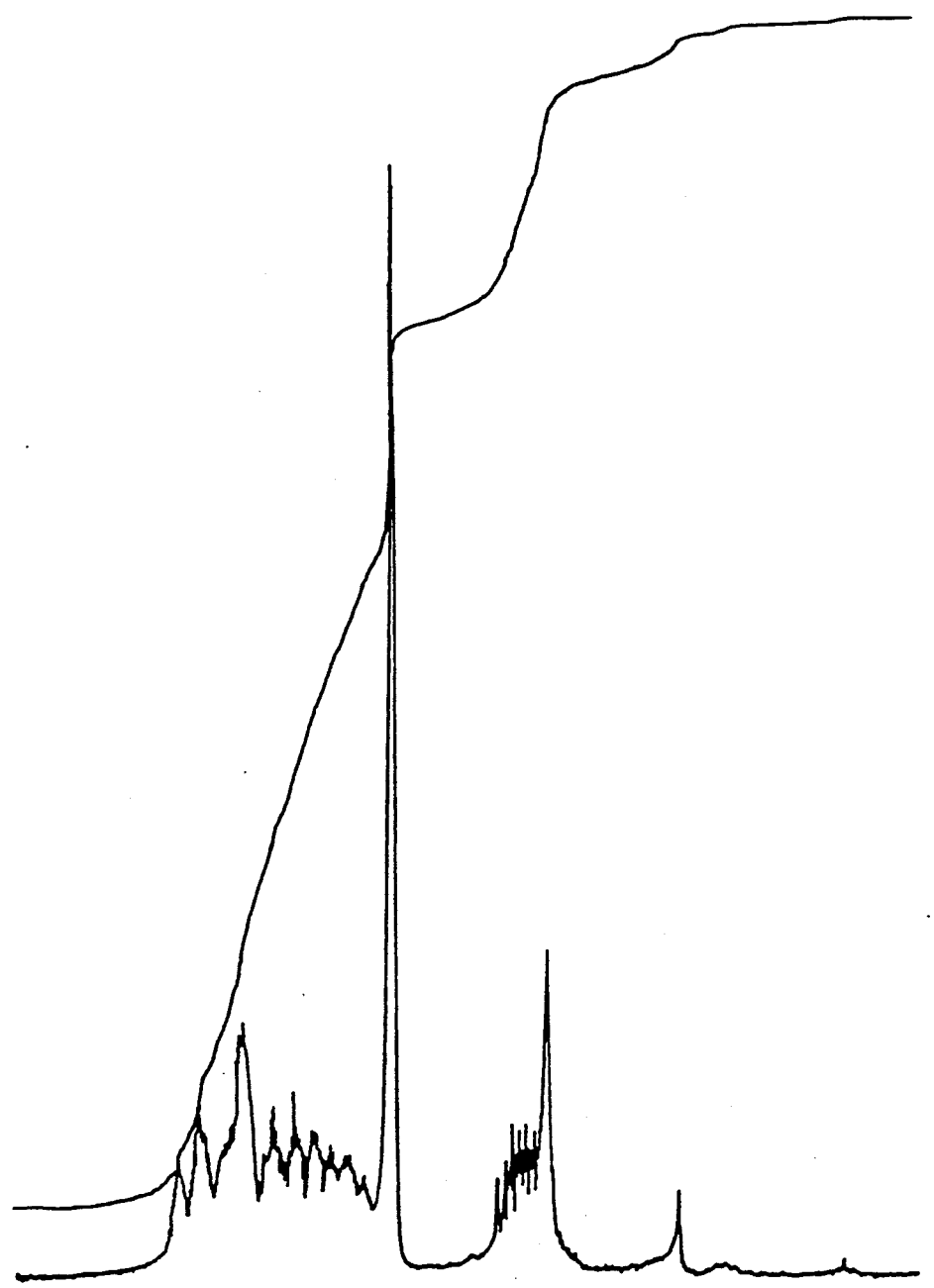

FIG. 48 is the NMR spectrum for the compound having the structure:

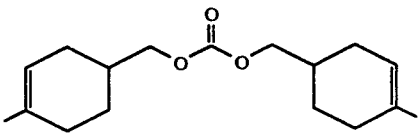

indicated by reference numeral 374 on FIG. 43.

FIG. 48A is the detailed portion "A" of the NMR spectrum of FIG. 48.

FIG. 48B is the detailed portion "B" of the NMR spectrum of FIG. 48

FIG. 48C is the detailed portion "C" of the NMR spectrum of FIG. 48.

Figure 49:
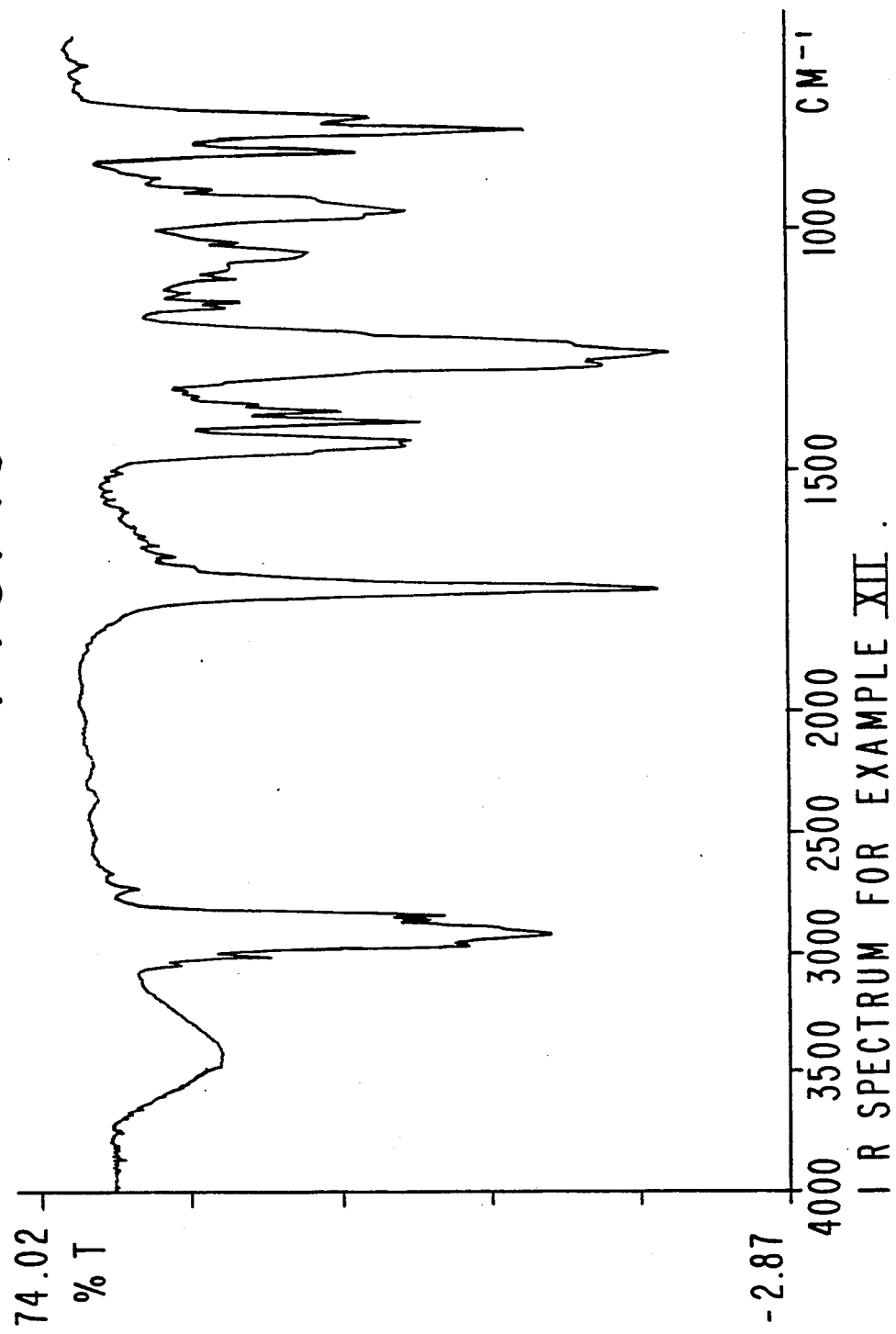

FIG. 49 is the infra-red spectrum for the compound having the structure:

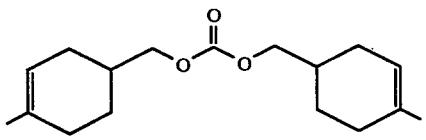

prepared according to Example XII.

Figure 50:
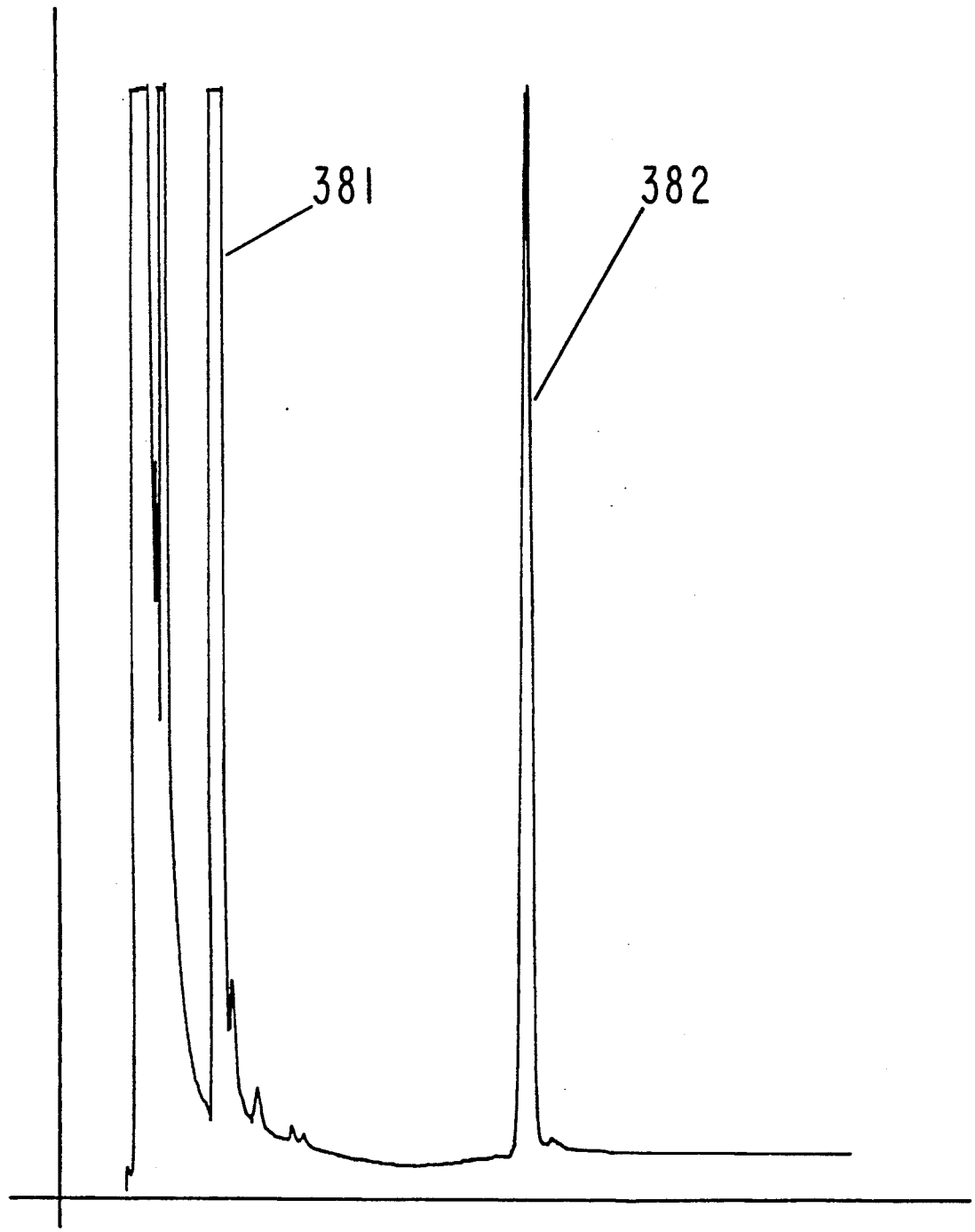

FIG. 50 is the GLC profile for the reaction product of Example XIII containing the compounds having the structures:

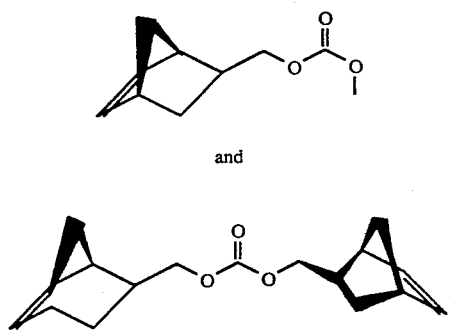

FIG. 51 is the NMR spectrum for the compound having the structure:

prepared according to Example XIII, the peak indicated by reference numeral 381 of FIG. 50.

Figures 51A, 51B:
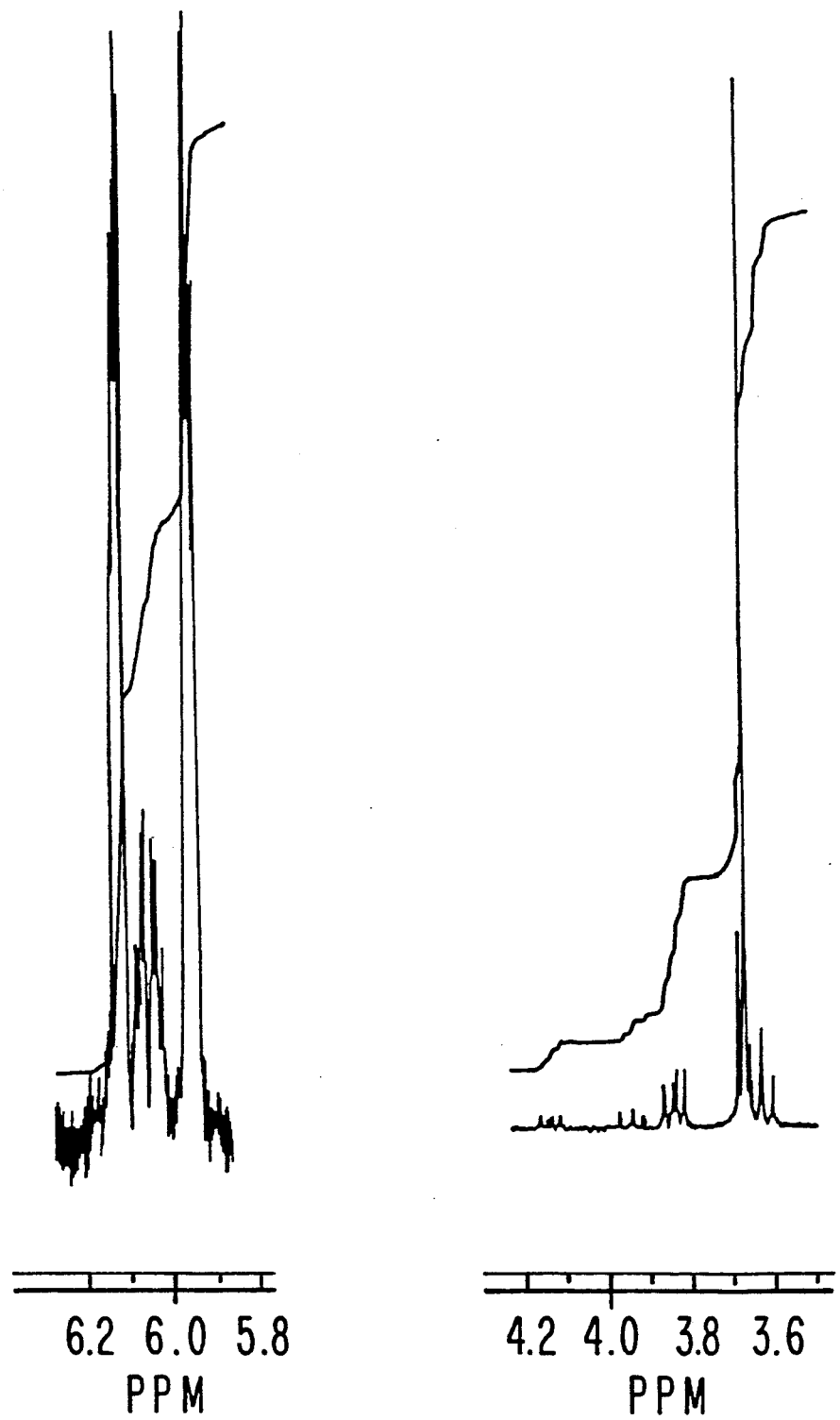

FIG. 51A is the detailed portion "A" of the NMR spectrum of FIG. 51

FIG. 51B is the detailed portion "B" of the NMR spectrum of FIG. 51.

FIG. 51C is the detailed portion "C" of the NMR spectrum of FIG. 51.

Figure 51D:
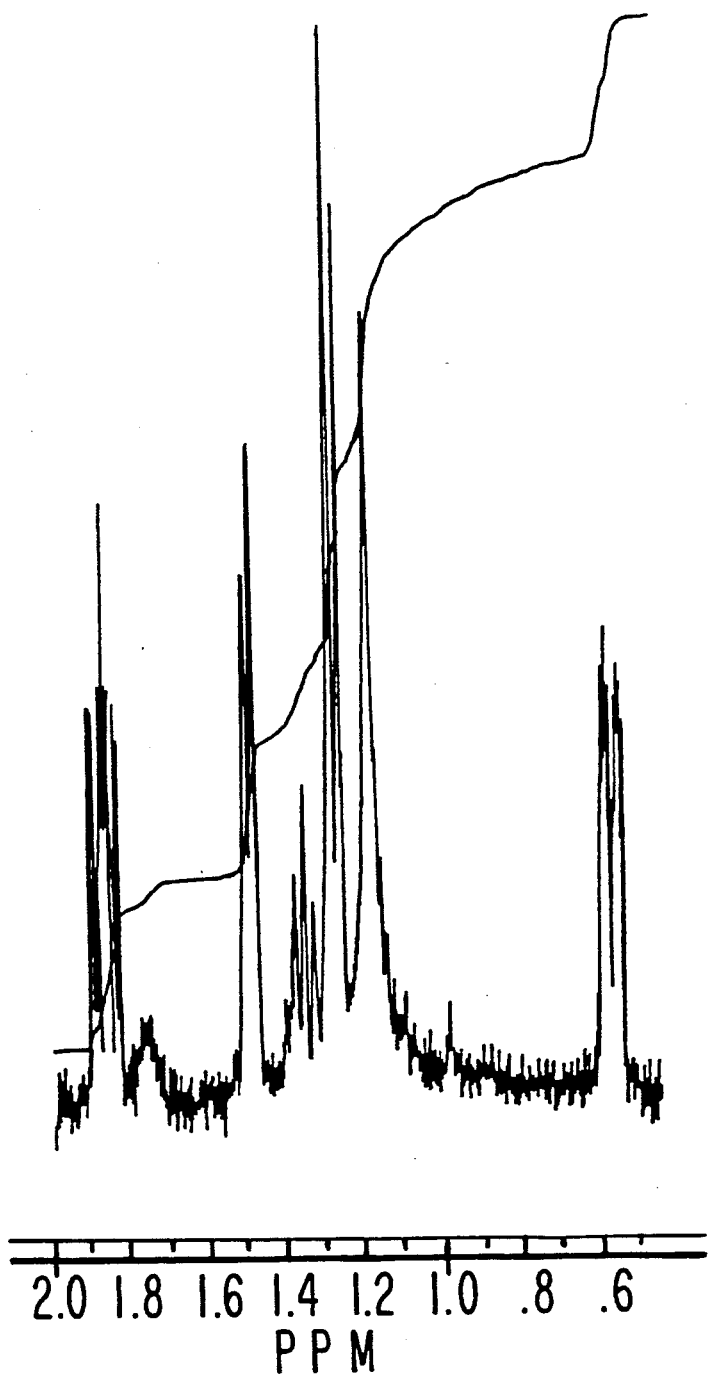

FIG. 51D is the detailed portion "D" of the NMR spectrum of FIG. 51.

Figure 52:
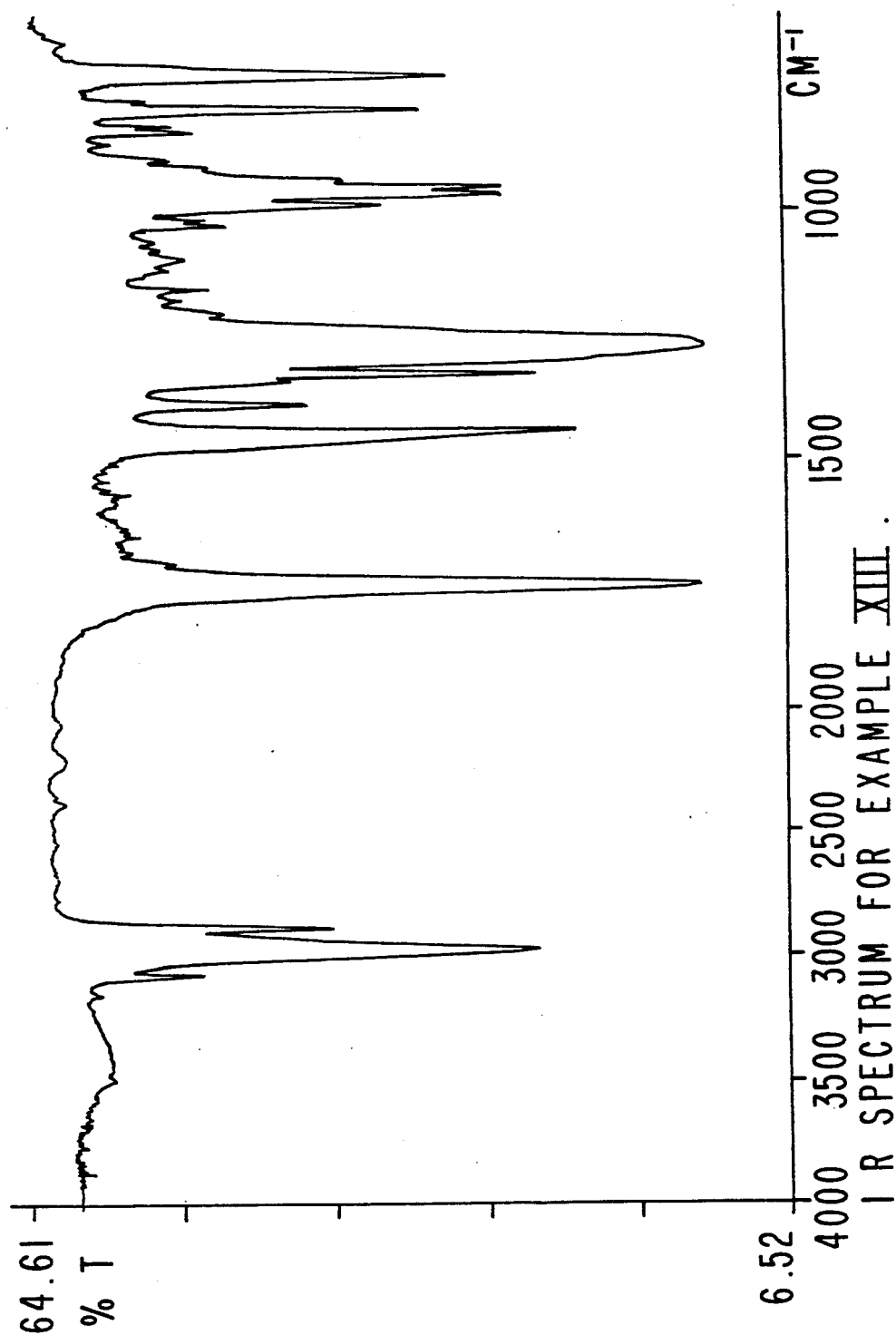

FIG. 52 is the infra-red spectrum for the compound having the structure:

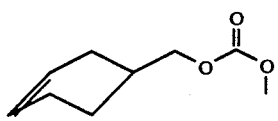

prepared according to Example XIII.

Figure 53:

FIG. 53 is the GLC profile for the reaction product of Example XIV containing the compound having the structure:

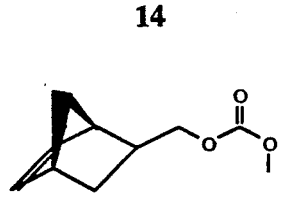

Figure 54A:
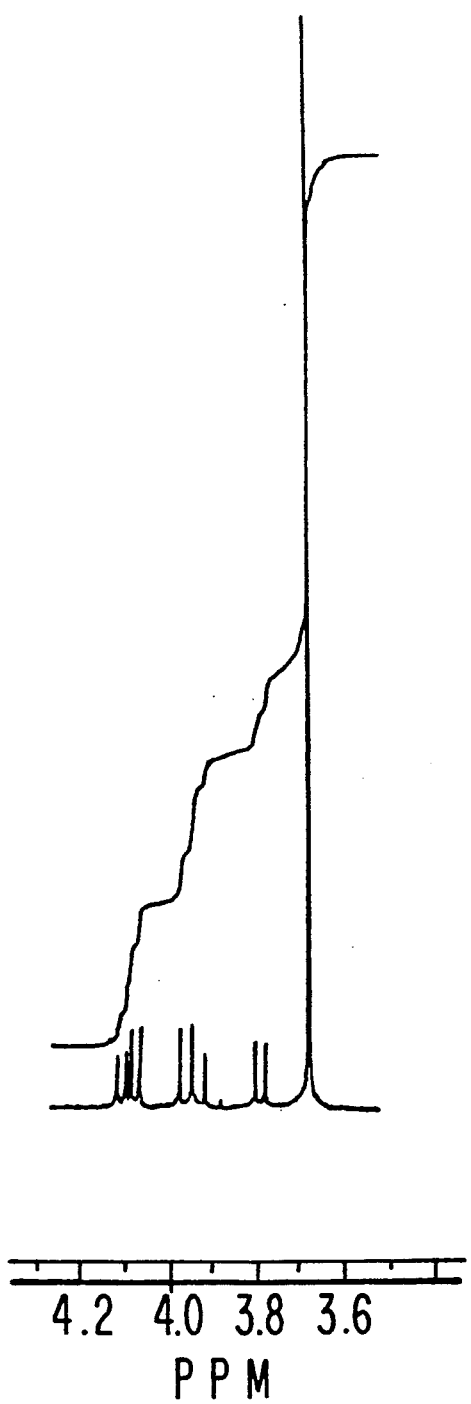
Figure 54:
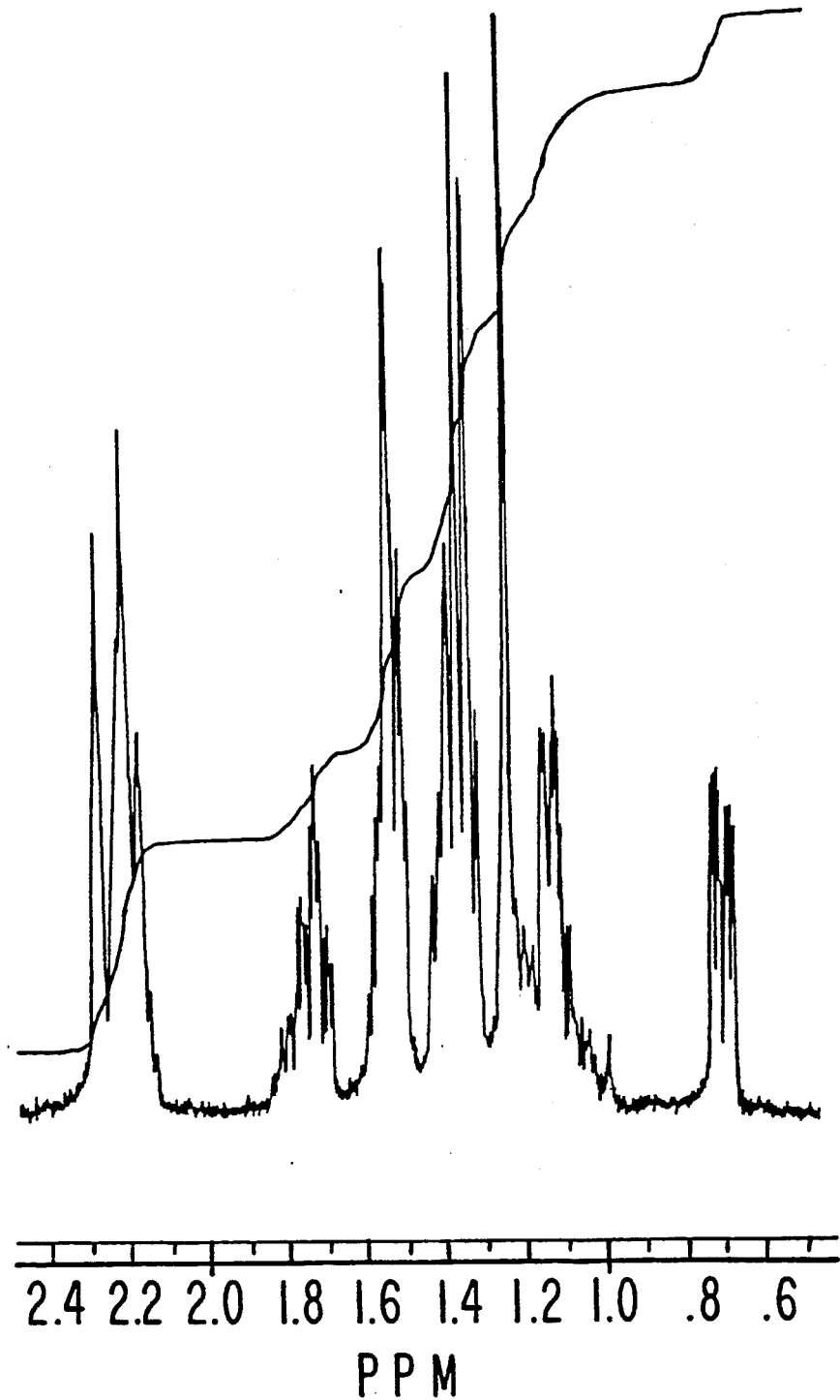

FIG. 54 is the NMR spectrum for the compound having the structure:

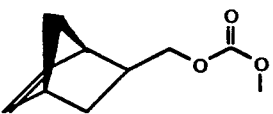

prepared according to Example XIV.

FIG. 54A is the detailed portion "A" of the NMR spectrum of FIG. 54.

FIG. 54B is the detailed portion "B" of the NMR spectrum of FIG. 54.

Figure 55:
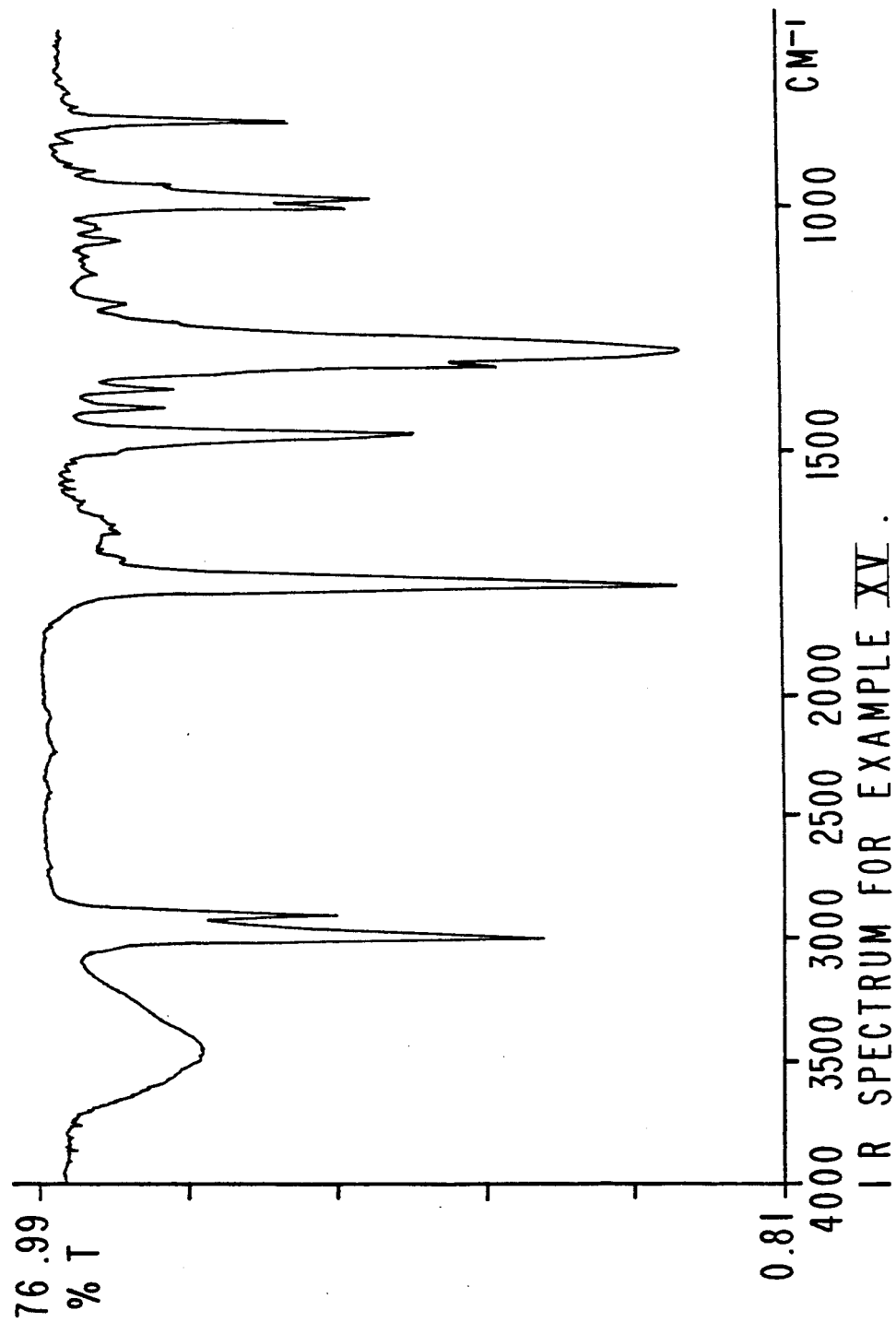

FIG. 55 is the infra-red spectrum for the compound having the structure:

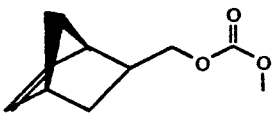

prepared according to Example XIV.

Figure 56:
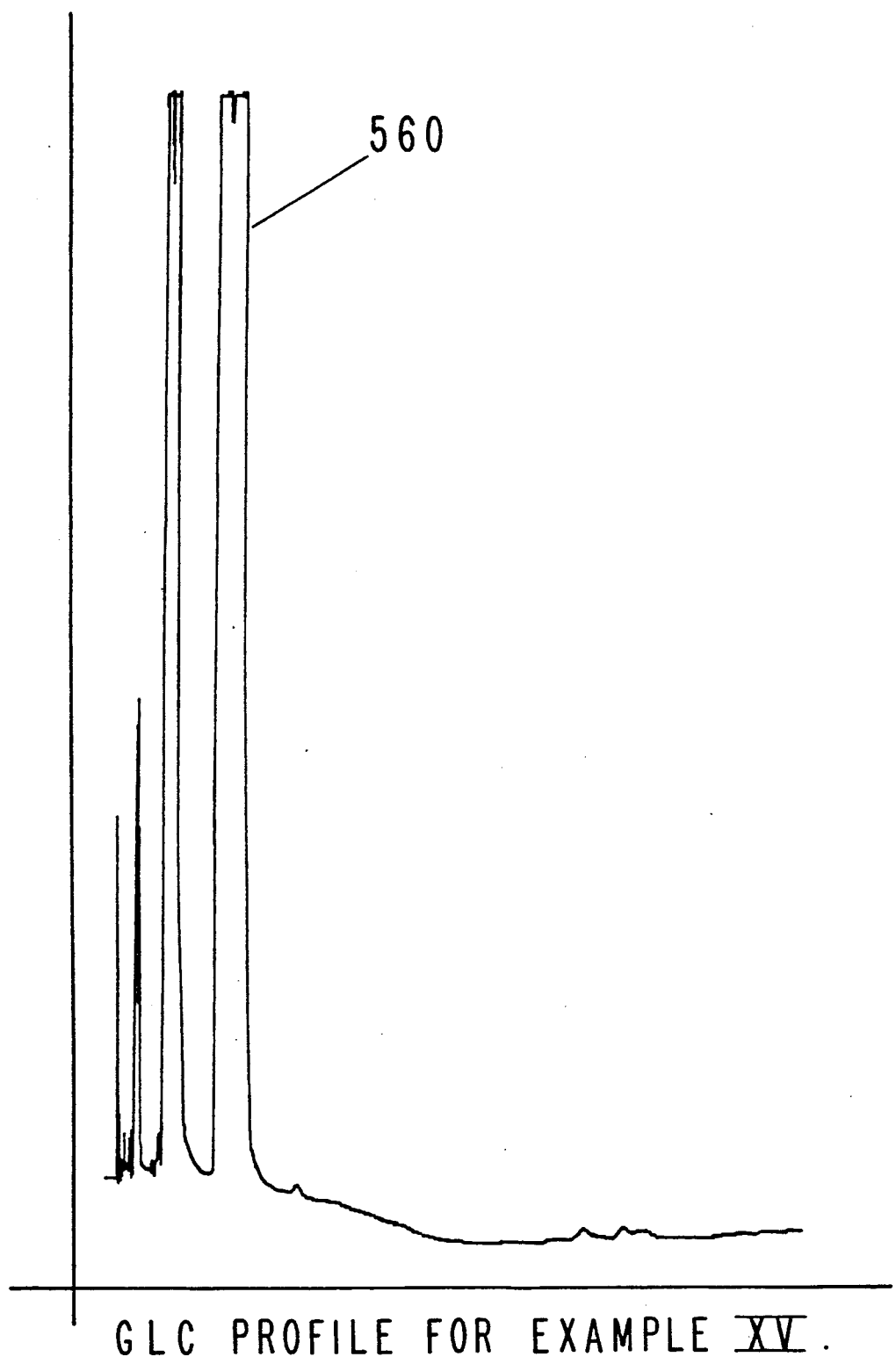

FIG. 56 is the GLC profile for the reaction product of Example XV containing the compound having the structure:

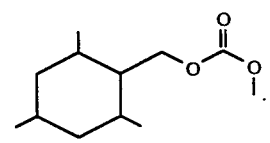

FIG. 57 is the NMR spectrum for the compound having the structure:

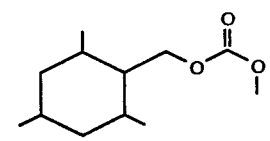

prepared according to Example XV.

Figure 57A:
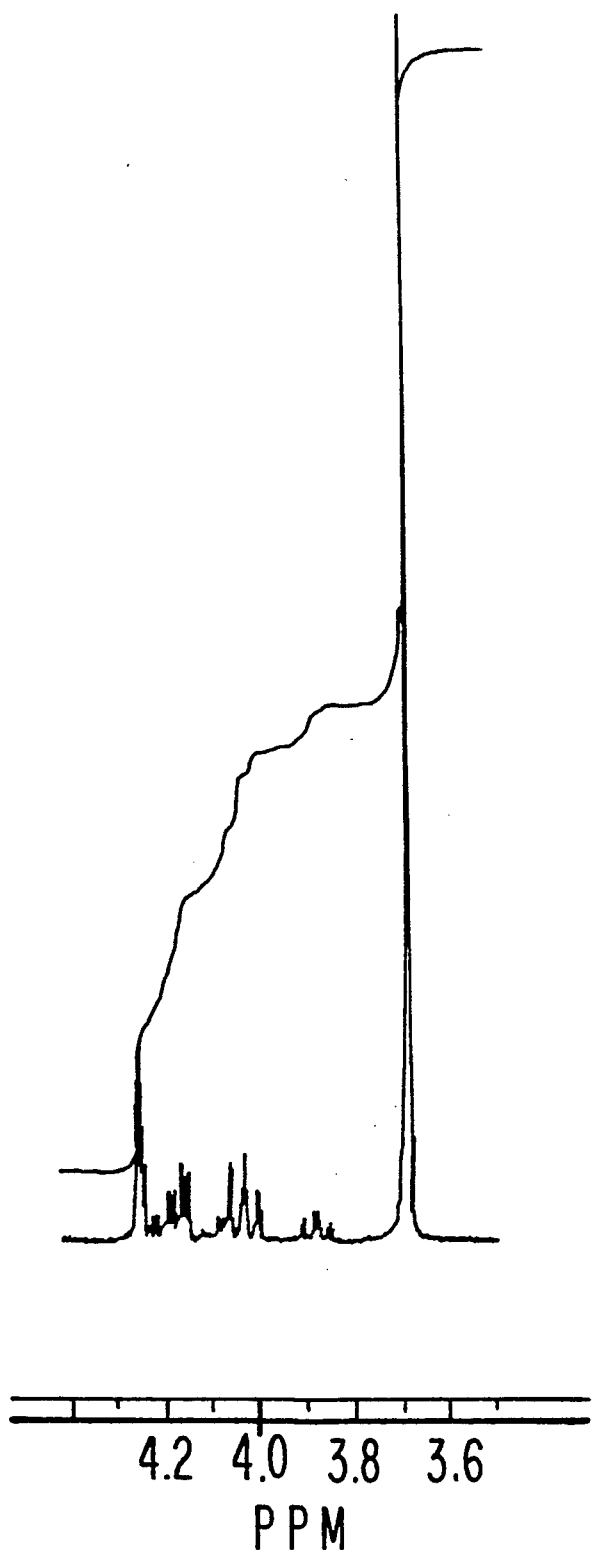

FIG. 57A is the detailed portion "A" of the NMR spectrum of FIG. 57.

Figure 57B:
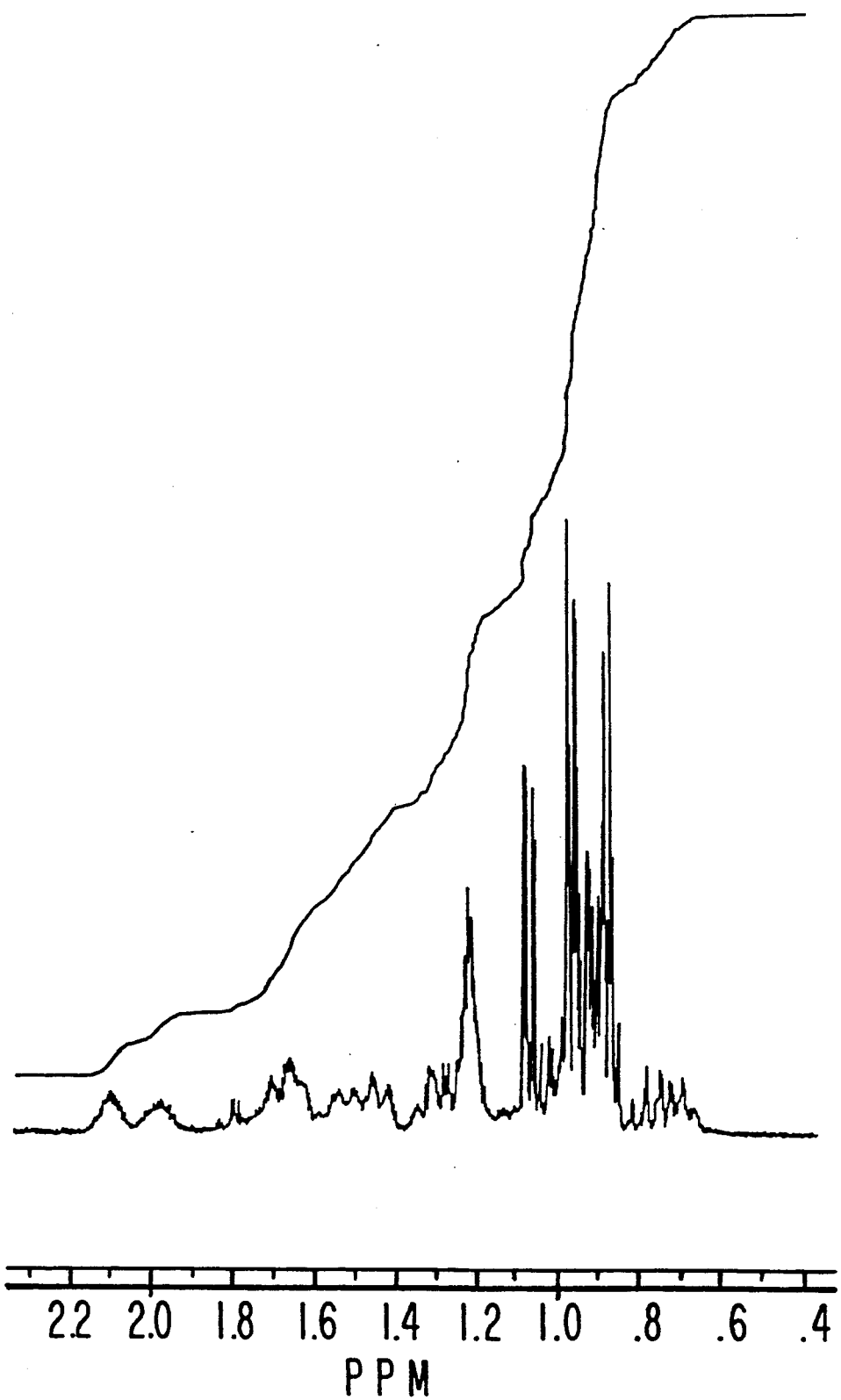

FIG. 57B is the detailed portion "B" of the NMR spectrum of FIG. 57.

FIG. 58 is the infra-red spectrum for the compound having the structure:

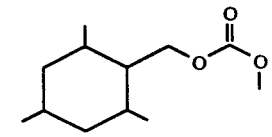

prepared according to Example XV.

FIG. 59 is the GLC profile of the reaction product of Example XVI containing a mixture of compounds defined according to the structure:

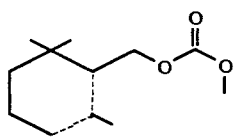

wherein the mixture, in each of the compounds one of the dashed lines is a carbon-carbon single bond and the other of the dashed lines is a carbon-carbon double bond.

FIG. 60 is the NMR spectrum for the compound having the structure:

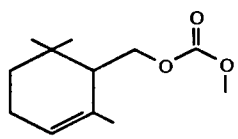

prepared according to Example XVI, peak 591 of FIG. 59.

FIG. 60A is the detailed portion "A" of the NMR spectrum of FIG. 60.

FIG. 60B is the detailed portion "B" of the NMR spectrum of FIG. 60.

Figure 60C:
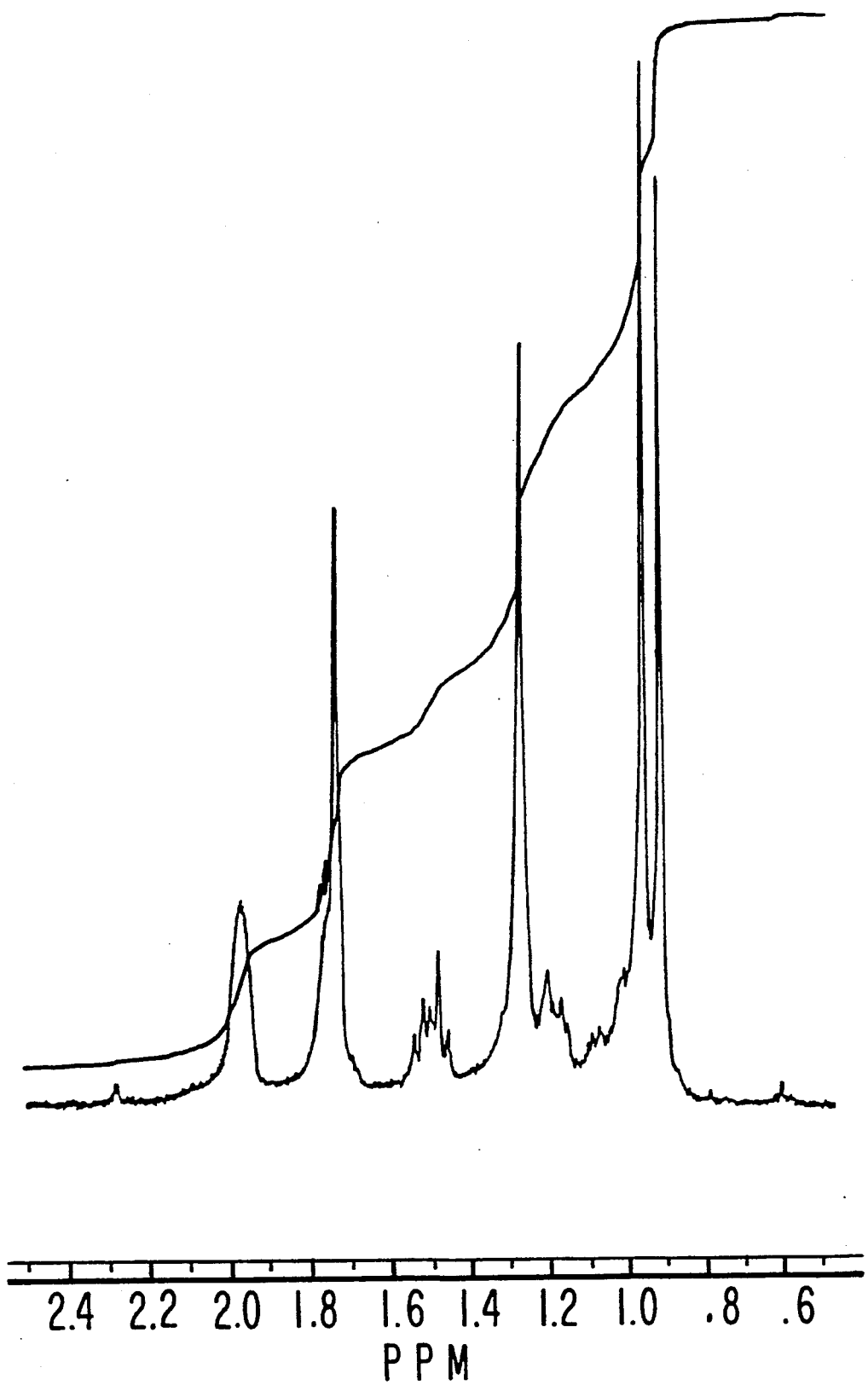

FIG. 60C is the detailed portion "C" of the NMR spectrum of FIG. 60.

FIG. 61 is the infra-red spectrum for the compound having the structure:

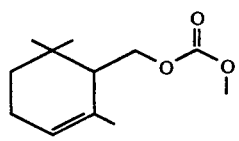

prepared according to Example XVI (peak 591 of FIG. 59).

Figure 62A:
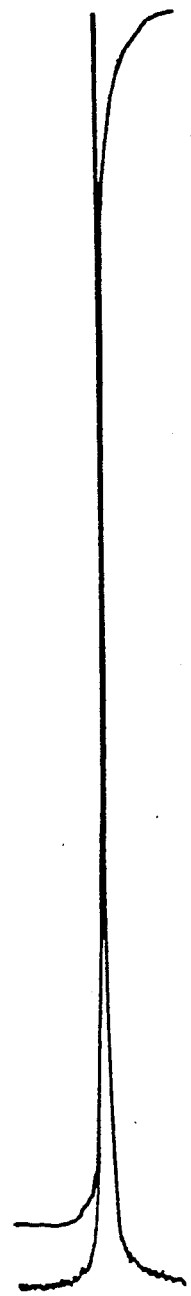
Figure 62B:
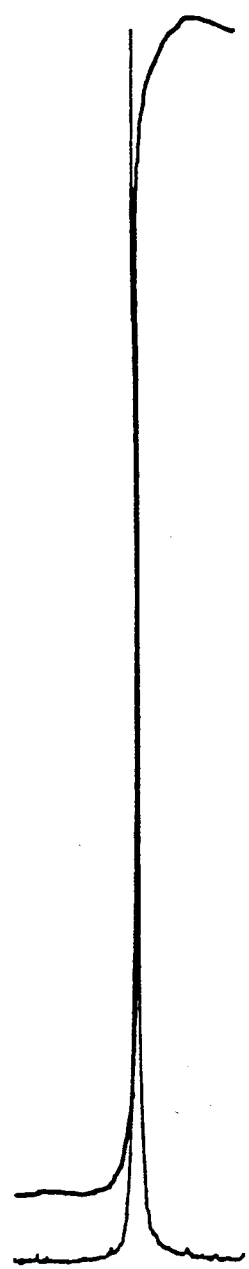
Figure 62:
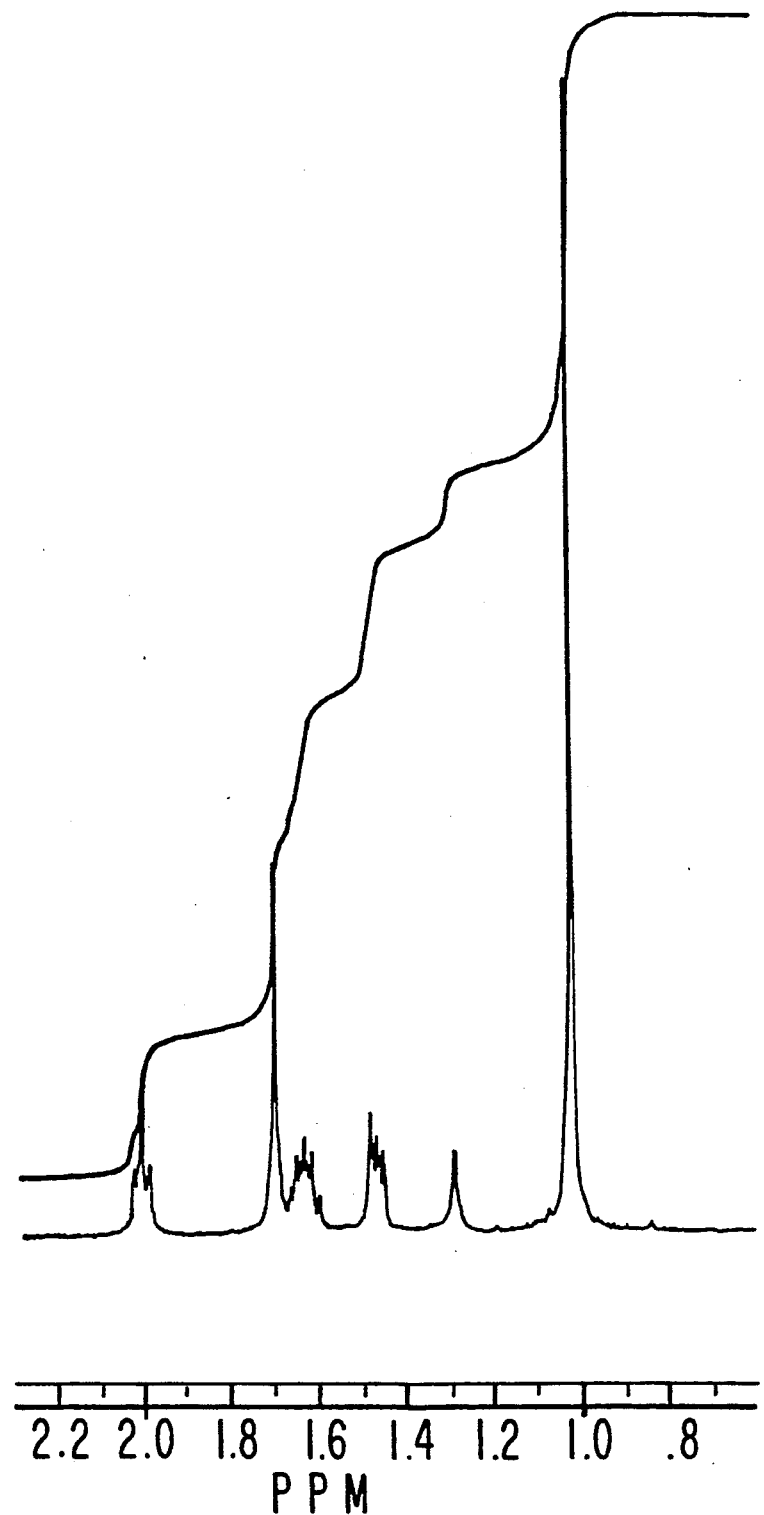

FIG. 62 is the NMR spectrum for the compound having the structure:

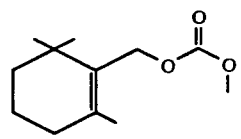

prepared according to Example XVI (peak 593 of FIG. 59).

FIG. 62A is the detailed portion "A" of the NMR spectrum of FIG. 62.

FIG. 62B is the detailed portion "B" of the NMR spectrum of FIG. 62.

FIG. 62C is the detailed portion "C" of the NMR spectrum of FIG. 62.

Figure 63:
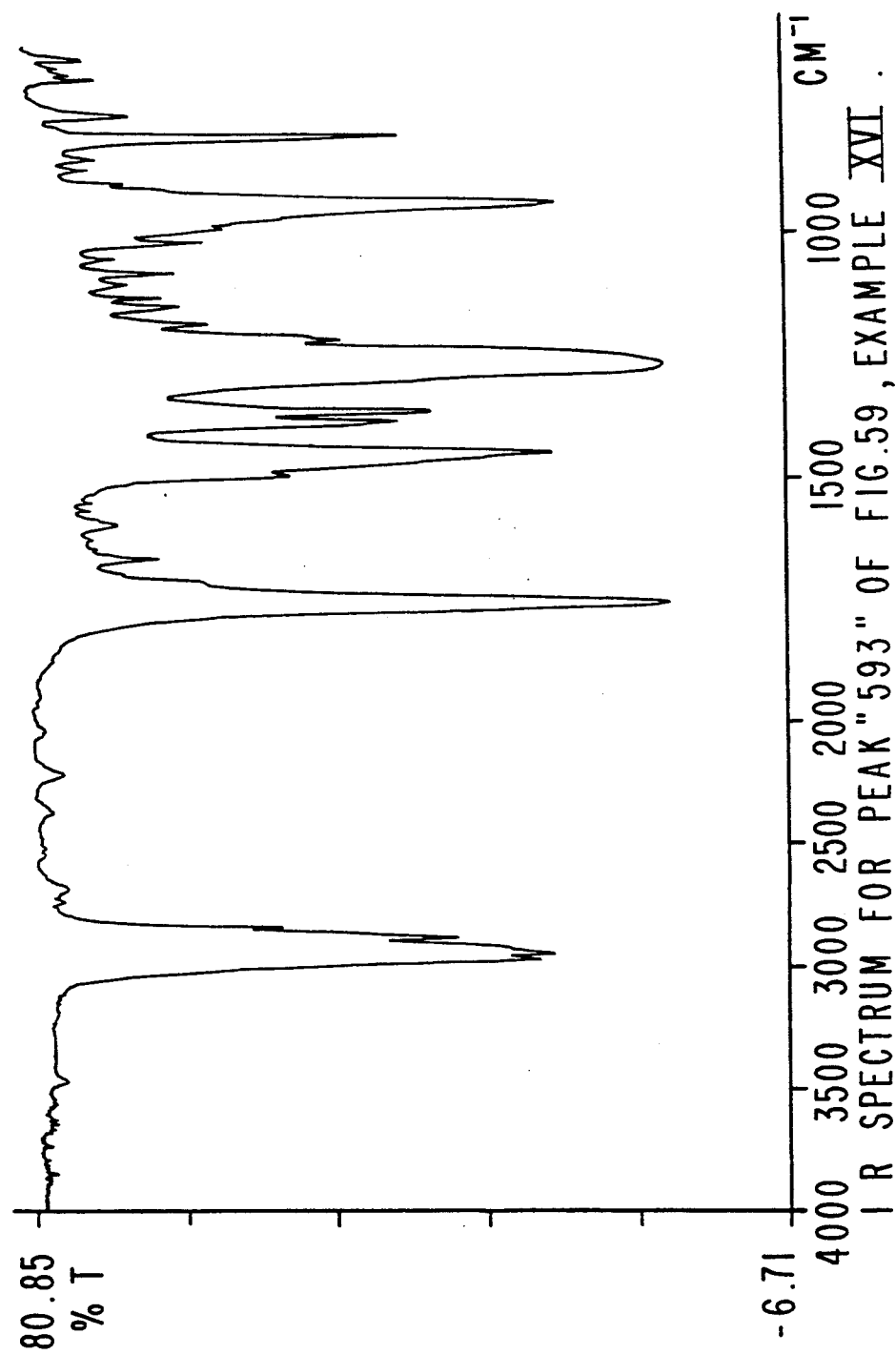

FIG. 63 is the infra-red spectrum for the compound having the structure:

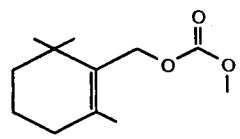

prepared according to Example XVI (peak 593 of FIG. 59).

Figure 64:
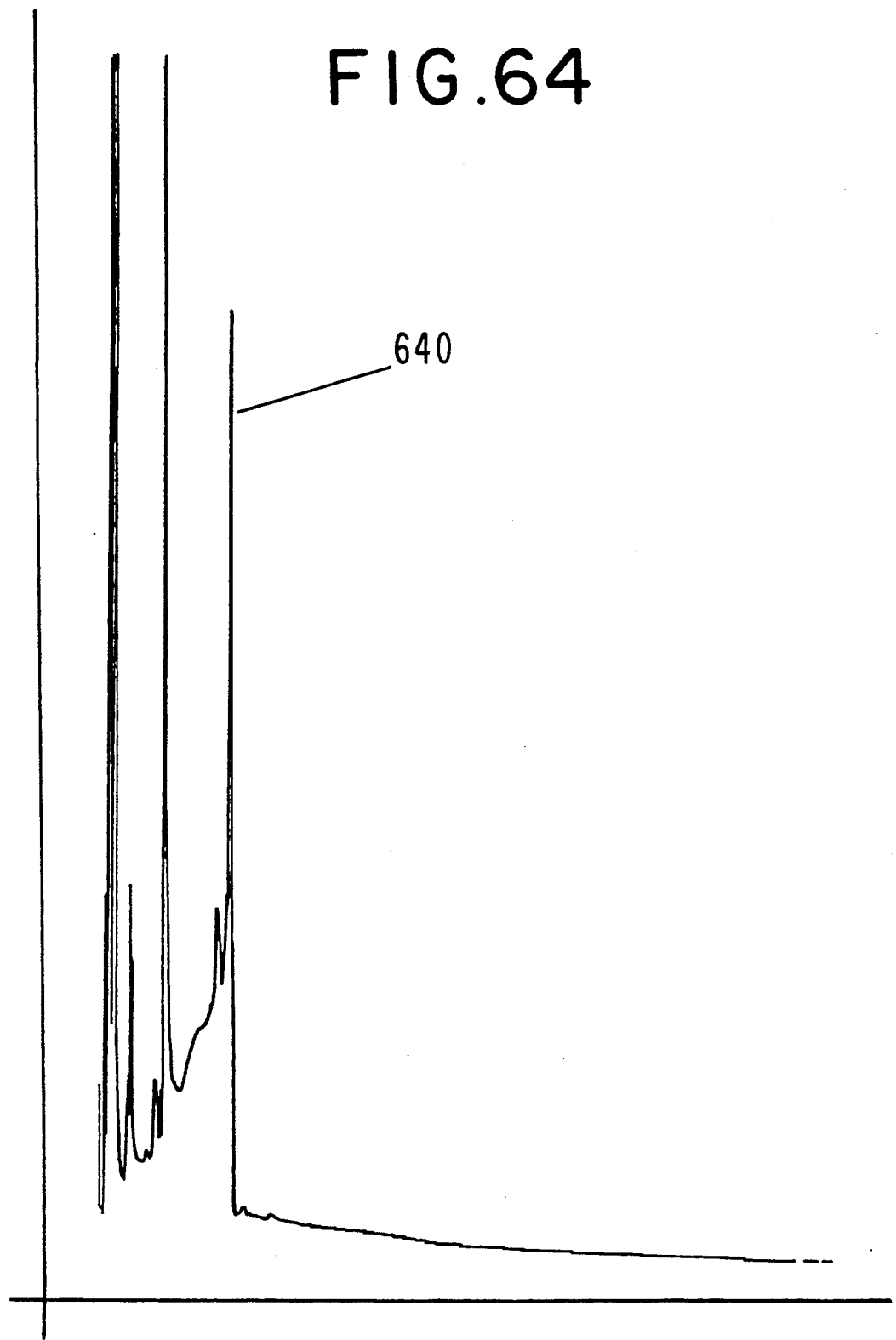

FIG. 64 is the GLC profile for the reaction product of Example XVII containing the compound having the structure:

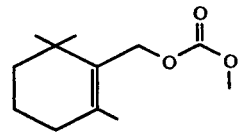

Figure 65:
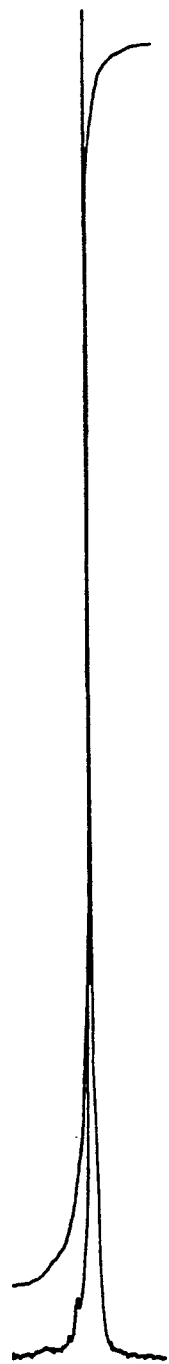
Figure 65:
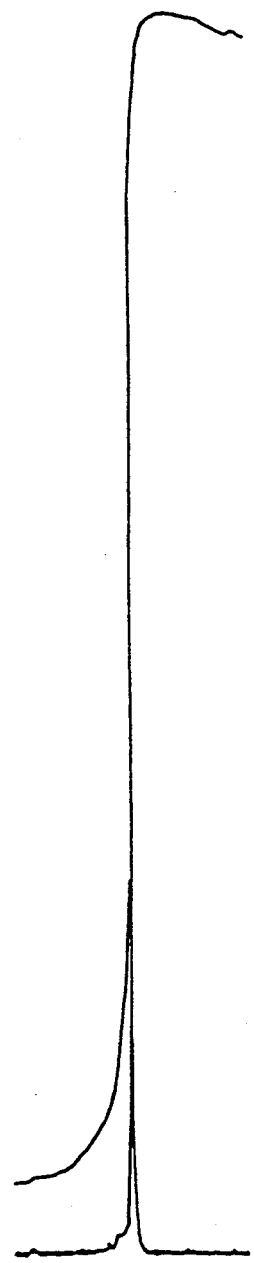

FIG. 65 is the NMR spectrum for the peak indicated by reference numeral 640 of FIG. 64 for the compound having the structure:

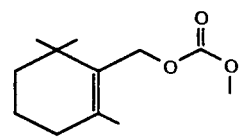

prepared according to Example XVII.

FIG. 65A is the detailed portion "A" of the NMR spectrum of FIG. 65.

FIG. 65B is the detailed portion "B" of the NMR spectrum of FIG. 65.

Figure 65C:
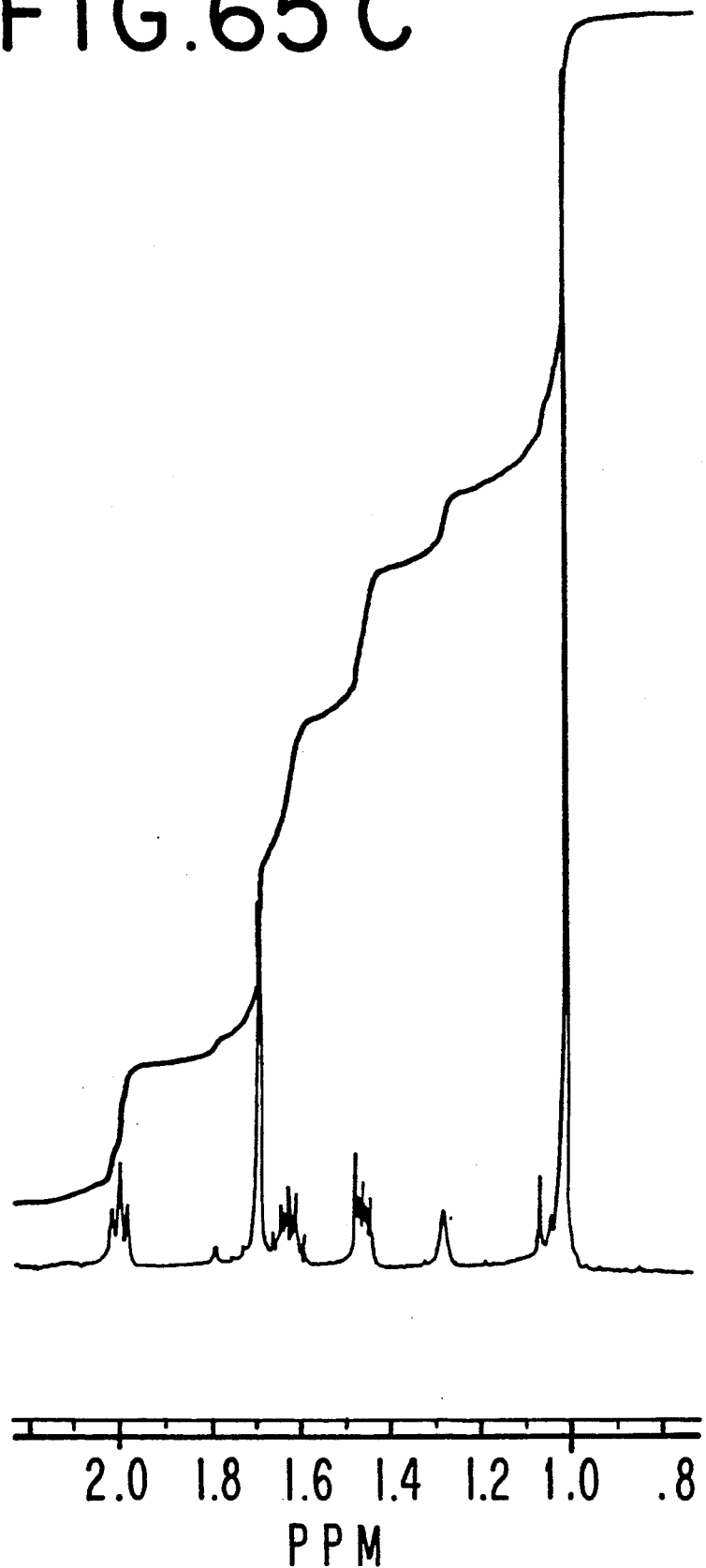

FIG. 65C is the detailed portion "C" of the NMR spectrum of FIG. 65.

FIG. 66 is the infra-red spectrum for the compound having the structure:

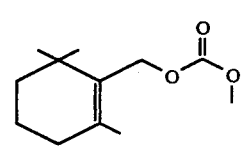

prepared according to Example XVII (peak 640 of FIG. 64).

DETAILED DESCRIPTION OF THE DRAWINGS

Figure 1:
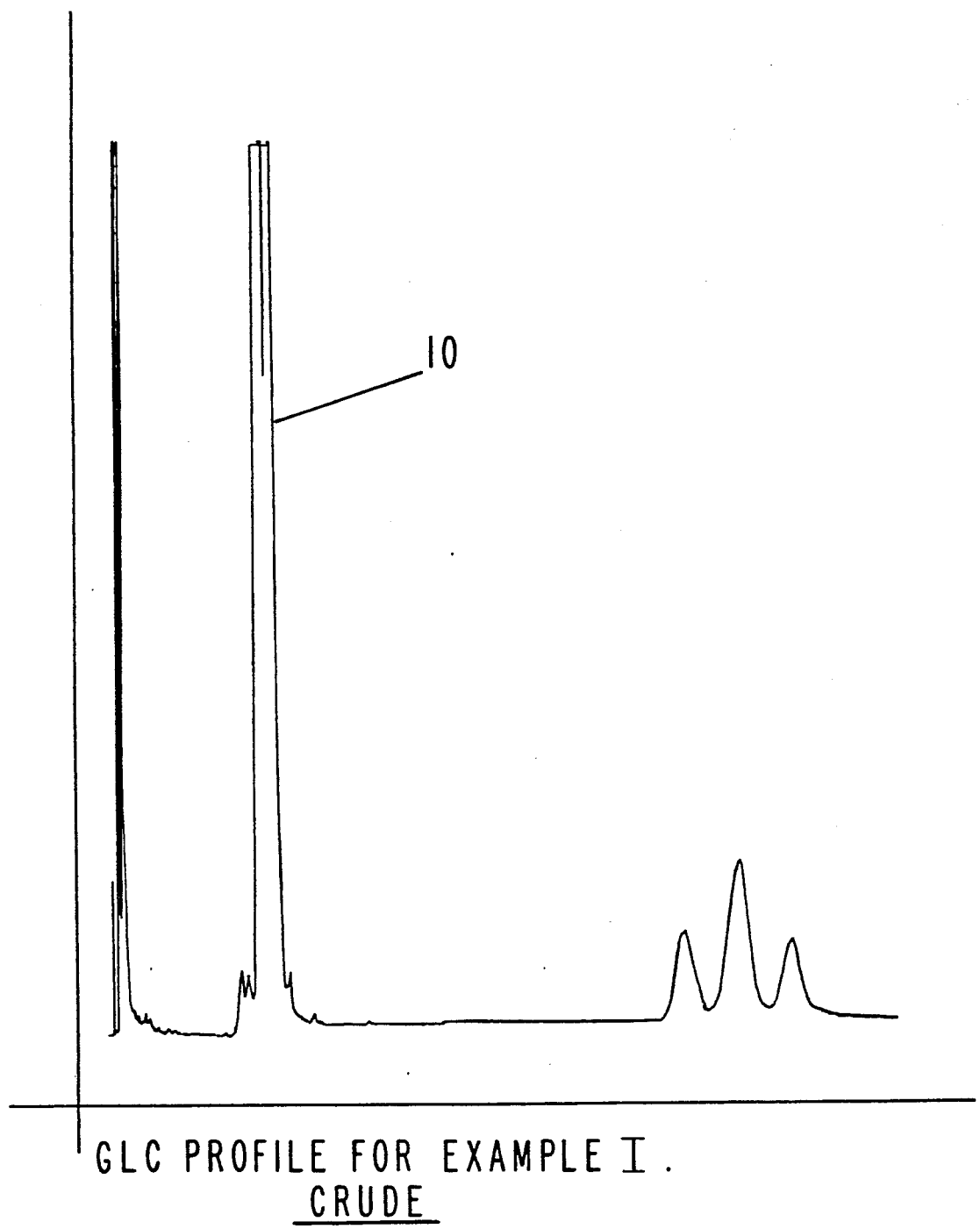
FIG. 1 is the GLC profile for the crude reaction product of Example I containing the compound having the structure.

FIG. 1 is the GLC profile for the crude reaction product of Example I containing the compound having the structure:

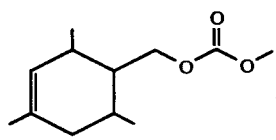

The peak indicated by reference numeral 10 is the peak for the compound having the structure:

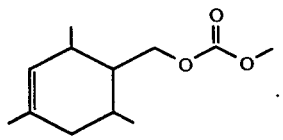

FIG. 2 is the GLC profile for bulked distillation fractions 7-12 containing isomers of the compound having the structure:

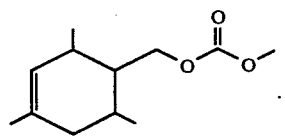

The peak indicated by reference numeral 21 is the peak for one of the isomers of the compound having the structure:

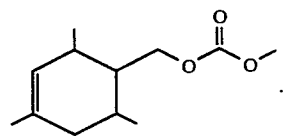

The peak indicated by reference numeral 22 is the peak for another of the isomers of the compound having the structure:

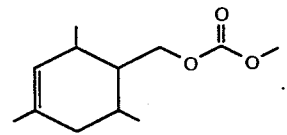

(Conditions: Carbowax column programmed at 150°-220° C. at 8° C. per minute). Thus, for example, one of the isomers of the compound having the structure:

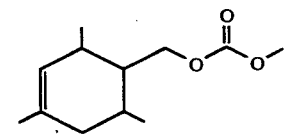

could be an isomer having the structure:

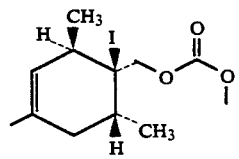

and another isomer could be the isomer having the structure:

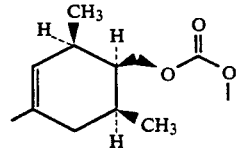

wherein the depiction of the isomers, the dashed lines represent moieties, e.g., hydrogen or methyl, beneath the plane of the cyclohexenyl moiety.

FIG. 7 is the GLC profile for the crude reaction product of Example II containing the compound having the structure:

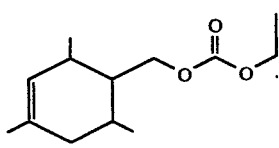

The peak indicated by reference numeral 17 is a peak for one of the isomers of the compound having the structure:

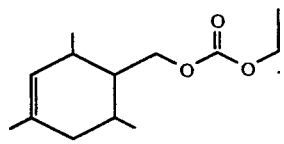

The peak indicated by reference numeral 72 is the peak for another of the isomers of the compound having the structure:

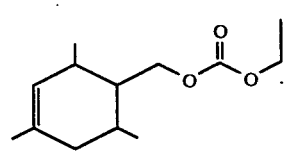

The peaks indicated by reference numerals 73, 74 and 75 are peaks for isomers of the compound having the structure:

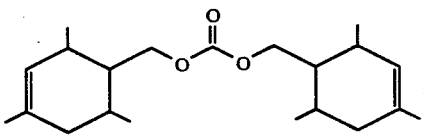

FIG. 9 is the NMR spectrum for peaks indicated by reference numerals 71 and 72 on the GLC profile of FIG. 7. The section of the NMR spectrum indicated by the letter "A" is shown in detail in FIG. 9A. The section of the NMR spectrum indicated by the letter "B" is shown in detail in FIG. 9B.

FIG. 10 is the GLC profile of the reaction product (crude) of Example III. The peaks indicated by reference numerals 103 and 104 are for isomers of the compound having the structure:

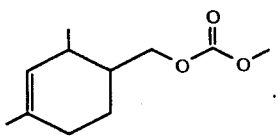

The peaks indicated by reference numerals 101 and 102 are for isomers of the starting material defined according to the structure:

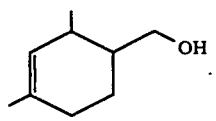

FIG. 13 is the GLC profile for the crude reaction product of Example IV. The peak indicated by reference numeral 132 is the peak for the compound having the structure:

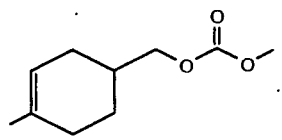

The peak indicated by reference numeral 133 is a peak for a side product defined according to the structure:

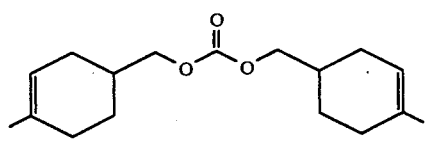

The peak indicated by reference numeral 131 is the peak for the starting material defined according to the structure:

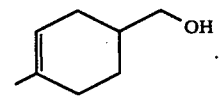

FIG. 16 is the GLC profile for the crude reaction product of Example V. The peak indicated by reference numeral 162 is the peak for the compound having the structure:

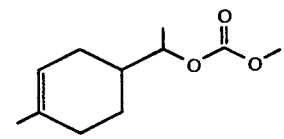

The peak indicated by reference numeral 161 is the peak for the starting material having the structure:

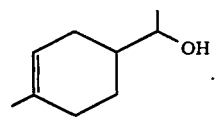

The peak indicated by reference numeral 160 is the peak for the reaction solvent which is a mixture of toluene, methyl alcohol and acetic acid.

FIG. 18 is the NMR spectrum for the peak indicated by reference numeral 162 of the GLC profile of FIG. 16 for the compound having the structure:

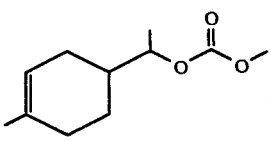

Sections marked "A", "B", "C" and "D" are shown in detailed form in, respectively, FIGS. 18A, 18B, 18C and 18D.

FIG. 19 is the GLC profile for the reaction product of Example VI (Conditions: SE-30 column programmed at 150°-220° C. at 8° C. per minute). The peak indicated by reference numeral 190 is the peak for the compound having the structure:

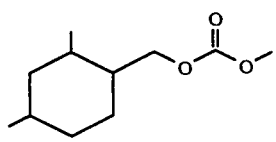

FIG. 20 is the NMR spectrum for the peak indicated by reference numeral 190 of the GLC profile of FIG. 19 for the compound having the structure:

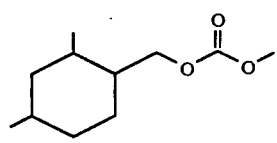

The sections of the NMR spectrum indicated by letters "A" and "B" are, respectively, shown in detail in FIGS. 20A and 20B.

FIG. 22 is the GLC profile for the crude reaction product of Example VII. The peak indicated by reference numeral 324 is for the compound having the structure:

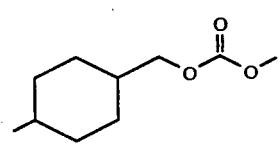

The peak indicated by reference numeral 323 is for the starting material, the compound having the structure:

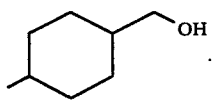

The peak indicated by reference numeral 325 is for the reaction side product having the structure:

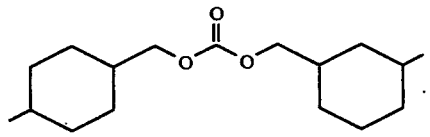

The peak indicated by reference numeral 322 is for the reaction solvent which is a mixture of methyl alcohol, toluene and acetic acid.

FIG. 23 is the NMR spectrum for the peak indicated by reference numeral 324 for the GLC profile of FIG. 22. The sections "A"0 and "B" of the NMR spectrum of FIG. 23 are shown in detailed form, respectively, in FIGS. 23A and 23B.

FIG. 25 is the NMR spectrum for the peak indicated by reference numeral 325 of the GLC profile of FIG. 22 for the compound having the structure:

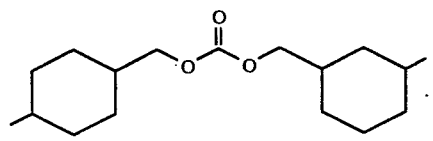

The sections of the NMR spectrum of FIG. 25 indicated by the letters "A" and "B" are, respectively, depicted in detailed form in FIGS. 25A and 25B.

Referring to FIGS. 27 and 28, in particular, the apparatus used in producing polymeric fragrances containing at least one of the alkyl cyclohexylmethyl and cyclohexenylmethyl carbonates of our invention comprises a device for forming scented polyolefin (for example) pellets, which comprises a vat or container 212 into which a mixture of polyolefins such as polyethylene and an aromatic substance or scented material is placed (e.g., at least one of the alkyl cyclohexylmethyl and cyclohexenylmethyl carbonates of our invention). The container is closed by an airtight lid 228 and clamped to the container by bolts 265. A stirrer 273 traverses the lid or cover 228 in an airtight manner and is rotated in a suitable manner. A surrounding cylinder 212 having heating coils 212A which are supplied with electric current through cable 224 from a rheostat or control 216 is operated to maintain a temperature inside the container 212 such that polyethylene or other thermoplastic polymer in the container will be maintained in the molten or liquid state. It has been found advantageous to employ a colorless, odorless polymer (e.g., polyethylene) with a viscosity ranging between 180 and 220 saybolt seconds and having a melting point in the range of 200°-280° F. The heater 212A is operated to maintain the upper portion of the container 212 within a temperature range of from 250°-350° F. The bottom portion of the container is heated by means of heating coils 212A heated through a control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scented aroma imparting material (e.g., at least one of the alkyl cyclohexylmethyl and cyclohexenylmethyl carbonates of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally bout 5-30% by weight of the scented material (e.g., at least one of the alkyl cyclohexylmethyl and cyclohexenylmethyl carbonates of our invention) is added to the polyolefin.

After the scent imparting material (e.g., a composition containing at least one of the alkyl cyclohexylmethyl and cyclohexenylmethyl carbonates of our invention) is added to the container 212, the mixture is stirred for a few minutes, for example, 5-15 minutes and maintained within the temperature range as indicated previously by heating coils 212A. The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234 adjacent to the lower side thereof. The outer end of the conduit 218/232 is closed so that the liquid polymer (e.g., polyolefin) and aroma imparting material (e.g., at least one of the alkyl cyclohexylmethyl and cyclohexenylmethyl carbonates of our invention) will continuously drop through orifices 234 downwardly from conduit 232. During this time the temperature of the polymer (e.g., polyethylene or polyolefin) and scent imparting material (e.g., at least one of the alkyl cyclohexylmethyl and cyclohexenylmethyl carbonates of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., at least one of the alkyl cyclohexylmethyl and cyclohexenylmethyl carbonates of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening of the conveyor belt 238 to insure rapid formation of the solid polymeric (e.g., polyolefin) scented pellets 244 without sticking to material which will not normally stick to a melted plastic. A moistening means 248 insures a sufficiently cold temperature of the belt surface for adequate formation of the pellets 244. The adequate moistening means comprises a container 250 which is continuously fed with water 254 to maintain a level for moistening a sponge element 256 which bears against the exterior of the belt 238.

FIG. 30 is the NMR spectrum for the compound having the structure:

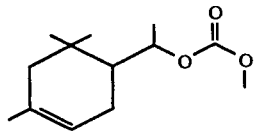

prepared according to Example VIII. Sections marked "A", "B" and "C" are shown in detailed form in, respectively, FIGS. 30A, 30B and 30C.

FIG. 31 is the GLC profile for the reaction product of Example IX (capillary GLC) (Conditions: Carbowax column programmed at 150°-220° C. at 8° C. per minute). The peak indicated by reference numeral 310 is the peak for the solvent, methyl alcohol. The peaks indicated by reference numerals 311 and 312 are for the starting material having the structure:

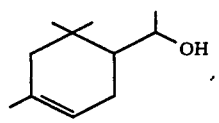

The peak indicated by reference numeral 314 is the peak for the compound having the structure:

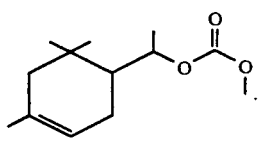

Peak 313 is also for an isomer of the starting material having the structure:

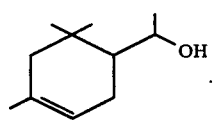

FIG. 32 is the GLC profile for the reaction product of Example IX, also (10 foot column used for trapping) - (Conditions: Carbowax column programmed at 150°-220° C. at 8° C. per minute). The peak indicated by reference numeral 315 is for the solvent, methyl alcohol. The peak indicated by reference numeral 316 is for the starting material having the structure:

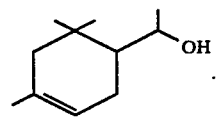

The peak indicated by reference numeral 317 is for the reaction product having the structure:

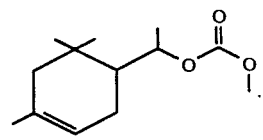

FIG. 33 is the NMR spectrum for the compound having the structure:

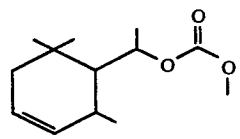

prepared according to Example IX. Sections marked "A", "B", "C" and "D" are shown in detailed form in, respectively, FIGS. 33A, 33B, 33C and 33D.

FIG. 10 is the GLC profile for the reaction product of Example X. The peak indicated by reference numeral 350 is for the methyl alcohol solvent. The peaks indicated by reference numerals 352 and 353 are for starting material having the structure:

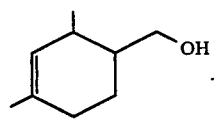

The peaks indicated by reference numerals 354 and 355 are for the reaction product defined according to the structure:

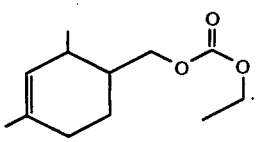

FIG. 37 is the NMR spectrum for the compound having the structure:

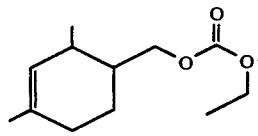

prepared according to Example X. Sections marked "A", "B" and "C" are shown in detailed form in, respectively, FIGS. 37A, 37B and 37C.

FIG. 38 is the GLC profile for the reaction product of Example XI. The peak indicated by reference numeral 360 is the peak for the reaction solvent, methyl alcohol. The peak indicated by reference numeral 362 is for the starting material having the structure:

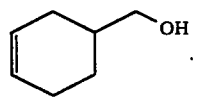

The peak indicated by reference numeral 364 is for the reaction product having the structure:

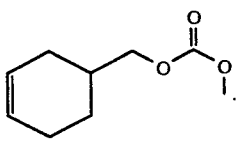

The peak indicated by reference numeral 366 is for the compound having the structure:

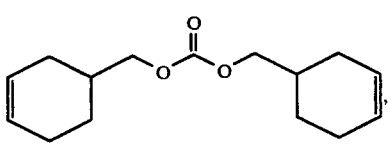

a bi-product.

FIG. 39 is the NMR spectrum for the compound having the structure:

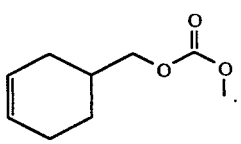

Sections marked "A", "B" and "C" are shown in detailed form in, respectively, FIGS. 39A, 39B and 39C.

FIG. 41 is the NMR spectrum for the compound having the structure:

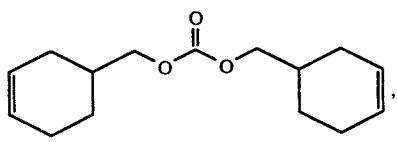

peak 366 of FIG. 38. Sections marked "A", "B" and "C" are shown in detailed form in, respectively, FIGS. 41A, 41B and 41C.

FIG. 43 is the GLC profile for the reaction product of Example XII. The peak indicated by reference numeral 370 is the peak for the reaction solvent, methyl alcohol. The peak indicated by reference numeral 371 is for the starting material having the structure:

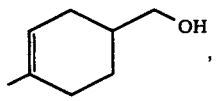

The peak indicated by reference numeral 372 is for the side product having the structure:

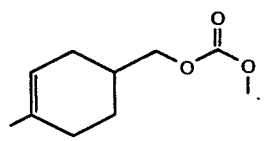

The peak indicated by reference numeral 373 is the peak for the reaction product having the structure:

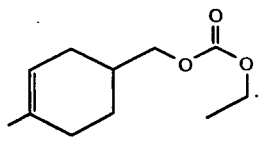

The peak indicated by reference numeral 374 is the peak for the bi-product having the structure:

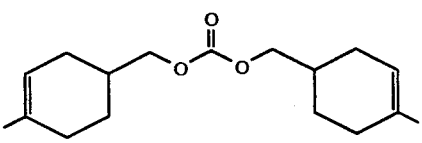

FIG. 44 is the NMR spectrum for the compound having the structure:

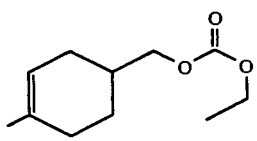

prepared according to Example XII. Sections marked "A", "B" and "C" are shown in detailed form in, respectively, FIGS. 44A, 44B and 44C.

FIG. 46 is the NMR spectrum for the compound having the structure:

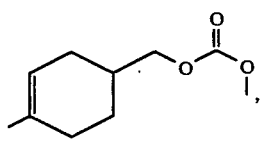

peak 372 of FIG. 43. Sections marked "A", "B" and "C" are shown in detailed form in, respectively, FIGS. 46A, 46B and 46C.

FIG. 48 is the NMR spectrum for the peak indicated by reference numeral 374 of FIG. 43, for the compound having the structure:

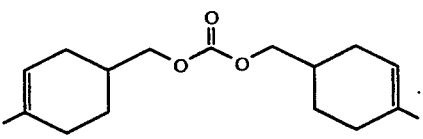

Sections marked "A", "B" and "C" are shown in detailed form in, respectively, FIGS. 48A, 48B and 48C.

FIG. 50 is the GLC profile for the reaction product of Example XIII. The peak indicated by reference numeral 381 is the peak for the compound having the structure:

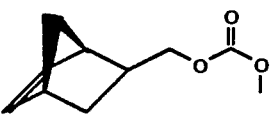

The peak indicated by reference numeral 382 is the peak for the bi-product having the structure:

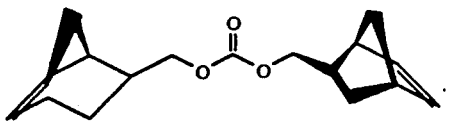

FIG. 51 is the NMR spectrum for the peak indicated by reference numeral 381 of FIG. 50 for the compound having the structure:

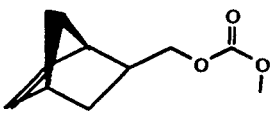

Sections marked "A", "B", "C" and "D" are shown in detailed form in, respectively, FIGS. 51A, 51B, 51C and 51D.

FIG. 54 is the NMR spectrum for the compound having the structure:

prepared according to Example XIV. Sections marked "A" and "B" are shown in detailed form in, respectively, FIGS. 54A and 54B.

FIG. 56 is the GLC profile for the reaction product of Example XV. The peak indicated by reference numeral 560 is for the compound having the structure:

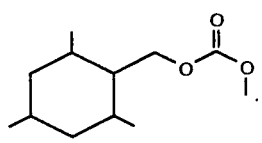

FIG. 57 is the NMR spectrum for the compound having the structure:

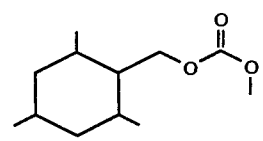

prepared according to Example XV. Sections marked "A" and "B" are shown in detailed form in, respectively, FIGS. 57A and 57B.

FIG. 59 is the GLC profile for the reaction product of Example XVI. The peak indicated by reference numeral 591 is the peak for the compound having the structure:

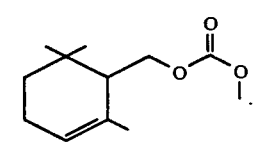

The peak indicated by reference numeral 593 is the peak for the compound having the structure:

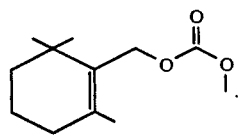

FIG. 60 is the NMR spectrum for the compound having the structure:

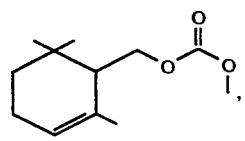

peak 591 of FIG. 59, prepared according to Example XVI. Sections marked "A", "B" and "C" are shown in detailed form in, respectively, FIGS. 60A, 60B and 60C.

FIG. 62 is the NMR spectrum for the compound having the structure:

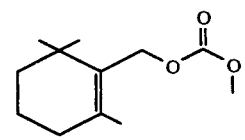

prepared according to Example XVI. Sections marked "A", "B" and "C" are shown in detailed form, in, respectively, FIGS. 62A, 62B and 62C.

FIG. 64 is the GLC profile for the reaction product of Example XVII. The peak indicated by reference numeral 640 is the peak for the compound having the structure:

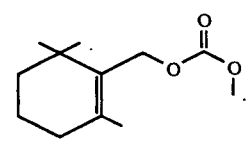

FIG. 65 is the NMR spectrum for the compound having the structure:

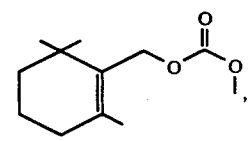

of peak 640 of FIG. 64. Sections marked "A", "B" and "C" are shown in detailed form, in, respectively, FIGS. 65A, 65B and 65C.

THE INVENTION

We have determined that certain alkyl cyclohexylmethyl and cyclohexenylmethyl carbonates defined according to the generic structure:

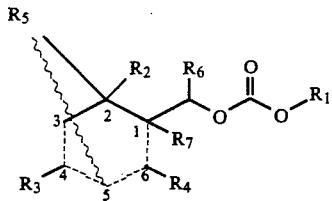

wherein $R_1$ is ethyl or methyl; $R_2$, $R_3$, $R_4$ and $R_6$ represent hydrogen or methyl; $R_5$ represents hydrogen, methyl or methylenes; and $R_7$ represents hydrogen or $C_1$–$C_4$ straight chain lower alkyl or isopropyl or $R_7$ is no moiety; the dashed lines represent carbon-carbon single bonds or carbon-carbon double bonds; and the wavy line represents a carbon-carbon single bond or no bond; with the provisos that:

(a) at least three of the dashed lines represent carbon-carbon single bonds;

(b) when $R_7$ is no moiety, the dashed line at the "1–6" position is a carbon-carbon double bond; and (c) when the wavy line is a carbon-carbon single bond, $R_5$ is methylene and the carbon-carbon bonds at the "4–5" and "5–6" positions are carbon-carbon single bonds;

are capable of imparting a variety of fragrances to various consumable materials and are also capable of augmenting or enhancing a variety of fragrances of various consumable materials.

Briefly, our invention contemplates augmenting or enhancing the fragrances of consumable materials such as perfumes, perfumed articles (e.g., solid or liquid anionic, cationic, nonionic or zwitterionic detergents, dryer-added fabric softeners and cosmetics) and colognes by adding thereto a small but effective amount of at least one of the alkyl cyclohexylmethyl and/or cyclohexenylmethyl carbonates defined according to the generic structure:

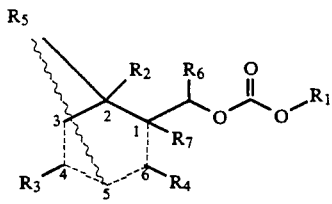

wherein $R_1$, $R_2$, $R_3$, $R_4$, $R_5$, $R_6$ and $R_7$ are defined, supra, and wherein the dashed and wavy lines are defined, supra.

The alkyl cyclohexylmethyl and cyclohexenylmethyl carbonates of our invention augment or enhance earthy, minty, eucalyptus, leathery, myrrh-like, sweet, green, herbal, fruity, banana, blueberry, ozoney, fresh air-dried clothing, floral, rose, violet, tulip, spicy, anisic, lavender, sweet, basic, woody, camphoraceous, winey and cognac aromas with floral, rose, green, cognac-like, balsamic, rum-like, sweet, air-dried clothing, ozoney and anisic topnotes and early morning forest path, earthy, rooty, eucalyptus, camphoraceous, minty, floral, rose, violet, tulip, green, sweet, aubepine, anisic, stemmy, fruity, pear-like, figgy, woody, spicy and clove-like undertones of perfumes, perfumed articles, such as cationic, anionic, nonionic or zwitterionic detergents and drier-added fabric softener articles and colognes.

The alkyl cyclohexylmethyl and cyclohexenylmethyl carbonates of our invention are produced according to techniques disclosed in U.S. Pat. No. 4,397,789 issued on Aug. 9, 1983 the specification for which is incorporated by reference herein as well as U.S. Pat. No. 4,033,993 issued on July 5, 1977 and U.S. Pat. No. 4,080,309 issued on Mar. 21, 1978 the specifications for which are incorporated by reference herein. More specifically, the alkyl cyclohexylmethyl and cyclohexenylmethyl carbonates of our invention are produced by reacting an alcohol derivative defined according to the generic structure:

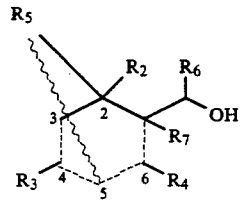

with a carbonate defined according to the structure:

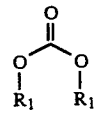

in the presence of an alkali metal alkoxide such as sodium methylate in a solvent such as methyl alcohol according to the reaction:

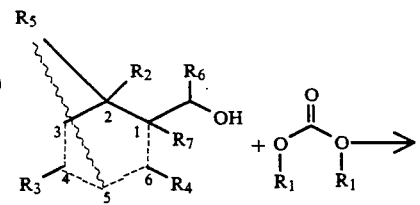

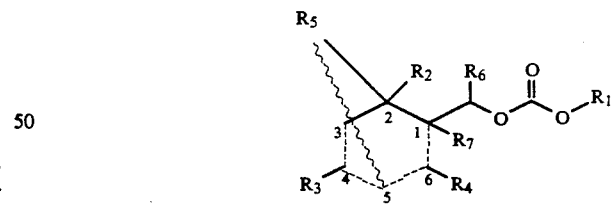

wherein $R_1$, $R_2$, $R_3$, $R_4$, $R_5$, $R_6$ and $R_7$ are defined, supra, and wherein the dashed lines and the wavy line are defined, supra.

At the end of the reaction the reaction mass is neutralized with weak acid such as acetic acid and then fractionally distilled in order to provide materials useful for augmenting or enhancing the aroma of perfume compositions, perfumed articles, or colognes.

The reaction useful in preparing the alkyl cyclohexylmethyl and cyclohexenylmethyl carbonates of our invention also prepare side products which are also useful in augmenting or enhancing the aroma of perfume compositions, colognes or perfumed articles and are useful as fixatives for perfumes as well as insect attractants or repellents. Such side products are defined according to the generic structures:

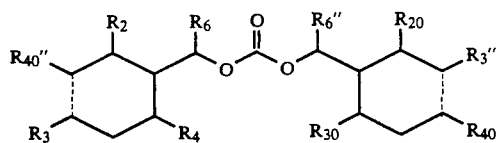

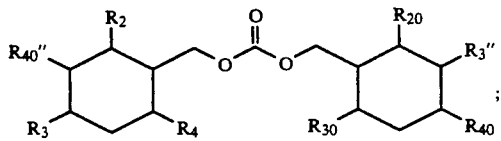

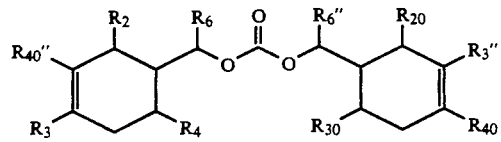

and

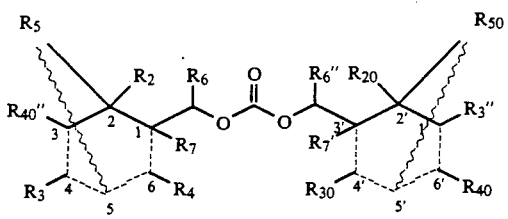

wherein $R_2$, $R_3$, $R_4$, $R_5$, $R_6$ and $R_7$ are defined, supra; wherein the wavy lines are defined, supra; wherein the dashed lines are defined, supra; wherein $R_2$ is the same as $R_{20}$; wherein $R_5$ is the same as $R_{50}$; wherein $R_3$ is the same as $R_{40}$; wherein $R_4$ is the same as $R_{30}$; wherein $R_7$ is the same as $R_7'$; wherein $R_3''$ and $R_{40}''$ are the same or different hydrogen or methyl.

The alkyl cyclohexylmethyl and cyclohexenylmethyl carbonates of our invention are pure isomers or mixtures of isomers defined according to the generic structures, for example, the generic structures:

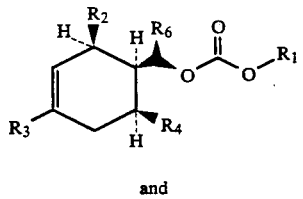

and

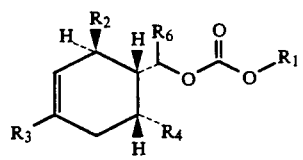

wherein the dashed lines show moieties below the plane of the cyclohexenyl moiety.

Examples of the alkyl cyclohexylmethyl and cyclohexenylmethyl carbonates of our invention and their organoleptic characteristics are as follows:

TABLE I

| Structure of Compound: | Fragrance Characteristics |
|---|---|
| The compound having the structure: [structure] prepared according to Example I. | A green, fruity, floral, rose, tulip, spicy and anisic aroma with floral, rose, tulip, green, stemmy, fruity, pear-like, spicy and clove-like undertones. |
| The compound having the structure: [structure] prepared according to Example II. | A green and fruity aroma with floral topnotes. |
| The compound having the structure: [structure] prepared according to Example III. | A green aroma with green topnotes. |
| The compound having the structure: [structure] prepared according to Example IV. | A green, fruity, anisic and lavender aroma with green and fruity undertones. |
| The compound having the structure: [structure] prepared according to Example V. | A sweet, anisic, herbal, basil, winey and cognac aroma profile with cognac-like and rum-like topnotes. |
| The compound having the structure: [structure] prepared according to Example VII. | A sweet, anisic aroma with sweet, "air-dried clothing", ozoney and anisic topnotes. |
| The compound having the structure: [structure] prepared according to Example VI. | An intense herbal, green, spicy, woody and cognac-like aroma with figgy and woody undertones. |
| The compound having the structure: | A leathery, myrrh-like aroma with balsamic and warm floral |

TABLE I-continued

| Structure of Compound: | Fragrance Characteristics |
|---|---|
| 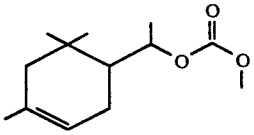 prepared according to Example VIII. | topnotes. |
| The compound having the structure: 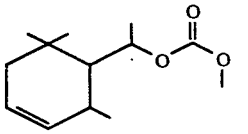 prepared according to Example IX. | An earthy, minty, eucalyptus, sweet, woody, camphoraceous aroma with early morning forest path, earthy, rooty, woody, eucalyptus and camphoraceous undertones. |
| The compound having the structure: 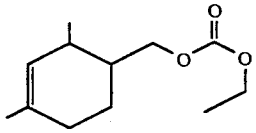 prepared according to Example X. | A fresh, green, herbaceous, and rose aroma. |
| The compound having the structure: 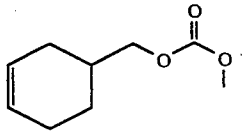 prepared according to Example XI. | A green, fruity, anisic, and violet aroma profile. |
| The compound having the structure: 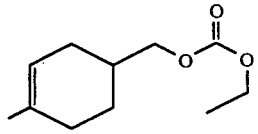 prepared according to Example XII. | A green, sweet, anisic aroma with green, sweet, aubepine, anisic undertones. |
| The compound having the structure: 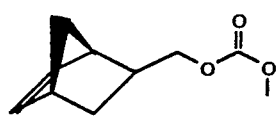 prepared according to Example XIII. | A fruity, banana, blueberry, green and violet aroma profile with fruity, green and violet undertones. |
| The compound having the structure: 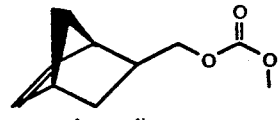 prepared according to Example XIV. | A fruity, violet aroma with fruity, minty and violet undertones. |
| The compound having the structure: 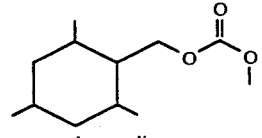 prepared according | A fresh, green, rose, ozoney and fresh air-dried clothing aroma with rose and green topnotes. |

TABLE I-continued

| Structure of Compound: | Fragrance Characteristics |
|---|---|
| to Example XV. | |

Thus, the alkyl cyclohexylmethyl and cyclohexenylmethyl carbonates of our invention can be used to contribute earthy, minty, eucalyptus, leathery, myrrh-like, sweet, green, herbal, fruity, banana, blueberry, ozoney, fresh air-dried clothing, floral, rose, violet, tulip, spicy, anisic, lavender, sweet, basic, woody, camphoraceous, winey and cognac aromas, with floral, rose, green, cognac-like, balsamic, rum-like, sweet, air-dried clothing, ozoney and anisic topnotes and early morning forest path, earthy, rooty, eucalyptus, camphoraceous, minty, floral, rose, violet, tulip, green, sweet, aubepine, anisic, stemmy, fruity, pear-like, figgy, woody, spicy and clove-like undertones to perfumes, perfumed articles and colognes.

As olfactory agents, the alkyl cyclohexylmethyl and cyclohexenylmethyl carbonates of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils, esters other than the esters of our invention and frequently hydrocarbons which are admixed so that the combined odors of the individual components produce a pleasant or desired fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of at least one of the alkyl cyclohexylmethyl and cyclohexenylmethyl carbonates of our invention which will be effective in perfume compositions depends on many factors, including the other ingredients, their amounts and the effects which are desired. It has been found that perfume compositions containing as little as 0.5% of at least one of the alkyl cyclohexylmethyl and cyclohexenylmethyl carbonates of our invention, or even less, can be used to impart interesting earthy, minty, eucalyptus, leathery, myrrh-like, sweet, green, herbal, fruity, banana, blueberry, ozoney, fresh air-dried clothing, floral, rose, violet, tulip, spicy, anisic, lavender, sweet, basil, woody, camphoraceous, winey and cognac aromas, with floral, rose, green, cognac-like, balsamic, rum-like, sweet, air-dried clothing, ozoney and anisic topnotes and early morning forest path, earthy, rooty, eucalyptus, camphoraceous, minty, floral, rose, violet, tulip, green, sweet, aubepine, anisic, stemmy, fruity, pear-like, figgy, woody, spicy and clove-like undertones to soaps, liquid and solid anionic, cationic, nonionic or zwitterionic detergents, cosmetics, powders, liquid and solid fabric softeners, optical brightener compositions and other products. The amount employed can range up to 50% or higher and will depend on considerations of cost, nature of the end product, and the effect desired on the finished product and particular fragrance sought.

The alkyl cyclohexylmethyl and cyclohexenylmethyl carbonates of our invention can be used alone or in a perfume composition as an olfactory component in detergents and soaps, space odorants and deodorants; perfumes, colognes, toilet waters; bath salts; hair preparations such as lacquers, brilliantines, pomades and shampoos; cosmetic preparations such as creams, deodorants, hand lotions, and sun screens; powders such as talcs, dusting powders, face powder, and the like. When used as an olfactory component of a perfumed article, as little as 0.01% of one or more of the alkyl cyclohexylmethyl and cyclohexenylmethyl carbonates of our invention will suffice to impart an interesting earthy, minty, eucalyptus, leathery, myrrh-like, sweet, green, herbal, fruity, banana, blueberry, ozoney, fresh air-dried clothing, floral, rose, violet, tulip, spicy, anisic, lavender, sweet, basil, woody, camphoraceous, winey and cognac aromas, with floral, rose, green, cognac-like, balsamic, rum-like, sweet, air-dried clothing, ozoney and anisic topnotes and early morning forest path, earthy, rooty, eucalyptus, camphoraceous, minty, floral, rose, violet, tulip, green, sweet, aubepine, anisic, stemmy, fruity, pear-like, figgy, woody, spicy and clove-like undertones. Generally no more than 0.5% is required. Thus, the percentage in perfumed articles of the alkyl cyclohexylmethyl and cyclohexenylmethyl carbonates of our invention ranges from 0.01% up to about 0.5% based on the weight of the perfumed article.

In addition, the perfume compositions of our invention can contain a vehicle or carrier for one or more of the alkyl cyclohexylmethyl and cyclohexenylmethyl carbonates of our invention taken alone or taken together with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil, by means of coacervation.

It will thus be apparent that one or more of the alkyl cyclohexylmethyl and cyclohexenylmethyl carbonates of our invention can be utilized to alter, modify, augment or enhance sensory properties particularly organoleptic properties such as fragrances of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

PREPARATION OF METHYL ISOCYCLOGERANIOL CARBONATE

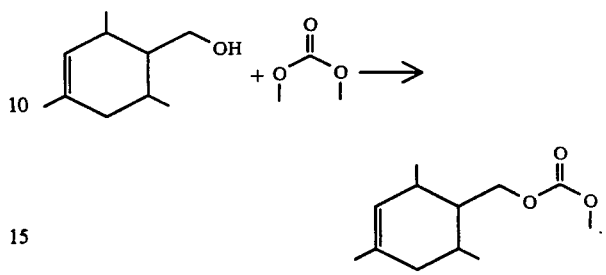

Into a 3 liter flask equipped with stirrer, thermometer, reflux condenser, heating mantle and equipped with nitrogen blanket provision apparatus are placed 500 grams of isocyclogeraniol having the structure:

(3.24 moles) and 885.0 grams of dimethyl carbonate (9.72 moles).

Over a 2.5 hour period while maintaining the reaction mass at 55°-60° C., 70.0 grams of a 25% solution of sodium methoxide is added to the reaction mass.

The reaction mass is then heated to 75°-80° C. and maintained at that temperature for a period of 0.5 hours. The reaction mass is then heated to 95°-100° C. (reflux) and maintained at reflux conditions for a period of six hours.

At the end of the six hour refluxing period, the reaction mass is cooled and 500 ml toluene taken together with 500 ml of 5% aqueous acetic acid is added to the reaction mass. The reaction mass is stirred for a period of 15 minutes and one 500 ml portion of 5% aqueous sodium bicarbonate followed by two 500 ml portions of 5% aqueous sodium chloride are added to the reaction mass. The organic phase is then separated from the aqueous phase and the organic phase is fractionally distilled yielding the following fractions:

| Fraction No. | Vapor Temp. (°C.) | Liquid Temp. (°C.) | Vacuum mm/Hg. Pressure |
|---|---|---|---|
| 1 | 87/90 | 110/109 | 1.35 |
| 2 | 89 | 106 | 1.18 |
| 3 | 88 | 104 | 1.26 |
| 4 | 85 | 100 | 0.735 |
| 5 | 78 | 89 | 0.625 |
| 6 | 75 | 95 | 0.557 |
| 7 | 74 | 92 | 0.550 |
| 8 | 73 | 88 | 0.537 |
| 9 | 78 | 102 | 0.530 |
| 10 | 70 | 93 | 0.4700 |
| 11 | 70 | 94 | 0.480 |
| 12 | 70 | 93 | 0.477 |
| 13 | 68 | 98 | 0.473 |
| 14 | 68 | 108 | 0.477 |
| 15 | 64 | 150 | 0.473 |
| 16 | 175 | 187 | 1.39 |
| 17 | 185 | 225 | 2.20 |

Fractions 7-12 are bulked. The bulked distillation fractions have a green, fruity, floral, rose, tulip, spicy, and anisic aroma, with floral, rose, tulip, green, stemmy, fruity, pear-like, spicy and clove-like undertones.

FIG. 1 is the GLC profile of the crude reaction product. The peak indicated by reference numeral 10 is the peak for isomers of the compound having the structure:

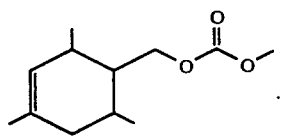

FIG. 2 is the GLC profile for bulked distillation fractions 7-12. The peaks indicated by reference numerals 21 and 22 are peaks for isomers of the compound having the structure:

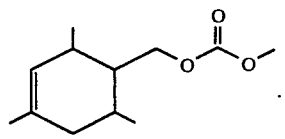

FIG. 3 is the NMR spectrum for the peak indicated by reference numeral 22 of the GLC profile of FIG. 2 for one of the isomers of the compound having the structure:

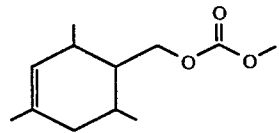

FIG. 4 is the infra-red spectrum for peak 22 of the GLC profile of FIG. 2 for one of the isomers of the compound having the structure:

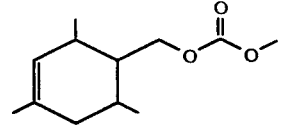

FIG. 5 is the NMR spectrum for peak 21 of the GLC profile of FIG. 2 for one of the isomers of the compound having the structure:

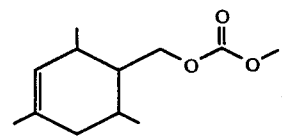

FIG. 6 is the infra-red spectrum for peak 21 of the GLC profile of FIG. 2 for one of the isomers of the compound having the structure:

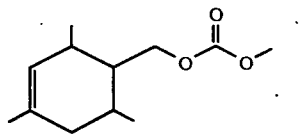

EXAMPLE II

PREPARATION OF ETHYL ISOCYCLOGERANIOL CARBONATE

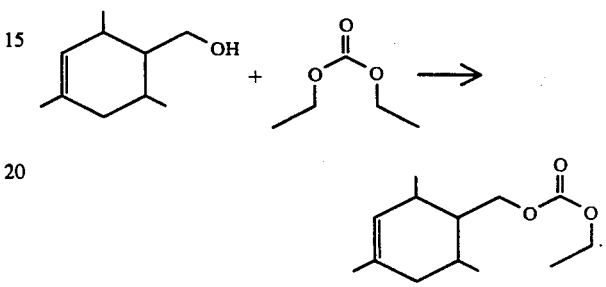

Into a 5 liter reaction vessel equipped with stirrer, thermometer, reflux condenser and provided with nitrogen blanket apparatus are placed 500.0 grams of isocyclogeraniol having the structure:

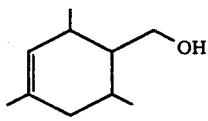

(3.24 moles) and 1160.0 grams of diethyl carbonate (9.72 moles). While maintaining the reaction mass at 40°-45° C. over a period of 0.5 hours, 105.0 grams of a 25% solution of sodium ethoxide in ethyl alcohol is added to the reaction mass (0.324 moles). The reaction mass is then heated to 70°-75° C. and maintained at that temperature for a period of 4.5 hours. At the end of the 4.5 hours, the reaction mass is heated to 101° C. (reflux conditions) and maintained at reflux conditions for a period of 12 hours. At the nd of the refluxing period (12 hour period) the reaction mass is cooled to room temperature and washed with 1000 ml of 5% aqueous acetic acid and 500 ml toluene. The reaction mass is then stirred for a period of 0.5 hours. The organic phase is separated from the aqueous phase and the organic phase is washed in sequence with one 700 ml portion of 5% sodium bicarbonate, followed by one 700 ml portion of aqueous sodium chloride. The reaction mass is then distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 77/80 | 108/108 | 0.505 | 9:1 |
| 2 | 82 | 108 | 0.553 | 9:1 |
| 3 | 84 | 108 | 0.550 | 9:1 |
| 4 | 87 | 110 | 0.537 | 9:1 |
| 5 | 87 | 112 | 0.525 | 4:1 |
| 6 | 87 | 108 | 0.520 | 4:1 |
| 7 | 80 | 105 | 0.495 | 4:1 |
| 8 | 78 | 104 | 0.490 | 4:1 |
| 9 | 78 | 104 | 0.488 | 4:1 |

| Fraction No. | Vapor Temp. (°C.) | Liquid Temp. (°C.) | Vacuum mm/Hg. Pressure | Reflux Ratio |
|---|---|---|---|---|
| 10 | 78 | 104 | 0.484 | 4:1 |
| 11 | 78 | 104 | 0.484 | 4:1 |
| 12 | 81 | 106 | 0.480 | 4:1 |
| 13 | 81 | 106 | 0.480 | 4:1 |
| 14 | 81 | 106 | 0.480 | 4:1 |
| 15 | 81 | 106 | 0.47 | 4:1 |
| 16 | 81 | 110 | 0.48 | 4:1 |
| 17 | 83 | 110 | 0.480 | 4:1 |
| 18 | 83 | 110 | 0.484 | 4:1 |
| 19 | 83 | 110 | 0.484 | 4:1 |
| 20 | 81 | 110 | 0.484 | 4:1. |

Distillation factions 8-16 are bulked and the bulked distillation fractions 8-16 have a green and fruity aroma with floral topnotes.

FIG. 7 is the GLC profile for the crude reaction product. The peaks indicated by reference numerals 71 and 72 are peaks for isomers of the compound having the structure:

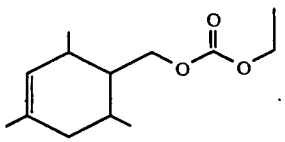

The peaks indicated by reference numerals 73, 74 and 75 are peaks for the side product having the structure:

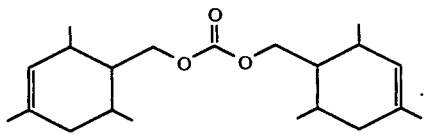

FIG. 8 is the infra-red spectrum for peaks 71 and 72 of the GLC profile of FIG. 7.

FIG. 9 is the NMR spectrum for peaks 71 and 72 of the GLC profile of FIG. 7. Sections "A" and "B" of FIG. 9 are set forth in detail, respectively, in FIGS. 9A and 9B.

EXAMPLE III

PREPARATION OF 2,4-DIMETHYL-3-CYCLOHEXENE-1-METHANOL, METHYL CARBONATE ESTER

Reaction:

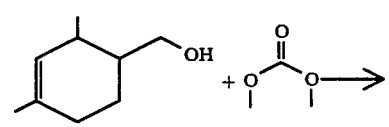

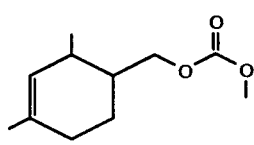

Into a 5liter reaction flask equipped with stirrer, thermometer, reflux condenser and provided with a nitrogen blanket apparatus are added 445.0 grams of the compound having the structure:

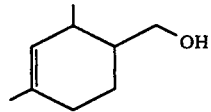

(3.17 moles) and 635 rams of dimethyl carbonate (6.97 moles). With stirring, over a period of 0.75 hours while maintaining the reaction mass at 35°-40° C., 70.0 grams of a 25% solution of sodium methoxide in methyl alcohol is added to the reaction mass (0.32 moles).

The temperature of the reaction mass is then increased to 50°-55° C. and maintained at that temperature for a period of 4.5 hours. At the end of the 4.5 hour period, the reaction mass is cooled to room temperature. The reaction mass is mixed with 500 ml 5% aqueous acetic acid and stirred for a period of 0.25 hours. The reaction mass is then mixed with 500 ml of toluene and stirred for a period of 0.25 hours.

The organic phase is separated from the aqueous phase and the organic phase is washed with one 500 cc volume of 5% acetic acid followed by two 500 cc volumes of 5% aqueous sodium bicarbonate followed by two 500 cc portions of aqueous saturated sodium chloride.

The organic phase is separated from the aqueous phase and the organic phase is distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 70/72 | 100/100 | 0.890 | 19:1 |
| 2 | 72 | 98 | 0.880 | 19:1 |
| 3 | 86 | 103 | 0.868 | 19:1 |
| 4 | 86 | 103 | 0.845 | 19:1 |
| 5 | 71 | 100 | 0.830 | 19:1 |
| 6 | 72 | 102 | 0.820 | 9:1 |
| 7 | 73 | 103 | 0.815 | 9:1 |
| 8 | 79 | 104 | 0.810 | 9:1 |
| 9 | 83 | 105 | 0.874 | 9:1 |
| 10 | 82 | 104 | 0.800 | 9:1 |
| 11 | 85 | 104 | 1.00 | 9:1 |
| 12 | 82 | 103 | 0.795 | 9:1 |
| 13 | 82 | 103 | 0.790 | 9:1 |
| 14 | 82 | 104 | 1.05 | 9:1 |
| 15 | 82 | 104 | 1.03 | 9:1 |
| 16 | 82 | 103 | 0.972 | 9:1 |
| 17 | 82 | 103 | 0.945 | 9:1 |
| 18 | 82 | 104 | 0.936 | 9:1 |
| 19 | 82 | 107 | 0.930 | 9:1 |
| 20 | 82 | 113 | 0.948 | 9:1 |
| 21 | 82 | 133 | 0.966 | 9:1 |
| 22 | 80 | 175 | 0.885 | 9:1 |
| 23 | 80 | 205 | 0.868 | 9:1. |

Fractions 10-20 are bulked. The bulked fractions 10-20 have a green aroma with green topnotes.

FIG. 10 is the GLC profile for the crude reaction product prior to distillation. The peaks indicated by reference numerals 103 and 104 are for isomers of the compound having the structure:

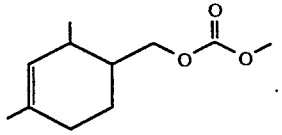

The peaks indicated by reference numerals 101 and 102 are for isomers of the compound having the structure:

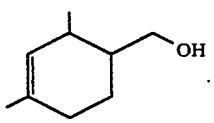

FIG. 11 is the NMR spectrum for peaks 103 and 104 of the GLC profile of FIG. 10.

FIG. 12 is the infra-red spectrum for peaks 103 and 104 of the GLC profile of FIG. 10.

EXAMPLE IV

PREPARATION OF 4-METHYL-3-CYCLOHEXENE-1-METHANOL, METHYL CARBONATE ESTER

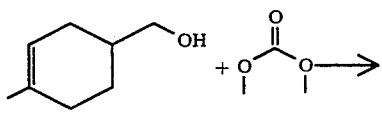

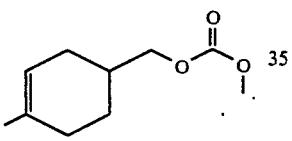

Into a 3 liter reaction vessel equipped with stirrer, thermometer, reflux condenser, heating mantle and provided with a nitrogen blanket apparatus, and under a nitrogen blanket are placed 500 grams of the compound having the structure:

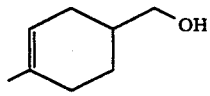

(3.96 moles) and 715.0 grams of dimethyl carbonate (7.92 moles). The reaction mass, with stirring, under a nitrogen blanket apparatus is then heated to 35°–40° C. Over a period of 0.5 hours with stirring while maintaining the reaction temperature at 35°–40° C., 86.0 grams of a 25% solution of sodium methoxide in methanol is added to the reaction mass (0.396 moles).

The reaction mass is then heated to 40°–45° C. and maintained at 40°–45° C. for a period of 4.5 hours. At the end of the 4.5 hour period, the reaction mass is cooled to room temperature and 1 liter of 5% aqueous acetic acid is added to the reaction mass. The reaction mass is stirred for a period 0.25 hours and the aqueous phase is separated from the organic phase. The organic phase is then washed with 1 liter of 5% aqueous sodium carbonate followed by two portions (1 liter each) of saturated sodium chloride.

The organic phase is separated from the aqueous phase and the organic phase is then distilled on an 18" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | /61 | /84 | 0.868 | 9:1 |
| 2 | 61 | 85 | 0.862 | 9:1 |
| 3 | 61 | 85 | 0.845 | 9:1 |
| 4 | 61 | 85 | 0.830 | 9:1 |
| 5 | 60 | 86 | 0.9 | 9:1 |
| 6 | 62 | 88 | 0.9 | 9:1 |
| 7 | 63 | 89 | 0.9 | 9:1 |
| 8 | 64 | 91 | 1.1 | 9:1 |
| 9 | 81 | 107 | 0.805 | 9:1 |
| 10 | 84 | 108 | 0.785 | 9:1 |
| 11 | 77 | 98 | 0.775 | 9:1 |
| 12 | 74 | 95 | 0.775 | 9:1 |
| 13 | 75 | 95 | 0.765 | 9:1 |
| 14 | 74 | 94 | 0.755 | 9:1 |
| 15 | 73 | 93 | 0.745 | 1:1 |
| 16 | 76 | 95 | 0.730 | 1:1 |
| 17 | 77 | 96 | 0.735 | 1:1 |
| 18 | 79 | 98 | 0.800 | 1:1 |
| 19 | 78 | 97 | 0.720 | 1:1 |
| 20 | 78 | 97 | 0.715 | 1:1 |
| 21 | 78 | 97 | 0.715 | 1:1 |
| 22 | 78 | 97 | 0.745 | 1:1 |
| 23 | 78 | 99 | 0.740 | 1:1 |
| 24 | 76 | 170 | 1.00 | 1:1 |
| 25 | 76 | 200 | 0.800 | 1:1. |

Fractions 16–21 are bulked. Bulked distillations fractions 16–21 have a green, fruity, anisic and lavender aroma with green and fruity undertones.

FIG. 13 is the GLC profile for the crude reaction product prior to distillation. The peak indicated by reference numeral 131 is the peak for the starting material having the structure:

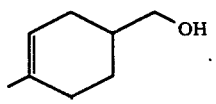

The peak indicated by reference numeral 132 is the peak for the reaction product having the structure:

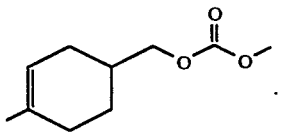

The peak indicated by reference numeral 133 is the peak for the side product having the structure:

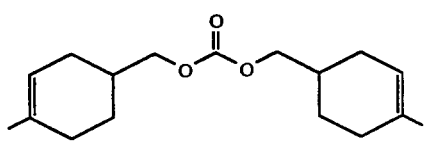

FIG. 14 is the NMR spectrum for the peak indicated by reference numeral 132 of the GLC profile of FIG. 13 for the compound having the structure:

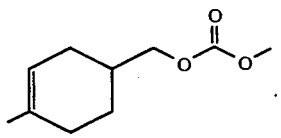

FIG. 15 is the infra-red spectrum for the peak indicated by reference numeral 132 of the GLC profile of FIG. 13 for the compound having the structure:

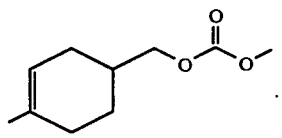

EXAMPLE V

PREPARATION OF THE METHYL ESTER OF METHYL(4-METHYL-3-CYCLOHEXENE-1-YL)CARBONIC ACID

Reaction:

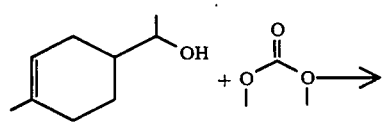

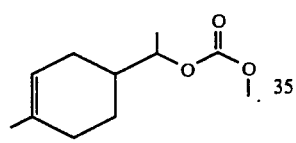

Into a 3 liter reaction vessel equipped with stirrer, thermometer, reflux condenser, heating mantle and supplied with a nitrogen blanket apparatus, and under a nitrogen blanket are added 370.0 grams of the compound having the structure:

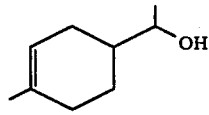

(2.64 moles) and 720 grams of dimethyl carbonate (7.92 moles).

With stirring the reaction mass is heated to 45°-50° C. and while maintaining the reaction mass at 45°-50° C. under a nitrogen blanket, 114.0 grams of a 25% solution of sodium methoxide in anhydrous methanol (0.528 moles) is added to the reaction mass over a period of one hour.

At the end of the one hour period, the reaction mass is heated to reflux (74° C.) and maintained under reflux conditions for a period of two hours. At the end of the two hour period, the reaction mass is cooled to room temperature and a mixture of 300 ml toluene and 500 ml 5% aqueous acetic acid is added to the reaction mass. The reaction mass is stirred for a period of 0.5 hours at room temperature. At the end of the 0.5 hour period, the organic phase is separated from the aqueous phase and the organic phase is washed with one 800 ml portion of saturated sodium chloride.

The organic phase is separated from the aqueous phase and the organic phase is distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 52/65 | 90/94 | 0.615 | 9:1 |
| 2 | 67 | 94 | 0.590 | 9:1 |
| 3 | 68 | 94 | 0.580 | 9:1 |
| 4 | 70 | 95 | 0.580 | 9:1 |
| 5 | 68 | 95 | 0.577 | 9:1 |
| 6 | 68 | 95 | 0.577 | 9:1 |
| 7 | 68 | 95 | 0.578 | 9:1 |
| 8 | 68 | 96 | 0.615 | 9:1 |
| 9 | 70 | 98 | 0.615 | 9:1 |
| 10 | 70 | 96 | 0.660 | 9:1 |
| 11 | 70 | 98 | 0.650 | 4:1 |
| 12 | 70 | 108 | 0.627 | 4:1 |
| 13 | 70 | 111 | 0.673 | 4:1 |
| 14 | 70 | 120 | 0.630 | 4:1 |
| 15 | 70 | 107 | 0.650 | 4:1 |
| 16 | 65 | 170 | 0.650 | 4:1. |

Fractions 4-13 are bulked.

Bulked distillation fractions 4-13 have a sweet, anisic, herbal, basil, winey and cognac aroma profile, with cognac-like and rum-like topnotes.

FIG. 16 is the GLC profile of the crude reaction product prior to distillation. The peak indicated by reference numeral 160 in the peak for the reaction solvent. The peak indicated by reference numeral 161 is the peak for the starting material having the structure:

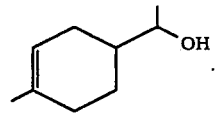

The peak indicated by reference numeral 162 is the peak for the reaction product having the structure:

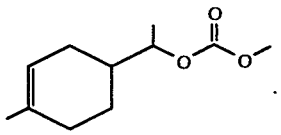

FIG. 17 is the infra-red spectrum for the peak indicated by reference numeral 162 of the GLC profile of FIG. 16 for the compound having the structure:

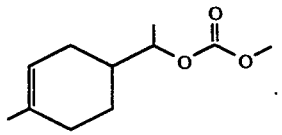

FIG. 18 is the NMR spectrum for the peak indicated by reference numeral 162 of the GLC profile of FIG. 16 for the compound having the structure:

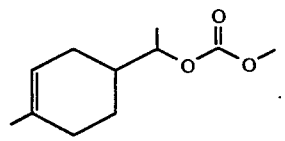

The sections of the NMR spectrum marked "A", "B", "C" and "D" are indicated in detail in FIGS. 18A, 18B, 18C and 18D, respectively.

EXAMPLE VI

PREPARATION OF THE METHYL ESTER OF METHYL(2,4-DIMETHYL CYCLOHEXYL)CARBONIC ACID

Reaction:

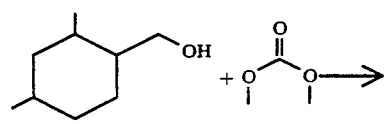

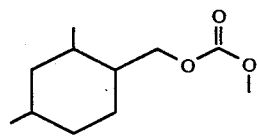

Into a 3 liter reaction vessel equipped with stirrer, thermometer, reflux condenser, heating mantle and provided with a nitrogen blanket apparatus, under a nitrogen blanket are placed 500.0 grams of the compound having the structure:

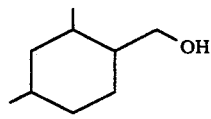

(3.52 moles) and 960.0 grams of dimethyl carbonate (10.5 moles). The reaction mass, with stirring, under nitrogen blanket is heated to 45°-50° C. While maintaining the reaction mass at 45°-50° C., over a period of one hour, 152.0 grams of a 25% solution of sodium methoxide is methanol (0.70 moles) is added to the reaction mass. At the end of the one hour period, the reaction mass is heated to reflux (82° C.) and maintained at reflux for a period of 2.5 hours. At the end of the 2.5 hour period, the reaction mass is cooled to room temperature and 500 ml toluene followed by 800 ml of 5% aqueous acetic acid (added dropwise) is added to the reaction mass. The reaction mass is then stirred for a period of 0.5 hours. The organic phase is then separated from the aqueous phase and the organic phase is washed with one 800 cc portion of saturated sodium chloride.

The organic phase is separated from the aqueous phase and the organic phase is distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 67/61 | 89/78 | 0.810 | 4:1 |
| 2 | 80 | 90 | 0.770 | 4:1 |
| 3 | 78 | 89 | 0.750 | 3:2 |

-continued

| Fraction No. | Vapor Temp. (°C.) | Liquid Temp. (°C.) | Vacuum mm/Hg. Pressure | Reflux Ratio |
|---|---|---|---|---|
| 4 | 82 | 95 | 0.750 | 3:2 |
| 5 | 88 | 106 | 0.856 | 3:2 |
| 6 | 95 | 100 | 0.850 | 3:2 |
| 7 | 65 | 85 | 0.735 | 3:2 |
| 8 | 64 | 85 | 0.730 | 3:2 |
| 9 | 66 | 87 | 0.730 | 3:2 |
| 10 | 65 | 87 | 0.725 | 3:2 |
| 11 | 65 | 87 | 0.725 | 3:2 |
| 12 | 65 | 87 | 0.725 | 3:2 |
| 13 | 66 | 87 | 0.725 | 7:3 |
| 14 | 70 | 91 | 0.725 | 7:3 |
| 15 | 70 | 91 | 0.725 | 7:3 |
| 16 | 70 | 91 | 0.725 | 7:3 |
| 17 | 70 | 93 | 0.705 | 4:1 |
| 18 | 65 | 90 | 0.690 | 4:1 |
| 19 | 64 | 97 | 0.680 | 4:1. |

Fractions 7-16 are bulked. Bulked distillation fractions 7-16 have an intense, herbal, green, spicy, woody and cognac-like aroma with figgy and woody undertones.

FIG. 19 is the GLC profile of the crude reaction product prior to distillation. The peak indicated by reference numeral 190 is the peak for the compound having the structure:

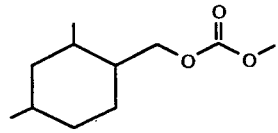

FIG. 20 is the NMR spectrum for the peak indicated by reference numeral 190 of the GLC profile of FIG. 19 for the compound having the structure:

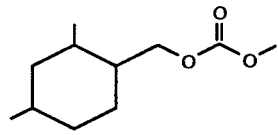

Sections "A" and "B" of the NMR spectrum of FIG. 20 are shown in detail, respectively, in FIGS. 20A and 20B.

FIG. 21 is the infra-red spectrum for the peak indicated by reference numeral 190 of the GLC profile of FIG. 19 for the compound having the structure:

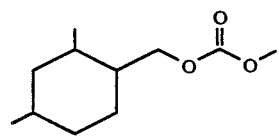

EXAMPLE VII

PREPARATION OF THE METHYL ESTER OF METHYL (4-METHYL CYCLOHEXYL) CARBONIC ACID

Reaction:

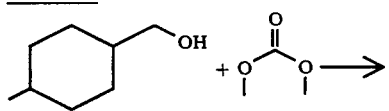

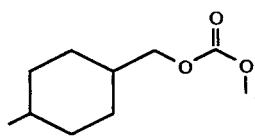

Into a 3 liter reaction vessel equipped with stirrer, thermometer, reflux condenser, heating mantle and provided with a nitrogen blanket apparatus, under a nitrogen blanket are added 532.0 grams of the compound having the structure:

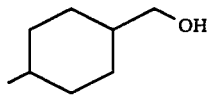

(4.15 moles) and 1135.0 grams of dimethyl carbonate (12.45 moles). Under a nitrogen blanket the reaction mass is heated to 50°-55° C. Over a period of one hour with stirring at 50°-55° C., 108.0 grams of a 25% solution of sodium methoxide in methanol is added to the reaction mass. At the end of the one hour period, the reaction mass is heated to reflux (70°-74° C. and refluxed for a period of 12 hours). At the end of the 12 hour period, the reaction mass is cooled to room temperature. 600 ml of 5% Aqueous acetic acid is added to the reaction mass followed by 250 ml toluene. The organic phase is then washed in sequence with one 800 ml portion of 5% aqueous sodium bicarbonate followed by one 800 ml portion of saturated sodium chloride.

The aqueous phase is separated from the organic phase and the organic phase is then distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 52/61 | 81/84 | 0.785 | 9:1 |
| 2 | 63 | 76 | 0.755 | 9:1 |
| 3 | 71 | 83 | 0.700 | 9:1 |
| 4 | 70 | 82 | 0.690 | 9:1 |
| 5 | 68 | 82 | 0.685 | 4:1 |
| 6 | 68 | 84 | 0.69 | 4:1 |
| 7 | 68 | 84 | 0.69 | 4:1 |
| 8 | 70 | 85 | 0.685 | 4:1 |
| 9 | 75 | 88 | 1.02 | 4:1 |
| 10 | 85 | 92 | 0.669 | 4:1 |
| 11 | 85 | 92 | 0.67 | 4:1 |
| 12 | 85 | 92 | 0.67 | 4:1 |
| 13 | 85 | 92 | 0.67 | 4:1 |
| 14 | 85 | 92 | 0.67 | 4:1 |
| 15 | 85 | 92 | 0.67 | 4:1 |
| 16 | 60 | 80 | 0.765 | 4:1 |
| 17 | 60 | 82 | 0.730 | 4:1 |
| 18 | 69 | 83 | 0.740 | 4:1 |
| 19 | 58 | 82 | 0.710 | 4:1. |

Fractions 5-15 are bulked. Bulked distillation fractions 5-15 have a sweet, anisic aroma, with sweet, "air-dried clothing"-like, ozoney and anisic topnotes.

FIG. 22 is the GLC profile for the crude reaction product prior to distillation. The peak indicated by reference numeral 324 is the peak for the reaction product having the structure:

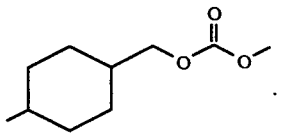

The peak indicated by reference numeral 323 is the peak for the starting material having the structure:

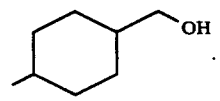

The peak indicated by reference numeral 322 is the peak for the reaction solvent. The peak indicated by reference numeral 325 is the peak for the bi-product of the reaction having the structure:

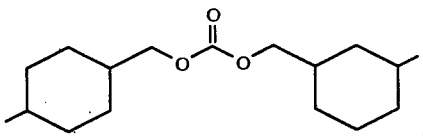

FIG. 23 is the GLC profile for the peak indicated by reference numeral 324 of the GLC profile of FIG. 22 for the compound having the structure:

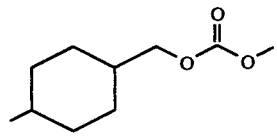

The sections of the NMR spectrum "A" and "B" are shown in detail, respectively, in FIGS. 23A and 23B.

FIG 24 is the infra-red spectrum for the peak indicated by reference numeral 324 of the GLC profile of FIG. 22 for the compound having the structure:

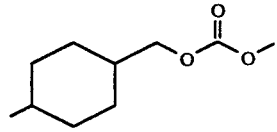

FIG. 25 is the NMR spectrum for the peak indicated by reference numeral 325 of the GLC profile of FIG. 22 for the compound having the structure:

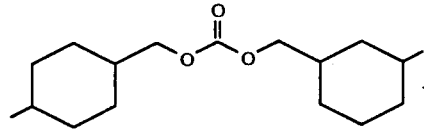

The sections of the NMR spectrum, "A" and "B", are shown in detail, respectively, on FIGS. 25A and 25B.

FIG. 26 is the infra-red spectrum for the peak indicated by reference numeral 325 of the GLC profile of FIG. 22 for the compound having the structure:

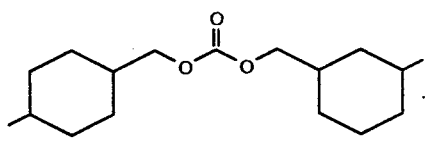

EXAMPLE VIII

PREPARATION OF ALPHA,4,6,6-TETRAMETHYL-3-CYCLOHEXENE-1-METHANOL, METHYL CARBONATE

Reaction:

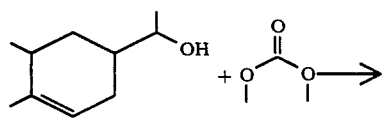

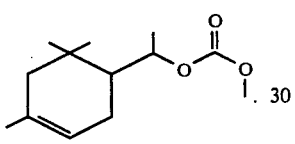

Into a 1 liter flask equipped with stirrer, thermometer, heating mantle and Bidwell water trap are placed 723 grams (1.63 moles) of the compound having the structure:

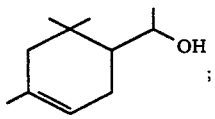

300 grams (3.33 moles) of dimethyl carbonate; and 40 grams of 25% sodium methylate. The reaction mass is then heated with stirring to 80° C. while removing water. The reaction mass is maintained at 75°-80° C. with stirring for a period of five hours. At the end of the five hour period, the reaction mass is quenched with 10 grams of acetic acid and then washed with saturated sodium chloride (equal volume). The reaction mass is then fractionated on a 4" splash column yielding the following fractions:

| Fraction No. | Vapor Temp. (°C.) | Liquid Temp. (°C.) | Vacuum mm/Hg. Pressure |
|---|---|---|---|
| 1 | 26/ | 85/ | 8.0 |
| 2 | 77 | 106 | 6.0 |
| 3 | 105 | 145 | 2.5 |
| 4 | 110 | 160 | 2.5 |
| 5 | 105 | 182 | 1.1. |

Fractions 3, 4 and 5 are bulked and redistilled on a spinning band column yielding the following fractions:

| Fraction No. | Vapor Temp. (°C.) | Liquid Temp. (°C.) | Vacuum mm/Hg. Pressure |
|---|---|---|---|
| 1 | 60/ | 120/ | 1.8 |
| 2 | 62 | 123 | 1.8 |
| 3 | 60 | 121 | 1.8 |
| 4 | 80 | 120 | 3.4 |
| 5 | 80 | 120 | 1.8 |
| 6 | 80 | 120 | 2.2 |
| 7 | 88 | 136 | 1.6 |
| 8 | 87 | 132 | 1.8 |
| 9 | 94 | 134 | 2.4 |
| 10 | 92 | 135 | 2.4 |
| 11 | 93 | 132 | 2.4 |
| 12 | 92 | 130 | 2.4 |
| 13 | 100 | 127 | 4.0 |
| 14 | 100 | 128 | 4.0 |
| 15 | 88 | 124 | 2.1 |
| 16 | 88 | 126 | 2.0 |
| 17 | 88 | 124 | 1.6 |
| 18 | 78 | 148 | |
| 19 | 125 | 173 | 1.4. |

Fractions 9-14 are bulked.

Bulked distillation Fractions 9-14 have a leathery, myrrh-like aroma with balsamic and warm floral topnotes.

FIG. 29 is the GLC profile of the reaction product containing the compound having the structure:

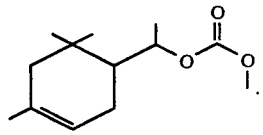

FIG. 30 is the NMR spectrum for the compound having the structure:

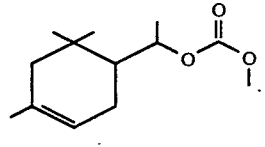

EXAMPLE IX

PREPARATION OF ALPHA,2,6,6-TETRAMETHYL-3-CYCLOHEXENE-1METHANOL, METHYL CARBONATE

Reaction:

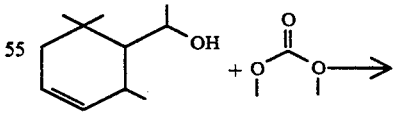

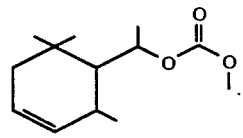

Into a 3 liter flask equipped with stirrer, thermometer, reflux condenser and heating mantle are placed 315 grams (1.85 moles) of the compound having the structure:

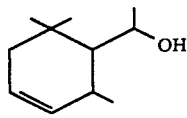

and 505 grams of dimethyl carbonate.

With stirring, allowing the temperature to rise to 35°-40° C., 40 grams of a 25% solution of sodium methoxide in methanol (0.185 moles) is added to the reaction mass over a period of two hours. At the end of the two hour period, the reaction mass is heated to 70°-75° C. and reflux at 75° C. for a period of twelve hours.

At the end of the twelve hour period, the reaction mass is cooled and 500 cc of 5% acetic acid followed by 200 cc toluene are admixed with the reaction mass. The reaction mass is agitated for twenty minutes. The organic phase is then separated from the aqueous phase and the organic phase is washed as follows:

1-500 cc volume of 5% acetic acid;
1-500 cc portion of 5S sodium bicarbonate,
2-500 cc portions of saturated sodium chloride.

The reaction mass is then distilled on a 12" Goodloe column yielding the following fractions:

| Fraction No. | Vapor Temp. (°C.) | Liquid Temp. (°C.) | Vacuum mm/Hg. Pressure |
|---|---|---|---|
| 1 | /72 | /102 | 1.86 |
| 2 | 81 | 102 | 1.86 |
| 3 | 82 | 100 | 1.86 |
| 4 | 86 | 105 | 2.06 |
| 5 | 86 | 105 | — |
| 6 | 86 | 105 | — |
| 7 | 84 | 99 | 1.49 |
| 8 | 83 | 104 | 0.79 |
| 9 | 83 | 104 | 0.76 |

Fractions 6 and 7 are bulked.

Bulked distillation Fractions 6 and 7 have an earthy, minty, eucalyptus, sweet, woody, camphoraceous aroma, with early morning forest path, earthy, rooty, woody, eucalyptus, and camphoraceous undertones.

FIG. 31 is the GLC profile for the reaction product containing the compound having the structure:

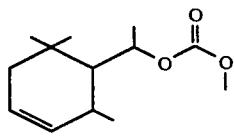

The peak indicated by reference numeral 314 is the peak for the reaction product having the structure:

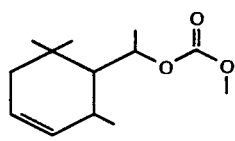

FIG. 9 is also a GLC profile for the reaction product. The peak indicated by reference numeral 317 is the peak for the compound having the structure:

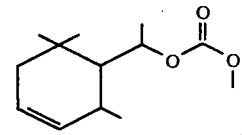

FIG. 33 is the NMR spectrum for the compound having the structure:

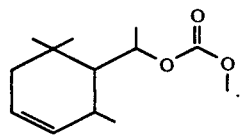

FIG. 34 is the infra-red spectrum for the compound having the structure:

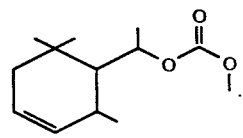

EXAMPLE X

PREPARATION OF 2,4-DIMETHYL-3-CYCLOHEXENE-1-METHANOL ETHYL CARBONATE

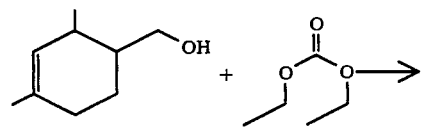

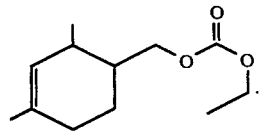

Into a 5 liter reaction vessel equipped with stirrer, thermometer, reflux condenser and heating mantle are placed 700 grams of the compound having the structure:

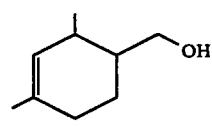

and 1,790 grams of diethyl carbonate. With stirring, the reaction mass is heated to 50°-55° C. Over a one hour period, 108 grams of a 25% solution of sodium methoxide in methyl alcohol is added to the reaction mass.

The reaction mass temperature is then increased to 85°-90° C. and maintained at 88°-92° C. with refluxing for a period of twelve hours.

The reaction mass is then quenched with 1000 cc of 5% acetic acid followed by 250 cc of toluene. The reaction mass is then washed as follows:

1-800 cc volume of acetic acid;

1 volume of 5% sodium bicarbonate.

The organic phase is separated from the aqueous phase and the organic phase is distilled on a fractionation column yielding the following fractions:

| Fraction No. | Vapor Temp. (°C.) | Liquid Temp. (°C.) | Vacuum mm/Hg. Pressure |
|---|---|---|---|
| 1 | 105/106 | 122/120 | 1.02 |
| 2 | 100 | 112 | 0.675 |
| 3 | 91 | 104 | 0.610 |
| 4 | 85 | 102 | 0.565 |
| 5 | 83 | 103 | 0.550 |
| 6 | 79 | 108 | 0.500 |
| 7 | 78 | 110 | 0.495 |
| 8 | 66 | 165 | 0.645 |
| 9 | 69 | 182 | 1.28 |

Fraction 4–7 are bulked. Bulked distillation Fractions 4–7 have a fresh, green, herbaceous and rose aroma profile.

FIG. 35 is the GLC profile for the reaction product. The peaks indicated by reference numerals 354 and 355 are for the reaction product having the structure:

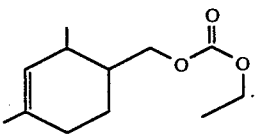

FIG. 36 is the infra-red spectrum for the compound having the structure:

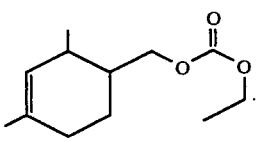

FIG. 37 is the NMR spectrum for the compound having the structure:

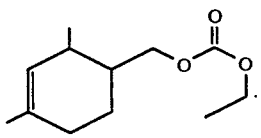

EXAMPLE XI

PREPARATION OF THE METHYL ESTER OF [3-CYCLOHEXENE-1-YL] METHYL CARBONIC ACID

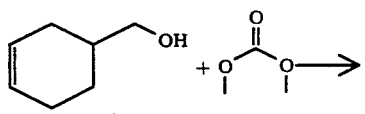

Into a 3 liter reaction vessel equipped with stirrer, thermometer, reflux condenser and heating mantle and nitrogen blanket apparatus is placed 200 cc toluene; 395 grams of the compound having the structure:

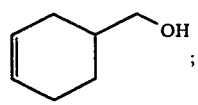

and 38.0 grams of sodium methoxide (powder).

The reaction mass is heated to 70°–75° C. with stirring. Over a period of one hour, 960 grams of dimethyl carbonate is added to the reaction mass with stirring while maintaining the temperature at 70°–75° C.

At the end of the feed, the reaction temperature is maintained at 70°–75° C. The reaction mass is then maintained at reflux at 74° C. for a period of six hours. At the end of the six hour period, the reaction mass is cooled to 60° C. and 300 cc toluene followed by 700 cc of 5% acetic acid is added to the reaction mass. The organic phase is separated from the aqueous phase and the organic phase is washed as follows:

1–700 cc volume of 5% acetic acid;
1–700 cc volume of saturated sodium chloride.

The organic phase is then fractionally distilled on a 12″ Goodloe column yielding the following fractions:

| Fraction No. | Vapor Temp. (°C.) | Liquid Temp. (°C.) | Vacuum mm/Hg. Pressure |
|---|---|---|---|
| 1 | 40/71 | 70/68 | 0.645 |
| 2 | 59 | 74 | 0.627 |
| 3 | 57 | 75 | 0.610 |
| 4 | 40 | 72 | 0.605 |
| 5 | 45 | 76 | 0.593 |
| 6 | 56 | 78 | 0.745 |
| 7 | 57 | 80 | 0.920 |
| 8 | 57 | 80 | 0.750 |
| 9 | 57 | 76 | 0.868 |
| 10 | 55 | 73 | 0.663 |
| 11 | 54 | 73 | 0.780 |
| 12 | 50 | 73 | 0.573 |
| 13 | 53 | 73 | 0.720 |
| 14 | 49 | 72 | 0.533 |
| 15 | 53 | 73 | 0.850 |
| 16 | 60 | 73 | 1.12 |
| 17 | 60 | 73 | 1.05 |
| 18 | 53 | 73 | 0.650 |
| 19 | 53 | 73 | 0.689 |
| 20 | 65 | 85 | 1.44 |

Fractions 6–16 are bulked.

Bulked distillation Fractions 6–16 have a green, fruity, anisic, floral and violet aroma profile.

FIG. 38 is the GLC profile for the reaction product. The peak indicated by reference numeral 364 is the peak for the compound having the structure:

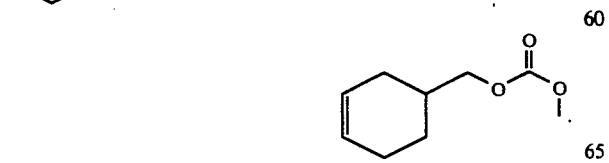

The peak indicated by reference numeral 366 is the peak for the compound having the structure:

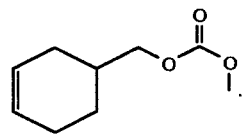

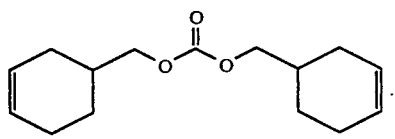

FIG. 39 is the NMR spectrum for the compound having the structure:

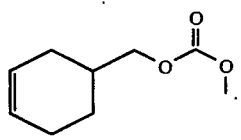

FIG. 40 is the infra-red spectrum for the compound having the structure:

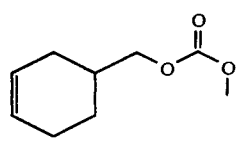

FIG. 41 is the NMR spectrum for the compound having the structure:

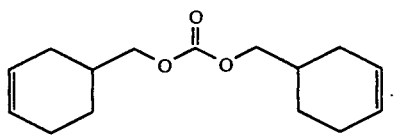

FIG. 42 is the infra-red spectrum for the compound having the structure:

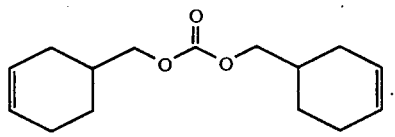

EXAMPLE XII

PREPARATION OF 4-METHYL-3-CYCLOHEXENE-1-METHANOL, ETHYL CARBONATE

Reaction:

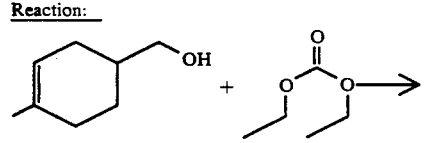

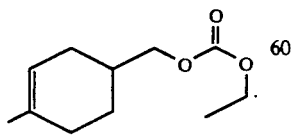

Into a 3 liter reaction vessel equipped with nitrogen blanket apparatus, stirrer, thermometer, reflux condenser and heating mantle are placed 415 grams of the compound having the structure:

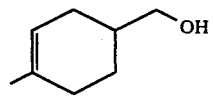

and 1178 grams of diethyl carbonate. The reaction mass is heated to 50°-55° C. with stirring. Over a period of one hour, 72 grams of sodium methoxide (25% solution in methanol) is added to the reaction mass.

The reaction mass is then heated to 85°-90° C. and maintained at 87°-96° C. for a period of ten hours. At the end of the ten hour period, the reaction mass is cooled and quenched with 500 cc of 5% acetic acid followed by 250 cc of toluene.

The reaction mass is then washed as follows:
1-600 cc volume of 5% sodium bicarbonate;
1-600 cc volume of saturated sodium chloride solution.

The reaction mass is then distilled on a 4" splash column yielding the following fractions:

| Fraction No. | Vapor Temp. (°C.) | Liquid Temp. (°C.) | Vacuum mm/Hg. Pressure |
|---|---|---|---|
| 1 | 110/110 | 123/122 | 21.0 |
| 2 | 98 | 112 | 13.2 |
| 3 | 83 | 98 | 2.20 |
| 4 | 80 | 90 | 1.69 |
| 5 | 86 | 100 | 1.65 |
| 6 | 85 | 100 | 1.64 |
| 7 | 85 | 100 | 1.70 |
| 8 | 85 | 104 | 1.63 |
| 9 | 85 | 104 | 1.64 |
| 10 | 85 | 104 | 1.64 |
| 11 | 85 | 129 | 1.58 |
| 12 | 72 | 150 | 1.52. |

Fractions 3-11 are bulked.

Distillation Fractions 3-11 containing primarily the compound having the structure:

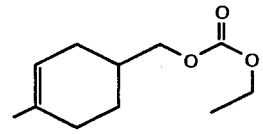

have a green, sweet, anisic aroma, with green, sweet, aubepine and anisic undertones.

FIG. 43 is the GLC profile of the reaction product of Example XXI. The peak indicated by reference numeral 373 is the peak for the compound having the structure:

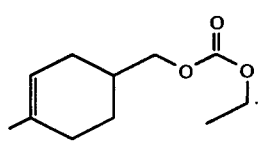

The peak indicated by reference numeral 372 is the peak for the compound having the structure:

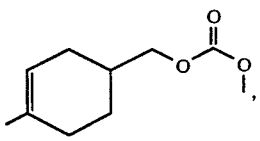

a side product resulting from the presence of the methanol solvent. The peak indicated by reference numeral 371 is for the starting material having the structure:

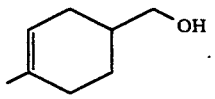

The peak indicated by reference numeral 374 is for another bi-product having the structure:

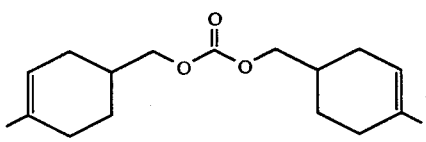

FIG. 44 is the NMR spectrum for the compound having the structure:

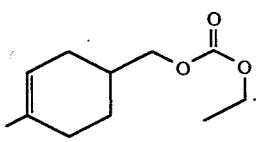

FIG. 45 is the infra-red spectrum for the compound having the structure:

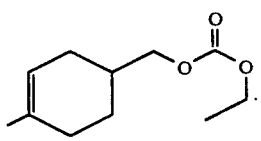

FIG. 46 is the NMR spectrum for the compound having the structure:

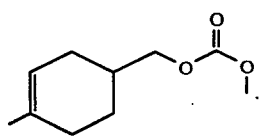

FIG. 47 is the infra-red spectrum for the compound having the structure:

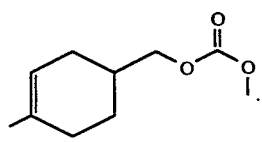

FIG. 48 is the NMR spectrum for the compound having the structure:

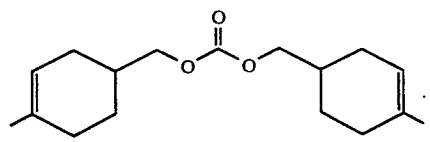

FIG. 49 is the infra-red spectrum for the compound having the structure:

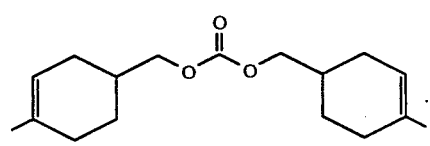

EXAMPLE XIII

PREPARATION OF 5-NORBORNENE-2-METHANOL, METHYL CARBONATE

Reaction:

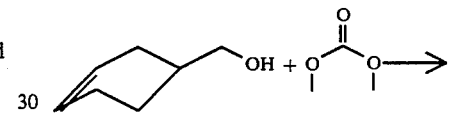

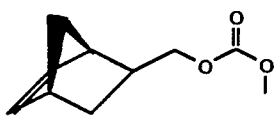

Into a 3 liter reaction vessel equipped with nitrogen blanket apparatus, stirrer, thermometer, reflux condenser and heating mantle are placed 500 grams of 5-norbornene-2-methanol having the structure:

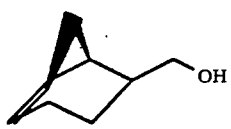

and 1080 grams of dimethyl carbonate. With stirring, the mixture is heated to 50°-55° C. Over a period of one hour, 173 grams of a 25% solution of sodium methoxide and methanol is added to the reaction mass. The reaction mass with stirring is heated to 100°110° C. and maintained at a temperature of 90°-100° C. for a period of seven hours while refluxing and removing methanol, using a Dean-stark trap.

The reaction mass is then cooled to room temperature and 300 cc toluene and 500 cc 5% aqueous acetic acid are added to the reaction mass. The organic phase is separated from the aqueous phase and the organic phase is then washed with one 500 cc portion of 5% acetic acid followed by one 500 cc portion of saturated sodium chloride solution.

The organic phase is then fractionally distilled using a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 57/67 | 88/94 | 1.35 | 9:1 |
| 2 | 63 | 89 | 1.31 | 7:3 |
| 3 | 63 | 90 | 1.31 | 7:3 |
| 4 | 63 | 90 | 1.30 | 7:3 |
| 5 | 63 | 90 | 1.29 | 7:3 |
| 6 | 63 | 91 | 1.29 | 7:3 |
| 7 | 62 | 92 | 1.29 | 7:3 |
| 8 | 63 | 92 | 1.27 | — |
| 9 | 63 | 92 | 1.28 | — |
| 10 | 62 | 96 | 1.28 | — |
| 11 | 62 | 97 | 1.27 | — |
| 12 | 62 | 100 | 1.28 | — |
| 13 | 62 | 105 | 1.28 | — |
| 14 | 62 | 112 | 1.27 | — |
| 15 | 60 | 129 | 1.27 | — |
| 16 | 60 | 160 | 1.26 | — |
| 17 | 100 | 163 | 1.26 | — |
| 18 | 139 | 176 | 1.22 | 7:3 |
| 19 | 139 | 175 | 1.21 | 7:3 |
| 20 | 139 | 175 | 1.20 | 7:3 |
| 21 | 139 | 177 | 1.20 | 7:3 |

Fractions 5–15 are bulked.

Bulked distillation Fractions 5–15 have a fruity, banana, blueberry, green and violet aroma profile, with fruity, green and violet undertones.

FIG. 50 is the GLC profile of the reaction product. The peak indicated by reference numeral 381 is the peak for the compound having the structure:

The peak indicated by reference numeral 382 is the peak for the compound having the structure:

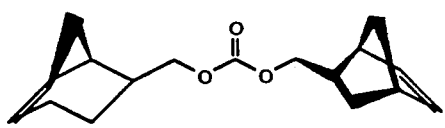

FIG. 51 is the NMR spectrum for the compound having the structure:

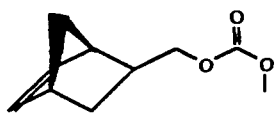

FIG. 52 is the infra-red spectrum for the compound having the structure:

EXAMPLE XIV

PREPARATION OF METHYL-2-NORBORNYLMETHYL ESTER OF CARBONIC ACID

Reaction:

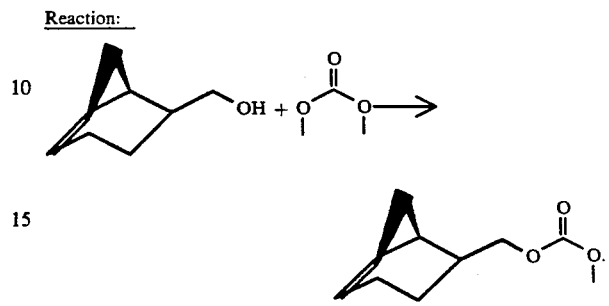

Into a 3 liter reaction vessel equipped with nitrogen blanket apparatus, stirrer, thermometer, reflux condenser and heating mantle are placed 500 grams of the compound having the structure:

and 1050 grams of dimethyl carbonate together with 300 cc of toluene.

Over a one hour period, 42 grams of powdered sodium methoxide is added to the reaction mass.

The reaction mass with stirring is heated to 70°–80° C. The reaction mass is then maintained at 90°–100° C. (refluxing) and continue to reflux at 86° C. for a period of five hours.

At the end of the five hour period, 200 cc toluene is added to the reaction mass. This is followed by 700 cc of 5% acetic acid.

The organic phase is separated from the aqueous phase.

The organic phase is washed with one 700 cc volume of saturated sodium chloride and then distilled using a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 57/62 | 91/91 | 0.856 | 4:1 |
| 2 | 66 | 92 | 0.895 | 4:1 |
| 3 | 61 | 89 | 0.840 | 4:1 |
| 4 | 60 | 88 | 0.825 | 4:1 |
| 5 | 60 | 88 | 0.825 | 4:1 |
| 6 | 60 | 88 | 0.820 | 4:1 |
| 7 | 60 | 88 | 0.815 | — |
| 8 | 60 | 90 | 0.820 | — |
| 9 | 60 | 90 | 0.815 | — |
| 10 | 60 | 90 | 0.815 | — |
| 11 | 60 | 90 | 0.815 | — |
| 12 | 62 | 95 | 1.17 | — |
| 13 | 63 | 98 | 1.15 | 4:1 |
| 14 | 62 | 102 | 1.14 | 4:1 |
| 15 | 61 | 117 | 1.13 | 4:1 |

Fractions 4–5 are bulked.

Bulked Fractions 4–15 have a fruity, violet aroma with fruity, minty and violet undertones.

FIG. 53 is the GLC profile for the reaction product containing the compound having the structure:

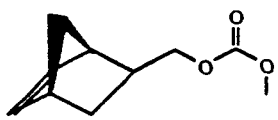

FIG. 54 is the NMR spectrum for the compound having the structure:

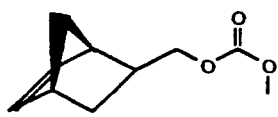

FIG. 55 is the infra-red spectrum for the compound having the structure:

EXAMPLE XV

PREPARATION OF THE METHYL CARBONATE OF DIHYDROISOCYCOGERANIOL

Reaction:

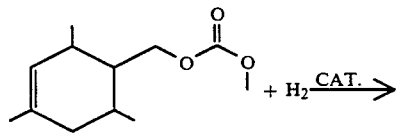

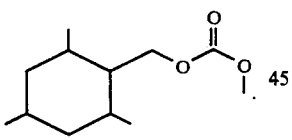

Into a 1 liter high pressure autoclave is placed 504.0 grams of the compound having the structure:

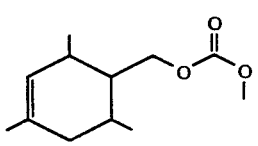

and 10.0 grams of a Raney nickel catalyst (grade E 480P, Lot 480-748P, CALSICAT®).

At a temperature of 115° C. and a pressure of 350 psig hydrogen is pumped into the autoclave. The autoclave is stirred for a period of two hours. At the end of the two hour period, the contents of the autoclave are cooled and the autoclave is depressurized and opened. The contents are filtered and the resulting filtrate is then distilled on a spinning band column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 96/30 | 141/111 | 0.600 | 20:1 |
| 2 | 52 | 113 | 0.500 | 20:1 |
| 3 | 50 | 112 | 0.450 | 20:1 |
| 4 | 48 | 113 | 0.350 | 200:1 |
| 5 | 48 | 114 | 0.350 | 20:1 |
| 6 | 48 | 115 | 0.350 | 20:1 |
| 7 | 48 | 115 | 0.350 | 20:1 |
| 8 | 48 | 115 | 0.350 | 50:1 |
| 9 | 48 | 115 | 0.320 | 50:1 |
| 10 | 48 | 113 | 0.300 | 50:1 |
| 11 | 48 | 113 | 0.340 | — |
| 12 | 48 | 113 | 0.320 | 50:1 |
| 13 | 48 | 113 | 0.370 | 50:1 |
| 14 | 48 | 113 | 0.300 | — |
| 15 | 50 | 116 | 0.325 | 20:1 |
| 16 | 58 | 117 | 0.310 | 20:1 |
| 17 | 52 | 117 | 0.300 | 200:1 |
| 18 | 56 | 118 | 0.290 | 30:1 |
| 19 | 92 | 118 | 3.80 | 30:1 |
| 20 | 60 | 120 | 0.300 | 30:1 |
| 21 | 42 | 110 | 0.260 | 50:1 |
| 22 | 42 | 110 | 0.250 | — |
| 23 | 42 | 110 | 0.250 | 50:1 |
| 24 | 43 | 111 | 0.250 | 50:1 |
| 25 | 44 | 120 | 0.250 | —. |

Distillation Fractions 6-18 are bulked.

Bulked distillation Fractions 6-18 have a fresh, green, rose, ozoney, fresh air-dried clothing aroma, with rose and green topnotes.

FIG. 56 is the GLC profile of the reaction product prior to distillation. The peak indicated by reference numeral 560 is the peak for the compound having the structure:

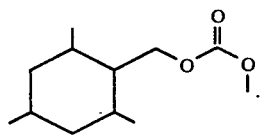

FIG. 57 is the NMR spectrum for the compound having the structure:

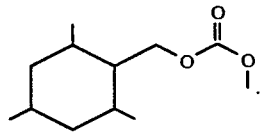

FIG. 58 is the infra-red spectrum for the compound having the structure:

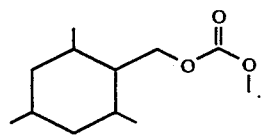

Other members of the genus:

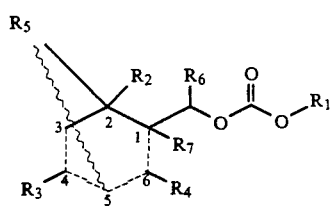

wherein each of the dashed lines is a carbon-carbon single bond can be produced from compounds wherein one of the dashed lines is a carbon-carbon double bond by means of the reaction:

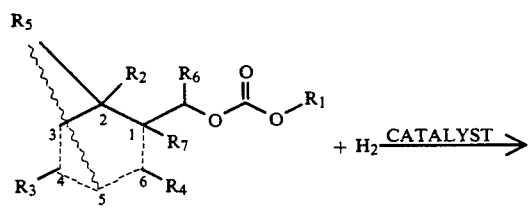

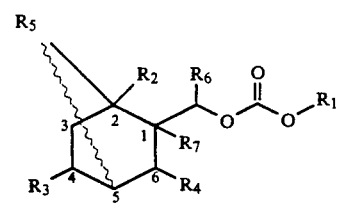

Such a reaction uses the standard hydrogenation catalyst such as Raney nickel or palladium supported on carbon. The reaction temperature may vary between about 80° C. and 130° C. with a pressure varying between about 250 psig and 400 psig.

Accordingly, compounds defined according to the genus:

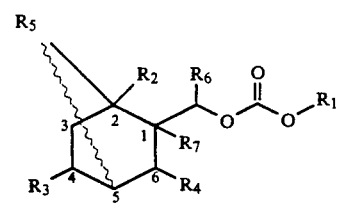

may be prepared from their corresponding alcohols or from their corresponding unsaturated precursors as set forth in Example XV, supra.

By the same token such compounds as are prepared using Example XV are produced, for example, according to the reaction:

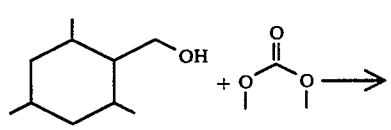

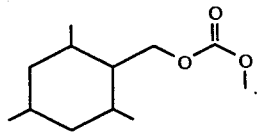

In the situation where $R_7$ is alkyl, such compounds as the compound having the structure:

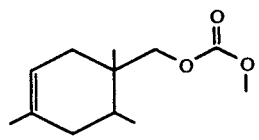

or the compound having the structure:

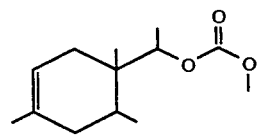

may be prepared, respectively, precursors having the structure:

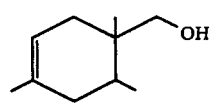

and

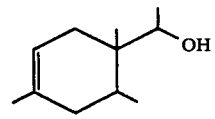

according to the reactions, respectively, to wit:

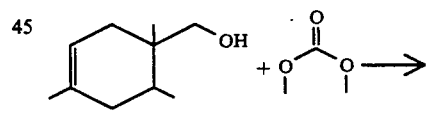

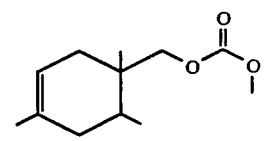

and

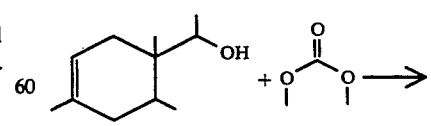

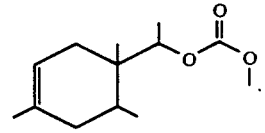

The precursors having the structures:

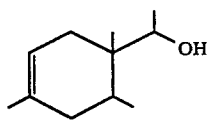

and

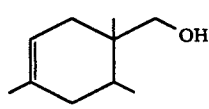

are produced according to the procedures of European Application 199,330 published on Apr. 21, 1986 and granted on Dec. 9, 1990 as European Patent 199,330 or by means of Dutch Published Application 87/01489 published on June 25, 1987 (abstracted at Chemical Abstracts, Volume 110:236970g).

EXAMPLE XVI

PREPARATION OF METHYL]2,6,6-TRIMETHYL-1-CYCLOHEXENE-1-YL] METHYL ESTER OF CARBONIC ACID

Reaction:

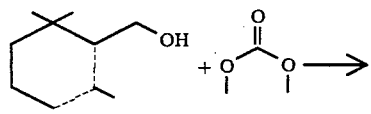

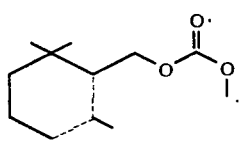

wherein, in the compounds having the structures:

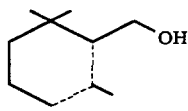

and

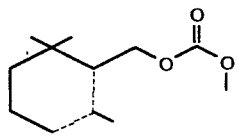

these structures represent mixtures and in the mixtures in each of the compounds one of the dashed lines is a carbon-carbon double bond and each of the other of the dashed lines represent carbon-carbon single bonds.

Into a 3 liter reaction vessel equipped with stirrer, thermometer, reflux condenser, heating mantle and nitrogen blanket apparatus are placed 670 grams of the mixture of compounds defined according to the generic structure:

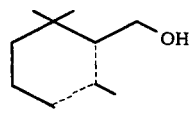

and 1170 grams of dimethyl carbonate. The mixture is stirred for a period of 15 minutes while being heated to 50°–55° C.

Over a period of 0.75 hours while maintaining the temperature at 50°–55° C., 195 grams of a 25% solution of sodium methoxide is added to the reaction mass.

The reaction mass is then heated to reflux (70° C.) and maintained at reflux (70°–76° C.) for a period of ten hours.

At the end of the ten hour period, the reaction mass is cooled and 1100 cc of a 5% acetic acid solution is added to the reaction mass.

The organic phase is separated from the aqueous phase and the organic phase is washed with 800 cc of saturated sodium chloride solution.

The organic phase is then fractionally distilled yielding the following fractions:

| Fraction No. | Vapor Temp. (°C.) | Liquid Temp. (°C.) | Vacuum mm/Hg. Pressure |
|---|---|---|---|
| 1 | 80/103 | 113/113 | 3.23 |
| 2 | 106 | 116 | 2.66 |
| 3 | 106 | 116 | 2.67 |
| 4 | 107 | 119 | 3.20 |
| 5 | 112 | 123 | 4.73 |
| 6 | 110 | 123 | 3.85 |
| 7 | 109 | 133 | 5.07 |
| 8 | 108 | 117 | 10.9 |
| 9 | 100 | 106 | 8.18. |

FIG. 59 is the GLC profile for the reaction mass prior to distillation. The peak indicated by reference numeral 591 is the peak for the compound having the structure:

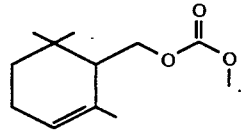

The peak indicated by reference numeral 593 is the peak for the compound having the structure:

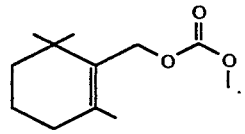

FIG. 60 is the NMR spectrum for the compound having the structure:

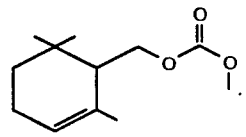

FIG. 61 is the infra-red spectrum for the compound having the structure:

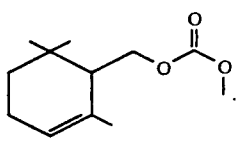

FIG. 59 is the NMR spectrum for the compound having the structure:

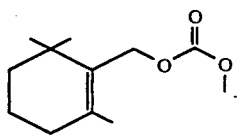

FIG. 63 is the infra-red spectrum for the compound having the structure:

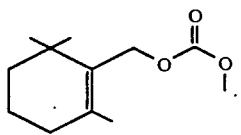

EXAMPLE XVII

PREPARATION OF METHYL[2,6,6-TRIMETHYL-1-CYCLOHEXENE-1-YL] METHYL ESTER OF CARBONIC ACID

Reaction:

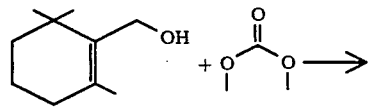

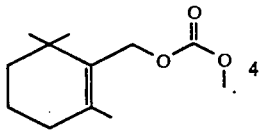

Into a 2 liter reaction flash equipped with stirrer, thermometer, reflux condenser and nitrogen blanket apparatus are placed 323 grams of betacyclogeraniol and 546 grams of dimethyl carbonate. The reaction mass is heated to 40°-45° C. While maintaining the reaction mass at 40°-45° C. over a period of one hour, 87.0 grams of sodium methoxide solution (25% in methanol) is added to the reaction mass. At the end of the one hour period, the reaction mass is heated to reflux (70°-72° C.) and maintained at reflux conditions for a period of five hours. At the end of the five hour period, the reaction mass is admixed with 500 cc of 55 aqueous acetic acid.

The reaction mass is then admixed with 200 cc of toluene. The organic phase is separated from the aqueous phase and the organic phase is washed with one 500 cc portion of saturated sodium chloride.

The organic phase is then fractionally distilled yielding the following fractions:

| Fraction No. | Vapor Temp. (°C.) | Liquid Temp. (°C.) | Vacuum mm/Hg. Pressure |
|---|---|---|---|
| 1 | 84/78 | 105/95 | 0.885 |
| 2 | 83 | 100 | 0.577 |
| 3 | 85 | 104 | 0.533 |
| 4 | 80 | 138 | 0.755 |
| 5 | 80 | 147 | 0.856. |

Fractions 2-4 are bulked.

FIG. 64 is the GLC profile of the reaction mass prior to distillation. The peak indicated by reference numeral 640 is the peak for the compound having the structure:

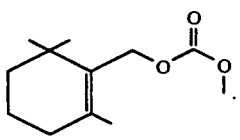

FIG. 65 is the NMR spectrum for the compound having the structure:

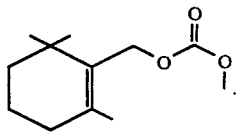

FIG. 66 is the infra-red spectrum for the compound having the structure:

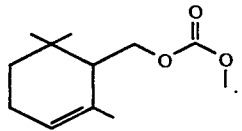

EXAMPLE XVIII

JASMINE PERFUME COMPOSITION

The following mixture is prepared:

| Ingredients | XVIII(A) | XVIII(B) | XVIII(C) |
|---|---|---|---|
| The compound having the structure: <br> prepared according to Example I, bulked distillation fractions 7-12. | 230 | 0 | 0 |
| The compound having the structure: <br> prepared according to Example II, bulked distillation fractions 8-16. | 0 | 230 | 0 |
| The compound having the structure: | 0 | 0 | 230 |

-continued

| Ingredients | XVIII(A) | XVIII(B) | XVIII(C) |
|---|---|---|---|
| 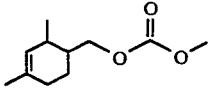 prepared according to Example III, bulked distillation fractions 10-20. | | | |
| Benzyl acetate | 150 | 150 | 150 |
| Linalool | 60 | 60 | 60 |
| Linalyl acetate | 60 | 60 | 60 |
| Hydroxy citronellal | 60 | 60 | 60 |
| Ylang oil | 40 | 40 | 40 |
| Methyl jasmonate | 25 | 25 | 25 |
| Benzyl salicylate | 15 | 15 | 15 |
| Geranyl acetate | 25 | 25 | 25 |
| n-undecanal | 25 | 25 | 25 |
| Para-cresyl phenyl acetate | 10 | 10 | 10 |
| Phenylethyl acetate | 20 | 20 | 20 |
| Phenylethyl alcohol | 50 | 50 | 50 |
| Indol | 20 | 20 | 20 |
| Coumarin | 12 | 12 | 12. |

The compound having the structure:

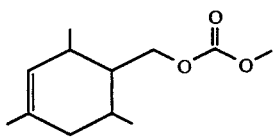

produced according to Example I, bulked fractions 7-12 imparts to this jasmine perfume composition green, fruity, floral, rose, tulip, spicy and anisic topnotes, with floral, rose, tulip, green, stemmy, fruity, pear-like, spicy and clove-like undertones. Accordingly, the perfume composition of Example (XVIII(A) can be described as "jasmine, with green, fruity, floral, rose, tulip, spicy and anisic topnotes, and floral, rose, tulip, green, stemmy, fruity, pear-like, spicy and clove-like" undertones.

The compounds of Example II having the structure:

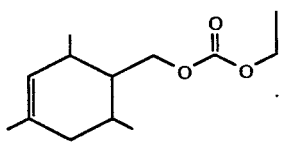

bulked fractions 8-16 imparts to this jasmine perfume formulation green and fruity undertones with floral topnotes. Accordingly, the perfume formulation of Example XVIII(B) can be described as "jasmine, with green and fruity undertones and floral topnotes".

The compound of Example III, bulked distillation fractions 10-20 having the structure:

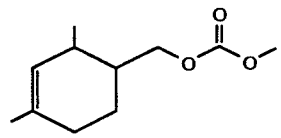

imparts to this jasmine perfume formulation a green undertone with green topnotes. Accordingly, the perfume formulation of Example XVIII(C) can be described as "jasmine having green undertones and green topnotes".

EXAMPLE XIX

HERBAL FRAGRANCE FORMULATION

The following mixture is prepared:

| Ingredients | XIX(A) | XIX(B) | XIX(C) |
|---|---|---|---|
| Amyl cinnamic aldehyde | 20 | 20 | 20 |
| Phenyl acetaldehyde dimethyl acetal | 4 | 4 | 4 |
| Thyme oil white | 8 | 8 | 8 |
| Sauge sclaree French | 8 | 8 | 8 |
| Galbanum oil | 4 | 4 | 4 |
| Juniper berry oil | 10 | 10 | 10 |
| Methyl octin carbonate | 4 | 4 | 4 |
| Linalyl acetate | 2 | 2 | 2 |
| Dihydro methyl jasmonate | 10 | 10 | 10 |
| The compound having the structure: 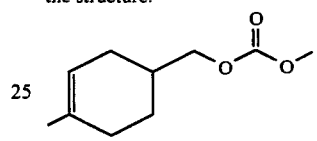 produced according to Example IV, bulked distillation fractions 16-21. | 10 | 0 | 0 |
| The compound having the structure: 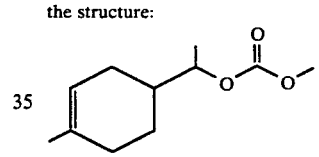 prepared according to Example V, bulked distillation fractions 4-13. | 0 | 10 | 0 |
| The compound having the structure: 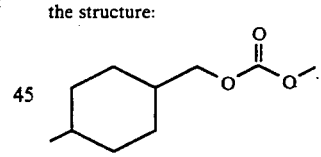 prepared according to Example VII, bulked distillation fractions 5-15. | 0 | 0 | 10 |

The compound having the structure:

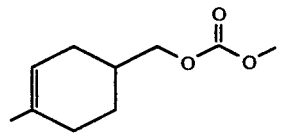

prepared according to Example IV, bulked distillation fractions 16-21 imparts to this herbal fragrance formulation green, fruity, anisic and lavender topnotes with green and fruity undertones. Accordingly, the fragrance formulation of Example XIX(A) can be described as "herbal, having green, fruity, anisic and lavender topnotes with green and fruity undertones".

The compound having the structure:

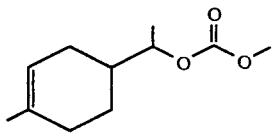

prepared according to Example V, bulked distillation fractions 4–13 imparts to this herbal formulation sweet, anisic, herbal, basil, winey and cognac undertones, with cognac-like and rum-like topnotes. Accordingly, the herbal formulation of Example XIX(B) can be described as "herbal, with sweet, anisic, herbal, basil, winey and cognac undertones and cognac-like and rum-like topnotes".

The compound having the structure:

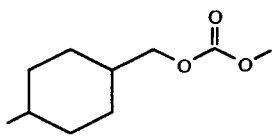

prepared according to Example VII, bulked fractions 5–15 imparts to this herbal formulation sweet and anisic undertones with sweet, "air-dried clothing"-like, ozoney and anisic topnotes. Accordingly, the fragrance of Example XIX(C) can be described as "herbal, with sweet and anisic undertones and sweet, "air-dried clothing"-like, ozoney and anisic topnotes".

EXAMPLE XX

JASMINE PERFUME COMPOSITION

The following mixture is prepared:

| Ingredients | XX(A) | XX(B) | XX(C) |
|---|---|---|---|
| The compound having the structure: 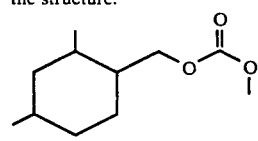 prepared according to Example VI. | 230 | 0 | 0 |
| The compound having the structure: 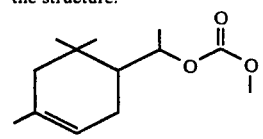 prepared according to Example VIII. | 0 | 230 | 0 |
| The compound having the structure: 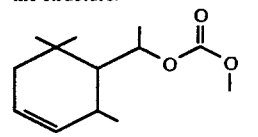 prepared according to Example IX. | 0 | 0 | 230 |
| Benzyl acetate | 150 | 150 | 150 |
| Linalool | 60 | 60 | 60 |
| Linalyl acetate | 60 | 60 | 60 |
| Hydroxy citronellal | 60 | 60 | 60 |
| Ylang oil | 40 | 40 | 40 |
| Methyl jasmonate | 25 | 25 | 25 |
| Benzyl salicylate | 15 | 15 | 15 |
| Geranyl acetate | 25 | 25 | 25 |
| n-undecanal | 25 | 25 | 25 |
| Para-cresyl phenyl acetate | 10 | 10 | 10 |
| Phenylethyl acetate | 20 | 20 | 20 |
| Phenylethyl alchool | 50 | 50 | 50 |
| Indol | 20 | 20 | 20 |
| Coumarin | 12 | 12 | 12. |

The compound having the structure:

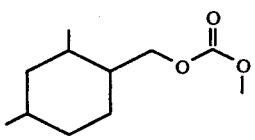

produced according to Example VI, imparts to this jasmine perfume composition herbal, green, spicy, woody and cognac-topnotes, with figgy and woody undertones. Accordingly, the perfume composition of Example XX(A) can be described as "jasmine, with herbal, green, spicy, woody and cognac-like topnotes and figgy and woody undertones".

The compound having the structure:

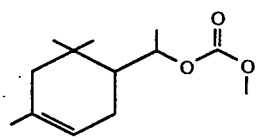

prepared according to Example VIII, imparts to this jasmine perfume formulation leathery and myrrh-like undertones with balsamic and warm floral topnotes. Accordingly, the perfume formulation of Example XX(B) can be described as "jasmine, with leathery and myrrh-like undertones and balsamic and warm floral topnotes".

The compound the structure:

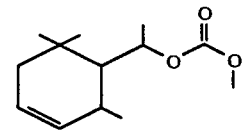

prepared according to Example IX, imparts to this jasmine perfume formulation earthy, minty, eucalyptus, sweet, woody and camphoraceous topnotes and early morning forest path, earthy, rooty, woody, eucalyptus and camphoraceous undertones. Accordingly, the perfume formulation of Example XX(C) can be described as "jasmine having earthy, minty, eucalyptus, sweet, woody and camphoraceous topnotes and early morning forest path, earthy, rooty, woody, eucalyptus and camphoraceous undertones".

EXAMPLE XXI

HERBAL FRAGRANCE FORMULATION

The following mixture is prepared:

| Ingredients | Parts by Weight | | |
|---|---|---|---|
| | XXI(A) | XXI(B) | XXI(C) |
| Amyl cinnamic aldehyde | 20 | 20 | 20 |
| Phenyl acetaldehyde dimethyl acetal | 4 | 4 | 4 |
| Thyme oil white | 8 | 8 | 8 |
| Sauge sclaree French | 8 | 8 | 8 |
| Galbanun oil | 4 | 4 | 4 |
| Juniper berry oil | 10 | 10 | 10 |
| Methyl octin carbonate | 4 | 4 | 4 |
| Linalyl acetate | 2 | 2 | 2 |
| Dihydro methyl jasmonate | 10 | 10 | 10 |
| The compound having the structure: | 10 | 0 | 0 |

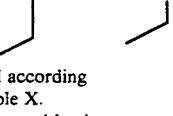

produced according to Example X.

| The compound having the structure: | 0 | 10 | 0 |

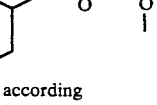

prepared according to Example XI.

| The compound having the structure: | 0 | 0 | 10 |

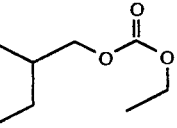

prepared according to Example XII.

The compound having the structure:

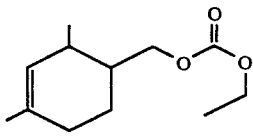

prepared according to Example X, imparts to this herbal fragrance formulation a fresh, green, herbaceous and rose undertone. Accordingly, the perfume formulation of Example XXI(A) can be described as "herbal, with a fresh, green and rose undertone".

The compound having the structure:

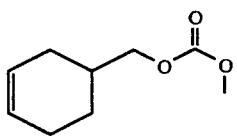

prepared according to EXAMPLE XI, imparts to this herbal formulation fruity, anisic, floral and violet undertones. Accordingly, the perfume formulation of Example XXI(B) can be described as "herbal, with fruity, anisic, floral and violet undertones".

The compound having the structure:

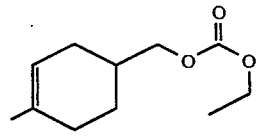

prepared according to Example XII, imparts to this herbal formulation sweet, anisic topnotes, and sweet, aubepine and anisic undertones. Accordingly, the formulation of Example XXI(C) can be described as "herbal, with sweet, anisic topnotes and sweet, aubepine and anisic undertones".

EXAMPLE XXII

JASMINE PERFUME COMPOSITION

The following mixture is prepared:

| Ingredients | XXII(A) | XXII(B) | XXII(C) |
|---|---|---|---|
| The compound having the structure: | 230 | 0 | 0 |

prepared according to Example XIII.

| The compound having the structure: | 0 | 230 | 0 |

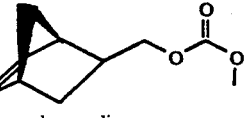

prepared according to Example XIV.

| The compound having the structure: | 0 | 0 | 230 |

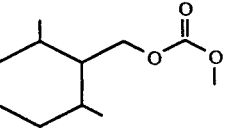

prepared according to Example XV.

| Benzyl acetate | 150 | 150 | 150 |
| Linalool | 60 | 60 | 60 |
| Linalyl acetate | 60 | 60 | 60 |
| Hydroxy citronellal | 60 | 60 | 60 |
| Ylang oil | 40 | 40 | 40 |
| Methyl jasmonate | 25 | 25 | 25 |
| Benzyl salicylate | 15 | 15 | 15 |
| Geranyl acetate | 25 | 25 | 25 |
| n-undecanal | 25 | 25 | 25 |
| Para-cresyl phenyl acetate | 10 | 10 | 10 |
| Phenylethyl acetate | 20 | 20 | 20 |
| Phenylethyl alcohol | 50 | 50 | 50 |
| Indol | 20 | 20 | 20 |
| Coumarin | 12 | 12 | 12. |

The compound having the structure:

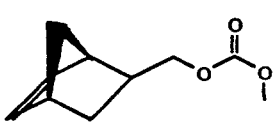

prepared according to Example XIII, imparts to this jasmine formulation fruity, banana, blueberry, green and violet topnotes and fruity, green and violet undertones. Accordingly, the perfume formulation of Example XXII(A) can be described as "jasmine, having fruity, banana, blueberry, green and violet topnotes, with fruity, green and violet undertones".

The compound having the structure:

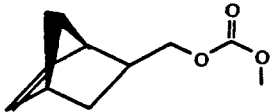

prepared according to Example XIV, imparts to this jasmine formulation fruity and violet topnotes, with fruity, minty and violet undertones. Accordingly, the perfume formulation of Example XXII(B) can be described as "jasmine, having fruity and violet topnotes and fruity, minty and violet undertones".

The compound having the structure:

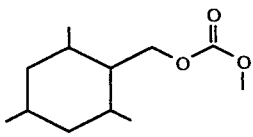

prepared according to Example XV, imparts to this jasmine formulation fresh, green, rose, ozoney and fresh air-dried clothing undertones and rose and green topnotes. Accordingly, the perfume formulation of Example XXII(C) can be described as "jasmine, having rose and green topnotes and fresh, green, rose, ozoney and fresh air-dried clothing undertones".

EXAMPLE XXIII

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below.

TABLE II

| Substance | Aroma Description |
|---|---|
| The compound having the structure:<br><br>prepared according to Example I, bulked distillation fractions 7–12. | A green, fruity, floral, rose, tulip, spicy and anisic aroma with floral, rose, tulip, green, stemmy, fruity, pear-like, spicy and clove-like undertones. |
| The compound having the structure:<br><br>prepared according to Example II, bulked distillation fractions 8–16. | A green and fruity aroma with floral topnotes. |

TABLE II-continued

| Substance | Aroma Description |
|---|---|
| The compound having the structure:<br><br>prepared according to Example III, bulked distillation fractions 10–20. | A green aroma with green topnotes. |
| The compound having the structure:<br><br>prepared according to Example IV, bulked distillation fractions 16–21. | A green, fruity, anisic, lavender aroma, with green and fruity undertones. |
| The compound having the structure:<br><br>prepared according to Example V, bulked distillation fractions 4–13. | A sweet, anisic, herbal, basil, winey and cognac aroma profile with cognac-like and rum-like topnotes. |
| The compound having the structure:<br><br>prepared according to Example VII, bulked distillation fractions 5–15. | A sweet, anisic aroma with sweet, "air-dried clothing"-like, ozoney, and anisic topnotes. |
| The compound having the structure:<br><br>prepared according to Example VIII. | A leathery, myrrh-like aroma with balsamic and warm floral topnotes. |
| The compound having the structure:<br><br>prepared according to Example IX. | An earthy, minty, eucalyptus sweet, woody and camphoraceous aroma with early morning forest path, earthy, rooty, woody, eucalyptus and camphoraceous undertones. |
| The compound having the structure:<br><br>prepared according to Example X. | A fresh, green, herbaceous and rose aroma profile. |
| The compound having | A green, fruity, anisic, |

TABLE II-continued

| Substance | Aroma Description |
|---|---|
| the structure:<br>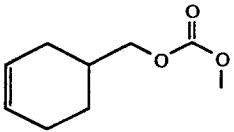<br>prepared according to Example XI. | floral and violet aroma profile. |
| The compound having the structure:<br>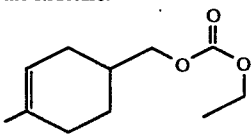<br>prepared according to Example XII. | A green, sweet, anisic aroma with green, sweet, aubepine, anisic undertones. |
| The compound having the structure:<br>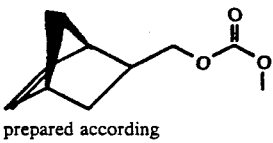<br>prepared according to Example XIII. | A fruity, banana, blueberry green and violet aroma profile with fruity, green and violet undertones. |
| The compound having the structure:<br>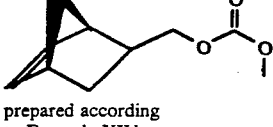<br>prepared according to Example XIV. | A fruity and violet aroma with fruity, minty and violet undertones. |
| The compound having the structure:<br>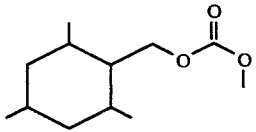<br>prepared according to Example XV. | A fresh, green, rose, ozoney and fresh air-dried clothing aroma with rose and green topnotes. |
| Perfume composition of Example XVIII(A). | Jasmine, with green, fruity, floral, rose, tulip, spicy and anisic topnotes, and foral, rose, tulip, green, stemmy, fruity, pear-like, spicy and clove-like undertones. |
| Perfume composition of Example XVIII(B). | Jasmine, with green and fruity undertones and floral topnotes. |
| Perfume composition of Example XVIII(C). | Jasmine having green undertones and green topnotes. |
| Perfume composition of Example XIX(A). | Herbal, having green, fruity, anisic and lavender topnotes with green and fruity undertones. |
| Perfume composition of Example XIX(B). | Herbal, with sweet, anisic, herbal, basil, winey and cognac undertones and cognac-like and rum-like undertones. |
| Perfume composition of Example XIX(C). | Herbal, with sweet and anisic undertones and sweet, "air-dried clothing"-like, ozoney and anisic topnotes. |
| Perfume composition of Example XX(A). | Jasmine, with herbal, green, spicy, woody and cognac-like topnotes and figgy and woody undertones. |
| Perfume composition of Example XX(B). | Jasmine, with leathery and myrrh-like undertones and balsamic and warm floral topnotes. |
| Perfume composition of Example XX(C). | Jasmine, having earthy, minty, eucalyptus, sweet, woody and camphoraceous topnotes and early morning forest path, earthy, rooty, woody, eucalyptus and camphoraceous undertones. |
| Perfume composition of Example XXI(A). | Herbal, with a fresh, green, and rose undertone. |
| Perfume composition of Example XXI(B). | Herbal, with fruity, anisic, floral and violet undertones. |
| Perfume composition of Example XXI(C). | Herbal, with sweet, anisic, topnotes and sweet, aubepine anisic undertones. |
| Perfume composition of Example XXII(A). | Jasmine, having fruity, banana, blueberry, green and violet topnotes, with fruity, green and violet undertones. |
| Perfume composition of Example XXII(B). | Jasmine, having fruity and violet topnotes and fruity, minty and violet undertones. |
| Perfume consumption of Example XXII(C). | Jasmine, having rose and green topnotes and fresh, green, rose, ozoney and fresh air-dried clothing undertones. |

EXAMPLE XXIV

PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976 incorporated by reference herein) with aroma nuances as set for in Table II of Example XXIII, are prepared containing 0.105, 0.15%, 0.20%, 0.25%, 0.30% and 0.35% of the substance set forth in Table II of Example XXIII. They are prepared by adding and homogeneously mixing the appropriate quantity of substance set forth in Table II of Example XXIII in the liquid detergent. The detergents all possess excellent aromas as set forth in Table II of Example XXIII, the intensity increasing with greater concentrations of substance as set forth in Table II of Example XXIII.

EXAMPLE XXV

PREPARATION OF COLOGNES AND HANDKERCHIEF PERFUMES

Compositions as set forth in Table II of Example XXIII are incorporated into colognes at concentrations of 2.0%, 2.5%, 3.0%, 3.5%, 4.0%, 4.5% and 5.05 in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example XXIII are imparted to the colognes and to the handkerchief perfumes at all levels indicated.

EXAMPLE XXVI

PREPARATION OF SOAP COMPOSITIONS

One hundred grams of soap chips (per sample) (IVORY ® produced by the Proctor & Gamble Company of Cincinnati, Ohio), are each mixed with one gram samples of substances as set forth in Table II of Example XXIII until homogeneous compositions are obtained. In each of the cases, the homogeneous compositions are heated under 8 atmospheres pressure at 180° C. for a period of three hours and the resulting liquids are placed into soap molds. The resulting soap cakes, on cooling, manifest aromas as set forth in Table II of Example XXIII.

EXAMPLE XXVII

PREPARATION OF SOLID DETERGENT COMPOSITIONS

Detergents are prepared using the following ingredients according to Example I of Canadian Patent No. 1,007,948 (incorporated by reference herein):

| Ingredient | Percent by Weight |
|---|---|
| NEODOL ® 45-11 (a $C_{14-15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example XXIII. Each of the detergent samples has an excellent aroma as indicated in Table II of Example XXIII.

EXAMPLE XXVIII

Utilizing the procedure of Example I at column 15 of U.S. Pat. No. 3,632,396 (the disclosure of which is incorporated herein by reference), nonwoven cloth substrates useful as drier-added fabric softening articles of manufacture are prepared wherein the substrate, the substrate coating, the outer coating and the perfume material are as follows:

1. A water "dissolvable" paper ("Dissolvo Paper");
2. Adogen 448 (m.p. about 140° F.) as the substrate coating; and
3. An outer coating having the following formulation (m.p. about 150° F.);
   57%—$C_{20-22}$ HAPS
   22%—isopropyl alcohol
   20%—antistatic agent of one of the substances as set forth in Table II of Example XXIII.

Fabric softening compositions prepared according to Example I at column 15 of U.S. Pat. No. 3,632,396 having aroma characteristics as set forth in Table II of Example XXIII, supra, consist of a substrate coating having a weight of about 3 grams per 100 square inches of substrate; a first coating located directly on the substrate coating consisting of about 1.85 grams per 100 square inches of substrate; and an outer coating coated on the first coating consisting of about 1.4 grams per 100 square inches of substrate. One of the substances of Table II of Example XXIII is admixed in each case with the outer coating mixture, thereby providing a total aromatized outer coating weight ratio to substrate of about 0.5:1 by weight of the substrate. The aroma characteristics are imparted in a pleasant manner to the head space in a drier on operation thereof in each case using said drier-added fabric softener non-woven fabrics and these aroma characteristics are described in Table II of Example XXIII, supra.

EXAMPLE XXIX

HAIR SPRAY FORMULATIONS

The following hair spray formulation is prepared by first dissolving PVP/VA E-735 copolymer manufactured by the GAF Corporation of 140 West 51st Street, New York, N.Y. in 91.62 grams of 95% food grade ethanol. 8.0 Grams of the polymer is dissolved in the alcohol. The following ingredients are added to the PVP/VA alcoholic solution:

| | Weight Percent |
|---|---|
| Dioctyl sebacate | 0.05 |
| Benzyl alcohol | 0.10 |
| Dow Corning 473 fluid (prepared by the Dow Corning Corporation) | 0.10 |
| Tween 20 surfactant (prepared by ICI America Corporation) | 0.03 |
| One of the perfumery substances as set forth in Table II of Example XXIII. | 0.10 |

The perfuming substances as set forth in Table II of Example XXIII add aroma characteristics as set forth in Table II of Example XXIII which are rather intense and aesthetically pleasing to the users of the soft-feel, good-hold pump hair sprays.

What is claimed is:

1. A alkyl cyclohexylmethyl and cyclohexenylmethyl carbonate defined according to the structure:

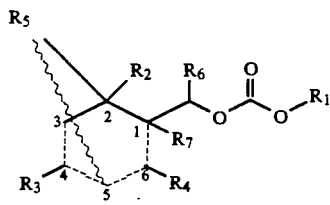

wherein $R_1$ is ethyl or methyl; $R_2$, $R_3$, $R_4$ and $R_6$ represent hydrogen or methyl; $R_5$ represents hydrogen, methyl or methylene; $R_7$ represent hydrogen or $C_1$-$C_4$ straight chain lower alkyl or isopropyl or $R_7$ is no moiety; the dashed lines represent carbon-carbon single bonds or carbon-carbon double bonds; and the wavy line represents a carbon-carbon single bond or no bond; with the provisos that:

(a) at least three of the dashed lines represent carbon-carbon single bonds;

(b) when $R_7$ is a moiety, the dashed lines at the "1-6" position is a carbon-carbon single bond;

(c) when the wavy line is a carbon-carbon single bond then $R_5$ is methylene and the carbon-carbon bonds at the "4-5" position and at the "5-6" position are carbon-carbon single bonds (d) when the wavy line is no bond and each of the dashed lines represent carbon-carbon single bonds, at least one of $R_2$ or $R_5$ is hydrogen.

2. The carbonate of claim 1 having the structure:

3. The carbonate of claim 1 having the structure:

4. The carbonate of claim 1 having the structure:

5. The carbonate of claim 1 having the structure:

6. The carbonate of claim 1 having the structure:

7. The carbonate of claim 1 having the structure:

8. The carbonate of claim 1 having the structure:

9. The carbonate of claim 1 having the structure:

10. The carbonate of claim 1 having the structure:

wherein one of the dashed lines represents a carbon-carbon double bond and the other of the dashed lines represents a carbon-carbon single bond.

11. The carbonate of claim 1 having the structure:

12. The carbonate of claim 1 having the structure:

13. The carbonate of claim 1 having the structure:

14. The carbonate of claim 1 having the structure:

15. A dimer defined according to the structure:

wherein the dashed lines represent carbon-carbon single bonds or carbon-carbon double bonds; the wavy lines represent carbon-carbon single bonds or no bonds; the molecule is symmetrical; $R_2$, $R_3$, $R_4$, $R_{20}$, $R_3''$, $R_{40}$ and $R_{30}$ each represents hydrogen or methyl; $R_5$ represents hydrogen, methyl or methylene; $R_{50}$ represents hydrogen, methyl or methylene; $R_7$ and $R_7'$ represent hydrogen, $C_1$–$C_4$ straight chain alkyl or isopropyl or $R_7$ and $R_7'$ represent no moiety; $R_6$ and $R_6''$ represents hydrogen or methyl; with the provisos that:

(a) at least six of the dashed lines are carbon-carbon single bonds;

(b) when $R_7$ and $R_7'$ represent no moieties, the dashed lines at the "1-6" position and at the "3'-4'" position are carbon-carbon double bonds; and (c) when the wavy lines are carbon-carbon single bonds, $R_5$ and $R_{50}$ are each methylene and the carbon-carbon bonds at the "4-5", "5-6", "4'-5'" and "5'-6'" positions are carbon-carbon single bonds.

16. The carbonate of claim 15 having the structure:

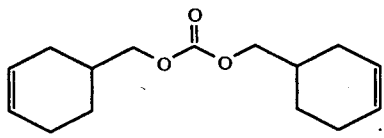

17. The carbonate of claim 15 having the structure:

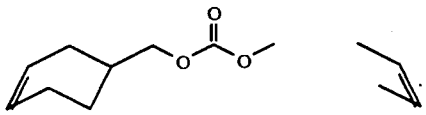

18. A perfume composition comprising a perfume base and intimately admixed therewith, an aroma augmenting, enhancing or imparting quantity of at least one alkyl cyclohexylmethyl and/or cyclohexenylmethyl carbonate defined according to claim 1.

19. A perfumed article comprising a perfumed article base and intimately admixed therewith, an aroma augmenting, enhancing or imparting quantity of at least one alkyl cyclohexylmethyl and/or cyclohexenylmethyl carbonate defined according to claim 1.

20. A cologne comprising water, ethyl alcohol and an aroma augmenting, enhancing or imparting quantity of at least one alkyl cyclohexylmethyl and/or cyclohexenylmethyl carbonate defined according to claim 1.

21. A process for augmenting or enhancing the aroma of a perfume composition, cologne or perfumed article comprising the step of intimately admixing with said perfume composition, cologne or perfumed article, an aroma augmenting, enhancing or imparting quantity of at least one alkyl cyclohexylmethyl and/or cyclohexenylmethyl carbonate defined according to claim 1.

22. A perfumed polymer comprising at least one microporous polymer and intimately admixed therewith in the pores thereof at least one alkyl cyclohexylmethyl and/or cyclohexenylmethyl carbonate defined according to claim 1.

* * * * *